(12) United States Patent
Silverman et al.

(10) Patent No.: US 9,845,474 B2
(45) Date of Patent: Dec. 19, 2017

(54) ENGINEERING OF MULTI-CARBON SUBSTRATE UTILIZATION PATHWAYS IN METHANOTROPHIC BACTERIA

(71) Applicant: Calysta, Inc., Menlo Park, CA (US)

(72) Inventors: Joshua A. Silverman, Los Altos Hills, CA (US); Effendi Leonard, Randolph, MA (US); Renee M. Saville, Mountain View, CA (US)

(73) Assignee: Calysta, Inc., Menlo Park, CA (US)

( * ) Notice: Subject to any disclaimer, the term of this patent is extended or adjusted under 35 U.S.C. 154(b) by 117 days.

(21) Appl. No.: 14/438,537

(22) PCT Filed: Oct. 24, 2013

(86) PCT No.: PCT/US2013/066665
§ 371 (c)(1),
(2) Date: Apr. 24, 2015

(87) PCT Pub. No.: WO2014/066670
PCT Pub. Date: May 1, 2014

(65) Prior Publication Data
US 2015/0275219 A1    Oct. 1, 2015

Related U.S. Application Data

(60) Provisional application No. 61/718,024, filed on Oct. 24, 2012.

(51) Int. Cl.
| | |
|---|---|
| C12N 15/52 | (2006.01) |
| C12N 1/20 | (2006.01) |
| C12N 9/00 | (2006.01) |
| C12N 9/12 | (2006.01) |
| C12N 9/04 | (2006.01) |

(52) U.S. Cl.
CPC ............... *C12N 15/52* (2013.01); *C12N 1/20* (2013.01); *C12N 9/0006* (2013.01); *C12N 9/1205* (2013.01); *C12N 9/93* (2013.01); *C12Y 101/01008* (2013.01); *C12Y 101/01027* (2013.01); *C12Y 207/0103* (2013.01); *C12Y 602/01001* (2013.01)

(58) Field of Classification Search
None
See application file for complete search history.

(56) References Cited

U.S. PATENT DOCUMENTS

| | | | |
|---|---|---|---|
| 4,490,465 | A | 12/1984 | Limbach et al. |
| 6,555,353 | B2 | 4/2003 | Koffas et al. |
| 6,689,601 | B2 | 2/2004 | Koffas et al. |
| 6,818,424 | B2 | 11/2004 | DiCosimo et al. |
| 7,098,005 | B2 | 8/2006 | Dicosimo et al. |
| 2003/0003528 | A1 | 1/2003 | Brzostowicz et al. |
| 2006/0057726 | A1 | 3/2006 | Sharpe |
| 2008/0026005 | A1 | 1/2008 | Miguez et al. |
| 2008/0292918 | A1 | 11/2008 | Finnerty et al. |
| 2009/0253192 | A1 | 10/2009 | Emptage et al. |
| 2010/0221813 | A1 | 9/2010 | Miguez et al. |
| 2011/0143408 | A1 | 6/2011 | Yang |
| 2012/0034594 | A1 | 2/2012 | Semrau et al. |
| 2012/0129241 | A1 | 5/2012 | Zhang et al. |

FOREIGN PATENT DOCUMENTS

| | | |
|---|---|---|
| EP | 0 296 484 A2 | 12/1988 |
| WO | 02/18617 A2 | 3/2002 |
| WO | 2007/003574 A1 | 1/2007 |
| WO | 2014/047209 A1 | 3/2014 |

OTHER PUBLICATIONS

Belova et al., "Acetate Utilization as a survival strategy of peat-inhabiting *Methylcystis* spp.", Env. Micro. Reports, 2011, 3(1):36-46. doi:10.1111/j.1758-2229.2010.00180.x.*
Prather et al., "De novo biosynthetic pathways: rational design of microbial chemical factories", Current Opinion in Biotechnology 2008, 19:468-474. DOI 10.1016/j.copbio.2008.07.009.*
Kizer et al., "Application of Functional Genomics to Pathway Optimization for Increased Isoprenoid Production", Applied and Environmental Microbiology, May 2008, vol. 74, No. 10, p. 3229-3241. doi:10.1128/AEM.02750-07.*
Semrau et al., "Facultative methanotrophy: false leads, true results, and suggestions for future research", FEMS Microbiol. Lett, 2011, 323:1-12. DOI:10.1111/j.1574-6968.2011.02315.x.*
Abram et al., "Proteomic Analyses of a *Listeria monocytogenes* Mutant Lacking $\sigma^B$ Identify New Components of the $\sigma^B$ Regulon and Highlight a Role for $\sigma^B$ in the Utilization of Glycerol," *Applied and Environmental Microbiology* 74(3):594-604, 2008.
Akhverdyan et al., "Application of the bacteriophage Mu-driven system for the integration/amplification of target genes in the chromosomes of engineered Gram-negative bacteria—mini review," *Appl Microbiol Biotechnol* 91:857-871, 2011.
Albers et al., "Glucose Transport in the Extremely Thermoacidophilic *Sulfolobus solfataricus* Involves a High-Affinity Membrane-Integrated Binding Protein," *Journal of Bacteriology* 181(14):4285-4291, 1999.
Ali et al., "Development and validation of promoter-probe vectors for the study of methane monooxygenase gene expression in *Methylococcus capsulatus* Bath," *Microbiology* 155:761-771, 2009.
Ali et al., "Duplication of the *mmoX* gene in Methylosinus sporium: cloning, sequencing and mutational analysis," *Microbiology* 152:2931-2942, 2006.
Asai et al., "Regulation of the transport system for $C_4$-dicarboxylic acids in *Bacillus subtilis*," *Microbiology* 146:263-271, 2000.
Bott et al., "Methylmalonyl-CoA decarboxylase from *Propionigenium modestum* Cloning and sequencing of the structural genes and purification of the enzyme complex," *Eur. J. Biochem* 250:590-599, 1997.
Bott et al., "Regulation of anaerobic citrate metabolism in *Klebsiella pneumoniae*," *Molecular Microbiology* 18(3):533-546, 1995, (article abstract) 1 page.
Bott, "Anaerobic citrate metabolism and its regulation in enterobacteria," *M. Arch Microbiol* 167(2-3):78-88, 1997 (article abstract), 2 pages.
Brosius, "Toxicity of an overproduced foreign gene product in *Escherichia coli* and its use in plasmid vectors for the selection of transcription terminators," *Gene.* 27:161-172, 1984.

(Continued)

*Primary Examiner* — Suzanne M Noakes
(74) *Attorney, Agent, or Firm* — Seed Intellectual Property Law Group LLP

(57) ABSTRACT

The present disclosure relates to genetically engineered methanotrophic bacteria with the capability of growing on a multi-carbon substrate as a primary or sole carbon source and methods for growing methanotrophic bacteria on a multi-carbon substrate.

34 Claims, 1 Drawing Sheet

(56) References Cited

OTHER PUBLICATIONS

Brown et al., "A Second Transport System for L-Arabinose in *Escherichia coli* B/r Controlled by the *araC* Gene," *Journal of Bacteriology* 111(2): 606-613, 1972.
Brown et al., "Characterization of the $_L$-Lactate Dehydrogenase from *Aggregatibacter actinomycetemcomitans*," *PLoS One* 4(11):e7864, 2009, 5 pages.
Bryant et al., "Growth of Desulfovibrio in Lactate or Ethanol Media Low in Sulfate in Association with $H_2$-Utilizing Methanogenic Bacteria," *Applied and Environmental Microbiology* 33(5):1162-1169, 1977.
Chai et al., "A Widely Conserved Gene Cluster Required for Lactate Utilization in *Bacillus subtilis* and Its Involvement in Biofilm Formation," *Journal of Bacteriology* 191(8):2423-2430, 2009.
Charrier et al., "Cloning and Sequencing of two Enterococcal *glpK* Genes and Regulation of the Encoded Glycerol Kinases by Phosphoenolpyruvate-dependent, Phosphotransferase System-catalyzed Phosphorylation of a Single Histidyl Residue," *The Journal of Biological Chemistry* 272(22):14166-14174, 1997.
Chevance et al., "Mlc of *Thermus thermophilus*: a Glucose-Specific Regulator for a Glucose/Mannose ABC Transporter in the Absence of the Phosphotransferase System," *Journal of Bacteriology* 188(18): 6561-6571, 2006.
Crueger (Brock Ed.), *Biotechnology : a textbook of industrial microbiology*, $2^{nd}$ Edition, Sinauer Associates Inc., Sunderland, MA, 1969, (book abstract) 1 page.
Darbon et al., "Antitermination by GlpP, catabolite repression via CcpA and inducer exclusion triggered by P~GlpK dephosphorylation control *Bacillus subtilis glpFK* expression," *Molecular Microbiology* 43(4):1039-1052, 2002.
Darbon et al., "Glycerol transport and phosphoenolpyruvate dependent enzyme I- and HPr-catalysed phosphorylation of glycerol kinase in *Thermus flavus*," *Microbiology* 145:3205-3212, 1999.
Dedysh et al., "*Methylocella palustris* gen. nov., sp. nov., a new methane-oxidizing acidophilic bacterium from peat bogs, representing a novel subtype of serine-pathway methanotrophs," *International Journal of Systematic and Evolutionary Microbiology* 50:955-969, 2000.
Dedysh et al., "*Methylocella* Species Are Facultatively Methanotrophic," *Journal of Bacteriology* 187(13):4665-4670, 2005.
Denger et al., "New motile anaerobic bacteria growing by succinate decarboxylation to propionate," *Arch Microbiol.* 154(6):550-555, 1990.
Deshpande, "Ethanol production from cellulose by coupled saccharification/fermentation using *Saccharomyces cerevisiae* and cellulose complex from *Sclerotiun rolfsii* UV-8 mutant," *Applied Biochemistry and Biotechnology* 36(3):227-234, 1992, (article abstract) 3 pages.
Drider et al., "Genetic organization and expression of citrate permease in lactic acid bacteria," *Genet. Mol. Res.* 3(2)273-281, 2004.
Duetz et al., "Inducibility of the TOL Catabolic Pathway in *Pseudomonas putida*(pWW0) Growing on Succinate in Continuous Culture: Evidence of Carbon Catabolite Repression Control," *Journal of Bacteriology* 176(8):2354-2361, 1994.
Englesberg et al., "$_L$-Arabinose-Sensitive, $_L$-Ribulose 5-Phosphate 4-Epimerase-Deficient Mutants of *Escherichia coli*," *J. Bacteriol.* 84:137-146, 1962.
Erwin et al., "Oxidation of $_D$-Lactate and $_L$-Lactate by *Neisseria meningitidis*: Purification and Cloning of Meningococcal $_D$-Lactate Dehydrogenase," *Journal of Bacteriology* 175(20):6382-6391, 1993.
Essenberg et al., "*Brucella abortus* strain 2308 putative glucose and galactose transporter gene: cloning and characterization," *Microbiology* 143:1549-1555, 1997.
Exley et al., "Lactate Acquisition Promotes Successful Colonization of the Murine Genital Tract by *Neisseria gonorrhoeae*," *Infection and Immunity* 75(3): 1318-1324, 2007.
Föllner et al., "Expression of polyhydroxyalkanoic-acid-biosynthesis genes in methylotrophic bacteria relying on the ribulose monophosphate pathway," *Applied Microbiology and Biotechnology* 40:284-291, 1993.
Forward et al., "TRAP Transporters: a New Family of Periplasmic Solute Transport Systems Encoded by the *dctPQM* Genes of *Rhodobacter capsulatus* and by Homologs in Diverse Gram-Negative Bacteria," *Journal of Bacteriology* 179(17):5482-5493, 1997.
Fraenkel et al., "Glucose and Gluconate Metabolism in an *Escherichia coli* Mutant Lacking Phosphoglucose Isomerase," *Journal of Bacteriology* 93(5):1571-1578, 1967.
Fuhrer et al., "Experimental Identification and Quantification of Glucose Metabolism in Seven Bacterial Species," *Journal of Bacteriology* 187(5)1581-1590, 2005.
Futai et al., "Inducible Membrane-bound $_L$-Lactate Dehydrogenase from *Escherichia coli*," *The Journal of Biological Chemistry* 252(16):5820-5827, 1977.
Futai, "Membrane D-Lactate Dehydrogenase from *Escherichia coli*. Purification and Properties," *Biochemistry* 12(13):2468-2474, 1973, (first page only) 1 page.
Gallegos et al., "AraC/XylS Family of Transcriptional Regulators," *Microbiology and Molecular Biology Reviews* 61(4):393-410, 1997.
Garcia Sanchez et al., "Improved xylose and arabinose utilization by an industrial recombinant *Saccharomyces cerevisiae* strain using evolutionary engineering," *Biotechnology for Biofuels* 3(13): 2010, 11 pages.
Garvie, "Bacterial Lactate Dehydrogenases," *Microbiological Reviews* 44(1):106-139, 1980.
Gerstmeir et al., "Acetate metabolism and its regulation in *Corynebacterium glutamicum*," *Journal of Biotechnology* 104(1-3):99-122, 2003, 47 pages.
Gimenez et al., "The Gene *yjcG*, Cotranscribed with the Gene *acs*, Encodes an Acetate Permease in *Escherichia coli*," *Journal of Bacteriology* 185(21):6448-6455, 2003.
Glenn et al., "Short Communication | Succinate Uptake by Free-living and Bacteroid Forms of *Rhizobium leguminosarum*," *Journal of General Microbiology* 119:267-271, 1980.
Goldman et al., "Pathways of Glucose Catabolism in *Bacillus Subtilis*," *J. Bacteriol.* 86(2):303-311, 1963.
Gonzalez et al., "A new model for the anaerobic fermentation of glycerol in enteric bacteria: Trunk and auxiliary pathways in *Escherichia coli*," *Metabolic Engineering* 10(5):234-245, 2008, (article abstract) 3 pages.
Gustafsson et al., "Codon bias and heterologous protein expression," *Trends in Biotechnology* 22(7):346-353, 2004.
Gutowski et al., "Succinate Uptake and Related Proton Movements in *Escherichia coli* K12," *Biochem. J.* 152:647-654, 1975.
Henderson et al., "Transport of Galactose, Glucose and their Molecular Analogues by *Escherichia coli* K12," *Biochem. J.* 162:309-320, 1977.
Herzberg et al., "Unraveling a bacterial hexose transport pathway," *Current Opinion in Structural Biology* 4:814-822, 1994.
Hosie et al., "A Monocarboxylate Permease of *Rhizobium leguminosarum* Is the First Member of a New Subfamily of Transporters," *Journal of Bacteriology* 184(19):5436-5448, 2002.
Hua et al., "Responses of the Central Metabolism in *Escherichia coli* to Phosphoglucose Isomerase and Glucose-6-Phosphate Dehydrogenase Knockouts," *Journal of Bacteriology* 185(24):7053-7067, 2003.
Hugh et al., "The Taxonomic Significance of Fermentative Versus Oxidative Metabolism of Carbohydrates by Various Gram Negative Bacteria," *J. Bacteriol.* 66(1):24-26, 1953.
Im et al., "Characterization of a novel facultative *Methylocystis* species capable of growth on methane, acetate and ethanol," *Environmental Microbiology Reports* 3(2):174-181, 2011.
Ishiguro et al., "Cloning and Nucleotide Sequence of the Gene (*citC*) Encoding a Citrate Carrier from Several *Salmonella* serovars," *The Journal of Biological Chemistry* 267(14):9559-9564, 1992.
Janssen et al., "Succinate decarboxylation by *Propionigenium maris* sp. nov., a new anaerobic bacterium from an estuarine sediment" *Archives of Microbiology* 164(1):29-35, 1995, (article abstract) 2 pages.
Janssen, "Isolation of *Clostridium propionicum* strain 19acry3 and further characteristics of the species," *Archives of Microbiology* 155(6):566-571, 1991, (article abstract) 1 page.
Jolkver et al., "Identification and Characterization of a Bacterial Transport System for the Uptake of Pyruvate, Propionate, and Acetate in *Corynebacterium glutamicum*," *Journal of Bacteriology* 191(3):940-948, 2009.

(56) References Cited

OTHER PUBLICATIONS

Kawaguchi et al., "Identification and Functional Analysis of the Gene Cluster for $_L$-Arabinose Utilization in *Corynebacterium glutamicum*," *Applied and Environmental Microbiology* 75(11):3419-3429, 2009.
Kim et al., "Creating auxotrophic mutants in *Methylophilus methylotrophus* AS1 by combining electroporation and chemical mutagenesis," *Appl Microbiol Biotechnol* 48:105-108, 1997.
Kline et al., "The Lactic Dehydrogenases of *E. coli*," *Ann NY Acad Sci.* 119(3):905-919, 1965, (first page only) 1 page.
Kohn et al., "Mechanisms of Active Transport in Isolated Bacterial Membrane Vesicles | XV. Purification and Properties of the Membrane-Bound $_D$-Lactate Dehydrogenase from *Escherichia coli*," *The Journal of Biological Chemistry* 248(20):7012-7017, 1973.
Korithoski et al., "Transport and Metabolism of Citrate by *Streptococcus mutans*," *Journal of Bacteriology* 187(13):4451-4456, 2005.
Lee et al., "Crystalline $_L$-Ribulose 5-Phosphate 4-Epimerase from *Escherichia coli*," *The Journal of Biological Chemistry* 243(18):4700-4705, 1968.
Lin et al., "Utilization of L-α-Glycerophosphate by *Escherichia coli* Without Hydrolysis," *Proceedings of the National Academy of Sciences* 48:2145-2150, 1962.
Lloyd et al., "Heterologous expression of soluble methane monooxygenase genes in methanotrophs containing only particulate methane monooxygenase," *Arch Microbiol* 171:364-370, 1999.
Lo, "The molecular mechanism if dicarboxylic acid transport in *Escherichia coli* k 12," *Journal of Supramolecular Structure* 7(3-4):463-480, 1977, (article abstract) 1 page.
Lolkema et al., "Transport of citrate catalyzed by the sodium-dependent citrate carrier of *Klebsiella pneumoniae* is obligatory coupled to the transport of two sodium ions," *Eur. J. Biochem* 220:469-475, 1994.
Magni et al., "The properties of citrate transport catalyzed by CitP of *Lactococcus lactis* ssp. *lactis* biovar *diacetylactis*," *FEMS Microbiology Letters* 142:265-269, 1996.
Martin et al., "CitI, a Transcription Factor Involved in Regulation of Citrate Metabolism in Lactic Acid Bacteria," *Journal of Bacteriology* 187(15):5146-5155, 2005.
Martin et al., "Methane monooxygenase mutants of *Methylosinus trichosporium* constructed by marker-exchange mutagenesis," *FEMS Microbiology Letters* 127:243-248, 1995.
Molinari et al., "The Lactic Dehydrogenase of *Propionibacterium pentosaceum*," *Biochem. J.* 75:57-65, 1960.
Motoyama et al., "Effects of the amplification of the genes coding for the L-threonine biosynthetic enzymes on the L-threonine production from methanol by the gram-negative obligate methylotroph, *Methylobacillus glycogenes*," *Appl Microbiol Biotechnol* 42:67-72, 1994.
Murarka et al., "Fermentative Utilization of Glycerol by *Escherichia coli* and Its Implications for the Production of Fuels and Chemicals," *Applied and Environmental Microbiology* 74(4):1124-1135, 2008.
Myers et al., "Bacterial Manganese Reduction and Growth with Manganese Oxide as the Sole Electron Acceptor," *Science* 240(4857):1319-1321, 1988.
Núñez et al., "The gene *yghK* linked to the *glc* operon of *Escherichia coli* encodes a permease for glycolate that is structurally and functionally similar to $_L$-lactate permease," *Microbiology* 147:1069-1077, 2001.
Pinchuk et al., "Genomic reconstruction of *Shewanella oneidensis* MR-1 metabolism reveals a previously uncharacterized machinery for lactate utilization," *Proceedings of the National Academy of Sciences* 106(8):2874-2879, 2009.
Poysti et al., "*Sinorhizobium meliloti* pSymB carries genes necessary for arabinose transport and catabolism," *Microbiology* 153:727-736, 2007.
Rawls et al., "Activity and Transcriptional Regulation of Bacterial Protein-Like Glycerol-3-Phosphate Dehydrogenase of the Haloarchaea in *Haloferax volcanii*," *Journal of Bacteriology* 193(17):4469-4476, 2011.
Rittmann et al., "Engineering of a Glycerol Utilization Pathway for Amino Acid Production by *Corynebacterium glutamicum*," *Applied and Environmental Microbiology* 74(20):6216-6222, 2008.
Ruíz-Herrera et al., "Regulation of Succinate Dehydrogenase in *Escherichia coli*," *Journal of General Microbiology* 72:29-35, 1972.
Saier Jr., "Bacterial Phosphoenolpyruvate: Sugar Phosphotransferase Systems: Structural, Functional, and Evolutionary Interrelationships," *Bacteriological Reviews* 41(4):856-871, 1977.
Sá-Nogueira et al., "The *Bacillus subtilis* $_L$-arabinose (ara) operon: nucleotide sequence, genetic organization and expression," *Microbiology* 143:957-969, 1997.
Sarker et al., "Primary Structure and Properties of the Na$^+$/Glucose Symporter (SglS) of *Vibrio parahaemolyticus*," *Journal of Bacteriology* 179(5):1805-1808, 1997.
Schleif, "Regulation of the $_L$-arabinose operon of *Escherichia coli*," *Trends Genet.* 16(12):559-565, 2000.
Schweizer et al., "Regulation of Glycerol Metabolism in *Pseudomonas aeruginosa*: Characterization of the *glpR* Repressor Gene," *Journal of Bacteriology* 178(17):5215-5221, 1996.
Sedlak et al., "Expression of *E. coli* araBAD operon encoding enzymes for metabolizing L-arabinose in *Saccharomyces cerevisiae*:" *Enzyme and Microbial Technology* 28:16-24, 2001.
Shamanna et al., "Uptake and Catabolism of $_D$-Xylose in *Salmonella typhimurium* LT2," *Journal of Bacteriology* 139(1):64-70, 1979.
Sharp et al., "Variation in the strength of selected codon usage bias among bacteria," *Nucleic Acids Research* 33(4):1141-1153, 2005.
Sher et al., "Glycerol metabolism in the extremely halophilic bacterium *Salinibacter ruber*," *FEMS Microbiology Letters* 232:211-215, 2004.
Spector et al., "[55] L-Glycerol-3-phosphate dehydrogenase from *Escherichia coli*," *Methods in Enzymology* 41:249-254, 1975, (article abstract) 2 pages.
Springer et al., "Sequence and characterization of *mxaB*, a response regulator involved in regulation of methanol oxidation, and of *mxaW*, a methanol-regulated gene in *Methylobacterium extorquens* AM1," *FEMS Microbiology Letters* 160:119-124, 1998.
Stein et al., "Genome Sequence of the Obligate Methanotroph *Methylosinus trichosporium* Strain OB3b," *Journal of Bacteriology* 192(24):6497-6498, 2010.
Stolyar et al., "Role of multiple gene copies in particulate methane monooxygenase activity in the methane-oxidizing bacterium *Methylococcus capsulatus* Bath," *Microbiology* 145:1235-1244, 1999.
Stolyar et al., "Search for Systems of Genetic Exchange in Methane-Oxidizing Bacteria," *Microbiology* 64(5):584-588, 1995, translated from *Mikrobiologiya* 64(5):686-691, 1995.
Stoner et al., "Transcription start site and induction kinetics of the *araC* regulatory gene in *Escherichia coli* K12," *Journal of Molecular Biology* 170(4):1049-1053, 1983, (article abstract) 1 page.
Subtil et al., "Improving L-arabinose utilization of pentose fermenting *Saccharomyces cerevisiae* cells by heterologous expression of L-arabinose transporting sugar transporters," *Biotechnology for Biofuels* 4:38, 2011, 10 pages.
Takahashi et al., "Glucose and Lactate Metabolism by Actinomyces Naeslundii," *Crit Rev Oral Biol Med* 10(4):487-503, 1999.
Teramoto et al., "Identification of a Gene Encoding a Transporter Essential for Utilization of $C_4$ Dicarboxylates in *Corynebacterium glutamicum*," *Applied and Environmental Microbiology* 74(17):5290-5296, 2008.
Theisen et al., "Regulation of methane oxidation in the facultative methanotroph *Methylocella silvestris* BL$_2$," *Molecular Microbiology* 58(3),682-692, 2005.
Tomlinson et al., "The metabolism of carbohydrates by extremely halophilic bacteria: glucose metabolism via a modified Entner-Doudoroff pathway," *Canadian Journal of Microbiology* 20(8):1085-1091, 1974, (article abstract) 1 page.
Toyama et al., "Construction of insertion and deletion *mxa* mutants of *Methylobacterium extorquens* AM1 by electroporation," *FEMS Microbiology Letters* 166:1-7, 1998.
Toyama et al., "*pqqA* is not required for biosynthesis of pyrroloquinoline quinone in *Methylobacterium extorquens* AM1," *Microbiology* 144:183-191, 1998.
Toyama et al., "Sequence analysis of *pqq* genes required for biosynthesis of pyrroloquinoline quinone in *Methylobacterium extorquens* AM1 and the purification of a biosynthetic intermediate," *Microbiology* 143:595-602, 1997.

(56) References Cited

OTHER PUBLICATIONS van der Rest et al., "Nucleotide Sequence and Functional Properties of a Sodium-dependent Citrate Transport System from *Klebsiella pneumoniae*," *The Journal of Biological Chemistry* 267(13)8971-8976, 1992.
Van Dien et al., "Reconstruction of $C_3$ and $C_4$ metabolism in *Methylobacterium extorquens* AM1 using transposon mutagenesis," *Microbiology* 149:601-609, 2003.
van Gylswyk et al., "*Schwartzia succinivorans* gen. nov., sp. nov., Another Ruminal Bacterium Utilizing Succinate as the Sole Energy Source," *International Journal of Systematic Bacteriology* 47(1):155-159, 1997.
van Hylckama Vlieg et al., "Natural diversity and adaptive responses of *Lactococcus lactis*," *Current Opinion in Biotechnology* 17:183-190, 2006.
Villalobos et al., "Gene Designer: a synthetic biology tool for constructing artificial DNA segments," *BMC Bioinformatics* 7:285, 2006, 8 pages.
Voegele et al., "Glycerol Kinase of *Escherichia coli* Is Activated by Interaction with the Glycerol Facilitator," *Journal of Bacteriology* 175(4): 1087-1094, 1993.
Vuilleumier et al., "Genome Sequence of the Haloalkaliphilic Methanotrophic Bacterium *Methylomicrobium alcaliphilum* 20Z," *Journal of Bacteriology* 194(2):551-552, 2012.
Wanner et al., "Genetic Identification of Three ABC Transporters as Essential Elements for Nitrate Respiration in *Haloferax volcanii*," *Genetics* 152:1417-1428, 1999.
Ward et al., "Genomic Insights into Methanotrophy: The Complete Genome Sequence of *Methylococcus capsulatus* (Bath)," *PLoS Biology* 2(10):e303, pp. 1616-1628, 2004.
Warner et al., "Catabolite Repression and Induction of the $Mg^{2+}$-Citrate Transporter CitM of *Bacillus subtilis*," *Journal of Bacteriology* 182(21):6099-6105, 2000, 13 pages.
Weiss, "Catabolic Activities of *Neisseria meningitidis*: Utilization of Succinate," *Journal of Bacteriology* 101(1):133-137, 1970.
Weissenborn et al., "Structure and Regulation of the *glpFK* Operon Encoding Glycerol Diffusion Facilitator and Glycerol Kinase of *Escherichia coli* K-12," *The Journal of Biological Chemistry* 267(9):6122-6131, 1992.
Welch et al., "Design Parameters to Control Synthetic Gene Expression in *Escherichia coli*," *PLoS One* 4(9):e7002, 2009, 10 pages.
Weyant et al., *Identification of Unusual Pathogen Gram-Negative Aerobic and Facultatively Anaerobic Bacteria*, $2^{nd}$ Edition, Williams and Wilkins, Baltimore, MD, 1995, pp. 5-7, 3 pages.
Wu et al., "SGDB: a database of synthetic genes re-designed for optimizing protein over-expression," *Nucleic Acids Research* 35(Database Issue):D76-D79, 2007.
Yamamoto et al., "The CitST two-component system regulates the expression of the Mg-citrate transporter in *Bacillus subtilis*," *Molecular Microbiology* 37(4): 898-912, 2000.
Yoshida et al., "Improved conditions for the transformation by electroporation of the extracellular polysaccharide-producing methylotroph *Methylobacillus* sp.," *Biotechnology Letters* 23:787-791, 2001.
Zhao et al., "Variants of the Obligate Methanotroph Isolate 761M Capable of Growth on Glucose in the Absence of Methane," *Applied and Environmental Microbiology* 48(4):807-812, 1984.

\* cited by examiner

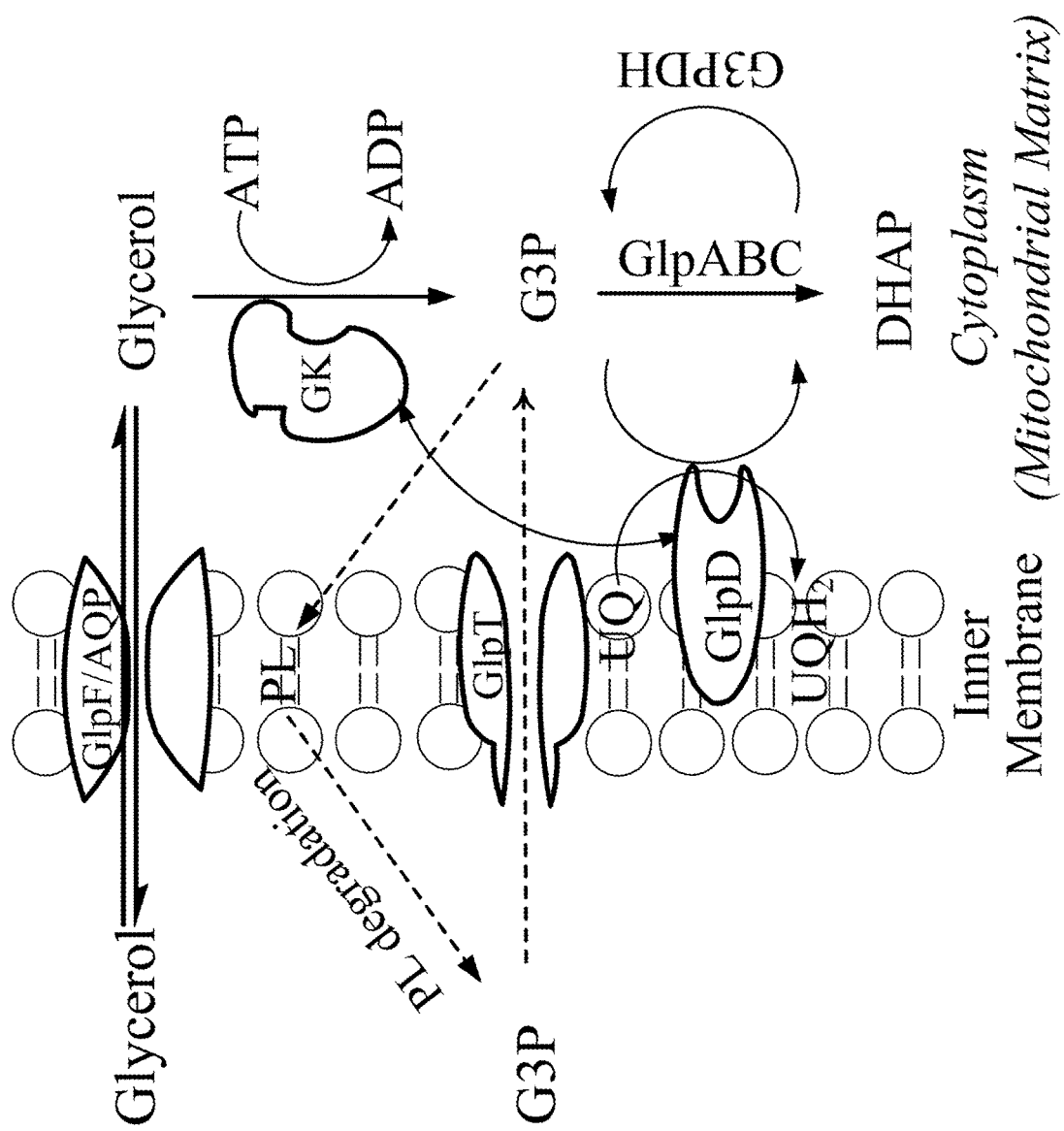

ENGINEERING OF MULTI-CARBON SUBSTRATE UTILIZATION PATHWAYS IN METHANOTROPHIC BACTERIA

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200206_402USPC_SEQUENCE_LISTING.txt. The text file is 399 KB, was created on Apr. 24, 2015, and is being submitted electronically via EFS-Web.

BACKGROUND

Technical Field

The present disclosure relates to genetically engineered methanotrophic bacteria capable of growing on multi-carbon substrates and methods for growing methanotrophic bacteria on multi-carbon substrates.

Description of the Related Art

Methanotrophic bacteria generally rely on methane as their sole carbon and energy source. The low solubility of methane is a major limiting factor in achieving high cell density and rapid growth in methanotrophic bacteria. The slow growth of methanotrophs and their requirement for methane, a potentially explosive substrate, has hampered their industrial application. For many industrial applications, such as chemical catalysis or other biological transformations, it is desirable to achieve high amounts of methanotroph biomass, regardless of the carbon source used.

In view of the limitations associated with methanotrophic bacteria growth, there is a need in the art for methanotrophs that can utilize alternative, preferably inexpensive, substrates as carbon and energy sources. The present disclosure provides a solution by providing genetically engineered methanotrophic bacteria that can utilize multi-carbon substrates, including glycerol.

SUMMARY OF INVENTION

In one aspect, the present disclosure provides for recombinant obligate methanotrophic bacteria including at least one exogenous nucleic acid encoding a multi-carbon substrate utilization pathway component, wherein the at least one exogenous nucleic acid is expressed in a sufficient amount to permit growth of the non-naturally occurring methanotrophic bacteria on the multi-carbon substrate as a primary carbon source. In certain embodiments, the multi-carbon substrate is a sole carbon source. In certain embodiments, the multi-carbon substrate may be glucose, acetate, lactate, arabinose, citrate, succinate, or glycerol.

In another aspect, the present disclosure provides for recombinant facultative methanotrophic bacteria including at least one exogenous nucleic acid encoding a multi-carbon substrate utilization pathway component, wherein the multi-carbon substrate is not utilized as a carbon source by a reference facultative methanotrophic bacterium, wherein the at least one exogenous nucleic acid encoding a multi-carbon substrate utilization pathway component is expressed in a sufficient amount to permit growth of the recombinant facultative methanotrophic bacteria on the multi-carbon substrate as a sole carbon source. In certain embodiments, the multi-carbon substrate may be glucose, glycerol, lactate, arabinose, acetate, succinate, or citrate.

In certain embodiments wherein the multi-carbon substrate is glucose, the recombinant methanotrophic bacteria include an exogenous nucleic acid encoding a glucose transporter.

In certain embodiments wherein the multi-carbon substrate is acetate, the recombinant methanotrophic bacteria include an exogenous nucleic acid encoding an acetate transporter. In further embodiments, the non-naturally occurring methanotrophic bacteria are further modified to overexpress acetyl-CoA synthase.

In certain embodiments wherein the multi-carbon substrate is lactate, the recombinant methanotrophic bacteria include an exogenous nucleic acid encoding a lactate transporter and an exogenous nucleic acid encoding a lactate dehydrogenase.

In certain embodiments wherein the multi-carbon substrate is arabinose, the recombinant methanotrophic bacteria include an exogenous nucleic acid encoding an L-arabinose isomerase, an exogenous nucleic acid encoding an L-ribulose kinase, an exogenous nucleic acid encoding an L-ribulose-5-phosphate epimerase, and an exogenous nucleic acid encoding an arabinose transporter. In further embodiments, the L-arabinose isomerase is AraA, the L-ribulose kinase is AraB, the L-ribulose-5-phosphate epimerase is AraD, and the arabinose transporter is AraE, AraFGH, or AraP.

In certain embodiments wherein the multi-carbon substrate is citrate, the recombinant methanotrophic bacteria include an exogenous nucleic acid encoding a citrate transporter.

In certain embodiments wherein the multi-carbon substrate is succinate, the recombinant methanotrophic bacteria include an exogenous nucleic acid encoding a succinate transporter.

In certain embodiments wherein the multi-carbon substrate is glycerol, the recombinant methanotrophic bacteria include at least two exogenous nucleic acids encoding glycerol utilization pathway components. In further embodiments, the at least two glycerol utilization components comprise glycerol kinase and glycerol-3-phosphate dehydrogenase. In a specific embodiment, the glycerol kinase is GlpK and glycerol-3-phosphate dehydrogenase is GlpD.

In further embodiments, the recombinant methanotrophic bacteria include three exogenous nucleic acids encoding glycerol utilization pathway components. In still further embodiments, the three glycerol utilization pathway components comprise glycerol uptake facilitator, glycerol kinase, and glycerol-3-phosphate dehydrogenase. In a specific embodiment, the glycerol uptake facilitator is GlpF, the glycerol kinase is GlpK, and the glycerol-3-phosphate dehydrogenase is GlpD.

In certain embodiments, the recombinant obligate methanotrophic bacteria are *Methylomonas, Methylobacter, Methylococcus, Methylosinus, Methylomicrobium,* or *Methanomonas.* In further embodiments, the recombinant obligate methanotrophic bacteria are *Methylosinus trichosporium* strain OB3b, *Methylococcus capsulatus* Bath strain, *Methylomonas methanica* 16A strain, *Methylosinus trichosporium* (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylomonas* sp AJ-3670 (FERM P-2400), *Methylacidiphilum infernorum,* or *Methylomicrobium alcaliphilum* 20Z.

In certain embodiments, the recombinant facultative methanotrophic bacteria are *Methylocella silvestris, Methylocella palustris, Methylocella tundrae, Methylocystis dal-* tona strain SB2, *Methylocystis bryophila*, *Methylocapsa aurea* KYG, or *Methylobacterium organophilum* (ATCC 27,886).

In certain embodiments, at least one exogenous nucleic acid encoding a multi-carbon substrate utilization pathway component is codon optimized for high expression in methanotrophic bacteria.

Additionally, the present disclosure provides methods for growing methanotrophic bacteria, comprising culturing the recombinant obligate methanotrophic bacteria according to any of the embodiments provided herein in the presence of a multi-carbon substrate, wherein the multi-carbon substrate is used as a primary carbon source by the recombinant obligate methanotrophic bacteria. In certain embodiments, the present disclosure provides methods for growing methanotrophic bacteria, comprising culturing the recombinant faculatative methanotrophic bacteria according to any of the embodiments provided herein in the presence of a multi-carbon substrate, wherein the multi-carbon substrate is used as a sole carbon source by the recombinant faculatative methanotrophic bacteria.

BRIEF DESCRIPTION OF THE DRAWING

FIG. 1 shows an exemplary glycerol utilization pathway (respiratory) for a genetically modified methanotrophic bacterium. Glycerol crosses the cell membrane (e.g., via a glycerol uptake facilitator such as GlpF), where it is phosphorylated by a glycerol kinase (GK) (e.g., GlpK) to form glycerol-3-phosphate (G3P), which is then oxidized by glycerol-3-phosphate dehydrogenase (e.g., GlpD) to dihydroxyacetone phosphate (DHAP), which is then isomerized by triose phosphate isomerase and may then enter endogenous sugar metabolism or gluconeogenesis pathways.

DETAILED DESCRIPTION

Prior to setting forth this disclosure in more detail, it may be helpful to an understanding thereof to provide definitions of certain terms to be used herein. Additional definitions are set forth throughout this disclosure.

In the present description, the term "about" means±20% of the indicated range, value, or structure, unless otherwise indicated. The term "consisting essentially of" limits the scope of a claim to the specified materials or steps and those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include" and "have" are used synonymously, which terms and variants thereof are intended to be construed as non-limiting. The term "comprise" means the presence of the stated features, integers, steps, or components as referred to in the claims, but that it does not preclude the presence or addition of one or more other features, integers, steps, components, or groups thereof.

As used herein, the term "recombinant" or "non-natural" refers to an organism, microorganism, cell, nucleic acid molecule, or vector that has at least one genetic alternation or has been modified by the introduction of an exogenous nucleic acid, or refers to a cell that has been altered such that the expression of an endogenous nucleic acid molecule or gene can be controlled, where such alterations or modifications are introduced by genetic engineering. Genetic alterations include, for example, modifications introducing expressible nucleic acid molecules encoding proteins or enzymes, other nucleic acid additions, nucleic acid deletions, nucleic acid substitutions, or other functional disruption of the cell's genetic material. Such modifications include, for example, coding regions and functional fragments thereof for heterologous or homologous polypeptides for the referenced species. Additional modifications include, for example, non-coding regulatory regions in which the modifications alter expression of a gene or operon. Exemplary proteins or enzymes include proteins or enzymes (i.e., components) within a multi-carbon substrate utilization pathway (e.g., a glycerol utilization pathway). Genetic modifications to nucleic acid molecules encoding enzymes, or functional fragments thereof, can confer a biochemical reaction capability or a metabolic pathway capability to the recombinant cell that is altered from its naturally occurring state.

As used herein, the term "host bacterium" or "host" refers to a microorganism (e.g., methanotrophic bacterium) that has not yet been genetically modified with the capability to utilize a multi-carbon substrate (e.g., glycerol) as a carbon and energy source. A host methanotrophic bacterium is selected for transformation with at least one exogenous nucleic acid encoding a multi-carbon substrate utilization pathway component to yield a recombinant methanotrophic bacterium with the capability to utilize a multi-carbon substrate as a carbon and energy source. A host methanotrophic bacterium may already possess other genetic modifications conferring it with desired properties, unrelated to the multi-carbon substrate utilization pathway disclosed herein. For example, a host methanotrophic bacterium may possess genetic modifications conferring high growth, tolerance of contaminants or particular culture conditions, ability to metabolize additional carbon substrates, or ability to synthesize desirable products or intermediates (e.g., propylene, crotonate, or crotonyl CoA, see, e.g., International Application Number PCT/US13/60460, incorporated herein by reference, in its entirety).

As used herein, the term "methanotrophic bacterium" refers to a methylotrophic bacterium that has the ability to oxidize methane as its sole carbon and energy source. As used herein, "methanotrophic bacteria" include "obligate methanotrophic bacteria" that can only utilize C1 substrates for carbon and energy sources and "facultative methanotrophic bacteria" that are naturally able to use multi-carbon substrates, such as acetate, pyruvate, succinate, malate, or ethanol, in addition to C1 substrates as their sole carbon and energy source. Facultative methanotrophs include some species of *Methylocella*, *Methylocystis*, and *Methylocapsa* (e.g., *Methylocella silvestris*, *Methylocella palustris*, *Methylocella tundrae*, *Methylocystis daltona* strain SB2, *Methylocystis bryophila*, and *Methylocapsa aurea* KYG), and *Methylobacterium organophilum* (ATCC 27,886).

As used herein, the term "reference facultative methanotrophic bacterium", as known as "wild type facultative methanotrophic bacterium" or "parent facultative methanotrophic bacterium", refers to a facultative methanotrophic bacterium that has not been genetically engineered with the capability to use an additional multi-carbon substrate other than its native substrates.

As used herein, the term "not utilized as a carbon source" means that the referenced carbon substrate cannot be used as a sole carbon source by the referenced bacteria.

As used herein, the term "C1 substrate" or "C1 compound" refers to any organic compound that lacks a carbon to carbon bond. C1 substrates include methane, methanol, formaldehyde, formic acid (formate), carbon monoxide, carbon dioxide, methylated amines (e.g., methylamine, dimethylamine, trimethylamine, etc.), methylated thiols, methyl halogens (e.g., bromomethane, chloromethane, iodomethane, dichloromethane, etc.), and cyanide.

As used herein, the term "multi-carbon substrate" or "multi-carbon compound" refers to an organic compound that contains at least one carbon to carbon bond. A multi-carbon substrate includes organic acids and carbohydrates. Exemplary multi-carbon substrates include glucose, acetate, lactate, arabinose, citrate, succinate, and glycerol.

As used herein, the term "glucose", also known as "D-glucose" or "dextrose", refers to a colorless, water soluble organic compound having the formula $C_6H_{12}O_6$ and that is the D-isomer or "right-handed form" of glucose. As used herein, glucose refers to both the open-chain form as well as cyclic isomers (e.g., α-D-glucopyranose, β-D-glucopyranose, α-D-glucofuranose, and β-D-glucofuranose).

As used herein, the term "acetate", also known as "ethanoate", refers to an organic compound that is a salt or ester of acetic acid (chemical formula $CH_3CO_2H$ (also written as $CH_3COOH$)). The formula for acetate anion is $CH_3CO_2^-$, $C_2H_3O_2^-$, or $CH_3COO^-$. Acetate may also be abbreviated as $OAc^-$ or $AcO^-$.

As used herein, the term "lactate" refers to a salt or ester of lactic acid. Lactic acid, also known as 2-hydroxypropanoic acid or sarcolactic acid, is a carboxylic acid with the chemical formula $C_3H_6O_3$. The lactate anion has the chemical formula $CH_3CH(OH)COO^-$. Lactate includes L-lactate and D-lactate optical isomers.

As used herein, the term "arabinose", also known as "pectinose", refers to a monosaccharide containing five carbon atoms including an aldehyde functional group (aldopentose). Arabinose has the chemical formula $C_5H_{10}O_5$. As used herein, arabinose includes L-arabinose and D-arabinose.

As used herein, the term "citrate" refers to a salt or ester of citric acid. Citric acid, also known as 2-hydroxypropane-1,2,3-tricarboxylic acid, is a weak organic acid that has the chemical formula $C_6H_8O_7$. The citrate anion has the chemical formula $C_3H_5O(COO)_3^{3-}$.

As used herein, the term "succinate" refers to a salt or ester of succinic acid. Succinic acid, also known as butanedioic acid or ethane-1,2-dicarboxylic acid, has the chemical formula $C_4H_6O_4$.

As used herein, the term "glycerol", also known as glycerine, glycerin, 1,2,3-propanetriol, glyceritol, glycyl alcohol, trihydroxypropane, propanetriol, osmoglyn, or 1,2,3-trihydroxypropane, refers to a tri-hydroxy sugar alcohol with the formula $C_3H_8O_3$. It is a colorless, odorless, viscous liquid. Glycerol is an intermediate in carbohydrate and lipid metabolism and is often used as a solvent, emollient, pharmaceutical agent, and sweetening agent. As used herein, glycerol includes both purified glycerol, the form used in pharmaceutical, food, and cosmetic industries, and crude glycerol. Crude glycerol, or g-phase, is a heavier separate liquid phase composed mainly of glycerol that is the by-product of biodiesel production. Crude glycerol generated by homogeneous base-catalyzed transesterification contains approximately 50-60% of glycerol, 12-16% of alkalies, especially in the form of alkali soaps and hydroxides, 15-18% of methyl esters, 8-12% of methanol, 2-3% water, and further components. Crude glycerol also contains a variety of elements, such as calcium, magnesium, phosphorus, or sulfur, originating from the primary oil. Larger quantities of sodium or potassium are also present, derived from the catalyst.

As used herein, "exogenous" means that the referenced molecule (e.g., nucleic acid) or referenced activity (e.g., enzyme activity or membrane transport) is introduced into a host methanotrophic bacterium by genetic engineering. The molecule can be introduced, for example, by introduction of a nucleic acid into the host genetic material such as by integration into a host chromosome or by introduction of a nucleic acid as non-chromosomal genetic material, such as on a plasmid. When the term is used in reference to expression of an encoding nucleic acid, it refers to introduction of the encoding nucleic acid in an expressible form into the host methanotrophic bacterium. When used in reference to an enzymatic or protein activity, the term refers to an activity that is introduced into the host reference bacterium. Therefore, the term "endogenous" or "native" refers to a referenced molecule or activity that is present in the host bacterium. The term "chimeric" when used in reference to a nucleic acid refers to any nucleic acid that is not endogenous, comprising sequences that are not found together in nature. For example, a chimeric nucleic acid may comprise regulatory sequences and coding sequences that are derived from different sources, or regulatory sequences and coding sequences that are derived from the same source, but arranged in a manner different than that found in nature. The term "heterologous" refers to a molecule or activity that is derived from a source other than the referenced species or strain whereas "homologous" refers to a molecule or activity derived from the host bacterium. Accordingly, a methanotrophic bacterium comprising an exogenous nucleic acid as provided in the present disclosure can utilize either a heterologous or homologous nucleic acid or both.

It is understood that when more than one exogenous nucleic acid is included in a bacterium that the more than one exogenous nucleic acid refers to the referenced encoding nucleic acid or protein activity, as discussed above. It is also understood that such more than one exogenous nucleic acid can be introduced into the host bacterium on separate nucleic acid molecules, on a polycistronic nucleic acid molecule, on a single nucleic acid molecule encoding a fusion protein, or a combination thereof, and still be considered as more than one exogenous nucleic acid. For example, as disclosed herein, a methanotrophic bacterium can be modified to express two or more exogenous nucleic acids encoding a desired multi-carbon substrate utilization pathway component (e.g., glycerol utilization pathway components). Where two exogenous nucleic acids encoding glycerol utilization pathway components are introduced into a host methanotrophic bacterium, it is understood that the two exogenous nucleic acids can be introduced as a single nucleic acid molecule, for example, on a single plasmid, on separate plasmids, can be integrated into the host chromosome at a single site or multiple sites, and still be considered two exogenous nucleic acids. Similarly, it is understood that more than two exogenous nucleic acid molecules can be introduced into a host bacterium in any desired combination, for example, on a single plasmid, on separate plasmids, can be integrated into the host chromosome at a single site or multiple sites, and still be considered as two or more exogenous nucleic acids. Thus, the number of referenced exogenous nucleic acids or enzymatic activities refers to the number of encoding nucleic acids or the number of protein activities, not the number of separate nucleic acid molecules introduced into the host bacterium.

As used herein, "nucleic acid", also known as polynucleotide, refers to a polymeric compound comprised of covalently linked subunits called nucleotides. Nucleic acids include polyribonucleic acid (RNA), polydeoxyribonucleic acid (DNA), both of which may be single or double stranded. DNA includes cDNA, genomic DNA, synthetic DNA, and semi-synthetic DNA.

As used herein, "multi-carbon substrate utilization pathway component" refers to any enzyme or protein that is involved (e.g., a protein or enzyme involved in transport or catalyzing an enzymatic reaction) in the ability of an organism to utilize the selected multi-carbon substrate as a carbon and energy source. Exemplary multi-carbon substrate utilization pathways include glucose, acetate, lactate, arabinose, citrate, succinate, and glycerol utilization pathways. Sources of nucleic acids encoding multi-carbon substrate utilization pathway components are well known in the art and may be derived from a variety of species, including bacteria, yeast, or other microorganisms.

As used herein, a "glucose transporter" refers to transport protein or transport system that transports glucose into a microorganism. Exemplary glucose transporters include phosphoenolpyruvate:sugar phosphotransferase system (PTS), which is involved in the uptake and concomitant phosphorylation of a variety of hexose sugars in bacteria, and members of the major facilitator family (e.g., glucose/galactose transporter (GluP), and galactose permease (GalP)).

As used herein, an "acetate transporter", also known as "monocarboxylic acid transporter", refers to a transport protein or transport system that transports acetate into a microorganism. Exemplary acetate transporters include acetate permeases and proton-linked monocarboxylate transporters of the sodium/solute symporter family (e.g., MctC, MctP, ActP).

As used herein, "acetyl-CoA synthase", also known as "acetyl-CoA synthetase", refers to an enzyme that ligates acetate to coenzyme A to form acetyl coenzyme A (acetyl-CoA).

As used herein, a "lactate transporter", also known as "monocarboxylic acid transporter", refers to a transport protein or transport system that transports lactate into a microorganism. Exemplary lactate transporters include lactate permease (e.g., LctP (also known as LacP)), and proton-linked monocarboxylate transporters of the sodium/solute symporter family (e.g., MctC, MctP, ActP).

As used herein, a "lactate dehydrogenase", refers to an NAD-independent enzyme that catalyzes the oxidation of lactate to pyruvate. As used herein, lactate dehydrogenase includes L-lactate and D-lactate dehydrogenase.

As used herein, an "arabinose operon", also known as "L-arabinose operon" or "ara operon", refers to a gene sequence encoding enzymes needed for the catabolism of arabinose to D-xylulose-5-phosphate, an intermediate of the pentose phosphate pathway.

As used herein, an "arabinose transporter" refers to a membrane transport protein or system that transports L-arabinose into a microorganism. An exemplary arabinose transporter includes the low affinity AraE transport protein and the AraFGH ATP-binding cassette (ABC) transporter system. AraF is a periplasmic arabinose-binding protein, AraG is an ATP-binding component, and AraH is a membrane-bound component.

As used herein, "glycerol utilization pathway component", also known as "glycerol metabolism pathway enzyme" or "glycerol fermentation pathway enzyme" refers to any enzyme or protein that is involved (e.g., transport or catalyzing enzymatic reaction) in the ability of an organism to utilize glycerol as a carbon and energy source. A glycerol utilization pathway component may be from an anaerobic pathway or aerobic pathway. A glycerol utilization pathway component includes, for example, glycerol uptake facilitators, glycerol kinase, glycerol-3-phosphate dehydrogenase, glycerol dehydrogenase, ATP- or phosphoenolpyruvate-dependent dihydroxyacetone kinase. Sources of nucleic acids encoding glycerol utilization pathway components are well known in the art and may be derived from a variety of species, including bacteria, yeast, or other microorganisms.

As used herein, "glycerol uptake facilitator", also known as "glycerol facilitator" refers to a cytoplasmic membrane protein that transports glycerol into a cell. It may be a member of the major intrinsic protein (MIP) family of transmembrane channel proteins. As used herein, a glycerol uptake facilitator may refer to a membrane protein that facilitates diffusion of or actively transports glycerol into a cell. The activity of glycerol uptake facilitator can be measured by a transport assay (see, e.g., Voegele and Boos, 1993, J. Bacteriol. 175:1087-1094).

As used herein, "glycerol kinase", also known as glycerokinase, refers to an enzyme that catalyzes the phosphorylation of glycerol to glycerol-3-phosphate (G3P). The activity of glycerol kinase can be measured as described in Lin et al., 1962, Proc. Natl. Acad. Sci. USA 48:2145-2150.

As used herein, "glycerol-3-phosphate dehydrogenase" refers to an enzyme that catalyzes the oxidation of glycerol-3-phosphate (G3P) to dihydroxyacetone phosphate. The activity of glycerol-3-phosphate dehydrogenase can be measured by the method of Spector and Pizer (1975, Methods Enzymol. 41:249-254). Glycerol-3-phosphate dehydrogenase includes both aerobic and anaerobic versions. In certain embodiments, the glycerol-3-phosphate is an aerobic enzyme.

As used herein, "transformation" refers to the transfer of a nucleic acid (e.g., exogenous nucleic acid) into the genome of a host bacterium, resulting in genetically stable inheritance. Host bacteria containing the transformed nucleic acids are referred to as "recombinant" or "non-naturally occurring" or "genetically engineered" or "transformed" or "transgenic" bacteria.

Methanotrophic Bacteria

In certain embodiments, obligate methanotrophic bacteria are genetically engineered with the capability to utilize a multi-carbon substrate as a carbon and energy source. In other embodiments, facultative methanotrophic bacteria are genetically engineered with the capacity to utilize a non-native multi-carbon substrate. Methanotrophic bacteria have the ability to oxidize methane as a carbon and energy source. Methanotrophic bacteria are classified into three groups based on their carbon assimilation pathways and internal membrane structure: type I (gamma proteobacteria), type II (alpha proteobacteria, and type X (gamma proteobacteria). Type I methanotrophs use the ribulose monophosphate (RuMP) pathway for carbon assimilation whereas type II methanotrophs use the serine pathway. Type X methanotrophs use the RuMP pathway but also express low levels of enzymes of the serine pathway. Methanotrophic bacteria are grouped into several genera: *Methylomonas, Methylobacter, Methylococcus, Methylocystis, Methylosinus, Methylomicrobium, Methanomonas*, and *Methylocella*. Methanotrophic bacteria include obligate methanotrophs, which can only utilize C1 substrates for carbon and energy sources, and facultative methanotrophs, which naturally have the ability to utilize some multi-carbon substrates as a sole carbon and energy source. Facultative methanotrophs include some species of *Methylocella, Methylocystis*, and *Methylocapsa* (e.g., *Methylocella silvestris, Methylocella palustris, Methylocella tundrae, Methylocystis daltona* strain SB2, *Methylocystis bryophila*, and *Methylocapsa aurea* KYG), and *Meth-*

*ylobacterium organophilum* (ATCC 27,886). Exemplary obligate methanotrophic bacteria include: *Methylococcus capsulatus* Bath strain, *Methylomonas* 16a (ATCC PTA 2402), *Methylosinus trichosporium* OB3b (NRRL B-11, 196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylomonas flagellata* sp AJ-3670 (FERM P-2400), *Methylacidiphilum infernorum* and *Methylomicrobium alcaliphilum* 20Z.

A selected methanotrophic host bacteria may also undergo strain adaptation under selective conditions to identify variants with improved properties for production. Improved properties may include increased growth rate, yield of desired products, and tolerance of likely process contaminants. In a particular embodiment, a high growth variant methanotrophic bacteria, which is an organism capable of growth on methane as the sole carbon and energy source and which possesses an exponential phase growth rate that is faster (i.e., shorter doubling time) than its parent, reference, or wild-type bacteria, is selected (see, e.g., U.S. Pat. No. 6,689,601).

Each of the methanotrophic bacteria of this disclosure may be grown as an isolated pure culture, with a heterologous organism(s) that may aid with growth, or one or more different strains of methanotrophic bacteria may be combined to generate a mixed culture.

Multi-carbon Substrate Utilization Pathway Enzymes Glycerol Utilization Pathway Enzymes Glycerol can be used as a source of carbon and energy by many microorganisms. As used herein, "glycerol utilization pathway component", also known as "glycerol metabolism pathway enzyme" or "glycerol fermentation pathway enzyme" refers to any enzyme or protein that is involved in the ability of an organism to utilize glycerol as a carbon and energy source. A glycerol utilization pathway component may include a number of enzymes and transport proteins from multiple glycerol utilization pathways, including for example, glycerol uptake facilitators, glycerol kinase, glycerol-3-phosphate dehydrogenase, glycerol dehydrogenase, and dihydroxyacetone kinase.

The initial step of glycerol utilization is its uptake by the microorganism. Glycerol can passively diffuse through membranes without a transport system. However, many microorganisms possess specific glycerol transporters. Glycerol transport can be mediated by a glycerol uptake facilitator (facilitated diffusion), or by an active glycerol transporter (e.g., ATP dependent transporter or proton glycerol symporter). Genes that encode glycerol transporters include, for example, glpF, glpT, aqp, gup1, gup2, mip, gtsA, gtsB, gtsC, and stl1. An exemplary amino acid sequence for a glycerol uptake facilitator comprises any one of SEQ ID NOS:1-21.

In most microorganisms that utilize glycerol, once glycerol has entered the cell, it is phosphorylated by glycerol kinase (GK) into glycerol-3-phosphate (G3P), which is then oxidized by glycerol-3-phosphate dehydrogenase to form dihydroxyacetone phosphate (DHAP) (i.e., in presence of electron acceptors, respiratory metabolism) (see, FIG. 1). In the respiratory glycerol utilization pathway, there are two forms of glycerol-3-phosphate dehydrogenase, aerobic and anaerobic (e.g., GlpD and GlpABC, respectively). Genes that encode glycerol kinase include, for example, glpK, gut1, and gykA. An exemplary amino acid sequence for a glycerol kinase comprises any one of SEQ ID NOS:22-42. Genes that encode glycerol-3-phosphate dehydrogenase include, for example, glpD, glpA, glpB, glpC, gpsA, glyC, and gpdA2. An exemplary amino acid sequence for a glycerol-3-phosphate dehydrogenase comprises any one of SEQ ID NOS:43-63. A small number of yeast and bacteria, however, use an alternative pathway in the absence of electron acceptors (i.e., fermentative metabolism), where glycerol is oxidized by glycerol dehydrogenase into dihydroxyacetone, which is then phosphorylated by dihydroxyacetone kinase into dihydroxyacetone phosphate.

Glucose Utilization Pathway Enzymes

Glucose utilization in bacteria is well characterized (see, e.g., Hugh and Leifson, 1953, J. Bacteriol. 66:24-26; Tomlinson et al., 1974, Canadian J. Microbiol. 20:1085-1091; Takahashi and Yamada, 1999, Crit. Rev. Oral Biol. Med. 10:487-503; Fuhrer et al., 2005, J. Bacteriol. 187:1581-1590; Goldman and Blumenthal, 1963, J. Bacteriol. 86:303-311; Fraenkel and Levisohn, 1967, J. Bacteriol. 93:1571-1578; Hua et al., 2003, J. Bacteriol. 185:7053-7067). The main pathway for glucose catabolism is the Embden-Meyerhof-Parnas (EMP) pathway, a type of glycolysis that converts glucose into pyruvate and is widely distributed in saccharolytic bacteria. Some bacteria may use another glycolytic pathway, the Entner-Doudoroff pathway, to convert glucose to pyruvate. An alternative pathway to glycolysis is the pentose phosphate pathway which converts glucose to ribulose-5-phosphate in an oxidative phase. A non-oxidative phase of the pentose phosphate pathway catalyzes the interconversion of phosphorylated sugars to xylulose-5-phosphate, ribulose-5-phosphate, and ribose-5-phosphate. Glucose-6-phosphate is a reaction component in the glycolytic pathways and pentose phosphate pathway.

Phosphoenolpyruvate:sugar phosphotransferase systems (PEP-sugar-PTS) are multi-component systems involving enzymes of the plasma membrane and in the cytoplasm that catalyze the concomitant transport and phosphorylation of hexose sugars (e.g., glucose) to hexose-6-phosphate (see, e.g., Herzberg and Klevit, 1994, Curr. Biol. 4:814-822; Takahashi and Yamada, 1999, Crit. Rev. Oral Biol. Med. 10:487-503; Saier, 1977, Bacteriological Rev. 41:856-871, disclosures of which are incorporated herein by reference, in their entirety). Cytoplasmic proteins enzyme EI and Histidine Protein (HPr) initiate phosphoryl transfer reactions and function in the transport and phosphorylation of all sugar substrates of the system. Enzymes II are sugar-specific permeases or transporters, commonly consisting two cytoplasmic domains EIIA and EIIB and an integral membrane domain EIIC. An exemplary amino acid sequence for components of PEP-glucose-PTS systems from *E. coli* comprises any one of SEQ ID NOS:64-67. Exemplary amino acid sequences for EI and HPr and EIIA components are provided in SEQ ID NOs: 64 and 65. Exemplary EIIB and EIIC components are provided in SEQ ID NOs: 66 and 67.

Alternative mechanisms for glucose uptake include glucose ion symporters (see, e.g., Sarker et al., 1997, J. Bacteriol. 179:1805-1808; Essenberg et al., 1997, Microbiology 143:1549-1555; Henderson et al., 1977, Biochem. J. 162: 309-320, disclosures of which are incorporated herein by reference, in their entirety) and ABC transporters (see, e.g., Albers et al., 1999, J. Bacteriol. 14:4285-4291; Chevance et al., 2006, J. Bacteriol. 188:6561-6571; Wanner and Soppa, 1999, Genetics 152:1417-1428, disclosures of which are incorporated herein by reference, in their entirety). An exemplary amino acid sequence for a glucose ion symporter or ABC transporter comprises any one of SEQ ID NOS:68-71. Glucose may be then be phosphorylated to glucose 6-phosphate by a separate gluco-kinase. An exemplary amino acid sequence for a gluco-kinase comprises SEQ ID NO:72 or 73.

Acetate Utilization Pathway Enzymes

The utilization of acetate as a carbon and energy source has been previously described (see, e.g., Gerstmeir et al., 2003, J. Biotechnol. 104:99-122). To grow on acetate, bacteria activate it to acetyl-CoA. Acetate may be converted to acetyl-phosphate and then to acetyl-CoA via acetate kinase and phosphotransacetylase enzymes, respectively. Acetate may also be converted directly to acetyl-CoA by acetyl-CoA synthase. An exemplary amino acid sequence for acetyl-CoA synthase comprises SEQ ID NO:74.

Bacterial transport systems for uptake of acetate include monocarboxylic transporters. Exemplary acetate transporters include ActP of *E. coli* (Gimenez et al., 2003, J. Bacteriol. 185:6448-6455, incorporated herein by reference, in its entirety), McTP of *Rhizobium leguminosarum* (Hosie et al, 2002, J. Bacteriol. 184:5436-5448, incorporated herein by reference, in its entirety), and MctC of *Corynebacterium glutamicum* (Jokver et al., 2009, J. Bacteriol. 191:940-948, incorporated herein by reference, in its entirety). An exemplary amino acid sequence for an acetate transporter comprises SEQ ID NO:75.

Lactate Utilization Pathway Enzymes

Many bacteria are able to utilize D- or L-lactate as a sole source of carbon and energy (see, e.g., Chai et al., 2009, J. Bacteriol. 191:2423-2430; Pinchuk et al., 2009, Proc. Natl. Acad. Sci. USA 106:2874-2879; Bryant et al., 1977, Appl. Environ. Microbiol. 33:1162-1169; Erwin and Gotschlich, 1993, J. Bacteriol. 175:6382-6391; Myers and Nealson, 1988, 240:1319-1321; Garvie, 1980, Microbiol. Rev. 44:106-139). To use lactate as a source of carbon, it is oxidized to pyruvate by lactate dehydrogenase. An exemplary amino acid sequence for a lactate dehydrogenase comprises SEQ ID NO:76.

Monocarboxylic transporters that transport acetate may also be capable of transporting lactate. Lactate transporters have been described and include, for example, LutP (formerly YvfH) (Chai et al., 2009, J. Bacteriol. 191:2423-2430, incorporated herein by reference, in its entirety), McTP (Hosie et al., 2002, J. Bacteriol. 184:5436-5448, incorporated herein by reference, in its entirety), GlcA (YghK) and LctP (LldP) (Nunez et al, 2001, Microbiol. 147:1069-1077, incorporated herein by reference, in its entirety). An exemplary amino acid sequence for a lactate transporter comprises SEQ ID NO:77 or 78.

Arabinose Utilization Pathway Enzymes

The utilization of arabinose as a carbon and energy source has been well characterized in a number of bacteria (see, e.g., Engelsberg et al., 1962, J. Bacteriol. 84:137-146; Brown et al., 1972, J. Bacteriol. 111:606-613; Stoner et al., 1983, J. Mol. Biol. 170:1049-1053; Gallegos et al., 1997, Microbiol. Mol. Biol. Rev. 61:393-410; Schleif R., 2000, Trends Genetc. 16:559-565; Sa-Nogueira et al., 1997, Microbiol. 143:957-969; Kawaguchi et al. 2009, Appl. Environ. Microbiol. 75:3419-3429; Vlieg et al., 2006, Curr. Opin. Biotechnol. 17:183-190; U.S. Patent Publication 2011/0143408, disclosures of which are incorporated herein by reference, in their entirety). The arabinose operon, also known as the L-arabinose operon or ara operon, is a gene sequence encoding enzymes needed for the catabolism of L-arabinose to D-xylulose 5-phosophate, an intermediate of the pentose phosphate pathway. The ara operon has both positive and negative regulation. In *E. coli*, the ara operon comprises of a regulator gene AraC, pC and pBAD promoters, and enzymes AraB, AraA, and AraD. AraA is an L-arabinose isomerase that converts arabinose to L-ribulose. AraB is a kinase that phosphorylates L-ribulose. AraD is an epimerase that converts L-ribulose-5-phosphate to D-xylulose-5-phosphate. AraE is a low affinity transporter that is bound to the inner membrane and uses the electrochemical potential to transport arabinose. AraFGH genes encode arabinose-specific components of a high-affinity ABC transporter. AraF is the periplasmic arabinose-binding protein. AraG is the ATP-binding component, and AraH is the membrane bound component. AraC regulates the arabinose catabolic genes (AraBAD) through interactions with the pBAD and pC promoter regions and is itself under arabinose-induced control (reviewed in Schleif R., 2002, SGM symposium 61: Signals, switches, regulons and cascades: control of bacterial gene expression. Ed. D. A. Hodgson, C. M. Thomas. Cambridge Univ. Press). Additional arabinose transporters include an arabinose permease AraP and arabinose transporter AraT. Exemplary amino acid sequences for AraB, AraA, AraD, AraE, AraF, AraG, and AraH comprise SEQ ID NOS: 79, 80, 81, 82, 83, 84, and 85, respectively.

Citrate Utilization Pathway Enzymes

Citrate metabolism pathways in bacteria have been well characterized (see, e.g., Martin et al., 2005, J. Bacteriol. 187:5146-5155; Drider et al., 2004, Genet. Mol. Res. 3:273-281; Bott, 1997, Arch. Microbiol. 167:78-88; Bott et al., 1995, Mol Microbiol. 18:533-546; Yamamoto et al., 2000, Mol. Microbiol. 37:898-912; Korithoski et al., 2005, J. Bacteriol. 2005, 187:4451-4456; Vlieg et al., 2006, Curr. Opin. Biotechnol. 17:183-190). Citrate uptake is mediated by citrate transporters including, for example, CitM (Warner et al., 2000, J. Bacteriol. 182:6099-6105; Korithoski et al., 2005, J. Bacteriol. 187:4451-4456, disclosures of which are incorporated herein by reference, in their entirety), CitS (van der Rest et al., 1992, J. Biol. Chem. 267:8971-8976; Lolkema et al., 1994, Eur. J. Biochem. 220:469-475, disclosures of which are incorporated herein by reference, in their entirety), CitP (Magni et al., 1996, FEMS Microbiol. Lett. 142:265-269, incorporated herein by reference, in its entirety), CitC (Ishiguro et al., 1992, J. Bio. Chem. 267:9559-9564, incorporated herein by reference, in its entirety), and CitH (Lolkema et al., 1994, Eur. J. Biochem. 220:469-475, incorporated herein by reference, in its entirety). An exemplary amino acid sequence for a citrate transporter comprises SEQ ID NO:86.

Succinate Utilization Pathway Enzymes

Bacterial utilization of succinate as a carbon and energy source has been described for a variety of bacteria (see, e.g., Janssen and Liesack, 1995, Arch. Microbiol. 164:29-35; Denger and Schink, 1990, Arch. Microbiol. 154:550-555; Jansen, 1991, Arch. Microbiol. 155:288-293; Gylswiyk et al., 1997, Int. J. Syst. Bacteriol. 47:155-9; Duetz et al., 1994, J. Bacteriol. 176:2354-2361).

Succinate is a component of the citric acid cycle or glyoxylate cycle for generating energy. Succinate is oxidized by succinate dehydrogenase to fumarate. In some bacteria, succinate is decarboxylated to propionate and $CO_2$ by methylmalonyl-CoA decarboxylase (see, e.g., Bott et al., 1997, Eur. J. Biochem. 250:590-599; Ruiz-Herrera and Garcia, 1972, J. Gen. Microbiol. 72:29-35).

Transport systems for $C_4$-dicarboxylates (e.g., succinate) have been described in a number of bacteria. For example, *E. coli* use anaerobic DcuA and DcuB and aerobic Dct dicarboxylate transport systems (Lo et al., 1977, J. Supramol. Struct. 7:463-480; Six et al., 1994, J. Bacteriol. 176:6470-6478, disclosures of which are incorporated herein by reference, in their entirety). YdbFG sensor-regulator and YdbH $C_4$-dicarboxylate transport protein have been described in *Bacillus subtilis* (Asai et al., 2000, Microbiol. 146:263-271, incorporated herein by reference, in its entirety). *Rhodobacter capsulatus* has a Dct transport system which consists of three proteins: $C_4$-dicarboxylate periplasmic binding protein, DctP, and two integral membrane proteins, DctQ and DctM (Forward et al., 1994, J. Bacteriol. 179:5482-5493, incorporated herein by reference, in its entirety). DcsT mediates uptake of C4 dicarbxylates, including succinate, in *Corynebacterium glutamicum* (Teramoto et al., 2008, Appl. Environ. Microbiol. 74:5290-5296, incorporated herein by reference, in its entirety). An exemplary amino acid sequence for a succinate transporter comprises SEQ ID NO:87 or 88.

Recombinant Methanotrophic Bacteria

Provided in the present disclosure are recombinant methanotrophic bacteria that may be produced by introducing (e.g., by transformation) into the host bacteria at least one expressible exogenous nucleic acid encoding a multi-carbon substrate utilization pathway component. Alternatively, if a selected methanotrophic host bacterium exhibits endogenous expression of one of more genes of a multi-carbon substrate utilization pathway, but is deficient in others, then an encoding nucleic acid is needed for the deficient component(s) to achieve the desired multi-carbon substrate utilization capability. Thus, a recombinant methanotrophic bacterium of the invention can be produced by introducing exogenous component activities to obtain a desired multi-carbon substrate utilization pathway or a desired multi-carbon substrate utilization pathway can be obtained by introducing one or more exogenous component activities which, together with one or more endogenous components, allow use of a multi-carbon substrate as a carbon source. However, it is understood that even if a host methanotrophic bacterium contains at least one multi-carbon substrate utilization pathway component, introduction of exogenous nucleic acids encoding components of a complete multi-carbon substrate utilization pathway may be included. In some embodiments, a recombinant methanotrophic bacterium as described herein can also include other genetic modifications that facilitate or optimize a multi-carbon substrate utilization pathway or that confer other useful functions onto the host. For example, if a selected host methanotrophic bacteria exhibits endogenous expression of a protein or enzyme that inhibits or competes with a multi-carbon substrate utilization pathway, then the host may be genetically modified so that it does not produce a functional protein or enzyme or a substantial amount of a functional protein or enzyme that inhibits or competes with the desired multi-carbon substrate utilization. In another example, selected host methanotrophic bacteria may be genetically modified to increase expression of an endogenous gene that enhances utilization of a desired multi-carbon substrate. Additionally, a host methanotrophic bacterium may possess other genetic modifications conferring it with other desirable properties, unrelated to multi-carbon substrate utilization. For example, a host methanotrophic bacterium may possess genetic modifications conferring high growth, tolerance of contaminants or particular culture conditions, ability to metabolize additional carbon substrates, or ability to synthesize desirable products or intermediates (e.g., propylene, crotonate, or crotonyl CoA, see, e.g., International Application Number PCT/US13/60460, incorporated herein by reference, in its entirety).

In certain embodiments, the present disclosure provides recombinant obligate methanotrophic bacteria or recombinant facultative methanotrophic bacteria including at least one exogenous nucleic acid encoding a multi-carbon substrate utilization pathway component, wherein the multi-carbon substrate is not utilized as a carbon source by a reference facultative methanotrophic bacterium, wherein the at least one exogenous nucleic acid encoding a multi-carbon substrate utilization pathway component is expressed in a sufficient amount to permit growth of the recombinant obligate methanotrophic bacteria on the multi-carbon substrate as a primary carbon source or the recombinant facultative methanotrophic bacteria on the multicarbon substrate as a sole carbon source. A multi-carbon substrate may be a carbohydrate or organic acid, including, for example, glucose, acetate, lactate, arabinose, citrate, succinate, and glycerol. Recombinant obligate methanotrophic bacteria use a selected multi-carbon substrate as a primary carbon source if the selected multi-carbon substrate is the source of at least 50% or more of carbon usage for the bacteria. In certain embodiments, the at least one exogenous nucleic acid encoding a multi-carbon substrate utilization pathway component is expressed in a sufficient amount to permit growth of the recombinant obligate methanotrophic bacteria on the multi-carbon substrate as a sole carbon source.

A reference facultative methanotrophic bacterium, also known as parent or wildtype facultative methanotrophic bacterium, is one that has not been genetically engineered with the capability to use an additional multi-carbon substrate other than its native substrates. A reference facultative methanotrophic bacterium may be selected for genetic engineering to introduce at least one exogenous nucleic acid encoding a multi-carbon substrate utilization pathway component for a multi-carbon substrate it does not naturally utilize (i.e., cannot grow on the selected multi-carbon substrate as sole carbon source) and becomes a recombinant facultative methanotrophic bacterium.

In certain embodiments wherein the multi-carbon substrate is glucose, recombinant methanotrophic bacteria include an exogenous nucleic acid encoding a glucose transporter. A number of methanotrophic bacterial genomes encode the enzymes of a complete glycolysis pathway necessary for utilization of D-glucose (see, e.g., Stein et al., 2010, J. Bacteriol. 192:6497-6498; U.S. Pat. No. 6,555,353; Ward et al., 2004, PLoS Biol. 2:e303; Vuilleumier et al., 2012, J. Bacteriol. 194:551-552). Methanotrophs have also been found to possess pentose phosphate pathway genes (Dedysh et al., 2000, Int. J. Syst. Evol. Microbiol. 50:955-969; Vuilleumier et al., 2012, J. Bacteriol. 194:551-552). However, methanotrophic bacteria lack glucose transporters that allow them to bring extracellular sugars into the cell, as well as enzymes to phosphorylate glucose. A glucose transporter suitable for introduction into a methanotrophic bacteria may be a phosphoenolpyruvate:glucose phosphotransferase system, a glucose ion symporter, or an ABC transporter. Exemplary amino acid sequences for phosphoenolpyruvate:glucose phosphotransferase system components comprise a sequence provided by SEQ ID NOS:64-67. Exemplary EI, HPr, and EIIA components comprise amino acid sequences provided by SEQ ID NO: 64 or 65; exemplary EIIC and EIIB components comprise amino acid sequences provided by SEQ ID NOs: 66 or 67. An exemplary amino acid sequence for glucose ion symporters and ABC transporters comprises SEQ ID NO:68, 69, 70, or 71. If the glucose transporter is not a phosphoenolpyruvate: glucose phosphotransferase system, then the recombinant methanotrophic bacterium may further include an exogenous nucleic acid encoding a gluco-kinase to phosphorylate imported glucose. An exemplary amino acid sequence for gluco-kinase comprises SEQ ID NO:72 or 73.

In certain embodiments wherein the multi-carbon substrate is acetate, recombinant methanotrophic bacteria include an exogenous nucleic acid encoding an acetate transporter. Examples of acetate transporters include ActP, MctP, and MctC. An exemplary amino acid sequence for an acetate transporter comprises SEQ ID NO:75. Methanotrophic bacteria lack acetate transporters but possess an acetyl-CoA synthase gene, which activates acetate to acetyl-CoA. Metabolism of acetate may be feasible if it is transported into the cell. In certain embodiments, the recombinant methanotrophic bacteria comprising an exogenous nucleic acid encoding an acetate transporter is further modified to overexpress acetyl-CoA synthase. Up-regulation or overexpression of an endogenous or exogenous nucleic acid encoding acetyl-CoA synthase may improve methanotrophic bacterial growth rate on exogenous acetate, as the endogenous enzyme may not be expressed at optimal levels for growth on this non-native substrate. An exemplary amino acid sequence for an acetyl-CoA synthase comprises SEQ ID NO:74.

In certain embodiments, wherein the multi-carbon substrate is lactate, recombinant methanotrophic bacteria include an exogenous nucleic acid encoding a lactate transporter and an exogenous nucleic acid encoding a lactate dehydrogenase. Examples of lactate transporters include LutP (formerly YvfH), MctP, GlcA (YghK), and LctP (LldP). A number of monocarboxylic acid transporters that transport acetate are capable of transporting lactate also. An exemplary amino acid sequence for lactate transporter comprises SEQ ID NO:77 or 78. A nucleic acid encoding lactate dehydrogenase is introduced into recombinant methanotrophic bacteria to convert imported lactate to pyruvate, which may then enter endogenous pyruvate metabolic pathways of the recombinant methanotrophic bacteria. An exemplary amino acid sequence for lactate dehydrogenase comprises SEQ ID NO:76.

In certain embodiments, wherein the multi-carbon substrate is arabinose, recombinant methanotrophic bacteria include an exogenous nucleic acid encoding an L-arabinose isomerase (e.g., AraA), an exogenous nucleic acid encoding an L-ribulose kinase (e.g., AraB), an exogenous nucleic acid encoding a L-ribulose-5-phosphate epimerase (e.g., AraD), and an exogenous nucleic acid encoding an arabinose transporter. Exemplary amino acid sequences for AraB, AraA, and AraD comprise SEQ ID NOs: 79, 80, and 81, respectively. An arabinose transporter, for example, AraE, AraFGH, or AraP, is used to transport arabinose into the recombinant methanotrophic bacteria. Exemplary AraE, AraF, and AraG, and AraH amino acid sequences comprise SEQ ID NOs: 82, 83, 84, and 85, respectively. AraA is an L-arabinose isomerase that converts arabinose to L-ribulose. AraB is a kinase that phosphorylates L-ribulose. AraD is an epimerase that converts L-ribulose-5-phosphate to D-xylulose-5-phosphate. D-xylulose-5-phosphate is a pre-cursor to ribulose-5-phosphate, a key intermediate in the ribulose monophosphate (RuMP) pathway employed by Type I and Type X methanotrophic bacteria, and is likely to be used efficiently by recombinant methanotrophic bacteria. In further embodiments, the L-arabinose isomerase is AraA, the L-ribulose kinase is AraB, and L-ribulose-5-phosphate epimerase is AraD, and the arabinose transporter is AraE, AraFGH, or AraP.

In certain embodiments, wherein the multi-carbon substrate is citrate, recombinant methanotrophic bacteria include an exogenous nucleic acid encoding a citrate transporter. Examples of citrate transporters include CitM, CitS, CitP, CitC, and CitH. An exemplary amino acid sequence for a citrate transporter comprises SEQ ID NO:86. Once citrate is imported into the cell, recombinant methanotrophs are expected to grow, as they possess enzymes for utilizing citrate.

In certain embodiments, wherein the multi-carbon substrate is succinate, recombinant methanotrophic bacteria include an exogenous nucleic acid encoding a succinate transporter. Examples of succinate transporters include DcuA, DcuB, Dct, YdbH, Dct, and DcsT. An exemplary amino acid sequence for a succinate transporter comprises SEQ ID NO:87 or 88. Once succinate is imported into the cell, recombinant methanotrophs are expected to grow, as they possess enzymes for succinate utilization.

In certain embodiments wherein the multi-carbon substrate is glycerol, the recombinant methanotrophic bacteria includes at least two exogenous nucleic acids encoding glycerol utilization pathway components. In certain embodiments the at least two exogenous nucleic acids are expressed in an amount sufficient to permit growth of the recombinant methanotrophic bacteria on glycerol as a sole carbon source. In certain embodiments, the at least two glycerol utilization pathway components comprise components that are from the respiratory glycerol metabolism pathway. In certain embodiments, the at least two glycerol utilization pathway components comprise glycerol kinase and glycerol-3-phosphate dehydrogenase. The glycerol-3-phophate dehydrogenase may be preferably, aerobic, or anaerobic. In a specific embodiment, the glycerol kinase is GlpK and the glycerol-3-phosphate dehydrogenase is GlpD. Exemplary glycerol kinase and glycerol-3-phosphate dehydrogenase amino acid sequences encoded by exogenous nucleic acids that may be used to transform host methanotrophic bacteria comprise any one of SEQ ID NOS:22-42 and SEQ ID NOS:43-63, respectively. In certain embodiments, the glycerol kinase comprises an amino acid sequence of SEQ ID NO:22 and the glycerol-3-phosphate dehydrogenase comprises an amino acid sequence of SEQ ID NO:43.

In certain embodiments, recombinant methanotrophic bacteria comprise three exogenous nucleic acids encoding glycerol utilization pathway components. The three exogenous nucleic acids encoding glycerol utilization pathway components may be expressed in an amount sufficient to permit growth of the recombinant methanotrophic bacterium on glycerol as a primary carbon source or as a sole carbon source. In certain embodiments, the three exogenous nucleic acids encoding glycerol utilization pathway components comprise glycerol uptake facilitator, glycerol kinase, and glycerol-3-phosphate dehydrogenase. In a specific embodiment, the glycerol uptake facilitator is GlpF, the glycerol kinase is GlpK, and the glycerol-3-phosphate dehydrogenase is GlpD. Exemplary glycerol uptake facilitator, glycerol kinase, and glycerol-3-phosphate dehydrogenase amino acid sequences encoded by exogenous nucleic acids that may be used to transform host methanotrophic bacteria comprise a sequence selected from SEQ ID NOS:1-21, SEQ ID NOS:22-42, and SEQ ID NOS:43-63, respectively. In certain embodiments, the glycerol uptake facilitator comprises an amino acid sequence of SEQ ID NO:1, the glycerol kinase comprises an amino acid sequence of SEQ ID NO:22, and the glycerol-3-phosphate dehydrogenase comprises an amino acid sequence of SEQ ID NO:43.

Recombinant methanotrophic bacteria comprising at least two exogenous nucleic acids encoding glycerol utilization pathway components, as described herein, are expected to exhibit rapid and efficient growth in the presence of glycerol. However, in the absence of glycerol (e.g., during growth on methane as a sole carbon source), it is possible for a glycerol utilization pathway to run in reverse, where intracellular DHAP from gluconeogenesis is reduced to glycerol-3-phosphate by glycerol-3-phosphate dehydrogenase, which is capable of catalyzing a reversible redox reaction. Glycerol- 3-phosphate may then be de-phosphorylated by glycerol-3-phosphatase into glycerol. Glycerol may then be secreted from the cell, thereby lowering the cellular growth rate. Therefore, in certain embodiments, expression of nucleic acids encoding glycerol utilization pathway components may be regulated (e.g., via inducible or repressible promoter) to provide for optimal bacterial growth under a variety conditions (e.g., presence of a particular carbon source). For example, expression of nucleic acids encoding glycerol utilization pathway components may be regulated so that they are not expressed in the absence of glycerol and expressed in the presence of glycerol.

In certain embodiments, recombinant methanotrophic bacteria of any of the embodiments disclosed herein comprise two, three, four, five, six, or more exogenous nucleic acids encoding multi-carbon substrate utilization pathway components, wherein the exogenous nucleic acids are expressed in an amount sufficient to permit growth of the recombinant methanotrophic bacteria on the multi-carbon substrate as a primary or sole carbon source. Each exogenous nucleic acid may encode a different type of multi-carbon substrate utilization pathway component (i.e., catalyze different enzymatic reactions or processes), or one or more nucleic acids may encode the same type of multi-carbon substrate utilization pathway component. For example, a recombinant methanotrophic bacterium may comprise two or more exogenous nucleic acids encoding a glycerol uptake facilitator, with each having a different sequence, in order to increase glycerol import capability of the bacterium. It is apparent to one of skill in the art that any combination of two or more nucleic acids encoding multi-carbon substrate utilization pathway components may be used to constitute a multi-carbon substrate utilization pathway in a recombinant methanotrophic bacterium, provided that the genetically engineered metabolic pathway provides the recombinant methanotrophic bacterium with the capability to metabolize the selected multi-carbon substrate (e.g., glycerol into dihydroxyacetone phosphate, arabinose to D-xylulose 5-phosophate).

In certain embodiments, the recombinant methanotrophic bacteria according to any of the embodiments disclosed herein is *Methylomonas*, *Methylobacter*, *Methylococcus*, *Methylosinus*, *Methylomicrobium*, or *Methanomonas*. In further embodiments, the recombinant methanotrophic bacteria is *Methylosinus trichosporium* strain OB3b, *Methylococcus capsulatus* Bath strain, *Methylomonas methanica* 16A strain, *Methylosinus trichosporium* (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylomonas* sp AJ-3670 (FERM P-2400), *Methylacidiphilum infernorum*, or *Methylomicrobium alcaliphilum* 20Z.

In certain embodiments, the recombinant methanotrophic bacteria according to any of the embodiments disclosed herein is *Methylocella silvestris*, *Methylocella palustris*, *Methylocella tundra*, *Methylocystis daltona*, *Methylocystis bryophila*, *Methylobacterium organophilum* (ATCC 27,886), or *Methylocapsa aurea*.

Sources of encoding nucleic acids for multi-carbon substrate utilization pathway components may include any bacterial, yeast, or other microorganism species where the encoded gene product is capable of catalyzing the referenced reaction in the multi-carbon substrate utilization pathway. Exemplary species for such sources are well known in the art.

Exemplary sources of encoding nucleic acids for glucose utilization pathway components include: *Escherichia coli*, *Bacillus subtilis*, *Corynebacterium glutamicum*, *Saccharomyces cerevisiae*, *Zymomonas mobilis*; *Agrobacterium tumefaciens*, *Sinorhizobium meliloti*; *Rhodobacter sphaeroides*; *Paracoccus versutus*; *Pseudomonas fluorescens*, *Pseudomonas putida*, *Salmonella enterica*, *Escherichia fergusonii*, *Salmonella enteric*, *Yersinia pestis*, *Yersinia pseudotuberculosis*, *Yersinia enterocolitica*, *Shigella flexneri*, *Shigella sonnei*, *Shigella boydii*, *Shigella dysenteriae*, *Pectobacterium atrosepticum*, *Pectobacterium wasabiae*, *Erwinia tasmaniensis*, *Erwinia pyrifoliae*, *Erwinia amylovora*, *Erwinia billingiae*, *Buchnera aphidicola*, *Enterobacter* sp. 638, *Enterobacter cloacae*, *Enterobacter asburiae*, *Enterobacter aerogenes*, *Cronobacter sakazakii*, *Cronobacter turicensis*, *Klebsiella pneumoniae*, *Klebsiella variicola*, *Klebsiella oxytoca*, *Citrobacter koseri*, *Citrobacter rodentium*, *Serratia proteamaculans*, *Serratia* sp. AS12, *Proteus mirabilis*, *Edwardsiella ictaluri*, *Edwardsiella tarda*, *Candidatus Hamiltonella defense*, *Dickeya dadantii*, *Dickeya zeae*, *Pantoea ananatis*, *Pantoea* sp. At-9b, *Pantoea vagans*, *Rahnella* sp. Y9602, *Haemophilus parasuis*, *Haemophilus parainfluenzae*, *Pasteurella multocida*, *Aggregatibacter aphrophilus*, *Aggregatibacter actinomycetemcomitans*, *Vibrio cholerae*, *Vibrio vulnificus*, *Vibrio parahaemolyticus*, *Vibrio harveyi*, *Vibrio splendidus*, *Photobacterium profundum*, *Vibrio anguillarum*, *Shewanella oneidensis*, *Shewanella denitrificans*, *Shewanella frigidimarina*, *Shewanella amazonensis*, *Shewanella baltica*, *Shewanella loihica*, *Shewanella* sp. ANA-3, *Shewanella* sp. MR-7, *Shewanella putrefaciens*, *Shewanella sediminis*, *Shewanella* sp. MR-4, *Shewanella* sp. W3-18-1, *Shewanella woodyi*, *Psychromonas ingrahamii*, *Ferrimonas balearica*, *Aeromonas hydrophile*, *Aeromonas salmonicida*, *Aeromonas veronii*, *Tolumonas auensis*, *Chromobacterium violaceum*, *Burkholderia* sp. CCGE1002, *Azospirillum* sp. B510, *Bacillus anthracis*, *Bacillus cereus*, *Bacillus cytotoxicus*, *Bacillus thuringiensis*, *Bacillus weihenstephanensis*, *Bacillus pseudofirmus*, *Bacillus megaterium*, *Staphylococcus aureus*, *Exiguobacterium sibiricum*, *Exiguobacterium* sp. AT1b, *Macrococcus caseolyticus*, *Paenibacillus polymyxa*, *Streptococcus pyogenes*, *Streptococcus pneumoniae*, *Streptococcus agalactiae*, *Streptococcus mutans*, *Streptococcus thermophilus*, *Streptococcus sanguinis*, *Streptococcus suis*, *Streptococcus gordonii*, *Streptococcus equi*, *Streptococcus uberis*, *Streptococcus dysgalactiae*, *Streptococcus gallolyticus*, *Streptococcus mitis*, *Streptococcus pseudopneumoniae*, *Lactobacillus johnsonii*, *Lactobacillus gasseri*, *Enterococcus faecalis*, *Aerococcus urinae*, *Carnobacterium* sp. 17-4, *Clostridium acetobutylicum*, *Clostridium perfringens*, *Clostridium tetani*, *Clostridium novyi*, *Clostridium botulinum*, *Desulfotomaculum reducens*, *Clostridium lentocellum*, *Erysipelothrix rhusiopathiae*, *Mycoplasma genitalium*, *Mycoplasma pneumoniae*, *Mycoplasma pulmonis*, *Mycoplasma penetrans*, *Mycoplasma gallisepticum*, *Mycoplasma mycoides*, *Mycoplasma synoviae*, *Mycoplasma capricolum*, *Mycoplasma crocodyli*, *Mycoplasma leachii*, *Mesoplasma forum*, *Propionibacterium acnes*, *Nakamurella multipartita*, *Borrelia burgdorferi*, *Borrelia garinii*, and *Borrelia afzelii*.

Exemplary sources of encoding nucleic acids for acetate utilization pathway components include: *Corynebacterium glutamicum*, *Escherichia coli*, and *Rhizobium leguminosarum*.

Exemplary sources of encoding nucleic acids for lactate utilization pathway components include: *Rhizobium leguminosarum*, *Bacillus subtilis*, *Staphylococcus aureus*, *Escherichia coli*, *Enterobacteriaceae*, *Propionibacterium*

*pentosaceum, Pseudomonas aeruginosa, Acetobacter peroxydans, Selenomonas ruminantium, Pseudomonas natriegens, Aerobacter aerogenes, Lactobacillus casei, Lactobacillus plantarum, Serratia, Aerobacter cloacae, Proteus vulgaris, Escherichia freundii, Klebsiella sp., Hafnia sp., Butyribacterium rettgeri, Streptococcus faecium, Streptococcus lactis, Pediococcus pentosaceum, Salmonella typhimurium, Aggregatibacter actinomycetemcomitans,* and *Neisseria gonorrhoeae.*

Sources of encoding nucleic acids for arabinose utilization pathway components include: *Escherichia coli, Bacillus subtilis, Scheffersomyces stipitis, Corynebacterium glutamicum, Lactococcus lactis, Pichia stipitis, Shigella flexneri, Shigella boydii, Shigella dysenteriae, Salmonella typhimurium, Salmonella enterica, Klebsiella pneumoniae, Klebsiella oxytoca, Enterobacter cancerogenus, Bacillus amyloliquefaciens, Rhizobium,* and *Agrobacterium.*

Sources of encoding nucleic acids for citrate utilization pathway components include: *Lactococcus lactis, Enterococcus, Lactobacillus plantarum, Oenococcus oeni, Leuconostoc mesenteroides, Weissella, Salmonella dublin, Salmonella pulloru, Salmonella enteritidis, Klebsiella pneumoniae, Salmonella typhimurium,* and *Bacillus subtilis.*

Sources of encoding nucleic acids for succinate utilization pathway components include: *Escherichia coli, Corynebacterium glutamicum, Rhodobacter capsulatus,* and *Bacillus subtilis.*

Sources of encoding nucleic acids for glycerol utilization pathway components include, for example: *Escherichia coli, Acinetobacter baumannii, Fusobacterium nucleatum* subsp. *vincentii, Pantoea* sp. Scl, *Pseudomonas aeruginosa, Shigella flexneri, Shewanella baltica* OS155, *Actinobacillus pleuropneumoniae serovar* 3 str. JL03, *Salmonella enterica* subsp. *enterica serovar Saintpaul* str. SARA29, *Yersinia bercovieri, Aeromonas veronii* B565, *Pseudomonas fluorescens, Serratia* sp. AS12, *Vibrio fischeri* SR5, *Haemophilus haemolyticus, Vibrio harveyi, Vibrio cholera, Pseudomonas putida* S16, *Pectobacterium carotovorum* subsp. *carotovorum* PC1, *Pseudomonas syringae, Acinetobacter* sp. ATCC 27244, *Photobacterium profundum* SS9, *Citrobacter freundii, Klebsiella pneumoniae, Enterobacter* sp., *Enterococcus casseliflavus, Enterococcus faecalis, Bacillus stearothermophilus, Bacillus subtilis, Streptococcus pyogenes, Haemophilus, influezae, Mycoplasma genitalium, Mycoplasma pneumonia, Mycoplasma mycoides, Yersinia mollaretii, Shigella dysenteriae, Shigella boydii, Shigella sonnei, Yersinia pestis, Yersinia intermedia, Yersinia frederiksenii, Serratia proteamaculans, Erwinia carotovora, Pseudomonas tolaasii, Yersinia enterolitica, Photorhabdus luminesens, Azotobacter vinelandii, Haemophilus ducreyi, Actinobacillus pleuropneumoniae, Aeromonas hydrophile, Photobacterium profundum, Aeromonas salmonicida, Vibrio angustum, Vibrio vulnificus, Vibrionales bacterium, Vibrio splendidus, Vibrio* sp. Ex25, *Vibrio alginolyticus, Vibrio parahaemolyticus, Shewanella* sp. W3-18-1, *Alteromonas macleodii, Sodalis glossinidius, Pasteurella multocida, Salmonella typhimurium, Lactobacillus casei, Rhadopseudomonas, Propionibacterium, Nocardia asteroides, Klebsiella aerogenes, Halobacterium cutirubrum, Gluconobacter oxydans, Staphylococcus aureus, Candida utilis, Candia mycodema, Saccharomyces cerevisiae, Pichia pastoris, Kluyveromyces lactis, Ashbya gossypii, Lodderomyces elongisporus, Debaryomyces hansenii, Candida albicans, Pichia guilliermondii, Pichia stipitis,* and *Fusarium oxysporum.*

However, with the complete genome sequence available for hundreds of microorganisms, the identification of genes encoding the requisite multi-carbon substrate utilization pathway in related or distant species, including for example, homologs, orthologs, paralogs, etc., is routine and well known in the art. Accordingly, exogenous nucleic acids encoding multi-carbon substrate utilization pathway components described herein with reference to particular nucleic acids from a particular organism can readily include other nucleic acids encoding multi-carbon substrate utilization pathway components from other microorganisms. For recombinant methanotrophic bacteria comprising at least two exogenous nucleic acids encoding multi-carbon substrate utilization components, each nucleic acid may be derived from the same microorganism or from different microorganisms.

Polypeptide sequences and encoding nucleic acids for proteins, protein domains, and fragments thereof described herein, such as a component of a multi-carbon substrate utilization pathway, may also include natural and recombinantly engineered variants. A nucleic acid variant refers to a nucleic acid that may contain one or more substitutions, additions, deletions, insertions, or may be or comprise fragment(s) of a reference nucleic acid. A reference nucleic acid refers to a selected nucleic acid encoding a multi-carbon substrate utilization pathway component. A variant nucleic acid may have 40%, 45%, 50%, 55%, 60%, 65%, 70%, 71%, 72%, 73%, 74%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to a reference nucleic acid, as long as the variant nucleic acid can still perform its requisite function or biological activity in the multi-carbon substrate utilization pathway (e.g., membrane transport). A variant polypeptide may have 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to a reference protein, as long as the variant polypeptide can still perform its requisite function or biological activity (e.g., membrane transport). In certain embodiments, a multi-carbon substrate utilization pathway component that is introduced into recombinant methanotrophs as provided herein encodes an amino acid sequence having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identity to an amino acid sequence selected from SEQ ID NOS:1-88. In certain embodiments, an exogenous nucleic acid encoding a multi-carbon substrate utilization pathway component that is introduced into recombinant methanotrophs comprises a nucleic acid sequence having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identity to a nucleic acid sequence provided in Tables 14-22. These variants may have improved function and biological activity (e.g., higher enzymatic activity or improved specificity for substrate) than the parent (or wildtype) protein. Due to redundancy in the genetic code, nucleic acid variants may or may not affect amino acid sequence. A nucleic acid variant may also encode an amino acid sequence comprising one or more conservative substitutions compared to a reference amino acid sequence. A conservative substitution may occur naturally in the polypeptide (e.g., naturally occurring genetic variants) or may be introduced when the polypeptide is recombinantly produced. A conservative substitution is where one amino acid is substituted for another amino acid that has similar properties, such that one skilled in the art would expect that the secondary structure and hydropathic nature of the polypeptide to be substantially unchanged.

Amino acid substitutions may generally be made on the basis of similarity in polarity, charge, solubility, hydrophobicity, and/or the amphipathic nature of the residues, and is known in the art. Amino acid substitutions, deletions, and additions may be introduced into a polypeptide using well-known and routinely practiced mutagenesis methods (see, e.g., Sambrook et al. *Molecular Cloning: A Laboratory Manual*, 3d ed., Cold Spring Harbor Laboratory Press, NY 2001). Oligonucleotide-directed site-specific (or segment specific) mutagenesis procedures may be employed to provide an altered polynucleotide that has particular codons altered according to the substitution, deletion, or insertion desired. Deletion or truncation variants of proteins may also be constructed by using convenient restriction endonuclease sites adjacent to the desired deletion. Alternatively, random mutagenesis techniques, such as alanine scanning mutagenesis, error prone polymerase chain reaction mutagenesis, and oligonucleotide-directed mutagenesis may be used to prepare polypeptide variants (see, e.g., Sambrook et al., supra). Variant nucleic acids may be naturally occurring or genetically engineered.

Nucleic acids encoding multi-carbon substrate utilization pathway components may be combined with other nucleic acid sequences, such as promoters, polyadenylation signals, restriction enzyme sites, multiple cloning sites, other coding segments, and the like.

Differences between a wild type (or parent or reference) nucleic acid or polypeptide and the variant thereof, may be determined by methods routinely practiced in the art to determine identity, which are designed to give the greatest match between the sequences tested. Methods to determine sequence identity can be applied from publicly available computer programs. Computer program methods to determine identity between two sequences include, for example, BLASTP, BLASTN (Altschul, S. F. et al., *J. Mol. Biol.* 215: 403-410 (1990), and FASTA (Pearson and Lipman Proc. Natl. Acad. Sci. USA 85; 2444-2448 (1988). The BLAST family of programs is publicly available from NCBI and other sources (*BLAST Manual*, Altschul, S., et al., NCBI NLM NIH Bethesda, Md.

Assays for determining whether a polypeptide variant folds into a conformation comparable to the non-variant polypeptide or fragment include, for example, the ability of the protein to react with mono- or polyclonal antibodies that are specific for native or unfolded epitopes, the retention of ligand-binding functions, the retention of enzymatic activity (if applicable), and the sensitivity or resistance of the mutant protein to digestion with proteases (see Sambrook et al., supra). Polypeptides, variants and fragments thereof, can be prepared without altering a biological activity of the resulting protein molecule (i.e., without altering one or more functional activities in a statistically significant or biologically significant manner). For example, such substitutions are generally made by interchanging an amino acid with another amino acid that is included within the same group, such as the group of polar residues, charged residues, hydrophobic residues, and/or small residues, and the like. The effect of any amino acid substitution may be determined empirically merely by testing the resulting modified protein for the ability to function in a biological assay, or to bind to a cognate ligand or target molecule.

Codon Optimization

Expression of recombinant proteins is often difficult outside their original host. For example, variation in codon usage bias has been observed across different species of bacteria (Sharp et al., 2005, Nucl. Acids. Res. 33:1141-1153). Over-expression of recombinant proteins even within their native host may also be difficult. In certain embodiments, at least one nucleic acid encoding a multi-carbon substrate utilization pathway component that is to be introduced into host methanotrophic bacteria according to any of the embodiments described herein is codon optimized to enhance protein expression in the methanotrophic bacteria. Codon optimization refers to alteration of codons in genes or coding regions of nucleic acids for transformation of a methanotrophic bacterium to reflect the typical codon usage of the host bacteria species without altering the polypeptide for which the DNA encodes. Codon optimization methods for optimum gene expression in heterologous hosts have been previously described (see, e.g., Welch et al., 2009, PLoS One 4:e7002; Gustafsson et al., 2004, Trends Biotechnol. 22:346-353; Wu et al., 2007, Nucl. Acids Res. 35:D76-79; Villalobos et al., 2006, BMC Bioinformatics 7:285; U.S. Patent Publication 2011/0111413; U.S. Patent Publication 2008/0292918; disclosure of which are incorporated herein by reference, in their entirety). One, two, three, or more nucleic acids encoding multi-carbon substrate utilization pathway components may be codon optimized. For example, wherein a recombinant methanotrophic bacterium comprises two glycerol utilization pathway components, one nucleic acid molecule (e.g., glycerol kinase) may be codon optimized, while the second nucleic acid molecule (e.g., glycerol-3-phosphate dehydrogenase) is not codon optimized, or vice versa. Alternatively, all nucleic acids encoding multi-carbon substrate (e.g., glycerol) utilization pathway components may be codon optimized.

Transformation Methods

Any of the recombinant methanotrophic bacteria described herein may be transformed to comprise at least one exogenous nucleic acid to provide the host bacterium with a new or enhanced activity (e.g., enzymatic activity) or may be genetically modified to remove or substantially reduce an endogenous gene function using a variety of methods known in the art.

Transformation refers to the transfer of a nucleic acid (e.g., exogenous nucleic acid) into the genome of a host bacterium, resulting in genetically stable inheritance. Host bacteria containing the transformed nucleic acid molecules are referred to as "non-naturally occurring" or "recombinant" or "transformed" or "transgenic" bacteria.

Expression systems and expression vectors useful for the expression of heterologous nucleic acids in methanotrophic bacteria are known.

Electroporation of C1 metabolizing bacteria has been previously described in Toyama et al., 1998, FEMS Microbiol. Lett. 166:1-7; Kim and Wood, 1997, Appl. Microbiol. Biotechnol. 48:105-108; Yoshida et al., 2001, Biotechnol. Lett. 23:787-791, and US2008/0026005.

Bacterial conjugation, which refers to a particular type of transformation involving direct contact of donor and recipient cells, is more frequently used for the transfer of nucleic acids into C1 metabolizing bacteria. Bacterial conjugation involves mixing "donor" and "recipient" cells together in close contact with each other. Conjugation occurs by formation of cytoplasmic connections between donor and recipient bacteria, with unidirectional transfer of newly synthesized donor nucleic acid molecules into the recipient cells. A recipient in a conjugation reaction is any cell that can accept nucleic acids through horizontal transfer from a donor bacterium. A donor in a conjugation reaction is a bacterium that contains a conjugative plasmid, conjugative transposon, or mobilized plasmid. The physical transfer of the donor plasmid can occur through a self-transmissible plasmid or with the assistance of a "helper" plasmid. Conjugations involving C1 metabolizing bacteria have been previously described in Stolyar et al., 1995, Mikrobiologiya 64:686-691; Motoyama et al., 1994, Appl. Micro. Biotech. 42:67-72; Lloyd et al., 1999, Archives of Microbiology 171:364-370; and Odom et al., PCT Publication WO 02/18617; Ali et al., 2006, Microbiol. 152:2931-2942.

Expression of heterologous nucleic acids in C1 metabolizing bacteria is known in the art (see, e.g., U.S. Pat. No. 6,818,424, US2003/0003528). Mu transposon based transformation of methylotrophic bacteria has been described (Akhverdyan et al., 2011, Appl. Microbiol. Biotechnol. 91:857-871). A mini-Tn7 transposon system for single and multicopy expression of heterologous genes without insertional inactivation of host genes in *Methylobacterium* has been described (US2008/0026005).

Various methods for inactivating, knocking-out, or deleting endogenous gene function in C1 metabolizing bacteria may be used. Allelic exchange using suicide vectors to construct deletion/insertional mutants in slow growing C1 metabolizing bacteria have also been described in Toyama and Lidstrom, 1998, Microbiol. 144:183-191; Stolyar et al., 1999, Microbiol. 145:1235-1244; Ali et al., 2006, Microbiology 152:2931-2942; Van Dien et al., 2003, Microbiol. 149:601-609.

Suitable homologous or heterologous promoters for high expression of exogenous nucleic acids may be utilized. For example, U.S. Pat. No. 7,098,005 describes the use of promoters that are highly expressed in the presence of methane or methanol for heterologous gene expression in C1 metabolizing bacteria. Additional promoters that may be used include deoxy-xylulose phosphate synthase methanol dehydrogenase operon promoter (Springer et al., 1998, FEMS Microbiol. Lett. 160:119-124); the promoter for PHA synthesis (Foellner et al. 1993, Appl. Microbiol. Biotechnol. 40:284-291); or promoters identified from native plasmid in methylotrophs (EP296484). Non-native promoters include the lac operon Plac promoter (Toyama et al., 1997, Microbiology 143:595-602) or a hybrid promoter such as Ptrc (Brosius et al., 1984, Gene 27:161-172). In certain embodiments, promoters or codon optimization are used for high constitutive expression of exogenous nucleic acids encoding glycerol utilization pathway enzymes in host methanotrophic bacteria. Regulated expression of an exogenous nucleic acid in the host methanotrophic bacterium may also be utilized. In particular, regulated expression of exogenous nucleic acids encoding glycerol utilization enzymes may be desirable to optimize growth rate of the non-naturally occurring methanotrophic bacteria. It is possible that in the absence of glycerol (e.g., during growth on methane as sole carbon source), for the glycerol utilization pathway to run in reverse, resulting in secretion of glycerol from the bacteria, thereby lowering growth rate. Controlled expression of nucleic acids encoding glycerol utilization pathway enzymes in response to the presence of glycerol may optimize bacterial growth in a variety of carbon source conditions. For example, an inducible/regulatable system of recombinant protein expression in methylotrophic and methanotrophic bacteria as described in US2010/0221813 may be used. Regulation of glycerol utilization genes in bacteria is well established (Schweizer and Po, 1996, J. Bacteriol. 178:5215-5221; Abram et al., 2008, Appl. Environ. Microbiol. 74:594-604; Darbon et al., 2002, Mol. Microbiol. 43:1039-1052; Weissenborn et al., 1992, J. Biol. Chem. 267:6122-6131). Glycerol utilization regulatory elements may also be introduced or inactivated in host methanotrophic bacteria for desired expression levels of exogenous nucleic acid molecules encoding glycerol utilization pathway enzymes.

Methods of screening are disclosed in Brock, supra. Selection methods for identifying allelic exchange mutants are known in the art (see, e.g., U.S. Patent Publication No. 2006/0057726, Stolyar et al., 1999, Microbiol. 145:1235-1244; and Ali et al., 2006, Microbiology 152:2931-2942.

Culture Methods

A variety of culture methodologies may be used for the recombinant methanotrophic bacteria described herein. For example, methanotrophic bacteria may be grown by batch culture and continuous culture methodologies. In certain embodiments, the cultures are grown in a controlled culture unit, such as a fermentor, bioreactor, hollow fiber membrane bioreactor, or the like.

A classical batch culturing method is a closed system where the composition of the media is set at the beginning of the culture and not subject to external alterations during the culture process. Thus, at the beginning of the culturing process, the media is inoculated with the desired methanotrophic bacteria and growth or metabolic activity is permitted to occur without adding anything to the system. Typically, however, a "batch" culture is batch with respect to the addition of carbon source and attempts are often made at controlling factors such as pH and oxygen concentration. In batch systems, the metabolite and biomass compositions of the system change constantly up to the time the culture is terminated. Within batch cultures, cells moderate through a static lag phase to a high growth logarithmic phase and finally to a stationary phase where growth rate is diminished or halted. If untreated, cells in the stationary phase will eventually die. Cells in logarithmic growth phase are often responsible for the bulk production of end product or intermediate in some systems. Stationary or post-exponential phase production can be obtained in other systems.

The Fed-Batch system is a variation on the standard batch system. Fed-Batch culture processes comprise a typical batch system with the modification that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measureable factors, such as pH, dissolved oxygen, and the partial pressure of waste gases such as $CO_2$. Batch and Fed-Batch culturing methods are common and known in the art (see, e.g., Thomas D. Brock, Biotechnology: A Textbook of Industrial Microbiology, $2^{nd}$ Ed. (1989) Sinauer Associates, Inc., Sunderland, Mass.; Deshpande, 1992, Appl. Biochem. Biotechnol. 36:227, herein incorporated by reference in its entirety).

Continuous cultures are "open" systems where a defined culture media is added continuously to a bioreactor and an equal amount of conditioned media is removed simultaneously for processing. Continuous cultures generally maintain the cells at a constant high liquid phase density where cells are primarily in logarithmic phase growth. Alternatively, continuous culture may be practiced with immobilized cells where carbon and nutrients are continuously added and valuable products, by-products, and waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limited nutrient, such as the carbon source or nitrogen level, at a fixed rate and allow all other parameters to modulate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art, and a variety of methods are detailed by Brock, supra.

Culture media must contain suitable carbon substrates for the methanotrophic bacteria. A culture media may comprise a selected multi-carbon substrate (e.g., glycerol) as the sole carbon source for the non-naturally occurring methanotrophic bacteria as described herein. Alternatively, a culture media may comprise two or more carbon substrates (mixed carbon substrates). Mixed carbon substrates may comprise a mixture of a C1 substrate and a multi-carbon substrate. For example, the culture media may comprise a mixture of glycerol and methane. Alternatively, mixed carbon substrates may comprise a mixture of more than one multi-carbon substrate or more than one C1 substrate or a combination thereof. For cultures containing mixed carbon substrates, a selected multi-carbon substrate (e.g., glycerol) is used as a primary carbon source by the recombinant methanotrophic bacteria as described herein. A carbon source, whether a multi-carbon substrate alone or a mixed composition, may be added to culture media initially, provided to culture media intermittently, or supplied continuously. Alternatively, recombinant methanotrophic bacteria may be initially grown in culture with methane as a sole carbon source and then a multi-carbon substrate added at a later time point to make a mixed carbon source or methane may be substituted by a multi-carbon substrate.

Glycerol compositions added to the culture may be purified glycerol or crude glycerol. Purified glycerol, the refined form used in pharmaceutical, food, and cosmetic industries, is at least 90%, 95%, 96%, 97%, 98%, 99%, or 99.5% pure. Crude glycerol is a by-product of biodiesel production that contains approximately 50-60% of glycerol, 12-16% of alkalies, especially in the form of alkali soaps and hydroxides, 15-18% of methyl esters, 8-12% of methanol, 2-3% water, and further components. Crude glycerol also contains a variety of elements, such as calcium, magnesium, phosphorus, or sulfur, originating from the primary oil. Larger quantities of sodium or potassium are also present, derived from the catalyst. Purified or crude glycerol may be added directly to the culture. Alternatively, impurities may be removed from crude glycerol by conventional separation techniques prior to addition to culture in order to increase the concentration of glycerol in solution to at least 50%, 55%, 60%, 65%, 70%, 75%, 80%, 85%, or 90%.

Methods for Growing Recombinant Methanotrophic Bacteria

In certain embodiments, methods for growing recombinant methanotrophic bacteria are provided, comprising: culturing any of the embodiments of recombinant methanotrophic bacteria disclosed herein in the presence of a multi-carbon substrate, wherein the multi-carbon substrate is used as a primary carbon source by the recombinant obligate methanotrophic bacteria or wherein the multi-carbon substrate is used as a sole carbon source by the recombinant facultative methanotrophic bacteria. A multi-carbon substrate may include glucose, acetate, lactate, arabinose, citrate, succinate, and glycerol. In certain embodiments, a selected multi-carbon substrate is used as a sole carbon source. In certain embodiments, the multi-carbon substrate is used as a sole carbon source by the recombinant obligate methanotrophic bacteria.

In certain embodiments wherein the multi-carbon substrate is glucose, the recombinant methanotrophic bacteria include at least one exogenous nucleic acid encoding a glucose transporter.

In certain embodiments wherein the multi-carbon substrate is acetate, the recombinant methanotrophic bacteria include at least one exogenous nucleic acid encoding an acetate transporter. In further embodiments, the recombinant methanotrophic bacterium is further modified to overexpress acetyl-CoA synthase.

In certain embodiments wherein the multi-carbon substrate is lactate, the recombinant methanotrophic bacteria include an exogenous nucleic acid encoding a lactate transporter and an exogenous nucleic acid encoding a lactate dehydrogenase.

In certain embodiments wherein the multi-carbon substrate is arabinose, the recombinant methanotrophic bacteria include an exogenous nucleic acid encoding an L-arabinose isomerase (e.g., AraA), an exogenous nucleic acid encoding an L-ribulose kinase (e.g., AraB), an exogenous nucleic acid encoding an L-ribulose-5-phosphate epimerase (e.g., AraD). An arabinose transporter includes AraE, AraFGH, and AraP.

In certain embodiments wherein the multi-carbon substrate is citrate, the recombinant methanotrophic bacteria include an exogenous nucleic acid encoding a citrate transporter.

In certain embodiments wherein the multi-carbon substrate is succinate, the recombinant methanotrophic bacteria include an exogenous nucleic acid encoding a succinate transporter.

In certain embodiments wherein the multi-carbon substrate is glycerol, the recombinant methanotrophic bacteria include at least two exogenous nucleic acids encoding glycerol utilization pathway components. The at least two exogenous nucleic acids encoding glycerol utilization pathway components may comprise glycerol kinase and glycerol-3-phosphate dehydrogenase. In a specific embodiment, glycerol kinase is GlpK and glycerol-3-phosphate dehydrogenase is GlpD. In another specific embodiment, glycerol kinase comprises an amino acid sequence of SEQ ID NO:22 and glycerol-3-phosphate dehydrogenase comprises an amino acid sequence of SEQ ID NO:43.

In certain embodiments, the recombinant methanotrophic bacteria includes three exogenous nucleic acids encoding glycerol utilization pathway components. The three exogenous nucleic acids encoding glycerol utilization pathway components may comprise glycerol uptake facilitator, glycerol kinase, and glycerol-3-phosphate dehydrogenase. In a specific embodiment, glycerol uptake facilitator is GlpF, glycerol kinase is GlpK, and glycerol-3-phosphate dehydrogenase is GlpD. In another specific embodiment, glycerol uptake facilitator comprises an amino acid sequence of SEQ ID NO:1, glycerol kinase comprises an amino acid sequence of SEQ ID NO:22, and glycerol-3-phosphate dehydrogenase comprises an amino acid sequence of SEQ ID NO:43.

Obligate methanotrophic bacteria for use according to any of the embodied methods disclosed herein include *Methylomonas, Methylobacter, Methylococcus, Methylosinus, Methylocystis, Methylomicrobium,* or *Methanomonas.* Exemplary obligate methanotrophic bacteria include: *Methylococcus capsulatus* Bath strain, *Methylomonas* 16a (ATCC PTA 2402), *Methylosinus trichosporium* OB3b (NRRL B-11, 196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylomonas* sp AJ-3670 (FERM P-2400), *Methylacidiphilum infernorum*( ), and *Methylomicrobium alcaliphilum* 20Z. Exemplary facultative methanotrophic bacteria for use according to any of the embodied methods disclosed herein include *Methylocella silvestris, Methylocella palustris, Methylocella tundra, Methylocystis daltona, Methylocystis bryophila, Methylobacterium organophilum* (ATCC 27,886), and *Methylocapsa aurea*.

In certain embodiments, one or more exogenous nucleic acids encoding a multi-carbon substrate utilization pathway component is codon optimized for high expression in methanotrophic bacteria.

Measuring Utilization of Multi-Carbon Substrates

Utilization of a selected multi-carbon substrate as a sole carbon source may be measured by determining growth rate, biomass yield, or increase in cell density using standard methods known in the art during culture of recombinant bacteria with the selected multi-carbon substrate as the sole carbon source.

Measuring Glycerol Utilization

Glycerol utilization by recombinant methanotrophic bacteria described herein may be determined by various methods known in the art. For example, enzyme activity assays of glycerol utilization pathway enzymes, e.g., glycerol kinase and glycerol-3-phosphate dehydrogenase, have been previously described (Rawls et al., 2011, J. Bacteriol. 193: 4469-4476; Rittman et al., 2008, Applied Environmental Microbiol. 74:6216-6222; Darbon et al., 1999, Microbiol. 145:3205-3212; Charrier et al., 1997, J. Biol. Chem. 272: 14166-14174).

Dihydroxyacetone phosphate (DHAP) levels may also be assayed via a coupled enzyme system: reduction with NADH-consuming glycerol-3-phosphate dehydrogenase enables determination of DHAP by measuring NADH concentration with UV spectroscopy (WO2007/003574).

The growth rate or biomass yield of recombinant methanotrophic using glycerol as a carbon source may also be measured as an indicator of glycerol utilization (Rittman et al., 2008, Applied Environmental Microbiol. 74:6216-6222; Muraka et al., 2008, Applied Environmental Microbiol. 74:1124-1135).

Glycerol depletion from the culture medium may also be measured over time. At various time points, aliquots of culture broth containing glycerol and non-naturally occurring methanotrophic bacteria described herein may be withdrawn, centrifuged, filtered, and analyzed by high-performance liquid chromatography to determine consumption of glycerol during bacterial growth in the medium (Rawls et al., 2011, J. Bacteriol. 193:4469-4476; Gonzalez et al., 2008, Metabolic Engineering 10:234-245; Rittman et al., 2008, Applied Environmental Microbiol. 74:6216-6222). Alternatively, radio-labeled glycerol substrate may be added to the culture media, and after different time points, radioactivity remaining in the culture or incorporated into bacteria may be measured (Sher et al., 2004, FEMS Microbiol. Lett. 232: 211-215; Muraka et al. 2008, Applied Environmental Microbiol. 74:1124-1135). Glycerol concentration in bacterial cell culture supernatant may also be measured at various time points using a free glycerol assay kit (see, e.g., Product #FG0100 from Sigma, St. Louis, Mo. or Product #ab65337 from Abcam, Cambridge Mass.).

Measuring Glucose Utilization

Glucose consumption may be measured by sampling culture medium over time for glucose or its corresponding fermentation by-products using HPLC (see, e.g., Garcia Sanchez et al., 2010, Biotechnology for Biofuels 3:13). Coupled enzyme assays, such as the one described in U.S. Pat. No. 4,490,465 or Amplex® Red Glucose/Glucose Oxidase Assay Kit (Invitrogen, Catalog #A22189), may be used to determine the amount of glucose in solution.

Measuring Acetate Utilization

Acetate agar may be used to test recombinant methanotrophic bacteria's ability to utilize acetate. The medium contains sodium acetate as the sole carbon source and inorganic ammonium salts as the sole nitrogen source. Bacterial growth is indicative of acetate utilization. When the bacteria metabolize acetate, the ammonium salts are broken down to ammonia, increasing alkalinity. The resulting increase in pH turns the bromothymol blue indicator in the medium from green to blue (see, e.g., Weyant et al. 1995, Identification of Unusual Pathogenic Gram-Negative Aerobic and Facultatively Anaerobic Bacteria, $2^{nd}$ ed., pp. 6-7, Williams & Wilkins, Baltimore, Md.).

Acetate utilization may also be measuring using a method as described in Dedysh et al. (2005, J. Bacteriol. 187:4665-4670). Briefly, recombinant methanotrophic bacteria are grown in basal salts medium DNMS (dilute nitrate mineral salts, pH 5.8) with sodium acetate at 0.04% wt/vol. Cultures are grown to an OD600 of >0.1 from an inoculation of <0.001 at 25° C. on a rotary shaker at 120 rpm. Samples are taken daily for determination of acetate concentrations, direct microscopic cell counts, OD600, and DNA extraction and quantitative real-time PCR to determination acetate utilization and bacterial cell growth. Acetate is measured on a Sykam high-performance liquid chromatography system with a refraction index detector. Measurement of growth yield and carbon conversion efficiency on acetate substrate has also been described in U.S. Patent Publication 2012/0034594. Assay kits for detecting acetate are commercially available (e.g., Catalog #K-ACETRM from Megazyme, Wicklow, Ireland)

Measuring Lactate Utilization

Lactate uptake assays may be used to measure lactate utilization. Briefly, radiolabelled lactate is added to cell culture and after different time intervals, samples are taken, filtered, washed, and counted on a scintillator (see, e.g., Nunez et al., 2001, Microbiol. 147:1069-1077; Exley et al., 2007, Infect. Immun. 75:1318-1324).

Lactate utilization may also be measuring by testing for conversion of lactate to pyruvate by lactate dehydrogenase and performing kinetic analysis (see, e.g., Garvie, 1980, Microbiol. Rev. 44:106-139; Brown and Whiteley, 2009, PLoS One 4:e7864; Futai, 1973, Biochemistry 12:2468-2474; Futai and Kimura, 1977, J. Biol. Chem. 252:5820-5827; Kohn and Kaback, 1973, J. Biol. Chem. 248:7012-7017; Molinari and Lara, 1960, Biochem. J. 75:57-65; Kline and Mahler, 1965, Ann. N.Y. Acad. Sci. 119:905-919). Coupled enzyme assays, such as the one described in U.S. Pat. No. 4,490,465 may be used to determine the amount of lactate in solution.

Measuring Arabinose Utilization

Arabinose utilization may be tested using an arabinose uptake assay (see, e.g. Subtil and Boles, 2011, Biotechnology for Biofuels, 4:38; U.S. Patent Publication 2012/0129241; Poysti et al., 2001, Microbiol. 153:727-736).

Briefly, recombinant methanotrophic bacteria are incubated with radiolabeled arabinose, and after different time intervals, cells are collected. The suspension is immediately filtered, washed, and radioactivity of the filtrate is measured in a scintillation counter.

Alternatively, arabinose utilization may be measured by determining L-arabinose isomerase (e.g., AraA), L-ribulose kinase (e.g., AraB), or L-ribulose 5-phosphate epimerase (e.g., AraD) enzyme activities (see, e.g., Sedlak and Ho, 2001, Enzyme and Microbial Technol. 28:16-24; Shamanna and Sanderson, 1979, J. Bacteriol. 139:64-70; Lee et al., 1968, J. Biol. Chem. 243:4700-4705).

Measuring Citrate Utilization

Citrate utilization as a sole carbon source may be detecting using a medium containing sodium citrate, a pH indicator (e.g., bromothymol blue), and inorganic ammonium salts as a sole nitrogen source. During its metabolism, citrate is converted to oxaloacetate and acetate. Production of $NaHCO_3$ and $NH_3$ from the use of sodium citrate and ammonium salts results in alkaline conditions, which is detected by a change of the medium's color from green to blue.

Measuring Succinate Utilization

Succinate utilization may be measuring by a succinate uptake by cells during culture using $^{14}$-labeled succinate (see, e.g., Weiss, 1970 J. Bacteriol. 101:133-137; Gutowski and Rosenberg, 1975, Biochem. J. 152:647-654; or Glenn et al., 1980, Microbiol. 119:267-271).

EXAMPLES

Example 1

Recombinant Methylosinus trichosporium Engineered to Grow on Glycerol

Preparation of NMS Media.

| | |
|---|---|
| $MgSO_4 \cdot 7H_2O$ | 1.0 g |
| $CaCl_2 \cdot 6H_2O$ | 0.20 g |
| Chelated Iron Solution (see below) | 2.0 ml |
| $KNO_3$ | 1.0 g |
| Trace Element Solution (see below) | 0.5 ml |
| $KH_2PO_4$ | 0.272 g |
| $Na_2HPO_4 \cdot 12H_2O$ | 0.717 g |
| Purified Agar (e.g., Oxoid L28) | 12.5 g |
| Distilled deionized water | 1.0 L |

Adjust pH to 6.8. Autoclave at 121° C. for 15 minutes.

Chelated Iron Solution:

| | |
|---|---|
| Ferric (III) ammonium citrate* | 0.1 g |
| EDTA, sodium salt | 0.2 g |
| HCl (concentrated) | 0.3 ml |
| Distilled deionized water | 100.0 ml |

*0.5 g of Ferric (III) chloride may be substituted.

Use 2.0 ml of this chelated iron solution per liter of final medium.

Trace Element Solution:

| | |
|---|---|
| EDTA | 500.0 mg |
| $FeSO_4 \cdot 7H_2O$ | 200.0 mg |
| $ZnSO_4 \cdot 7H_2O$ | 10.0 mg |
| $MnCl_2 \cdot 4H_2O$ | 3.0 mg |
| $H_3BO_3$ | 30.0 mg |
| $CoCl_2 \cdot 6H_2O$ | 20.0 mg |
| $CaCl_2 \cdot 2H_2O$ | 1.0 mg |
| $NiCl_2 \cdot 6H_2O$ | 2.0 mg |
| $Na_2MoO_4 \cdot 2H_2O$ | 3.0 mg |
| Distilled water | 1.0 L |

Autoclave at 121° C. for 15 minutes.

Growth and Conjugations. The procedure for conjugating plasmids from E. coli into methanotrophs was based on the method developed by Martin, H. & Murrell, J. C. (1995). Methane monooxygenase mutants of Methylosinus trichosporium constructed by marker exchange mutagenesis. FEMS Microbiol. Lett. 127:243-248.

Briefly, a mobilizing plasmid to be conjugated was first transformed into E. coli S17-1 using standard electroporation methods. Transformation was confirmed by selection of kanamycin-resistant colonies on LB-agar containing 20 ug/mL kanamycin. Transformed colonies were inoculated into LB media containing 20 ug/mL kanamycin and shaken overnight at 37° C. A 10 mL aliquot of the overnight culture was then collected on a sterile 47 mm nitrocellulose filter (0.2 mm pore size). The E. coli donor strain was washed on the filter with 50 mL sterile NMS media to remove residual media and antibiotic.

In parallel, a sample of the M. trichosporium OB3b recipient strain was inoculated into 100 mL serum bottles containing 20-50 mL NMS media. The headspace of the bottles was then flushed with a 1:1 mixture of oxygen and methane, and the bottles were sealed with butyl rubber septa and crimped. The bottles were shaken continuously in a 30° C. incubator until reaching an OD600 of approximately 0.3. The cells were then collected on the same filter as the E. coli donor strain. The filter was again washed with 50 mL of sterile NMS media. The filter was placed (cells up) on an NMS agar plate containing 0.02% (w/v) proteose peptone and incubated for 24 h at 30° C. in the presence of methane and oxygen. After 24 h, cells were resuspended in 10 mL sterile (NMS) medium before being concentrated by centrifugation. The pellet was resuspended in 1 mL sterile NMS media. Aliquots (100 µl) were spread onto NMS agar plates containing 10 ug/mL kanamycin.

The plates were incubated in sealed chambers containing a 1:1 mixture of methane and oxygen maintained at 30° C. The gas mixture was replenished every 2 days until colonies formed, typically after 7-14 days. Colonies were streaked onto NMS plates containing kanamycin to confirm kanamycin resistance as well as to further isolate transformed methanotroph cells from residual E. coli donor cells.

Introduction of Glycerol Utilization Pathway. Nucleic acids encoding GlpK, GlpD, and GlpF from E. coli were codon optimized for expression in Methylosinus trichosporium. The codon optimized nucleic acids encoding GlpK, GlpD, and GlpF are synthesized as an operon (SEQ ID NO:95; see Table 14 for components of operon) under control of an mdh promoter with appropriate intergenic regions (CAPITALIZED sequence) incorporating ribosome binding sequences.

TABLE 14

Glycerol Utilization Pathway Operon Codon Optimized for Methylosinus trichosporium

| SEQ ID NO: # | Gene Name | Nucleotide Sequence |
| --- | --- | --- |
| SEQ ID NO: 89 | MDH promoter | TTTGCCTCGATCGGCGGTCCTTGTGACAGGGAG<br>ATATTCCCGACGGATCCGGGGCATTCGAGCGGA<br>ACCGCCCGCCGTGGGAGTTTTTCCAGCGAGCAT<br>TCGAGAGTTTTTCAAGGCGGCTTCGAGGGGTTA<br>TTCCGTAACGCCGCCGACATGATCTGTCCCAGA<br>ATCTCCGCCGCTGTTCGTAGAGCGCCGATGCAG<br>GGTCGGCATCAATCATTCTTGGAGGAGACAC |
| SEQ ID NO: 90 | GlpK | atgaccgagaagaagtatatcgtcgcgctggaccagggcaccacctcgtcgc<br>gcgcggtcgtcatggaccatgacgcgaacatcatctcggtctcgcagcgcga<br>gttcgagcagatctatccgaagccgggctgggtcgagcatgacccgatggag<br>atctgggcgacccagtcgtcgaccctggtcgaggtcctggcgaaggcggac<br>atctcgtcggaccagatcgcggcgatcggcatcaccaaccagcgcgagacc<br>accatcgtctgggagaaggagaccggcaagccgatctataacgcgatcgtct<br>ggcagtgccgccgcaccgcggagatctgcgagcatctgaagcgcgacggc<br>ctggaggactatatccgctcgaacaccggcctggtcatcgacccgtatttctcg<br>ggcaccaaggtcaagtggatcctggaccatgtcgagggctcgcgcgagcgc<br>gcgcgccgcggcgagctgctgttcggcaccgtcgacacctggctgatctgga<br>agatgacccagggccgcgtccatgtcaccgactataccaacgcgtcgcgcac<br>catgctgttcaacatccataccctggactgggacgacaagatgctggaggtcc<br>tggacatcccgcgcgagatgctgccggaggtccgccgctcgtcggaggtcta<br>tggccagaccaacatcggcggcaagggcggcacccgcatcccgatctcgg<br>gcatcgcgggcgaccagcaggcggcgctgttcggccagctgtgcgtcaagg<br>agggcatggcgaagaacaccctatggcaccggctgcttcatgctgatgaacac<br>cggcgagaaggcggtcaagtcggagaacggcctgctgaccaccatcgcgtg<br>cggcccgaccggcgaggtcaactatgcgctggagggcgcggtcttcatggc<br>gggcgcgtcgatccagtggctgcgcgacgagatgaagctgatcaacgacgc<br>gtatgactcggagtatttcgcgaccaaggtccagaacaccaacgcgtctatg<br>tcgtcccggcgttcaccggcctgggcgcgccgtattgggacccgtatgcgcg<br>cggcgcgatcttcggcctgacccgcggcgtcaacgcgaaccatatcatccgc<br>gcgacctggagtcgatcgcgtatcagacccgcgacgtcctggaggcgatg<br>caggcggactcgggcatccgcctgcatgcgctgcgcgtcgacggcggcgc<br>ggtcgcgaacaacttcctgatgcagttccagtcggacatcctgggcacccgcg<br>tcgagcgcccggaggtccgcgaggtcaccgcgctgggcgcggcgtatctgg<br>cgggcctggcggtcggcttctggcagaacctggacgagctgcaggagaagg<br>cggtcatcgagcgcgagttccgcccgggcatcgagaccaccgagcgcaact<br>atcgctatgcgggctggaagaaggcggtcaagcgcgcgatggcgtgggag<br>gagcatgactga |
| SEQ ID NO: 91 | Intergenic region | TCATTCTTGGAGGAGACAC |
| SEQ ID NO: 92 | GlpD | atggagaccaaggacctgatcgtcatcggcggcggcatcaacggcgcgggc<br>atcgcggcggacgcggcggggccgcggcctgtcggtcctgatgctggaggc<br>gcaggacctggcgtgcgcgacctcgtcggcgtcgtcgaagctgatccatggc<br>ggcctgcgctttctggagcattatgagttccgcctggtctcggaggcgctggc<br>ggagcgcgaggtcctgctgaagatggcgccgcatatcgcgttcccgatgcgc<br>ttccgcctgccgcatcgcccgcatctgcgcccggcgtggatgatccgcatcg<br>gcctgttcatgtatgaccatctgggcaagcgcacctcgctgccgggctcgacc<br>ggcctgcgcttcggcgcgaactcggtcctgaagcggagatcaagcgcggc<br>ttcgagtattcggactgctgggtcgacgacgcgcgcctggtcctggcgaacg<br>cgcagatggtcgtccgcaagggcggcgaggtcctgacccgcacccgcgcg<br>acctcggcgcgccgcgagaacggcctgtggatcgtcgaggcggaggacat<br>cgacaccggcaagaagtattcgtggcaggcgcgcggcctggtcaacgcgac<br>cggcccgtgggtcaagcagttcttcgacgacggcatgcatctgccgtcgccgt<br>atggcatccgcctgatcaagggctcgcatatcgtcgtcccgcgcgtccatacc<br>cagaagcaggcgtatatcctgcagaacgaggacaagcgcatcgtcttcgtcat<br>cccgtggatggacgagttctcgatcatcggcaccaccgacgtcgagtataag<br>ggcgacccgaaggcggtcaagatcgaggagtcggagatcaactatctgctg<br>aacgtctataacacccatttcaagaagcagctgtcgcgcgacgacatcgtctg<br>gacctattcgggcgtccgcccgctgtgcgacgacgagtcggactcgccgca<br>ggcgatcacccgcgactatacccggacatccatgacgagaacggcaaggc<br>gccgctgctgtcggtcttcggcggcaagctgaccacctatcgcaagctggcg<br>gagcatgcgctggagaagctgaccccgtattatcagggcatcggcccggcgt<br>ggaccaaggagtcggtcctgccgggcggcgcgatcgagggcgaccgcga<br>cgactatgcggcgcctgcgccgcgctatccgttcctgaccgagtcgctg<br>gcgcgccattatgcgcgcacctatgctcgaactcggagctgctgctgggca<br>acgcgggcaccgtctcggacctgggcgaggacttcggccatgagttctatga<br>ggcggagctgaagtatctggtcgaccatgagtgggtccgccgcgcggacga<br>cgcgctgtggcgccgcaccaagcagggcatgtggctgaacgcggaccagc<br>agtcgcgcgtctcgcagtggctggtcgagtataccagcagcgcctgtcgctg<br>gcgtcgtga |

TABLE 14-continued

Glycerol Utilization Pathway Operon Codon Optimized for Methylosinus trichosporium

| SEQ ID NO: # | Gene Name | Nucleotide Sequence |
|---|---|---|
| SEQ ID NO: 93 | Intergenic region | TCATTCTTGGAGGAGACAC |
| SEQ ID NO: 94 | GlpF | atgtcgcagacctcgaccctgaagggccagtgcatcgcggagttcctgggca ccggcctgctgatcttcttcggcgtcggctgcgtcgcggcgctgaaggtcgcg ggcgcgtcgttcggccagtgggagatctcggtcatctggggcgtcg cgatggcgatctatctgaccgcgggcgtctcgggcgcgcatctgaacccggc ggtcaccatcgcgctgtggctgttcgcgtgcttcgacaagcgcaaggtcatcc cgttcatcgtctcgcaggtcgcgggcgcgttctgcgcggcggcgctggtctat ggcctgtattataaccctgttcttcgacttcgagcagaccatcatatcgtccgcg gctcggtcgagtcggtcgacctggcgggcaccttctcgacctatccgaaccc gcatatcaacttcgtccaggcgttcgcggtcgagatggtcatcaccgcgatcct gatgggcctgatcctggcgctgaccgacgacggcaacggcgtcccgcgcg gcccgctggcgccgctgctgatcggcctgctgatcgcggtcatcggcgcgtc gatgggcccgctgaccggcttcgcgatgaacccggcgcgcgacttcggccc gaaggtcttcgcgtggctggcgggctggggcaacgtcgcgttcaccggcgg ccgcgacatcccgtatttcctggtcccgctgttcggcccgatcgtcggcgcgat cgtcggcgcgttcgcgtatcgcaagctgatcggccgccatctgccgtgcgac atctgcgtcgtcgaggagaaggagaccaccaccccgtcggagcagaaggc gtcgctgtga |
| SEQ ID NO: 95 | Glycerol Utilization Pathway Operon | tttgcctcgatcggcggtccttgtgacagggagatattcccgacggatccggg gcattcgagcggaaccgcccgccgtgggagttttttccagcgagcattcgaga gtttttcaaggcggcttcgaggggttattccgtaacgccgccgacatgatctgtc ccagaatctccgccgctgttcgtagagcgccgatgcagggtcggcatcaatca ttcttggaggagacacatgaccgagaagaagtatatcgtcgcgctggaccag ggcaccacctcgtcgcgcgcggtcgtcatggaccatgacgcgaacatcatct cggtctcgcagcgcgagttcgagcagatctatccgaagccgggctgggtcga gcatgacccgatggagatctgggcgacccagtcgtcgaccctggtcgaggtc ctggcgaaggcggacatctcgtcggaccagatcgcggcgatcggcatcacc aaccagcgcgagaccaccatcgtctgggagaaggagaccggcaagcgat ctataacgcgatcgtctggcagtgccgccgcaccgcggagatctgcgagcat ctgaagcgcgacggcctggaggactatatccgctcgaacaccggcctggtca tcgacccgtatttctcgggcaccaaggtcaagtggatcctggaccatgtcgag ggctcgcgcgagcgcgcgccgcggcgagctgctgttcggcaccgtcga cacctggctgatctggaagatgacccagggccgcgtccatgtcaccgactata ccaacgcgtcgcgcaccatgctgttcaacatccatacccctggactgggacgac aagatgctggaggtcctggacatcccgcgcgagatgctgccggaggtccgc cgctcgtcggaggtctatggccagaccaacatcggcggcaagggcggcacc cgcatcccgatctcgggcatcgcgggcgaccagcaggcggcgctgttcggc cagctgtgcgtcaaggaggcatggcgaagaacacctatggcaccggctgc ttcatgctgatgaacaccggcgagaaggcggtcaagtcggagaacggcctg ctgaccaccatcgcgtgcgccgaccggcgaggtcaactatgcgctggag ggcgcggtcttcatggcgggcgcgtcgatccagtggctgcgcgacgagatg aagctgatcaacgacgcgtatgactcggagtatttcgcgaccaaggtccagaa caccaacggcgtctatgtcgtcccggcgttcaccggcctgggcgcgccgtatt gggacccgtatgcgcgcggcgcgatcttcggcctgacccgcggcgtcaacg cgaaccatatcatccgcgcgaccctggagtcgatcgcgtatcagaccccgcga cgtcctggaggcgatgcaggcggactcgggcatccgcctgcatgcgctgcg cgtcgacggcggcgcggtcgcgaacaacttcctgatgcagttccagtcggac atcctgggcacccgcgtcgagcgcccggaggtccgcgaggtcaccgcgctg ggcgcggcgtatctggcggggcctggcggtcggcttctggcagaacctggac gagctgcaggagaaggcggtcatcgagcgcgagttccgcccgggcatcga gaccaccgagcgcaactatcgctatgcgggctggaagaaggcggtcaagcg cgcgatggcgtgggaggagcatgactgatcattcttggaggagacacatgga gaccaaggacctgatcgtcatcggcggcggcatcaacggcgcgggcatcgc ggcggacgcggcgggccgcggcctgtcggtcctgatgctggaggcgcagg acctggcgtgcgcgacctcgtcggcgtcgtcgaagctgatccatggcggcct gcgctatctggagcattatgagttccgcctggtctcggaggcgctggcggagc gcgaggtcctgctgaagatggcccgcatatcgcgttcccgatgcgcttccgc ctgccgcatcgcccgcatctgcgcccggcgtggatgatccgcatcggcctgtt catgtatgaccatctgggcaagcgcacctcgctgccgggctcgaccggcctg cgcttcggcgcgaactcggtcctgaagccggagatcaagcgcggcttcgagt attcggactgctgggtcgacgacgcgcctggtcctggcgaacgcgcagat ggtcgtccgcaagggcggcgaggtcctgacccgcacccgcgcgacctcgg cgcgccgcgagaacggcctgtggatcgtcgaggcggaggacatcgacacc ggcaagaagtattcgtggcaggcgcgcggcctggtcaacgcgaccggccc gtgggtcaagcagttcttcgacgacggcatgcatctgccgtcgccgtatgca tccgcctgatcaagggctcgcatatcgtcgtcccgcgcgtccataccccagaag caggcgtatatcctgcagaacgaggacaagcgcatcgtcttcgtcatcccgtg gatgaacgagttctcgatcatcggcaccaccgacgtcgagtataagggcgac ccgaaggcggtcaagatcgaggagtcggagatcaactatctgctgaacgtct ataacacccattcaagaagcagctgtcgcgcgacgacatcgtctggaccatt |

TABLE 14-continued

Glycerol Utilization Pathway Operon Codon Optimized for Methylosinus trichosporium

| SEQ ID NO: # | Gene Name | Nucleotide Sequence |
|---|---|---|
| | | cgggcgtccgcccgctgtgcgacgacgagtcggactcgccgcaggcgatca
cccgcgactatacccctggacatccatgacgagaacggcaaggcgccgctgct
gtcggtcttcggcggcaagctgaccacctatcgcaagctggcggagcatgcg
ctggagaagctgaccccgtattatcagggcatcggcccggcgtggaccaag
gagtcggtcctgccgggcggcgcgatcgagggcgaccgcgacgactatgc
ggcgcgcctgcgccgccgctatccgttcctgaccgagtcgctggcgcgccat
tatgcgcgcacctatggctcgaactcggagctgctgctgggcaacgcgggca
ccgtctcggacctgggcgaggacttcggccatgagttctatgaggcggagct
gaagtatctggtcgaccatgagtgggtccgccgcgcggacgacgcgctgtg
gcgccgcaccaagcagggcatgtggctgaacgcggaccagcagtcgcgcg
tctcgcagtggctggtcgagtatacccagcagcgcctgtcgctggcgtcgtga
tcattcttggaggagacacatgtcgcagacctcgaccctgaagggccagtgca
tcgcggagttcctgggcaccggcctgctgatcttcttcggcgtcggctgcgtcg
cggcgctgaaggtcgcgggcgcgtcgttcggccagtgggagatctcggtcat
ctggggcctgggcgtcgcgatggcgatctatctgaccgcggggcgtctcgggc
gcgcatctgaacccggcggtcaccatcgcgctgtggctgttcgcgtgcttcga
caagcgcaaggtcatcccgttcatcgtctcgcaggtcgcgggcgcgttctgcg
cggcggcgctggtctatggcctgtattataacctgttcttcgacttcgagcagac
ccatcatatcgtccgcggctcggtcgagtcggtcgacctggcgggcaccttct
cgacctatccgaacccgcatatcaacttcgtccaggcgttcgcggtcgagatg
gtcatcaccgcgatcctgatgggcctgatcctggcgctgaccgacgacggca
acggcgtcccgcgcggcccgctggcgccgctgctgatcggcctgctgatcg
cggtcatcggcgcgtcgatgggcccgctgaccggcttcgcgatgaacccgg
cgcgcgacttcggcccgaaggtcttcgcgtggctggcgggctggggcaacg
tcgcgttcaccggcggccgcgacatcccgtatttcctggtcccgctgttcggcc
cgatcgtcggcgcgatcgtcggcgcgttcgcgtatcgcaagctgatcggccg
ccatctgccgtgcgacatctgcgtcgtcgaggagaaggagaccaccacccc
gtcggagcagaaggcgtcgctgtga |

The synthetic operon is then cloned and transformed as described above. Transformation is confirmed by resistance of the cells to antibiotic selection, and gene expression is confirmed by northern blot (to confirm RNA transcription), western blot, or ELISA methods (to confirm protein expression).

Growth on Glycerol as a Sole Carbon Source. Recombinant M. trichosporium transformed with a vector containing the synthetic operon encoding genes for glycerol utilization are inoculated into 100 mL shake flasks containing 20-50 mL NMS media, 1% glycerol and 10 ug/mL kanamycin. The flasks are then shaken continuously while being incubated at 30° C. Growth is confirmed by monitoring optical density of the culture over time. Note that because glycerol is the only carbon source provided to the cells, all cell mass produced must have been derived from glycerol.

Example 2

Recombinant Methylococcus capsulatus Bath Strain Engineered to Grow on Glycerol

Growth and Conjugations. The procedure for conjugating plasmids from E. coli into M. capsulatus was based on the method reported in Ali, H. & Murrell, J. C. (2009). Development and validation of promoter-probe vectors for the study of methane monooxygenase gene expression in Methylococcus capsulatus Bath. Microbiology (2009), 155:761-771.

Briefly, a mobilizing plasmid to be conjugated was first transformed into E. coli S17-1 using standard electroporation methods. Transformation was confirmed by selection of kanamycin-resistant colonies on LB-agar containing 20 ug/mL kanamycin. Transformed colonies were inoculated into LB media containing 20 ug/mL kanamycin and shaken overnight at 37° C. A 10 mL aliquot of the overnight culture was then collected on a sterile 47 mm nitrocellulose filter (0.2 mm pore size). The E. coli donor strain was washed on the filter with 50 mL sterile NMS to remove residual media and antibiotic.

In parallel, a sample of the M. capsulatus recipient strain was inoculated into 100 mL serum bottles containing 20-50 mL NMS media. The headspace of the bottles was then flushed with a 1:1 mixture of oxygen and methane, and the bottles were sealed with butyl rubber septa and crimped. The bottles were shaken continuously in a 45° C. incubator until reaching an $OD_{600}$ of approximately 0.3. The cells were then collected on the same filter as the E. coli donor strain. The filter was again washed with 50 mL of sterile NMS media. The filter was placed (cells up) on an NMS agar plate containing 0.02% (w/v) proteose peptone and incubated for 24 h at 37° C. in the presence of methane and oxygen. After 24 h, cells were resuspended in 10 mL sterile (NMS) medium before being concentrated by centrifugation. The pellet was resuspended in 1 mL sterile NMS media. Aliquots (100 ul) were spread onto NMS agar plates containing 10 ug/mL kanamycin.

The plates were incubated in sealed chambers containing a 1:1 mixture of methane and oxygen maintained at 45° C. The gas mixture was replenished every 2 days until colonies formed, typically after 7-14 days. Colonies were streaked onto NMS plates containing kanamycin to confirm kanamycin resistance as well as to further isolate transformed methanotroph cells from residual E. coli donor cells.

Introduction of Glycerol Utilization Pathway. Nucleic acid sequences encoding GlpK, GlpD, and GlpF from E. coli were codon optimized for expression in M. capsulatus. The codon optimized nucleic acids encoding GlpK, GlpD, and GlpF are synthesized as an operon (SEQ ID NO:102; see Table 15 for components of operon) under control of an mdh promoter with appropriate intergenic regions (CAPITALIZED sequence) incorporating ribosome binding sequences.

TABLE 15

Glycerol Utilization Pathway Operon Codon Optimized for *M. capsulatus*

| SEQ ID NO: # | Gene Name | Nucleotide Sequence |
|---|---|---|
| SEQ ID NO: 96 | MDH promoter | TTTGCCTCGATCGGCGGTCCTTGTGACAGGGAG<br>ATATTCCCGACGGATCCGGGGCATTCGAGCGG<br>AACCGCCCGCCGTGGGAGTTTTTCCAGCGAGCA<br>TTCGAGAGTTTTTCAAGGCGGCTTCGAGGGGTT<br>ATTCCGTAACGCCGCCGACATGATCTGTCCCAG<br>AATCTCCGCCGCTGTTCGTAGAGCGCCGATGCA<br>GGGTCGGCATCAATCATTCTTGGAGGAGACAC |
| SEQ ID NO: 97 | GlpK | atgaccgagaagaagtacatcgtcgccctggaccagggcaccaccagcagc<br>cgcgccgtcgtcatggaccacgacgccaacatcatcagcgtcagccagcgc<br>gagttcgagcagatctacccgaagccgggctgggtcgagcacgacccgatg<br>gagatctgggcacccagagcagcaccctggtcgaggtcctggccaaggcc<br>gacatcagcagcgaccagatcgccgccatcggcatcaccaaccagcgcga<br>gaccaccatcgtctgggagaaggagaccggcaagccgatctacaacgccat<br>cgtctggcagtgccgccgcaccgccgagatctgcgagcacctgaagcgcga<br>cggcctggaggactacatccgcagcaacaccggcctggtcatcgacccgta<br>cttcagcggcaccaaggtcaagtggatcctggaccacgtcgagggcagccg<br>cgagcgcgcccgccgcggcgagctgctgttcggcaccgtcgacacctggct<br>gatctggaagatgacccagggccgcgtccacgtcaccgactacaccaacgc<br>cagccgcaccatgctgttcaacatccacaccctggactgggacgacaagatg<br>ctggaggtcctggacatcccgcgcgagatgctgccggaggtccgccgcagc<br>agcgaggtctacgccagaccaacatcggcggcaagggcggcacccgcat<br>cccgatcagcggcatcgccggcgaccagcaggccgccctgttcggccagct<br>gtgcgtcaaggagggcatggccaagaacacctacggcaccggctgcttcat<br>gctgatgaacaccggcgagaaggccgtcaagagcgagaacggcctgctga<br>ccaccatcgcctgcgggcccgaccggcgaggtcaactacgccctggagggc<br>gccgtcttcatggccggcgccagcatccagtggctgcgcgacgagatgaag<br>ctgatcaacgacgcctacgacagcgagtacttcgccaccaaggtccagaaca<br>ccaacggcgtctacgtcgtcccggccttcaccggcctgggcgccccgtactg<br>ggacccgtacgcccgcggcgccatcttcggcctgacccgcggcgtcaacgc<br>caaccacatcatccgcgccaccctggagagcatcgcctaccagacccgcga<br>cgtcctggaggccatgcaggccgacagcggcatccgcctgcacgccctgcg<br>cgtcgacggcggcgccgtcgccaacaacttcctgatgcagttccagagcgac<br>atcctgggcacccgcgtcgagcgcccggaggtccgcgaggtcaccgccct<br>gggcgccgcctacctggccggcctggccgtcggcttctggcagaacctgga<br>cgagctgcaggtgaaggccgtcatcgagcgcgagttccgcccgggcatcg<br>agaccaccgagcgcaactaccgctacgccggctggaagaaggccgtcaag<br>cgcgccatggcctgggaggagcacgacgagtga |
| SEQ ID NO: 98 | Intergenic region | TCATTCTTGGAGGAGACAC |
| SEQ ID NO: 99 | GlpD | atggagaccaaggacctgatcgtcatcggcggcggcatcaacggcgccgg<br>catcgccgccgacgccgccggccgcggcctgagcgtcctgatgctggagg<br>cccaggacctggcctgcgccaccagcagcgccagcagcaagctgatccac<br>ggcggcctgcgctacctggagcactacgagttccgcctggtcagcgaggcc<br>ctggccgagcgcgaggtcctgctgaagatggccccgcacatcgccttcccg<br>atgcgcttccgcctgccgcaccgcccgcacctgcgcccggcctggatgatcc<br>gcatcggcctgttcatgtacgaccacctgggcaagcgcaccagcctgccgg<br>gcagcaccgcctgcgcttcggcgccaacagcgtcctgaagccggagatca<br>gcgcggcttcgagtacagcgactgctgggtcgacgacgcccgcctggtcct<br>ggccaacgcccagatggtcgtccgcaagggcggcgaggtcctgacccgca<br>cccgcgccaccagcgcccgccgcgagaacggcctgtggatcgtcgaggcc<br>gaggacatcgacaccggcaagaagtacagctggcaggcccgcggcctggt<br>caacgccaccggcccgtgggtcaagcagttcttcgacgacggcatgcacctg<br>ccgagcccgtacggcatccgcctgatcaagggcagccacatcgtcgtcccg<br>cgcgtcccacacccagaagcaggcctacatcctgcagaacgaggacaagcg<br>catcgtcttcgtcatcccgtggatggacgagttcagcatcatcggcaccaccg<br>acgtcgagtacaagggcgacccgaaggccgtcaagatcgaggagagcgag<br>atcaactacctgctgaacgtctacaacacccacttcaagaagcagctgagccg<br>cgacgacatcgtctggacctacagcggcgtccgcccgctgtgcgacgacga<br>gagcgacgacccgcaggccatcacccgcgactacaccctggacatccacga<br>cgagaacggcaaggcccgctgctgagcgtcttcggcggcaagctgaccac<br>ctaccgcaagctggccgagcacgccctggagaagctgaccccgtactacca<br>gggcatcggcccggcctggaccaaggagagcgtcctgccgggcggcgcc<br>atcgagggcgaccgcgacgactacgccgcccgcctgcgccgccgctaccc<br>gttcctgaccgagagcctggccgccactacgccccgacctacggcagcaa<br>cagcgagctgctgctgggcaacgccggcaccgtcagcgacctgggcgagg<br>acttcggccacgagttctacgaggccgagctgaagtacctggtcgaccacga<br>gtgggtccgccgcgccgacgacgccctgtggccgccaccaagcagggca<br>tgtggctgaacgccgaccagcagagccgcgtcagccagtggctggtcgagt<br>acacccagcagcgcctgagcctggccagcga |

TABLE 15-continued

Glycerol Utilization Pathway Operon Codon Optimized for M. capsulatus

| SEQ ID NO: # | Gene Name | Nucleotide Sequence |
|---|---|---|
| SEQ ID NO: 100 | Intergenic region | TCATTCTTGGAGGAGACAC |
| SEQ ID NO: 101 | GlpF | atgagccagaccagcaccctgaagggccagtgcatcgccgagttcctgggc<br>accggcctgctgatcttcttcggcgtcggctgcgtcgccgccctgaaggtcgc<br>cggcgccagcttcggccagtgggagatcagcgtcatcctggggcctgggcgt<br>cgccatggccatctacctgaccgccggcgtcagcggcgcccacctgaaccc<br>ggccgtcaccatcgccctgtggctgttcgcctgcttcgacaagcgcaaggtca<br>tcccgttcatcgtcagccaggtcgccggcgccttctgcgccgccgccctggtc<br>tacggcctgtactacaacctgttcttcgacttcgagcagaccccaccacatcgtc<br>cgcggcagcgtcgagagcgtcgacctggccggcaccttcagcacctacccg<br>aacccgcacatcaacttcgtccaggccttcgccgtcgagatggtcatcaccgc<br>catcctgatgggcctgatcctggccctgaccgacgacggcaacggcgtccc<br>gcgcggcccgctggcccgctgctgatcggcctgctgatcgccgtcatcggc<br>gccagcatgggcccgctgaccggcttcgccatgaacccggcccgcgacttc<br>ggccccgaaggtcttcgcctggctggccggctggggcaacgtcgccttcacc<br>ggccggccgcgacatcccgtacttcctggtcccgctgttcggcccgatcgtcg<br>gcgccatcgtcggcgccttcgcctaccgcaagctgatcggccgccacctgcc<br>gtgcgacatctgcgtcgtcgaggagaaggagaccaccaccccgagcgagc<br>agaaggccagcctatga |
| SEQ ID NO: 102 | Glycerol Utilization Pathway Operon | tttgcctcgatcggcggtccttgtgacagggagatattcccgacggatccggg<br>gcattcgagcggaaccgcccgccgtgggagttttttccagcgagcattcgaga<br>gtttttcaaggcggcttcgaggggttattccgtaacgccgccgacatgatctgt<br>cccagaatctccgccgctgttcgtagagcgccgatgcagggtcggcatcaat<br>cattcttggaggagacacatgaccgagaagaagtacatcgtcgccctggacc<br>agggcaccaccagcagccgcgccgtcgtcatggaccacgacgccaacatc<br>atcagcgtcagccagcgcgagttcgagcagatctacccgaagccgggctgg<br>gtcgagcacgacccgatggagatctgggccacccagagcagcaccctggtc<br>gaggtcctggccaaggccgacatcagcagcgaccagatcgccgccatcgg<br>catcaccaaccagcgcgagaccaccatcgtctgggagaaggagaccggca<br>gccgatctacaacgccatcgtctggcagtgccgccgcaccgccgagatctg<br>cgagcacctgaagcgcgacggcctggaggactacatccgcagcaacaccg<br>gcctggtcatcgacccgtacttcagcggcaccaaggtcaagtggatcctgga<br>ccacgtcgagggcagccgcgagcgcgcccgccgcggcgagctgctgttcg<br>gcaccgtcgacacctggctgatctggaagatgacccagggccgcgtccacg<br>tcaccgactacaccaacgccagccgcaccatgctgttcaacatccacaccctg<br>gactgggacgacaagatgctggaggtcctggacatcccgcgcgagatgctg<br>ccggaggtccgccgcagcagcgaggtctacggccagaccaacatcggcgg<br>caagggcggcacccgcatcccgatcagcggcatcgccggcgaccagcagg<br>ccgccctgttcggccagctgtgcgtcaaggagggcatggccaagaacacct<br>acggcaccggctgcttcatgctgatgaacaccggcgagaaggccgtcaaga<br>gcgagaacgccctgctgaccaccatcgcctgcgggcccgaccggcgaggtc<br>aactacgccctggagggcgccgtcttcatggccggcgccagcatccagtgg<br>ctgcgcgacgagatgaagctgatcaacgacgcctacgacagcgagtacttcg<br>ccaccaaggtccagaacaccaacggcgtctacgtcgtcccggccttcaccgg<br>cctgggcgccccgtactgggacccgtacgcccgcggcgccatcttcggcct<br>gacccgcggcgtcaacgccaaccacatcatccgcgccaccctggagagcat<br>cgcctaccagacccgcgacgtcctggaggccatgcaggccgacagcggca<br>tccgcctgcacgccctgcgcgtcgacggcggcgccgtcgccaacaacttcct<br>gatgcagttccagagcgacatcctgggcacccgcgtcgagcgcccggaggt<br>ccgcgaggtcaccgccctgggcgccgcctacctggccggcctggccgtcg<br>gcttctggcagaacctggacgagctgcaggagaaggccgtcatcgagcgcg<br>agttccgcccgggcatcgagaccaccgagcgcaactaccgctacgccggct<br>ggaagaaggccgtcaagcgcgccatggcctgggaggagcacgacgagtg<br>atcattcttggaggagacacatggagaccaaggacctgatcgtcatcggcgg<br>cggcatcaacggcgccggcatcgccgccgacgccgccggccgggcctg<br>agcgtcctgatgctggaggccaggacctggcctgcgccaccagcagcgcc<br>agcagcaagctgatccacggcggcctgcgctacctggagcactacgagttcc<br>gcctggtcagcgaggccctggccgagcgcgaggtcctgctgaagatggccc<br>cgcacatcgccttcccgatgcgcttccgcctgccgcaccgcccgcacctgcg<br>cccggcctgatgatccgcatcggcctgttcatgtacgaccacctgggcaag<br>cgcaccagcctgccgggcagcaccggcctgcgcttcggcgccaacagcgt<br>cctgaagccggagatcaagcgcggcttcgagtacagcgactgctgggtcga<br>cgacgcccgcctggtcctggccaacgcccagatggtcgtccgcaagggcg<br>gcgaggtcctgacccgcacccgcgccaccagcgcccgccgcgagaacgg<br>cctgtggatcgtcgaggccgaggacatcgacaccggcaagaagtacagctg<br>gcaggcccgcggcctggtcaacgccaccggcccgtgggtcaagcagttctt<br>cgacgacggcatgcacctgccgagcccgtacggcatccgcctgatcaaggg<br>cagccacatcgtcgtcccgcgcgtccacacccagaagcaggcctacatcctg<br>cagaacgaggacaagcgcatcgtcttcgtcatcccgtggatggacgagttca<br>gcatcatcggcaccaccgacgtcgagtacaagggcgacccgaaggccgtca<br>gatcgaggagagcgagatcaactacctgctgaacgtctacaacacccacttc<br>aagaagcagctgagccgcgacgacatcgtcctggacctacagcggcgtccgc |

TABLE 15-continued

Glycerol Utilization Pathway Operon Codon Optimized for *M. capsulatus*

| SEQ ID NO: # | Gene Name | Nucleotide Sequence |
|---|---|---|
| | | ccgctgtgcgacgacgagagcgacagcccgcaggccatcacccgcgacta |
| | | caccctggacatccacgacgagaacggcaaggccccgctgctgagcgtctt |
| | | cggcggcaagctgaccacctaccgcaagctggccgagcacgccctggaga |
| | | agctgaccccgtactaccagggcatcggcccggcctggaccaaggagagc |
| | | gtcctgccgggcggcgccatcgagggcgaccgcgacgactacgccgcccg |
| | | cctgcgccgccgctacccgttcctgaccgagagcctggcccgccactacgcc |
| | | cgcacctacggcagcaacagcgagctgctgctgggcaacgccggcaccgt |
| | | cagcgacctgggcgaggacttcggccacgagttctacgaggccgagctgaa |
| | | gtacctggtcgaccacgagtgggtccgccgcgccgacgacgccctgtggcg |
| | | ccgcaccaagcagggcatgtggctgaacgccgaccagcagagccgcgtca |
| | | gccagtggctggtcgagtacacccagcagcgcctgagcctggccagctgat |
| | | cattcttggaggagacacatgagccagaccagcaccctgaagggccagtgc |
| | | atcgccgagttcctgggcaccggcctgctgatcttcttcggcgtcggctgcgtc |
| | | gccgccctgaaggtcgccggcgccagcttcggccagtgggagatcagcgtc |
| | | atctggggcctgggcgtcgccatggccatctacctgaccgccggcgtcagcg |
| | | gcgcccacctgaacccggccgtcaccatcgccctgtggctgttcgcctgcttc |
| | | gacaagcgcaaggtcatcccgttcatcgtcagccaggtcgccggcgccttct |
| | | gcgccgccgccctggtctacggcctgtactacaacctgttcttcgacttcgagc |
| | | agacccaccacatcgtccgcggcagcgtcgagagcgtcgacctggccggc |
| | | accttcagcacctaccgaacccgcacatcaacttcgtccaggccttcgccgt |
| | | cgagatggtcatcaccgccatcctgatgggcctgatcctggccctgaccgac |
| | | gacggcaacggcgtcccgcgcggcccgctggcccccgctgctgatcggcct |
| | | gctgatcgccgtcatcggcgccagcatgggcccgctgaccggcttcgccatg |
| | | aacccggcccgcgacttcggcccgaaggtcttcgcctggctggccggctgg |
| | | ggcaacgtcgccttcaccggcggccgcgacatcccgtacttcctggtcccgct |
| | | gttcggcccgatcgtcggcgcgcatcgtcggcgccttcgcctaccgcaagctg |
| | | atcggccgccacctgccgtgcgacatctgcgtcgtcgaggagaaggagacc |
| | | accaccccgagcgagcagaaggccagcctgtga |

The synthetic operon is then cloned and transformed into *M. capsulatus* as described above. Transformation is confirmed by resistance of the cells to antibiotic selection, and gene expression is confirmed by northern blot (to confirm RNA transcription), western blot, or ELISA methods (to confirm protein expression).

Growth on Glycerol as a Sole Carbon Source. Recombinant *M. capsulatus* transformed with a vector containing the synthetic operon encoding genes for glycerol utilization are inoculated into 100 mL shake flasks containing 20-50 mL NMS media, 1% glycerol and 10 ug/mL kanamycin. The flasks are then shaken continuously while being incubated at 42° C. Growth is confirmed by monitoring optical density of the culture over time. Note that because glycerol is the only carbon source provided to the cells, all cell mass produced must have been derived from glycerol.

Example 3

Recombinant Methylomonas Methanica Engineered to Grow on Glycerol

Growth and Conjugations. The procedure for growth and conjugation of *Methylomonas methanica* was performed essentially identically to the procedures described for *M. capsulatus* (above).

Introduction of Glycerol Utilization Pathway. Nucleic acid sequences encoding GlpK, GlpD, and GlpF from *E. coli* were codon optimized for expression in *M. methanica*. The codon optimized nucleic acids encoding GlpK, GlpD, and GlpF are synthesized as an operon (SEQ ID NO:109; see Table 16 for components of operon) under control of an hps promoter with appropriate intergenic regions (CAPITALIZED sequence) incorporating ribosome binding sequences.

TABLE 16

Glycerol Utilization Pathway Operon Codon Optimized for *M. methanica*

| SEQ ID NO: # | Gene Name | Nucleotide Sequence |
|---|---|---|
| SEQ ID NO: 103 | HPS promoter | TTCGGAATCCCTGACGGGAATTGGCCCGA |
| | | AGAAGGCAGATGCCATCGTTCAGTATCGA |
| | | AAGGAACATGGGGATTTTCAGTCATTGAA |
| | | GGATCTGGAGAATGTCAGCGGCATTGGCG |
| | | AGAAAACCCTTCAGGCCAATGAAAAAGAC |
| | | ATTCGCTTCACGGATGATTTGAGCGATAAG |
| | | TCATCCGCGGAAAAAGGTGCGGTAGCTGT |
| | | GGATAAAAAAGGCGCCAGATAGTAAGCGC |
| | | TAAGGATTGGGGTGCGTCGCCGGTCGCGG |
| | | CGGCGCTCCTCGACGGCAGAGTTGGTGCC |
| | | AGGTTGGCGGATGATTGATGCCGAATATT |
| | | ACGCGACCAATTCTCGAGGCAAATGAACT |
| | | GTGAGCTACTGAGTTGCAGGCATTGACAG |
| | | CCATCCCATTTCTATCATACAGTTACGGAC |
| | | GCATCACGAGTAGGTGATAAGCCTAGCAG |

TABLE 16-continued

Glycerol Utilization Pathway Operon Codon Optimized for *M. methanica*

| SEQ ID NO: # | Gene Name | Nucleotide Sequence |
|---|---|---|
| | | ATTGCGGCAGTTGGCAAAATCAGCTATTAC<br>TAATAATTAAAAACTTTCGGAGCACATCAC |
| SEQ ID NO: 104 | GlpK | atgaccgaaaaaaatatatcgtcgcgttggatcaaggcaccaccag<br>cagccgcgcggtcgtcatggatcacgatgcgaacatcatcagcgtca<br>gccaacgcgaattcgaacaaatctatccgaaaccgggctgggtcgaa<br>cacgatccgatggaaatctgggcgacccaaagcagcaccttggtcga<br>agtcttggcgaaagcggatatcagcagcgatcaaatcgcggcgatcg<br>gcatcaccaaccaacgcgaaaccaccatcgtctgggaaaagaaac<br>cggcaaaccgatctataacgcgatcgtctggcaatgccgccgcaccg<br>cggaaatctgcgaacacttgaaacgcgatggcttggaagattatatcc<br>gcagcaacaccggcttggtcatcgatccgtatttcagcggcaccaaa<br>gtcaaatggatcttggatcacgtcgaaggcagccgcgaacgcgcgc<br>gccgcggcgaattgttgttcggcaccgtcgatacctggttgatctgga<br>aaatgacccaaggccgcgtccacgtcaccgattataccaacgcgagc<br>cgcaccatgttgttcaacatccacaccttggattgggatgataaaatgtt<br>ggaagtcttggatatcccgcgcgaaatgttgccggaagtccgccgca<br>gcagcgaagtctatggccaaaccaacatcggcggcaaaggcggca<br>cccgcatcccgatcagcggcatcgcgggcgatcaacaagcggcgtt<br>gttcggccaattgtgcgtcaaagaaggcatggcgaaaaacacctatg<br>gcaccggctgcttcatgttgatgaacaccggcgaaaaagcggtcaaa<br>agcgaaaacggcttgttgaccaccatcgcgtgcgccccgaccggcg<br>aagtcaactatgcgttggaaggcgcggtcttcatggcgggcgcgagc<br>atccaatggttgcgcgatgaaatgaaattgatcaacgatgcgtatgata<br>gcgaatatttcgcgaccaaagtccaaaacaccaacggcgtctatgtcg<br>tcccggcgttcaccggcttgggcgcgccgtattgggatccgtatgcgc<br>gcggcgcgatcttcggcttgacccgcggcgtcaacgcgaaccacat<br>catccgcgcgaccttggaaagcatcgcgtatcaaacccgcgatgtctt<br>ggaagcgatgcaagcggatagcggcatccgcttgcacgcgttgcgc<br>gtcgatggcggcgcggtcgcgaacaacttcttgatgcaattccaaagc<br>gatatcttgggcacccgcgtcgaacgcccggaagtccgcgaagtca<br>ccgcgttgggcgcggcgtatttggcgggcttggcggtcggcttctgg<br>caaaacttggatgaattgcaagaaaaagcggtcatcgaacgcgaattc<br>cgcccgggcatcgaaaccaccgaacgcaactatcgctatgcgggct<br>ggaaaaaagcggtcaaacgcgcgatggcgtgggaagaacacgatg<br>aataa |
| SEQ ID NO: 105 | Intergenic region | TAATAATTAAAAACTTTCGGAGCACATCAC |
| SEQ ID NO: 106 | GlpD | atggaaaccaaagatttgatcgtcatcggcggcggcatcaacggcgc<br>gggcatcgcggcggatgcggcgggccgcggcttgagcgtcttgatg<br>ttggaagcgcaagatttggcgtgcgcgaccagcagcgcgagcagca<br>aattgatccacggcggcttgcgctatttggaacactatgaattccgcttg<br>gtcagcgaagcgttggcggaacgcgaagtcttgttgaaaatggcgcc<br>gcacatcgcgttcccgatgcgcttccgcttgccgcaccgcccgcactt<br>gcgcccggcgtggatgatccgcatcggcttgttcatgtatgatcacttg<br>ggcaaacgcaccagcttgccgggcagcaccggcttgcgcttcggcg<br>cgaacagcgtcttgaaaccggaaatcaaacgcggcttcgaatatagc<br>gattgctgggtcgatgatgcgcgcttggtcttggcgaacgcgcaaatg<br>gtcgtccgcaaaggcggcgaagtcttgacccgcacccgcgcgacca<br>gcgcgcgccgcgaaaacggcttgtggatcgtcgaagcggaagatat<br>cgataccggcaaaaaatatagctggcaagcgcgcggcttggtcaac<br>gcgaccggcccgtgggtcaaacaattcttcgatgatggcatgcacttg<br>ccgagcccgtatggcatccgcttgatcaaaggcagccacatcgtcgt<br>cccgcgcgtccacacccaaaaacaagcgtatatcttgcaaaacgaag<br>ataaacgcatcgtcttcgtcatcccgtggatggatgaattcagcatcatc<br>ggcaccaccgatgtcgaatataaaggcgatccgaaagcggtcaaaat<br>cgaagaaagcgaaatcaactatttgttgaacgtctataacacccacttc<br>aaaaaacaattgagccgcgatgatatcgtctggacctatagcggcgtc<br>cgcccgttgtgcgatgatgaaagcgatagcccgcaagcgatcaccc<br>gcgattataccttggatatccacgatgaaaacggcaaagcgccgttgtt<br>gagcgtcttcggcggcaaattgaccacctatcgcaaattggcggaac<br>acgcgttggaaaaattgaccccgtattatcaaggcatcggcccggcgt<br>ggaccaaagaaagcgtcttgccgggcggcgcgatcgaaggcgatc<br>gcgatgartatgcggcgcgcttgccgccgcgctatccgttcttgaccg<br>aaagcttggcgcgccactatgcgcgcacctatggcagcaacagcga<br>attgttgttgggcaacgcgggcaccgtcagcgatttgggcgaagam<br>cggccacgaattctatgaagcggaattgaaatatttggtcgatcacgaa<br>tgggtccgccgcgcggatgatgcgttgtggcgccgcaccaaacaag<br>gcatgtggttgaacgcggatcaacaaagccgcgtcagccaatggttg<br>gtcgaatatacccaacaacgcttgagcttggcgagctaa |

TABLE 16-continued

Glycerol Utilization Pathway Operon Codon Optimized for *M. methanica*

| SEQ ID NO: # | Gene Name | Nucleotide Sequence |
|---|---|---|
| SEQ ID NO: 107 | Intergenic region | TAATAATTAAAAACTTTCGGAGCACATCAC |
| SEQ ID NO: 108 | GlpF | atgagccaaaccagcaccttgaaaggccaatgcatcgcggaattcttg<br>ggcaccggcttgttgatcttcttcggcgtcggctgcgtcgcggcgttga<br>aagtcgcgggcgcgagcttcggccaatgggaaatcagcgtcatctg<br>gggcttgggcgtcgcgatggcgatctatttgaccgcgggcgtcagcg<br>gcgcgcacttgaacccggcggtcaccatcgcgttgtggttgttcgcgt<br>gcttcgataaacgcaaagtcatcccgttcatcgtcagccaagtcgcgg<br>gcgcgttctgcgcggcggcgttggtctatggcttgtattataacttgttct<br>tcgatttcgaacaaacccaccacatcgtccgcggcagcgtcgaaagc<br>gtcgatttggcgggcaccttcagcacctatccgaacccgcacatcaac<br>ttcgtccaagcgttcgcggtcgaaatggtcatcaccgcgatcttgatgg<br>gcttgatcttggcgttgaccgatgatggcaacggcgtcccgcgcggc<br>ccgttggcgccgttgttgatcggcttgttgatcgcggtcatcggcgcga<br>gcatgggcccgttgaccggcttcgcgatgaacccggcgcgcgatttc<br>ggcccgaaagtcttcgcgtggttggcgggctggggcaacgtcgcgtt<br>caccggcggccgcgatatccgtatttcttggtcccgttgttcggcccg<br>atcgtcggcgcgatcgtcggcgcgttcgcgtatcgcaaattgatcggc<br>cgccacttgccgtgcgatatctgcgtcgtcgaagaaaaagaaaccac<br>caccccgagcgaacaaaaagcgagcttgtaa |
| SEQ ID NO: 109 | Glycerol Utilization Pathway Operon | TTCGGAATCCCTGACGGGAATTGGCCCGA<br>AGAAGGCAGATGCCATCGTTCAGTATCGA<br>AAGGAACATGGGGATTTTCAGTCATTGAA<br>GGATCTGGAGAATGTCAGCGGCATTGGCG<br>AGAAAACCCTTCAGGCCAATGAAAAAGAC<br>ATTCGCTTCACGGATGATTTGAGCGATAAG<br>TCATCCGCGGAAAAAGGTGCGGTAGCTGT<br>GGATAAAAAAGGCGCCAGATAGTAAGCGC<br>TAAGGATTGGGGTGCGTCGCCGGTCGCGG<br>CGGCGCTCCTCGACGGCAGAGTTGGTGCC<br>AGGTTGGCGGATGATTGATGCCGAATATT<br>ACGCGACCAATTCTCGAGGCAAATGAACT<br>GTGAGCTACTGAGTTGCAGGCATTGACAG<br>CCATCCCATTTCTATCATACAGTTACGGAC<br>GCATCACGAGTAGGTGATAAGCCTAGCAG<br>ATTGCGGCAGTTGGCAAAATCAGCTATTAC<br>TAATAATTAAAAACTTTCGGAGCACATCAC<br>atgaccgaaaaaaaatatatcgtcgcgttggatcaaggcaccaccag<br>cagccgcgcggtcgtcatggatcacgatgcgaacatcatcagcgtca<br>gccaacgcgaattcgaacaaatctatccgaaaccgggctgggtcgaa<br>cacgatccgatggaaatctgggcgacccaaagcagcaccttggtcga<br>agtcttggcgaaagcggatatcagcagcgatcaaatcgcggcgatcg<br>gcatcaccaaccaacgcgaaaccaccatcgtctgggaaaaagaaac<br>cggcaaaccgatctataacgcgatcgtctggcaatgccgccgcaccg<br>cggaaatctgcgaacacttgaaacgcgatggcttggaagattatatcc<br>gcagcaacaccggcttggtcatcgatccgtatttcagcggcaccaaa<br>gtcaaatggatcttggatcacgtcgaaggcagccgcgaacgcgcgc<br>gccgcggcgaattgttgttcggcaccgtcgataccctggttgatctgga<br>aaatgacccaaggccgcgtccacgtcaccgattataccaacgcgagc<br>cgcaccatgttgttcaacatccacaccttggattgggatgataaaatgtt<br>ggaagtcttggatatcccgcgcgaaatgttgccggaagtccgccgca<br>gcagcgaagtctatggccaaaccaacatcggcggcaaaggcggca<br>cccgcatcccgatcagcggcatcgcgggcgatcaacaagcggcgtt<br>gttcggccaattgtgcgtcaaagaaggcatggcgaaaaacacctatg<br>gcaccggctgcttcatgttgatgaacaccggcgaaaaagcggtcaaa<br>agcgaaaacggcttgttgaccaccatcgcgtgcggcccgaccggcg<br>aagtcaactatgcgttggaaggcgcggtcttcatggcgggcgcgagc<br>atccaatggttgcgcgatgaaatgaaattgatcaacgatgcgtatgata<br>gcgaatatttcgcgaccaaagtccaaaacaccaacggcgtctatgtcg<br>tcccggcgttcaccggcttgggcgcgccgtattgggatccgtatgcgc<br>gcggcgcgatcttcggcttgacccgcggcgtcaacgcgaaccacat<br>catccgcgcgaccttggaaagcatcgcgtatcaaacccgcgatgtctt<br>ggaagcgatgcaagcggatagcggcatccgcttgcacgcgttgcgc<br>gtcgatggcggcgcggtcgcgaacaacttcttgatgcaattccaaagc<br>gatatcttgggcacccgcgtcgaacgcccggaagtccgcgaagtca<br>ccgcgttgggcgcggcgtatttggcgggcttggcggtcggcttctgg<br>caaaacttggatgaattgcaagaaaaagcggtcatcgaacgcaattc<br>cgcccgggcatcgaaaccaccgaacgcaactatcgctatgcgggct<br>ggaaaaaagcggtcaaacgcgcgatggcgtgggaagaacacgatg<br>aataaTAATAATTAAAAACTTTCGGAGCACAT<br>CACatggaaaccaaagatttgatcgtcatcggcggcggcatcaac<br>ggcgcgggcatcgcggcggatgcggcgggccgcggcttgagcgtc |

TABLE 16-continued

Glycerol Utilization Pathway Operon Codon Optimized for *M. methanica*

SEQ ID
NO: #    Gene Name    Nucleotide Sequence

```
ttgatgttggaagcgcaagatttggcgtgcgcgaccagcagcgcgag
cagcaaattgatccacggcggcttgcgctatttggaacactatgaattc
cgcttggtcagcgaagcgttggcggaacgcgaagtcttgttgaaaatg
gcgccgcacatcgcgttcccgatgcgcttccgcttgccgcaccgccc
gcacttgcgcccggcgtggatgatccgcatcggcttgttcatgtatgat
cacttgggcaaacgcaccagcttgccgggcagcaccggcttgcgctt
cggcgcgaacagcgtcttgaaaccggaaatcaaacgcggcttcgaat
atagcgattgctgggtcgatgatgcgcgcttggtcttggcgaacgcgc
aaatggtcgtccgcaaaggcggcgaagtcttgacccgcacccgcgc
gaccagcgcgcgccgcgaaaacggcttgtggatcgtcgaagcgga
agatatcyataccggcaaaaaatatagctggcaagcgcgcggcttgg
tcaacgcgaccggcccgtgggtcaaacaattcttcgatgatggcatgc
acttgccgagcccgtatggcatccgcttgatcaaaggcagccacatc
gtcgtcccgcgcgtccacacccaaaaacaagcgtatatcttgcaaaac
gaagataaacgcatcgtcttcgtcatcccgtggatggatgaattcagca
tcatcggcaccaccgatgtcgaatataaaggcgatccgaaagcggtc
aaaatcgaagaaagcgaaatcaactatttgttgaacgtctataacaccc
acttcaaaaaacaattgagccgcgatgatatcgtctggacctatagcg
gcgtccgcccgttgtgcgatgatgaaagcgatagcccgcaagcgatc
acccgcgattataccttggatatccacgatgaaaacggcaaagcgcc
gttgttgagcgtcttcggcggcaaattgaccacctatcgcaaattggcg
gaacacgcgttggaaaaattgacccgtattatcaaggcatcggccc
ggcgtggaccaaagaaagcgtcttgccgggcggcgcgatcgaagg
cgatcgcgatgattatgcggcgcgcttgcgccgccgctatccgttcttg
accgaaagcttggcgcgccactatgcgcgcacctatggcagcaaca
gcgaattgttgttgggcaacgcgggcaccgtcagcgatttgggcgaa
gatttcggccacgaattctatgaagcggaattgaaatatttggtcgatca
cgaatgggtccgccgcgcggatgatgcgttgtggcgccgcaccaaa
caaggcatgtggttgaacgcggatcaacaaagccgcgtcagccaat
ggttggtcgaatatacccaacaacgcttgagcttggcgagctaaTA
ATAATTAAAAACTTTCGGAGCACATCACatg
agccaaaccagcaccttgaaaggccaatgcatcgcggaattcttggg
caccggcttgttgatcttcttcggcgtcggctgcgtcgcggcgttgaaa
gtcgcgggcgcgagcttcggccaatgggaaatcagcgtcatctggg
gcttgggcgtcgcgatggcgatctatttgaccgcgggcgtcagcggc
gcgcacttgaacccggcggtcaccatcgcgttgtggttgttcgcgtgc
ttcgataaacgcaaagtcatcccgttcatcgtcagccaagtcgcgggc
gcgttctgcgcggcggcgttggtctatggcttgtattataacttgttcttc
gatttcgaacaaacccaccacatcgtccgcggcagcgtcgaaagcgt
cgatttggcgggcaccttcagcacctatccgaacccgcacatcaactt
cgtccaagcgttcgcggtcgaaatggtcatcaccgcgatcttgatggg
cttgatcttggcgttgaccgatgatggcaacggcgtcccgcgcggcc
cgttggcgccgttgttgatcggcttgttgatcgcggtcatcggcgcga
gcatgggcccgttgaccggcttcgcgatgaacccggcgcgcgatttc
ggcccgaaagtcttcgcgtggttggcgggctggggcaacgtcgcgtt
caccggcggccgcgatatcccgtatttcttggtcccgttgttcggcccg
atcgtcggcgcgatcgtcggcgcgttcgcgtatcgcaaattgatcggc
cgccacttgccgtgcgatatctgcgtcgtcgaagaaaaagaaaccac
caccccgagcgaacaaaaagcgagcttgtaa
```

The synthetic operon is then cloned and transformed into *M. methanica* as described above. Transformation is confirmed by resistance of the cells to antibiotic selection, and gene expression is confirmed by northern blot (to confirm RNA transcription), western blot, or ELISA methods (to confirm protein expression).

Growth on Glycerol as a Sole Carbon Source. Recombinant *M. methanica* transformed with a vector containing the synthetic operon encoding genes for glycerol utilization are inoculated into 100 mL shake flasks containing 20-50 mL NMS media, 1% glycerol and 10 ug/mL kanamycin. The flasks are then shaken continuously while being incubated at 30° C. Growth is confirmed by monitoring optical density of the culture over time. Note that because glycerol is the only carbon source provided to the cells, all cell mass produced must have been derived from glycerol.

Example 4

Recombinant Methylosinus Trichosporium Engineered to Grow on Acetate

*M. trichosporium* cells are cultured and conjugated as described above.

Introduction of an Acetate Utilization Pathway. Nucleic acid sequences encoding AcsA (acetyl-CoA synthase) and ActP from *E. coli* were codon optimized for expression in *M. trichosporium*. The codon optimized nucleic acids encoding AcsA and ActP are synthesized as an operon (SEQ ID NO:114; see Table 17 for components of operon) under control of an mdh promoter with appropriate intergenic regions (CAPITALIZED sequence) incorporating ribosome binding sequences.

TABLE 17

Acetate Utilization Pathway Operon Codon Optimized for *M. trichosporium*

| SEQ ID NO: # | Gene Name | Nucleotide Sequence |
|---|---|---|
| SEQ ID NO: 110 | MDH promoter | TTTGCCTCGATCGGCGGTCCTTGTGACAGGGA GATATTCCCGACGGATCCGGGGCATTCGAGCG GAACCGCCCGCCGTGGGAGTTTTTCCAGCGAG CATTCGAGAGTTTTTCAAGGCGGCTTCGAGGG GTTATTCCGTAACGCCGCCGACATGATCTGTCC CAGAATCTCCGCCGCTGTTCGTAGAGCGCCGA TGCAGGGTCGGCATCAATCATTCTTGGAGGAG ACAC |
| SEQ ID NO: 111 | AcsA | atgtcagatccataagcataccatcccggcgaacatcgcggaccgctgc ctgatcaacccgcagcagtatgaggcgatgtatcagcagtcgatcaacgtcc cggacaccttctggggcgagcagggcaagatcctggactggatcaagccgt atcagaaggtcaagaacacctcgttcgcgccgggcaacgtctcgatcaagt ggtatgaggacggcaccctgaacctggcggcgaactgcctggaccgccat ctgcaggagaacggcgaccgcaccgcgatcatctgggagggcgacgacg cgtcgcagtcgaagcatatctcgtataaggagctgcatcgcgacgtctgccg cttcgcgaacaccctgctggagctgggcatcaagaagggcgacgtcgtcgc gatctatatgccgatggtcccggaggcggcggtcgcgatgctggcgtgcgc gcgcatcggcgcggtccattcggtcatcttcggcggcttctcgccggaggcg gtcgcgggccgcatcatcgactcgaactcgcgcctggtcatcacctcggac gagggcgtccgcgcgggccgctcgatcccgctgaagaagaacgtcgacg acgcgctgaagaacccgaacgtcacctcggtcgagcatgtcgtcgtcctga agcgcaccggcggcaagatcgactggcaggagggccgcgacctgtggtg gcatgacctggtcgagcaggcgtcggaccagcatcaggcggaggagatga acgcggaggaccgctgttcatcctgtataacctcgggctcgaccggcaagc cgaagggcgtcctgcataccaccggcggctatctggtctatgcggcgctga ccttcaagtatgtcttcgactatcatcccggggcgacatctattggtgcaccgcgg acgtcggctgggtcaccggccattcgtatctgctgtatgccccgctggccgtg cgggcgaccacccctgatgttcgagggcgtcccgaactggccgaccccgg cgcgcatggcgcaggtcgtcgacaagcatcaggtcaacatcctgtataccg cgccgaccgcgatccgcgcgctgatggcggagggcgacaaggcgatcga gggcaccgaccgctcgtcgctgcgcatcctgggctcggtcggcgagccga tcaacccggaggcgtgggagtggtattggaagaagatcggcaacgagaag tgcccggtcgtcgacacctggtggcagaccgagaccggcggcttcatgatc acccccgctgccgggcgcgaccgagctgaaggcgggctcggcgacccgcc cgttcttcggcgtccagccggcgctggtcgacaacgagggcaacccgctgg agggcgaccgagggctcgctggtcatcaccgactcgtggccgggccag gcgcgcaccctgttcggcgaccatgagcgcttcgagcagacctatttctcga ccttcaagaacatgtatttctcgggcgacggcgcgccgcgacgaggacg gctattattggatcaccggccgcgtcgacgacgtcctgaacgtctcgggcca tcgcctgggctccgcggagatcgagtcggcgcgtggtcgcgcatccgaaga tcgcggaggcggcggtcgtcggcatcccgcataacatcaagggccaggcg atctatgcgtatgtcaccctgaaccatggcgaggagccgtcgccggagctgt atgcggaggtccgcaactgggtccgcaaggagatcggcccgctggcgacc ccggacgtcctgcattggaccgactcgctgccgaagacccgctcgggcaa gatcatgcgccgcatcctgcgcaagatcgcggcgggcgacacctcgaacct gggcgacacctcgaccctggcggaccccgggcgtcgtcgagaagccgct ggaggagaagcaggcgatcgcgatgccgtcgtga |
| SEQ ID NO: 112 | Intergenic Region | TCATTCTTGGAGGAGACAC |
| SEQ ID NO: 113 | ActP | atgaagcgcgtcctgaccgcgctggcggcgaccctgccgttcgcggcgaa cgcggcggacgcgatctcgggcgcggtcgagcgccagccgaccaactgg caggcgatcatcatgttcctgatcttcgtcgtcttcccaccctgggcatcacctatt gggcgtcgaagcgcgtccgctcgcgctcggactattataccgcgggcggc aacatcaccggcttccagaacggcctggcgatcgcgggcgactatatgtcg gcggcgtcgttcctgggcatctcggcgctggtcttcaacctcgggctatgacg gcctgatctattcgctgggcttcctggtcggctggccgatcatcctgttcctgat cgcggagcgcctgcgcaaacctgggccgctataccttcgcggacgtcgcgtc gtatcgcctgaagcagggcccgatccgcatcctgtcggcgtgcggctcgct ggtcgtcgtcgcgctgtatctgatcgcgcagatggtcggcgcgggcaagct gatcgagctgctgttcggcctgaactatcatatcgcggtcgtcctggtcggcg tcctgatgatgatgtatgtcctgttcggcggcatgctggcgaccacctgggtc cagatcatcaaggcggtcctgctgctgttcggcgcgtcgttcatggcgttcat ggtcatgaagcatgtcggcttctcgttcaacaacctgttctcggaggcgatgg ccgtccatccgaagggcgtcgacatcatgaagccggccgggcctggtcaag gacccgatctcggcgctgtcgctgggcctgggcctgatgttcggcaccgcg ggcctgccgcatatcctgatgcgcttcttcaccgtctcggacgcgcgcgagg cgcgcaagtcggtcttctctatgcgaccggcttcatgggctgtatttctatatcctgac cttcatcatcggcttcggcgcgatcatgctggtcggcgcgaacccggagtat aaggacgcggcgggccatctgatcggcggcaacaacatggcggcggtcc atctggcgaacgcgtcggcggcaacctgttcctgggcttcatctcggcggt cgcgttcgcgaccatcctggcggtcgtcgcgggcctgaccctggcgggcg cgtcggcggtctcgcatgacctgtatgcgaacgtcttcaagaagggcgcga |

TABLE 17-continued

Acetate Utilization Pathway Operon Codon Optimized for *M. trichosporium*

| SEQ ID NO: # | Gene Name | Nucleotide Sequence |
|---|---|---|
| | | ccgagcgcgaggagctgcgcgtctcgaagatcaccgtcctgatcctgggcg<br>tcatcgcgatcatcctgggcgtcctgttcgagaaccagaacatcgcgttcatg<br>gtcggcctggcgttcgcgatcgcggcgtcgtgcaacttcccgatcatcctgct<br>gtcgatgtattggtcgaagctgaccacccgcggcgcgatgatgggcggctg<br>gctgggcctgatcaccgcggtcgtcctgatgatcctgggcccgaccatctgg<br>gtccagatcctgggccatgagaaggcgatcttcccgtatgagtatccggcgc<br>tgttctcgatcaccgtcgcgttcctgggcatctggttcttctcggcaccgaca<br>actcggcggagggcgcgcgcgagcgcgagctgttccgcgcgcagttcatc<br>cgctcgcagaccggcttcggcgtcgagcagggccgcgcgcattga |
| SEQ ID NO: 114 | Acetate Utilization Pathway Operon | TTTGCCTCGATCGGCGGTCCTTGTGACAGGGA<br>GATATTCCCGACGGATCCGGGGCATTCGAGCG<br>GAACCGCCCGCCGTGGGAGTTTTTCCAGCGAG<br>CATTCGAGAGTTTTTCAAGGCGGCTTCGAGGG<br>GTTATTCCGTAACGCCGCCGACATGATCTGTCC<br>CAGAATCTCCGCCGCTGTTCGTAGAGCGCCGA<br>TGCAGGGTCGGCATCAATCATTCTTGGAGGAG<br>ACACatgtcgcagatccataagcataccatcccggcgaacatcgcggac<br>cgctgcctgatcaacccgcagcagtatgaggcgatgtatcagcagtcgatca<br>acgtcccggacaccttctgggcgagcagggcaagatcctggactggatca<br>agccgtatcagaaggtcaagaacaccctcgttcgcgccgggcaacgtctcga<br>tcaagtggtatgaggacggcaccctgaacctggcggcgaactgcctggacc<br>gccatctgcaggagaacggcgaccgcaccgcgatcatctgggagggcga<br>cgacgcgtcgcagtcgaagcatatctcgtataaggagctgcatcgcgacgtc<br>tgccgcttcgcgaacaccctgctggagctgggcatcaagaagggcgacgtc<br>gtcgcgatctatatgccgatggtcccggaggcggcggtcgcgatgctggcg<br>tgcgcgcgcatcggcgcggtccattcggtcatcttcggcggcttctcgccgg<br>aggcggtcgcgggccgcatcatcgactcgaactcgcgcctggtcatcacct<br>cggacgagggcgtccgcgcgggccgctcgatcccgctgaagaagaacgt<br>cgacgacgcgctgaagaacccgaacgtcacctcggtcgagcatgtcgtcgt<br>cctgaagcgcaccggcggcaagatcgactggcaggagggccgcgacctg<br>tggtggcatgacctggtcgagcaggcgtcggaccagcatcaggcggagga<br>gatgaacgcggaggacccgctgttcatcctgtataccctcgggctcgaccgc<br>aagccgaagggcgtcctgcataccaccggcggctatctggtctatgcggcg<br>ctgaccttcaagtatgtcttcgactatcatcccgggcgacatctattggtgcacc<br>gcggacgtcggctgggtcaccggccattcgtatctgctgtatggcccgctgg<br>cgtgcggcgcgaccacccctgatgttcgagggcgtcccgaactggccgacc<br>ccggcgcgcatggcgcaggtcgtcgacaagcatcaggtcaacatcctgtat<br>accgcgccgaccgcgatccgcgcgctgatggcggagggcgacaaggcg<br>atcgagggcaccgaccgctcgtcgctgcgcatcctgggctcggtcggcga<br>gccgatcaacccggaggcgtgggagtggtattggaagaagatcggcaacg<br>agaagtgcccggtcgtcgacacctggtggcagaccgagaccggcggcttc<br>atgatcaccccgctgccgggcgcgaccgagctgaaggcgggctcggcga<br>cccgccgttcttcggcgtccagccggcgctggtcgacaacgagggcaac<br>ccgctggagggcgcgaccgagggctcgctggtcatcaccgactcgtggcc<br>gggccaggcgcgcaccctgttcggcgaccatgagcgcttcgagcagacct<br>atttctcgacctcaagaacatgtatttctcgggcgacggcgcgcgccgcgac<br>gaggacggctattattggatcaccggccgcgtcgacgacgtcctgaacgtct<br>cgggccatcgcctgggcaccgcggagatcgagtcggcgcgctggtcgcgcat<br>ccgaagatcgcggaggcggcggtcgtcggcatcccgcataacatcaaggg<br>ccaggcgatctatgcgtatgtcaccctgaacatggcgaggagccgtcgcc<br>ggagctgtatgcggaggtccgcaactgggtccgcaaggagatcggcccgc<br>tggcgacccccggacgtcctgcattggaccgactcgctgccgaagacccgct<br>cgggcaagatcatgcgccgcatcctgcgcaagatcgcggcgggcgacacc<br>tcgaacctgggcgacacctcgaccctggcggaccccgggcgtcgtcgagaa<br>gctgctggaggagaagcaggcgatcgcgatgccgtcgtgaTCATTCT<br>TGGAGGAGACACatgaagcgcgtcctgaccgcgctggcggcga<br>ccctgccgttcgcggcgaacgcggcgacgcgatctcgggcgcggtcga<br>gcgccagccgaccaactggcaggcgatcatcatgttcctgatcttcgtcgtct<br>tcaccctgggcatcacctattgggcgtcgaagcgcgtccgctcgcgctcgga<br>ctattataccgcgggcggcaacatcaccggcttccagaacggcctggcgat<br>cgcgggcgactatatgtcggcggcgtcgttcctggcatctcggcgctggtc<br>ttcacctcgggctatgacggcctgatctattcgctgggcttcctggtcggctgg<br>ccgatcatcctgttcctgatcgcggagcgcctgcgcaacctgggccgctata<br>ccttcgcggacgtcgcgtcgtatcgcctgaagcagggcccgatccgcatcct<br>gtcggcgtcggctcgctggtcgtcgtcgcgcgtgtatctgatcgcgcagatg<br>gtcggcgcgggcaagctgatcgagctgctgttcggcctgaactatcatatcg<br>cggtcgtcctggtcggcgtcctgatgatgatgtatgtcctgttcggcggcatg<br>ctggcgaccacctgggtccagatcatcaaggcggtcctgctgctgttcggcg<br>cgtcgttcatggcgttcatggtcatgaagcatgtcggcttcctcgttcaacaacct<br>gttctcggaggcgatggcggtccatccgaagggcgtcgacatcatgaagcc<br>gggcggcctggtcaaggacccgatctcggcgctgtcgctgggcctgggcct<br>gatgttcggcaccgcgggcctgccgcatatcctgatgcgcttcttcaccgtct<br>cggacgcgcgcgaggcgcgcaagtcggtcttctatgcgaccggcttcatgg<br>gctatttctatatcctgaccttcatcatcggcttcggcgcgatcatgctggtcgg |

TABLE 17-continued

Acetate Utilization Pathway Operon Codon Optimized for *M. trichosporium*

| SEQ ID NO: # | Gene Name | Nucleotide Sequence |
|---|---|---|
| | | cgcgaacccggagtataaggacgcggcgggccatctgatcggcggcaac<br>aacatggcggcggtccatctggcgaacgcggtcggcggcaacctgttcctg<br>ggcttcatctcggcggtcgcgttcgcgaccatcctggcggtcgtcgcgggcc<br>tgaccctggcgggcgcgtcggcggtctcgcatgacctgtatgcgaacgtctt<br>caagaagggcgcgaccgagcgcgaggagctgcgcgtctcgaagatcacc<br>gtcctgatcctgggcgtcatcgcgatcatcctgggcgtcctgttcgagaacca<br>gaacatcgcgttcatggtcggcctggcgttcgcgatcgcggcgtcgtgcaac<br>ttcccgatcatcctgctgtcgatgtattggtcgaagctgaccacccgcggcgc<br>gatgatgggcggctggctgggcctgatcaccgcggtcgtcctgatgatcctg<br>ggcccgaccatctgggtccagatcctgggccatgagaaggcgatcttccgt<br>atgagtatccggcgctgttctcgatcaccgtcgcgttcctgggcatctggttctt<br>ctcggcgaccgacaactcggcggagggcgcgcgcgagcgcgagctgttc<br>cgcgcgcagttcatccgctcgcagaccggcttcggcgtcgagcagggccg<br>cgcgcattga |

The synthetic operon is then cloned and transformed as described above. Transformation is confirmed by resistance of the cells to antibiotic selection, and gene expression is confirmed by northern blot (to confirm RNA transcription), western blot, or ELISA methods (to confirm protein expression).

Growth on Acetate as a Sole Carbon Source. Recombinant *M. trichosporium* transformed with a vector containing the synthetic operon encoding genes for acetate utilization are inoculated into 100 mL shake flasks containing 20-50 mL NMS media, 1% sodium acetate and 10 ug/mL kanamycin. The flasks are then shaken continuously while being incubated at 30° C. Growth is confirmed by monitoring optical density of the culture over time. Note that because acetate is the only carbon source provided to the cells, all cell mass produced must have been derived from acetate.

Example 5

Recombinant Methylococcus Capsulatus Bath Engineered to Grow on Acetate

*M. capsulatus* cells are cultured and conjugated as described above.

Introduction of an Acetate Utilization Pathway. Nucleic acid sequences encoding AcsA (acetyl-CoA synthase) and ActP from *E. coli* were codon optimized for expression in *M. trichosporium*. The codon optimized nucleic acids encoding AcsA and ActP are synthesized as an operon (SEQ ID NO:119; see Table 18 for components of operon) under control of an mdh promoter with appropriate intergenic regions (CAPITALIZED sequence) incorporating ribosome binding sequences.

TABLE 18

Acetate Utilization Pathway Operon Codon Optimized for *M. capsulatus*

| SEQ ID NO: # | Gene Name | Nucleotide Sequence |
|---|---|---|
| SEQ ID NO: 115 | MDH promoter | TTTGCCTCGATCGGCGGTCCTTGTGACAGGG<br>AGATATTCCCGACGGATCCGGGGCATTCGAG<br>CGGAACCGCCCGCCGTGGGAGTTTTTCCAGC<br>GAGCATTCGAGAGTTTTTCAAGGCGGCTTCG<br>AGGGGTTATTCCGTAACGCCGCCGACATGAT<br>CTGTCCCAGAATCTCCGCCGCTGTTCGTAGA<br>GCGCCGATGCAGGGTCGGCATCAATCATTCT<br>TGGAGGAGACAC |
| SEQ ID NO: 116 | AcsA | atgagccagatccacaagcacaccatcccggccaacatcgccgaccgct<br>gcctgatcaacccgcagcagtacgaggccatgtaccagcagagcatcaa<br>cgtcccggacaccttctggggcgagcagggcaagatcctggactggatc<br>aagccgtaccagaaggtcaagaacaccagcttcgccccgggcaacgtc<br>agcatcaagtggtacgaggacggcaccctgaacctggccgccaactgc<br>ctggaccgccacctgcaggagaacggcgaccgcaccgccatcatctgg<br>gagggcgacgacgccagccagagcaagcacatcagctacaaggagct<br>gcaccgcgacgtctgccgcttcgccaacaccctgctggagctgggcatc<br>aagaagggcgacgtcgtcgccatctacatgccgatggtcccggaggcc<br>gccgtcgccatgctggcctgcgcccgcatcggcgcgtccacagcgtca<br>tcttcggcggcttcagcccggaggccgtcgccggccgcatcatcgacag<br>caacagccgcctggtcatcaccagcgacgagggcgtccgcgccggcc<br>gcagcatcccgctgaagaagaacgtcgacgacgccctgaagaacccga<br>acgtcaccagcgtcgagcacgtcgtcgtcctgaagcgcaccggcggca<br>agatcgactggcaggagggccgcgacctgtggtggcacgacctggtcg<br>agcaggccagcgaccagccaccaggccgaggagatgaacgccgagga<br>cccgctgttcatcctgtacaccagcggcagcaccggcaagccgaaggg<br>cgtcctgcacaccaccggcggctacctggtctacgccgccctgacctca<br>agtacgtcttcgactaccaccccgggcgacatctactggtgcaccgccgac<br>gtcggctgggtcaccggccacagctacctgctgtacggcccgctggcct<br>gcggcgccaccaccctgatgttcgagggcgtcccgaactggccgaccc |

TABLE 18-continued

Acetate Utilization Pathway Operon Codon Optimized for *M. capsulatus*

| SEQ ID NO: # | Gene Name | Nucleotide Sequence |
|---|---|---|
| | | cggcccgcatggcccaggtcgtcgacaagcaccaggtcaacatcctgta<br>caccgccccgaccgccatccgcgccctgatggccgagggcgacaagg<br>ccatcgagggcaccgaccgcagcagcctgcgcatcctgggcagcgtcg<br>gcgagccgatcaacccggaggcctgggagtggtactggaagaagatcg<br>gcaacgagaagtgcccggtcgtcgacacctggtggcagaccgagaccg<br>gcggcttcatgatcaccccgctgccgggcgccaccgagctgaaggccg<br>gcagcgccaccgcccgttcttcggcgtccagccggccctggtcgacaa<br>cgagggcaacccgctggagggcgccaccgagggcagcctggtcatca<br>ccgacagctggccgggccaggcccgcaccctgttcggcgaccacgag<br>cgcttcgagcagacctacttcagcaccttcaagaacatgtacttcagcggc<br>gacggcgcccgccgcgacgaggacggctactactggatcaccggccg<br>cgtcgacgacgtcctgaacgtcagcggccaccgcctgggcaccgccga<br>gatcgagagcgccctggtcgcccaccgaagatcgccgaggccgccgt<br>cgtcggcatcccgcacaacatcaagggccaggccatctacgcctacgtc<br>accctgaaccacggcgaggagccgagcccggagctgtacgccgaggt<br>ccgcaactgggtccgcaaggagatcggcccgctggccaccccggacgt<br>cctgcactggaccgacagcctgccgaagacccgcagcggcaagatcat<br>gcgccgcatcctgcgcaagatcgccgccggcgacaccagcaacctggg<br>cgacaccagcaccctggccgacccgggcgtcgtcgagaagctgctgg<br>aggagaagcaggccatcgccatgccgagctga |
| SEQ ID NO: 117 | Intergenic Region | TCATTCTTGGAGGAGACAC |
| SEQ ID NO: 118 | ActP | atgaagcgcgtcctgaccgccctggccgccaccctgccgttcgccgcca<br>acgccgccgacgccatcagcggcgccgtcgagcgccagccgaccaac<br>tggcaggccatcatcatgttcctgatcttcgtcgtcttcaccctgggcatcac<br>ctactgggccagcaagcgcgtccgcagccgcagcgactactacaccgc<br>cggcggcaacatcaccggcttccagaacggcctggccatcgccggcga<br>ctacatgagcgccgccagcttcctgggcatcagcgccctggtcttcacca<br>gcggctacgacggcctgatctacagcctgggcttcctggtcggctggcc<br>gatcatcctgttcctgatcgccgagcgcctgcgcaacctgggccgctaca<br>ccttcgccgacgtcgccagctaccgcctgaagcagggcccgatccgcat<br>cctgagcgcctgcggcagcctggtcgtcgtcgccctgtacctgatcgccc<br>agatggtcggcgccggcaagctgatcgagctgctgttcggcctgaactac<br>cacatcgccgtcgtcctggtcggcgtcctgatgatgatgtacgtcctgttcg<br>gcggcatgctggccaccacctgggtccagatcatcaaggccgtcctgct<br>gctgttcggcgccagcttcatggccttcatggtcatgaagcacgtcggctt<br>cagcttcaacaacctgttcagcgaggccatggccgtccacccgaagggc<br>gtcgacatcatgaagccgggcggcctggtcaaggacccgatcagcgcc<br>ctgagcctgggcctgggcctgatgttcggcaccgccggcctgccgcaca<br>tcctgatgcgcttcttcaccgtcagcgacgcccgcgaggcccgcaagag<br>cgtcttctacgccaccggcttcatgggctactttctacatcctgaccttcatca<br>tcggcttcggcgccatcatgctggtcggcgccaacccggagtacaagga<br>cgccgccggccacctgatcggcggcaacaacatggccgccgtccacct<br>ggccaacgccgtcggcggcaacctgttcctgggcttcatcagcgccgtc<br>gccttcgccaccatcctggccgtcgtcgccggcctgaccctggccggcg<br>ccagcgccgtcagccacgacctgtacgccaacgtcttcaagaagggcgc<br>caccgagcgcgaggagctgcgcgtcagcaagatcaccgtcctgatcctg<br>ggcgtcatcgccatcatcctgggcgtcctgttcgagaaccagaacatcgc<br>cttcatggtcggcctggccttcgccatcgccgccagctgcaacttcccgat<br>catcctgctgagcatgtactggagcaagctgaccacccgcggcgccatg<br>atgggcggctggctgggcctgatcaccgccgtcgtcctgatgatcctggg<br>cccgaccatctgggtccagatcctgggccacgagaaggccatcttcccgt<br>acgagtacccggccctgttcagcatcaccgtcgccttcctgggcatctggt<br>tcttcagcgccaccgacaacagcgccgagggcgcccgcgagcgcgag<br>ctgttccgcgcccagttcatccgcagccagaccggcttcggcgtcgag<br>cagggccgcgcccactga |
| SEQ ID NO: 119 | Acetate Utilization Pathway Operon | TTTGCCTCGATCGGCGGTCCTTGTGACAGGG<br>AGATATTCCCGACGGATCCGGGGCATTCGAG<br>CGGAACCGCCCGCCGTGGGAGTTTTTCCAGC<br>GAGCATTCGAGAGTTTTTCAAGGCGGCTTCG<br>AGGGGTTATTCCGTAACGCCGCCGACATGAT<br>CTGTCCCAGAATCTCCGCCGCTGTTCGTAGA<br>GCGCCGATGCAGGGTCGGCATCAATCATTCT<br>TGGAGGAGACAcatgagccagatccacaagcacaccatccc<br>ggccaacatcgccgaccgctgcctgatcaacccgcagcagtacgaggc<br>catgtaccagcagagcatcaacgtcccggacaccttctggggcgagcag<br>ggcaagatcctggactggatcaagccgtaccagaaggtcaagaacacca<br>gcttcgcccccgggcaacgtcagcatcaagtggtacgaggacggcaccct<br>gaacctggccgccaactgcctggaccgccacctgcaggagaacggcga<br>ccgcaccgccatcatctgggagggcgacgacgccagccgagagcaagc<br>acatcagctacaaggagctgcaccgcgacgtctgccgcttcgccaacac<br>cctgctggagctgggcatcaagaagggcgacgtcgtcgccatctacatg |

TABLE 18-continued

Acetate Utilization Pathway Operon Codon Optimized for *M. capsulatus*

| SEQ ID NO: # | Gene Name | Nucleotide Sequence |
|---|---|---|
| | | ccgatggtcccggaggccgccgtcgccatgctggcctgcgcccgcatc<br>ggcgccgtccacagcgtcatcttcggcggcttcagcccggaggccgtcg<br>ccggccgcatcatcgacagcaacagccgcctggtcatcaccagcgacg<br>agggcgtccgcgccggccgcagcatcccgctgaagaagaacgtcgac<br>gacgccctgaagaacccgaacgtcaccagcgtcgagcacgtcgtcgtcc<br>tgaagcgcaccggcggcaagatcgactggcaggagggccgcgacctg<br>tggtggcacgacctggtcgagcaggccagcgaccagcaccaggccga<br>ggagatgaacgccgaggacccgctgttcatcctgtacaccagcggcagc<br>accggcaagccgaagggcgtcctgcacaccaccggcggctacctggtc<br>tacgccgccctgaccttcaagtacgtcttcgactaccacccgggcgacat<br>ctactggtgcaccgccgacgtcggctgggtcaccggccacagctacctg<br>ctgtacggcccgctggcctgcggcgccaccaccctgatgttcgagggcg<br>tcccgaactggccgaccccggcccgcatggcccaggtcgtcgacaagc<br>accaggtcaacatcctgtacaccgccccgaccgccatccgcgccctgat<br>ggccgagggcgacaaggccatcgagggcaccgaccgcagcagcctg<br>cgcatcctgggcagcgtcggcgagccgatcaacccggaggcctggga<br>gtggtactggaagaagatcggcaacgagaagtgcccggtcgtcgacac<br>ctggtggcagaccgagaccggcggcttcatgatcaccccgctgccggg<br>cgccaccgagctgaaggccggcagcgccacccgcccgttcttcggcgt<br>ccagccggccctggtcgacaacgagggcaacccgctggagggcgcca<br>ccgagggcagcctggtcatcaccgacagctggccgggccaggcccgc<br>accctgttcggcgaccacgagcgcttcgagcagacctacttcagcacctt<br>caagaacatgtacttcagcggcgacggcgcccgccgcgacgaggacg<br>gctactactggatcaccggccgcgtcgacgacgtcctgaacgtcagcgg<br>ccaccgcctgggcaccgccgagatcgagagcgccctggtcgcccaccc<br>gaagatcgccgaggccgccgtcgtcggcatcccgcacaacatcaaggg<br>ccaggccatctacgcctacgtcaccctgaaccacggcgaggagccgag<br>cccggagctgtacgccgaggtccgcaactgggtccgcaaggagatcgg<br>cccgctggccaccccggacgtcctgcactggaccgacagcctgccgaa<br>gacccgcagcggcaagatcatgcgccgcatcctgcgcaagatcgccgc<br>cggcgacaccagcaacctgggcgacaccagcaccctggccgacccgg<br>gcgtcgtcgagaagctgctggaggagaagcaggccatcgccatgccga<br>gctgaTCATTCTTGGAGGAGACACatgaagcgcgtcct<br>gaccgccctggccgccaccctgccgttcgccgccaacgccgccgacgc<br>catcagcggcgccgtcgagcgccagccgaccaactggcaggccatcat<br>catgttcctgatcttcgtcgtcttcaccctgggcatcacctactgggccagc<br>aagcgcgtccgcagccgcagcgactactacaccgccggcggcaacatc<br>accggcttccagaacggcctggccatcgccggcgactacatgagcgcc<br>gccagcttcctgggcatcagcgccctggtcttcaccagcggctacgacg<br>gcctgatctacagcctgggcttcctggtcggctggccgatcatcctgttcct<br>gatcgccgagcgcctgcgcaacctgggccgctacaccttcgccgacgtc<br>gccagctaccgcctgaagcagggcccgatccgcatcctgagcgcctgc<br>ggcagcctggtcgtcgtcgccctgtacctgatcgcccagatggtcggcgc<br>cggcaagctgatcgagctgctgttcggcctgaactaccacatcgccgtcg<br>tcctggtcggcgtcctgatgatgatgtacgtcctgttcggcggcatgctgg<br>ccaccacctgggtccagatcatcaaggccgtcctgctgctgttcggcgcc<br>agcttcatggccttcatggtcatgaagcacgtcggcttcagcttcaacaac<br>ctgttcagcgaggccatggccgtccacccgaagggcgtcgacatcatga<br>agccgggcggcctggtcaaggacccgatcagcgccctgagcctgggcc<br>tgggcctgatgttcggcaccgccggcctgccgcacatcctgatgcgcttct<br>tcaccgtcagcgacgcccgcgaggcccgcaagagcgtcttctacgccac<br>cggcttcatgggctacttctacatcctgaccttcatcatcggcttcggcgcc<br>atcatgctggtcggcgccaacccggagtacaaggacgccgccggccac<br>ctgatcggcggcaacaacatggccgccgtccacctggccaacgccgtc<br>ggcggcaacctgttcctgggcttcatcagcgccgtcgccttcgccaccat<br>cctggccgtcgtcgccggcctgaccctggccggcgccagcgccgtcag<br>ccacgacctgtacgccaacgtcttcaagaagggcgccaccgagcgcga<br>ggagctgcgcgtcagcaagatcaccgtcctgatcctgggcgtcatcgcc<br>atcatcctgggcgtcctgttcgagaaccagaacatcgccttcatggtcggc<br>ctggccttcgccatcgccgccagctgcaacttcccgatcatcctgctgagc<br>atgtactggagcaagctgaccacccgcggcgccatgatgggcggctgg<br>ctgggcctgatcaccgccgtcgtcctgatgatcctgggcccgaccatctg<br>ggtccagatcctgggccacgagaaggccatcttcccgtacgagtacccg<br>gccctgttcagcatcaccgtcgccttcctgggcatctggttcttcagcgcca<br>ccgacaacagcgccgagggcgcccgcgagcgcgagctgttccgcgcc<br>cagttcatccgcagccagaccggcttcggcgtcgagcagggccgcg<br>cccactga |

The synthetic operon is then cloned and transformed as described above. Transformation is confirmed by resistance of the cells to antibiotic selection, and gene expression is confirmed by northern blot (to confirm RNA transcription), western blot, or ELISA methods (to confirm protein expression).

Growth on Acetate as a Sole Carbon Source. Recombinant M. capsulatus transformed with a vector containing the synthetic operon encoding genes for acetate utilization are inoculated into 100 mL shake flasks containing 20-50 mL NMS media, 1% sodium acetate and 10 ug/mL kanamycin. The flasks are then shaken continuously while being incubated at 42° C. Growth is confirmed by monitoring optical density of the culture over time. Note that because acetate is the only carbon source provided to the cells, all cell mass produced must have been derived from acetate.

Example 6

Recombinant Methylomonas Methanica Engineered to Grow on Acetate

Growth and Conjugations. The procedure for growth and conjugation of *Methylomonas methanica* was performed essentially identically to the procedures described for *M. capsulatus* (above).

Introduction of Acetate Utilization Pathway. Nucleic acid sequences encoding AcsA (acetyl-CoA synthase) and ActP from *E. coli* were codon optimized for expression in *M. methanica*. The codon optimized nucleic acids encoding AcsA and ActP are synthesized as an operon (SEQ ID NO:124; see Table 19 for components of operon) under control of an hps promoter with appropriate intergenic regions (CAPITALIZED sequence) incorporating ribosome binding sequences.

TABLE 19

Acetate Utilization Pathway Operon Codon Optimized for *M. methanica*.

| SEQ ID NO: # | Gene Name | Nucleotide Sequence |
|---|---|---|
| SEQ ID NO: 120 | HPS promoter | TTCGGAATCCCTGACGGGAATTGGCCCGAAGAA<br>GGCAGATGCCATCGTTCAGTATCGAAAGGAACA<br>TGGGGATTTTCAGTCATTGAAGGATCTGGAGAA<br>TGTCAGCGGCATTGGCGAGAAAACCCTTCAGGC<br>CAATGAAAAGACATTCGCTTCACGGATGATTT<br>GAGCGATAAGTCATCCGCGGAAAAAGGTGCGGT<br>AGCTGTGGATAAAAAAGGCGCCAGATAGTAAGC<br>GCTAAGGATTGGGGTGCGTCGCCGGTCGCGGCG<br>GCGCTCCTCGACGGCAGAGTTGGTGCCAGGTTG<br>GCGGATGATTGATGCCGAATATTACGCGACCAA<br>TTCTCGAGGCAAATGAACTGTGAGCTACTGAGT<br>TGCAGGCATTGACAGCCATCCCATTTCTATCATA<br>CAGTTACGGACGCATCACGAGTAGGTGATAAGC<br>CTAGCAGATTGCGGCAGTTGGCAAAATCAGCTA<br>TTACTAATAATTAAAAACTTTCGGAGCACATCAC |
| SEQ ID NO: 121 | AcsA | atgagccaaatccacaaacacaccatcccggcgaacatcgcggatcgctgctt<br>gatcaacccgcaacaatatgaagcgatgtatcaacaaagcatcaacgtcccgg<br>ataccttctgggcgaacaaggcaaaatcttggattggatcaaaccgtatcaaaa<br>agtcaaaaacaccagcttcgcgccgggcaacgtcagcatcaaatggtatgaag<br>atggcaccttgaacttggcggcgaactgcttggatcgccacttgcaagaaaacg<br>gcgatcgcaccgcgatcatctgggaaggcgatgatgcgagccaaagcaaaca<br>catcagctataaagaattgcaccgcgatgtctgccgcttcgcgaacaccttgttg<br>gaattgggcatctaaaaaggcgatgtcgtcgcgatctatatgccgatggtcccg<br>gaagcggcggtcgcgatgttggcgtgcgcgcgcatcggcgcggtccacagc<br>gtcatcttcggcggcttcagcccggaagcggtcgcgggccgcatcatcgatag<br>caacagccgcttggtcatcaccagcgatgaaggcgtccgcgcgggccgcagc<br>atcccgttgaaaaaaaacgtcgatgatgcgttgaaaaacccgaacgtcaccagc<br>gtcgaacacgtcgtcgtcttgaaacgcaccggcggcaaaatcgattggcaaga<br>aggccgcgatttgtggtggcacgatttggtcgaacaagcgagcgatcaacacc<br>aagcggaagaaatgaacgcggaagatccgttgttcatcttgtataccagcggca<br>gcaccggcaaaccgaaaggcgtcttgcacaccaccggcggctatttggtctat<br>gcggcgttgaccttcaaatatgtcttcgattatcaccccgggcgatatctattggtgc<br>accgcggatgtcggctgggtcaccggccacagctatttgttgtatggcccgttg<br>gcgtgcggcgcgaccaccttgatgttcgaaggcgtcccgaactggccgaccc<br>cggcgcgcatggcgcaagtcgtcgataaacaccaagtcaacatcttgtataccg<br>cgccgaccgcgatccgcgcgttgatggcggaaggcgataaagcgatcgaag<br>gcaccgatcgcagcagcttgcgcatcttgggcagcgtcggcgaaccgatcaac<br>ccggaagcgtgggaatggtattggaaaaaaatcggcaacgaaaaatgccggg<br>tcgtcgatacctggtggcaaaccgaaaccggcggcttcatgatcaccccgttgc<br>cgggcgcgaccgaattgaaagcgggcagcgcgacccgcccgttcttcggcgt<br>ccaaccggcgttggtcgataacgaaggcaaccgttggaaggcgcgaccgaa<br>ggcagcttggtcatcaccgatagctggccgggccaagcgcgcaccttgttcgg<br>cgatcacgaacgcttcgaacaaacctatttcagcaccttcaaaaacatgtatttca<br>gcggcgatggcgcgcgccgcgatgaagatggctattattggatcaccggccg<br>cgtcgatgatgtcttgaacgtcagcggccaccgcttgggcaccgcggaaatcg<br>aaagcgcgttggtcgcgcacccgaaaatcgcggaagcggcggtcgtcggcat<br>cccgcacaacatcaaaggccaagcgatctatgcgtatgtcaccttgaaccacgg<br>cgaagaaccgatcccggaattgtatgcggaagtccgcaactgggtccgcaaa<br>gaaatcggcccgttggcgacccccggatgtcttgcactggaccgatagcttgccg<br>aaaacccgcagcggcaaaatcatgcgccgcatcttgcgcaaaatcgcggcgg<br>gcgataccagcaacttgggcgataccagcaccttggcggatccgggcgtcgtc<br>gaaaaattgttggaagaaaaacaagcgatcgcgatgccgagctaa |

TABLE 19-continued

Acetate Utilization Pathway Operon Codon Optimized for *M. methanica*.

| SEQ ID NO: # | Gene Name | Nucleotide Sequence |
|---|---|---|
| SEQ ID NO: 122 | Intergenic Region | TAATAATTAAAAACTTTCGGAGCACATCAC |
| SEQ ID NO: 123 | ActP | atgaaacgcgtcttgaccgcgttggcggcgaccttgccgttcgcggcgaacgc<br>ggcggatgcgatcagcggcgcggtcgaacgccaaccgaccaactggcaagc<br>gatcatcatgttcttgatcttcgtcgtcttcaccttgggcatcacctattgggcgag<br>caaacgcgtccgcagccgcagcgattattataccgcgggcggcaacatcacc<br>ggcttccaaaacggcttggcgatcgcgggcgattatatgagcgcggcgagctt<br>cttgggcatcagcgcgttggtcttcaccagcggctatgatggcttgatctatagct<br>tgggcttcttggtcggctggccgatcatcttgttcttgatcgcggaacgcttgcgc<br>aacttgggccgctataccttcgcggatgtcgcgagctatcgcttgaaacaaggc<br>ccgatccgcatcttgagcgcgtgcggcagcttggtcgtcgtcgcgttgtatttgat<br>cgcgcaaatggtcggcgcgggcaaattgatcgaattgttgttcggcttgaactat<br>cacatcgcggtcgtcttggtcggcgtcttgatgatgatgtatgtcttgttcggcgg<br>catgttggcgaccacctgggtccaaatcatcaaagcggtcttgttgttgttcggcg<br>cgagcttcatggccgttcatggtcatgaaacacgtcggcttcagcttcaacaacttg<br>ttcagcgaagcgatggcggtccacccgaaaggcgtcgatatcatgaaaccgg<br>gcggcttggtcaaagatccgatcagcgcgttgagcttgggcttgggcttgatgtt<br>cggcaccgcgggcttgccgcacatcttgatgcgcttcttcaccgtcagcgatgc<br>gcgcgaagcgcgcaaaagcgtcttctatgcgaccggcttcatgggctatttctat<br>atcttgaccttcatcatcggcttcggcgcgatcatgttggtcggcgcgaacccgg<br>aatataaagatgcggcgggccacttgatcggcggcaacaacatggcggcggt<br>ccacttggcgaacgcggtcggcggcaacttgttcttgggcttcatcagcgcggt<br>cgcgttcgcgaccatcttggcggtcgtcgcgggcttgaccttggcgggcgcga<br>gcgcggtcagccacgatttgtatgcgaacgtcttcaaaaaaggcgcgaccgaa<br>cgcgaagaattgcgcgtcagcaaaatcaccgtcttgatcttgggcgtcatcgcg<br>atcatcttgggcgtcttgttcgaaaaccaaaacatcgcgttcatggtcggcttggc<br>gttcgcgatcgcggcgagctgcaacttcccgatcatcttgttgagcatgtattgga<br>gcaaattgaccaccgcgggcgcgatgatgggcggctggttgggcttgatcacc<br>gcggtcgtcttgatgatcttgggcccgaccatctgggtccaaatcttgggccacg<br>aaaaagcgatcttcccgtatgaatatccggcgttgttcagcatcaccgtcgcgttc<br>ttgggcatctggttcttcagcgcgaccgataacagcgcggaaggcgcgcgcga<br>acgcgaattgttccgcgcgcaattcatccgcagccaaaccggcttcggcgtcga<br>acaaggccgcgcgcactaa |
| SEQ ID NO: 124 | Acetate Utilization Pathway Operon | TTCGGAATCCCTGACGGGAATTGGCCCGAAGAA<br>GGCAGATGCCATCGTTCAGTATCGAAAGGAACA<br>TGGGGATTTTCAGTCATTGAAGGATCTGGAGAA<br>TGTCAGCGGCATTGGCGAGAAAACCCTTCAGGC<br>CAATGAAAAAGACATTCGCTTCACGGATGATTT<br>GAGCGATAAGTCATCCGCGGAAAAAGGTGCGGT<br>AGCTGTGGATAAAAAAGGCGCCAGATAGTAAGC<br>GCTAAGGATTGGGGTGCGTCGCCGGTCGCGGCG<br>GCGCTCCTCGACGGCAGAGTTGGTGCCAGGTTG<br>GCGGATGATTGATGCCGAATATTACGCGACCAA<br>TTCTCGAGGCAAATGAACTGTGAGCTACTGAGT<br>TGCAGGCATTGACAGCCATCCCATTTCTATCATA<br>CAGTTACGGACGCATCACGAGTAGGTGATAAGC<br>CTAGCAGATTGCGGCAGTTGGCAAAATCAGCTA<br>TTACTAATAATTAAAAACTTTCGGAGCACATCAC<br>atgagccaaatccacaaacacaccatcccggcgaacatcgcggatcgctgctt<br>gatcaacccgcaacaatatgaagcgatgtatcaacaaagcatcaacgtcccgg<br>ataccttctggggcgaacaaggcaaaatcttggattggatcaaaccgtatcaaaa<br>agtcaaaaacaccagcttcgccgggcaacgtcagcatcaaatggtatgaag<br>atggcaccttgaacttggcggcgaactgcttggatcgccacttgcaagaaaacg<br>gcgatcgcaccgcgatcatctgggaaggcgatgatgcgagccaaagcaaaca<br>catcagctataaagaattgcaccgcgatgtctgccgcttcgcgaacaccttgttg<br>gaattgggcatcaaaaaaggcgatgtcgtcgcgatctatatgccgatggtcccg<br>gaagcggcgtcgcgatgttggcgtgcgcgcatcggcgcggtccacagc<br>gtcatcttcggcggcttcagcccggaagcggtcgcgggccgcatcatcgatag<br>caacagccgcttggtcatcaccagcgatgaaggcgttccgcgcgggccgcagc<br>atcccgttgaaaaaaaacgtcgatgatgcgttgaaaaacccgaacgtcaccagc<br>gtcgaacacgtcgtcgtcttgaaacgcaccggcggcaaaatcgattggcaaga<br>aggccgcgatttgtggtggcacgatttggtcgaacaagcgagcgatcaacacc<br>aagcggaagaaatgaacgcggaagatccgttgttcatcttgtataccagcggca<br>gcaccggcaaaccgaaaggcgtcttgcacaccaccggcggctatttggtctat<br>gcggcgttgaccttcaaatatgtcttcgattatcacccgggcgatatctattggtgc<br>accgcggatgtcggctgggtcaccggccacagctatttgttgtatggcccgttg<br>gcgtgcggcgcgaccaccttgatgttcgaaggcgtcccgaactggccgaccc<br>cggcgcgcatggcgcaagtcgtcgataaacaccaagtcaacatcttgtataccg<br>cgccgaccgcgatccgcgcgttgatggcggaaggcgataaagcgatcgaag<br>gcaccgatcgcagcagcttgcgcatcttgggcagcgtcggcgaaccgatcaac<br>ccggaagcgtgggaatggtattggaaaaaaatcggcaacgaaaaatgcccgg<br>tcgtcgataccggtggcaaaccgaaaccggcggcttcatgatcaccccgttgc |

TABLE 19-continued

Acetate Utilization Pathway Operon Codon Optimized for M. methanica.

| SEQ ID NO: | Gene # Name | Nucleotide Sequence |
|---|---|---|
| | | cgggcgcgaccgaattgaaagcgggcagcgcgacccgcccgttcttcggcgt<br>ccaaccggcgttggtcgataacgaaggcaacccgttggaaggcgcgaccgaa<br>ggcagcttggtcatcaccgatagctggccgggccaagcgcgcaccttgttcgg<br>cgatcacgaacgcttcgaacaaacctatttcagcaccttcaaaaacatgtatttca<br>gcggcgatggcgcgcgccgcgatgaagatggctattattggatcaccggccg<br>cgtcgatgatgtcttgaacgtcagcggccaccgcttgggcaccgcggaaatcg<br>aaagcgcgttggtcgcgcacccgaaaatcgcggaagcggcggtcgtcggcat<br>cccgcacaacatcaaaggccaagcgatctatgcgtatgtcaccttgaaccacgg<br>cgaagaaccgagcccggaattgtatgcggaagtccgcaactgggtccgcaaa<br>gaaatcggcccgttggcgaccccggatgtcttgcactggaccgatagcttgccg<br>aaaacccgcagcggcaaaatcatgcgccgcatcttgcgcaaaatcgcggcgg<br>gcgataccagcaacttgggcgataccagcaccttggcggatccgggcgtcgtc<br>gaaaaattgttggaagaaaaacaagcgatcgcgatgccgagctaaTAATA<br>ATTAAAAACTTTCGGAGCACATCACatgaaacgcgtctt<br>gaccgcgttggcggcgaccttgccgttcgcggcgaacgcggcggatgcgatc<br>agcggcgcggtcgaacgccaaccgaccaactggcaagcgatcatcatgttctt<br>gatcttcgtcgtcttcaccttgggcatcacctattgggcgagcaaacgcgtccgc<br>agccgcagcgattattataccgcgggcggcaacatcaccggcttccaaaacgg<br>cttggcgatcgcgggcgattatatgagcgcggcgagcttcttgggcatcagcgc<br>gttggtcttcaccagcggctatgatggcttgatctatagcttgggcttcttggtcgg<br>ctggccgatcatcttgttcttgatcgcggaacgcttgcgcaacttgggccgctata<br>ccttcgcggatgtcgcgagctatcgcttgaaacaaggcccgatccgcatcttga<br>gcgcgtgcggcagcttggtcgtcgtcgcgttgtatttgatcgcgcaaatggtcg<br>gcgcgggcaaattgatcgaattgttgttcggcttgaactatcacatcgcggtcgtc<br>ttggtcggcgtcttgatgatgatgtatgtcttgttcggcggcatgttggcgaccac<br>ctgggtccaaatcatcaaagcggtcttgttgttgttcggcgcgagcttcatggcgt<br>tcatggtcatgatacacgtcggcttcagcttcaacaacttgttcagcgaagcgat<br>ggcggtccacccgaaaggcgtcgatatcatgaaaccgggcggcttggtcaaa<br>gatccgatcagcgcgttgagcttgggcttgggcttgatgttcggcaccgcgggc<br>ttgccgcacatcttgatgcgcttcttcaccgtcagcgatgcgcgcgaagcgcgc<br>aaaagcgtcttctatgcgaccggcttcatgggctatttctatatcttgaccttcatca<br>tcggcttcggcgcgatcatgttggtcggcgcgaacccggaatataaagatgcg<br>gcgggccacttgatcggcggcaacaacatggcggcggtccacttggcgaacg<br>cggtcggcggcaacttgttcttgggcttcatcagcgcggtcgcgttcgcgaccat<br>cttggcggtcgtcgcgggcttgaccttggcgggcgcgagcgcggtcagccac<br>gatttgtatgcgaacgtcttcaaaaaaggcgcgaccgaacgcgaagaattgcg<br>cgtcagcaaaatcaccgtcttgatcttggcgtcatcgcgatcatcttgggcgtct<br>tgttcgaaaaccaaaacatcgcgttcatggtcggcttggcgttcgcgatcgcgg<br>cgagctgcaacttcccgatcatcttgttgagcatgtattggagcaaattgaccacc<br>cgcggcgcgatgatgggcggctggttgggcttgatcaccgcggtcgtcttgat<br>gatcttgggcccgaccatctgggtccaaatcttgggccacgaaaaagcgatctt<br>cccgtatgaatatccggcgttgttcagcatcaccgtcgcgttcttgggcatctggt<br>tcttcagcgcgaccgataacagcgcggaaggcgcgcgcgaacgcgaattgtt<br>ccgcgcgcaattcatccgcagccaaaccggcttcggcgtcgaacaaggccgc<br>gcgcactaa |

The synthetic operon is then cloned and transformed into M. methanica as described above. Transformation is confirmed by resistance of the cells to antibiotic selection, and gene expression is confirmed by northern blot (to confirm RNA transcription), western blot, or ELISA methods (to confirm protein expression).

Growth on Acetate as a Sole Carbon Source. Recombinant M. methanica transformed with a vector containing the synthetic operon encoding genes for acetate utilization are inoculated into 100 mL shake flasks containing 20-50 mL NMS media, 1% sodium acetate and 10 ug/mL kanamycin. The flasks are then shaken continuously while being incubated at 30° C. Growth is confirmed by monitoring optical density of the culture over time. Note that because acetate is the only carbon source provided to the cells, all cell mass produced must have been derived from acetate.

Example 7

Recombinant Methylosinus trichosporium Engineered to Grow on Lactate

M. trichosporium cells are cultured and conjugated as described above.

Introduction of Lactate Utilization Pathway. Nucleic acid sequences encoding lactate dehydrogenase D (LdhD) and a lactate permease (LctP) from E. coli were codon optimized for expression in M. trichosporium. The codon optimized nucleic acids encoding LdhD and LctP are synthesized as an operon (SEQ ID NO:129; see Table 20 for components of operon) under control of an mdh promoter with appropriate intergenic regions (CAPITALIZED sequence) incorporating ribosome binding sequences.

TABLE 20

Lactate Utilization Pathway Operon Codon Optimized for *M. trichosporium*

| SEQ ID NO: # | Gene Name | Nucleotide Sequence |
|---|---|---|
| SEQ ID NO: 125 | MDH promoter | TTTGCCTCGATCGGCGGTCCTTGTGACAGGGAG<br>ATATTCCCGACGGATCCGGGGCATTCGAGCGG<br>AACCGCCCGCCGTGGGAGTTTTTCCAGCGAGCA<br>TTCGAGAGTTTTTCAAGGCGGCTTCGAGGGGTT<br>ATTCCGTAACGCCGCCGACATGATCTGTCCCAG<br>AATCTCCGCCGCTGTTCGTAGAGCGCCGATGCA<br>GGGTCGGCATCAATCATTCTTGGAGGAGACAC |
| SEQ ID NO: 126 | LdhD | atgaagctggcggtctattcgaccaagcagtatgacaagaagtatctgcagca<br>ggtcaacgagtcgttcggcttcgagctggagttcttcgacttcctgctgaccga<br>gaagaccgcgaagaccgcgaacggctgcgaggcggtctgcatcttcgtcaa<br>cgacgacggctcgcgcccggtcctggaggagctgaagaagcatggcgtca<br>agtatatcgcgctgcgctgcgcgggcttcaacaacgtcgacctggacgcggc<br>gaaggagctgggcctgaaggtcgtccgcgtcccggcgtatgacccggagg<br>cggtcgcggagcatgcgatcggcatgatgatgaccctgaaccgccgcatcc<br>atcgcgcgtatcagcgcacccgcgacgcgaacttctcgctggagggcctga<br>ccggcttcaccatgtatgcaagaccgcgggcgtcatcggcaccggcaaga<br>tcggcgtcgcgatgctgcgcatcctgaagggcttcggcatgcgcctgctggc<br>gttcgacccgtatccgtcggcggcggcgctggagctgggcgtcgagtatgtc<br>gacctgccgaccctgttctcggagtcggacgtcatctcgctgcattgcccgct<br>gaccccggagaactatcatctgctgaacgaggcggcgttcgagcagatgaa<br>gaacggcgtcatgatcgtcaacacctcgcgcggcgcgctgatcgactcgca<br>ggcggcgatcgaggcgctgaagaaccagaagatcggctcgctgggcatgg<br>acgtctatgagaacgagcgcgacctgttcttcgaggacaagtcgaacgacgt<br>catccaggacgacgtcttccgccgcctgtcggcgtgccataacgtcctgttca<br>ccggccatcaggcgttcctgaccgcggaggcgctgacctcgatctcgcaga<br>ccaccctgcagaacctgtcgaacctggagaagggcgagacctgcccgaacg<br>agctggtctga |
| SEQ ID NO: 127 | Intergenic Region | TCATTCTTGGAGGAGACAC |
| SEQ ID NO: 128 | LctP | atgaacctgtggcagcagaactatgacccggcgggcaacatctggctgtcgt<br>cgctgatcgcgtcgctgccgatcctgttcttcttcttcgcgctgatcaagctgaa<br>gctgaagggctatgtcgcggcgtcgtggaccgtcgcgatcgcgctggcggt<br>cgcgctgctgttctataagatgccggtcgcgaacgcgctggcgtcggtcgtct<br>atggcttcttcatggcctgtggcgatcgcgtggatcatcatcgcggcggtctt<br>cgtctataagatctcggtcaagaccggccagttcgacatcatccgctcgtcgat<br>cctgtcgatcaccccggaccagcgcctgcagatgctgatcgtcggcttctgctt<br>cggcgcgttcctggagggcgcggcgggcttcggcgcgccggtcgcgatca<br>ccgcggcgctgctggtcggcctgggcttcaagccgctgtatgcggcgggcct<br>gtgcctgatcgtcaacaccgcgccggtcgcgttcggcgcgatgggcatcccg<br>atcctggtcgcggggccaggtcaccggcatcgactcgttcgagatcggccaga<br>tggtcggccgccagctgccgttcatgaccatcatcgtcctgttctggatcatgg<br>cgatcatggacggctggcgcggcatcaaggagacctggccggcggtcgtc<br>gtcgcgggcggctcgttcgcgatcgcgcagtatctgtcgtcgaacttcatcgg<br>cccggagctgccggacatcatctcgtcgctggtctcgctgctg<br>tgcctgaccctgttcctgaagcgctggcagccggtccgcgtcttccgcttcgg<br>cgacctgggcgcgtcgcaggtcgacatgaccctggcgcataccggctatac<br>cgcggggccaggtcctgcgcgcgtggaccccgttcctgttcctgaccgcgacc<br>gtcaccctgtggtcgatcccgccgttcaaggcgctgttcgcgtcgggcggcg<br>cgctgtatgagtgggtcatcaacatcccggtcccgtatctggacaagctggtc<br>gcgcgcatgccgccggtcgtctcggaggcgaccgcgtatgcggcggtcttc<br>aagttcgactggttctcggcgaccggcaccgcgatcctgttcgcggcgctgct<br>gtcgatcgtctggctgaagatgaagcgtcggacgcgatctcgaccttcggct<br>cgaccctgaaggagctggcgctgccgatctattcgatcggcatggtcctggc<br>gttcgcgttcatctcgaactattcgggcctgtcgtcgaccctggcgctggcgct<br>ggcgcataccggccatgcgttcaccttcttctcgccgttcctgggctggctggg<br>cgtcttcctgaccggctcggacacctcgtcgaacgcgctgttcgcggcgctgc<br>aggcgaccgcggcgcagcagatcggcgtctcggacctgctgctggtcgcg<br>gcgaacaccaccggcggcgtcaccggcaagatgatctcgccgcagtcgatc<br>gcgatcgcgtgcgcggcggtcggcctggtcggcaaggagtcggacctgttc<br>cgcttcaccgtcaagcattcgctgatcttcacctgcatcgtcggcgtcatcacca<br>CCctgcaggcgtatgtcctgacctggatgatcccgtga |
| SEQ ID NO: 129 | Lactate Utilization Pathway Operon | TTTGCCTCGATCGGCGGTCCTTGTGACAGGGAG<br>ATATTCCCGACGGATCCGGGGCATTCGAGCGG<br>AACCGCCCGCCGTGGGAGTTTTTCCAGCGAGCA<br>TTCGAGAGTTTTTCAAGGCGGCTTCGAGGGGTT<br>ATTCCGTAACGCCGCCGACATGATCTGTCCCAG<br>AATCTCCGCCGCTGTTCGTAGAGCGCCGATGCA<br>GGGTCGGCATCAATCATTCTTGGAGGAGACACa<br>tgaagctggcggtctattcgaccaagcagtatgacaagaagtatctgcagcag<br>gtcaacgagtcgttcggcttcgagctggagttcttcgacttcctgctgaccgag<br>aagaccgcgaagaccgcgaacggctgcgaggcggtctgcatcttcgtcaac |

TABLE 20-continued

Lactate Utilization Pathway Operon Codon Optimized for *M. trichosporium*

| SEQ ID NO: # | Gene Name | Nucleotide Sequence |
|---|---|---|
| | | gacgacggctcgcgcccggtcctggaggagctgaagaagcatggcgtcaa<br>gtatatcgcgctgcgctgcgcgggcttcaacaacgtcgacctggacgcggcg<br>aaggagctgggcctgaaggtcgtccgcgtcccggcgtatgacccggaggc<br>ggtcgcggagcatgcgatcggcatgatgatgaccctgaaccgccgcatccat<br>cgcgcgtatcagcgcacccgcgacgcgaacttctcgctggagggcctgacc<br>ggcttcaccatgtatggcaagaccgcgggcgtcatcggcaccggcaagatc<br>ggcgtcgcgatgctgcgcatcctgaagggcttcggcatgcgcctgctggcgt<br>tcgacccgtatccgtcggcgggcggcgctggagctgggcgtcgagtatgtcga<br>cctgccgaccctgttctcggagtcggacgtcatctcgctgcattgcccgctgac<br>cccggagaactatcatctgctgaacgaggcggcgttcgagcagatgaagaa<br>cggcgtcatgatcgtcaacacctcgcgcggcgcgctgatcgactcgcaggc<br>ggcgatcgaggcgctgaagaaccagaagatcggctcgctgggcatggacgt<br>ctatgagaacgagcgcgacctgttcttcgaggacaagtcgaacgacgtcatcc<br>aggacgacgtcttccgccgcctgtcggcgtgccataacgtcctgttcaccggc<br>catcaggcgttcctgaccgcggaggcgctgacctcgatctcgcagaccaccc<br>tgcagaacctgtcgaacctggagaagggcgagacctgcccgaacgagctg<br>gtctgaTCATTCTTGGAGGAGACAtgaacctgtggcagc<br>agaactatgacccggcgggcaacatctggctgtcgtcgctgatcgcgtcgct<br>gccgatcctgttcttcttcttcgcgctgatcaagctgaagctgaagggctatgtc<br>gcggcgtcgtggaccgtcgcgatcgcgctggcggtcgcgctgctgttctata<br>agatgccggtcgcgaacgcgctggcgtcggtcgtctatggcttcttctatggc<br>ctgtggccgatcgcgtggatcatcatcgcggcggtcttcgtctataagatctcg<br>gtcaagaccggccagttcgacatcatccgctcgtcgatcctgtcgatcacccc<br>ggaccagcgcctgcagatgctgatcgtcggcttctgcttcggcgcgttcctgg<br>agggcgcggcgggcttcggcgcgccggtcgcgatcaccgccggcgctgctg<br>gtcggcctgggcttcaagccgctgtatgcggcgggcctgtgcctgatcgtcaa<br>caccgcgccggtcgcgttcggcgcgatgggcatcccgatcctggtcgcggg<br>ccaggtcaccggcatcgactcgttcgagatcggccagatggtcggccgcca<br>gctgccgttcatgaccatcatcgtcctgttctggatcatggcgatcatggacgg<br>ctggcgcggcatcaaggagacctggccggcggtcgtcgtcgcgggcggct<br>cgttcgcgatcgcgcagtatctgtcgtcgaacttcatcggcccggagctgccg<br>gacatcatctcgtcgctggtctcgctgctgtgcctgaccctgttcctgaagcgct<br>ggcagccggtccgcgtcttccgcttcggcgacctgggcgcgctgcaggtcg<br>acatgaccctggcgcataccggctataccgcgggccaggtcctgcgcgcgt<br>ggaccccgttcctgttcctgaccgcgaccgtcaccctgtggtcgatcccgccg<br>ttcaaggcgctgttcgcgtcgggcggcgcgctgtatgagtgggtcatcaacat<br>cccggtcccgtatctggacaagctggtcgcgcgcatgccgccggtcgtctcg<br>gaggcgaccgcgtatgcggcggtcttcaagttcgactggttctcggcgaccg<br>gcaccgcgatcctgttcgcggcgctgctgtcgatcgtctggctgaagatgaag<br>ccgtcggacgcgatctcgaccttcggctcgaccctgaaggagctggcgctgc<br>cgatctattcgatcggcatggtcctggcgttcgcgttcatctcgaactattcggg<br>cctgtcgtcgaccctggcgctggcgctggcgcataccggccatgcgttcacct<br>tcttctcgccgttcctgggctggctgggcgtcttcctgaccggctcggacacct<br>cgtcgaacgcgctgttcgcggcgctgcaggcgaccgcggcgcagcagatc<br>ggcgtctcggacctgctgctggtcgcggcgaacaccaccggcggcgtcacc<br>ggcaagatgatctcgccgcagtcgatcgcgatcgcgtgcgcggcggtcggc<br>ctggtcggcaaggagtcggacctgttccgcttcaccgtcaagcattcgctgat<br>cttcacctgcatcgtcggcgtcatcaccaccctgcaggcgtatgtcctga<br>cctggatgatcccgtga |

Example 8

Recombinant Methylococcus Capsulatus Bath Engineered to Grow on Lactate

*M. capsulatus* cells are cultured and conjugated as described above.

Introduction of Lactate Utilization Pathway. Nucleic acid sequences encoding lactate dehydrogenase D (LdhD) and a lactate permease (LctP) from *E. coli* were codon optimized for expression in *M. trichosporium*. The codon optimized nucleic acids encoding LdhD and LctP are synthesized as an operon (SEQ ID NO:134; see Table 21 for components of operon) under control of an mdh promoter with appropriate intergenic regions (CAPITALIZED sequence) incorporating ribosome binding sequences.

The synthetic operon is then cloned and transformed as described above. Transformation is confirmed by resistance of the cells to antibiotic selection, and gene expression is confirmed by northern blot (to confirm RNA transcription), western blot, or ELISA methods (to confirm protein expression).

Growth on Lactate as a Sole Carbon Source. Recombinant *M. trichosporium* transformed with a vector containing the synthetic operon encoding genes for lactate utilization are inoculated into 100 mL shake flasks containing 20-50 mL NMS media, 1% sodium lactate and 10 ug/mL kanamycin. The flasks are then shaken continuously while being incubated at 30° C. Growth is confirmed by monitoring optical density of the culture over time. Note that because lactate is the only carbon source provided to the cells, all cell mass produced must have been derived from lactate.

TABLE 21

Lactate Utilization Pathway Operon Codon Optimized for *M. capsulatus*

| SEQ ID NO: # | Gene Name | Nucleotide Sequence |
|---|---|---|
| SEQ ID NO: 130 | MDH promoter | TTTGCCTCGATCGGCGGTCCTTGTGACAGGGAG<br>ATATTCCCGACGGATCCGGGGCATTCGAGCGGA<br>ACCGCCCGCCGTGGGAGTTTTTCCAGCGAGCAT<br>TCGAGAGTTTTTCAAGGCGGCTTCGAGGGGTTA<br>TTCCGTAACGCCGCCGACATGATCTGTCCCAGA<br>ATCTCCGCCGCTGTTCGTAGAGCGCCGATGCAG<br>GGTCGGCATCAATCATTCTTGGAGGAGACAC |
| SEQ ID NO: 131 | LdhD | atgaagctggccgtctacagcaccaagcagtacgacaagaagtacctgcagc<br>aggtcaacgagagcttcggcttcgagctggagttcttcgacttcctgctgaccg<br>agaagaccgccaagaccgccaacggctgcgaggccgtctgcatcttcgtcaa<br>cgacgacggcagccgcccggtcctggaggagctgaagaagcacggcgtca<br>agtacatcgccctgcgctgcgccggcttcaacaacgtcgacctggacgccgc<br>caaggagctgggcctgaaggtcgtccgcgtcccggcctacgacccggaggc<br>cgtcgccgagcacgccatcggcatgatgatgaccctgaaccgccgcatccac<br>cgcgcctaccagcgcacccgcgacgccaacttcagcctggagggcctgacc<br>ggcttcaccatgtacggcaagaccgccggcgtcatcggcaccggcaagatc<br>ggcgtcgccatgctgcgcatcctgaagggcttcggcatgcgcctgctggcctt<br>cgacccgtacccgagcgccgccgccctggagctgggcgtcgagtacgtcga<br>cctgccgaccctgttcagcgagagcgacgtcatcagcctgcactgcccgctg<br>accccggagaactaccacctgctgaacgaggccgccttcgagcagatgaag<br>aacggcgtcatgatcgtcaacaccagccgcggcgccctgatcgacagccag<br>gccgccatcgaggccctgaagaaccagaagatcggcagcctgggcatgga<br>cgtctacgagaacgagcgcgacctgttcttcgaggacaagagcaacgacgtc<br>atccaggacgacgtcttccgccgcctgagcgcctgccacaacgtcctgttcac<br>cggccaccaggccttcctgaccgccgaggccctgaccagcatcagccagac<br>caccctgcagaacctgagcaacctggagaagggcgagacctgcccgaacg |
| SEQ ID NO: 132 | Intergenic Region | TCATTCTTGGAGGAGACAC |
| SEQ ID NO: 133 | LctP | atgaacctgtggcagcagaactacgacccggccggcaacatctggctgagc<br>agcctgatcgccagcctgccgatcctgttcttcttcttcgccctgatcaagctga<br>agctgaagggctacgtcgccgccagctggaccgtcgccatcgccctggccgt<br>cgccctgctgttctacaagatgccggtcgccaacgccctggccagcgtcgtct<br>acggcttcttctacggcctgtggccgatcgcctggatcatcatcgccgccgtctt<br>cgtctacaagatcagcgtcaagaccggccagttcgacatcatccgcagcagc<br>atcctgagcatcaccccggaccagcgcctgcagatgctgatcgtcggcttctg<br>cttcggcgccttcctggagggcgccgccggcttcggcgccccggtcgccatc<br>accgccgccctgctggtcggcctgggcttcaagccgctgtacgccgccggcc<br>tgtgcctgatcgtcaacaccgccccggtcgccttcggcgccatgggcatcccg<br>atcctggtcgccggccaggtcaccggcatcgacagcttcgagatcggccaga<br>tggtcggccgccagctgccgttcatgaccatcatcgtcctgttctggatcatgg<br>ccatcatggacggctggcgcggcatcaaggagacctggccggccgtcgtcg<br>tcgccggcggcagcttcgccatcgcccagtacctgagcagcaacttcatcgg<br>cccggagctgccggacatcatcagcagcctggtcagcctgctgtgcctgacc<br>ctgttcctgaagcgctggcagccggtccgcgtcttccgcttcggcgacctggg<br>cgccagccaggtcgacatgaccctggcccacaccggctacaccgccggcca<br>ggtcctgcgcgcctggaccccgttcctgttcctgaccgccaccgtcaccctgt<br>ggagcatcccgccgttcaaggccctgttcgccagcggcggcgccctgtacga<br>gtgggtcatcaacatcccggtcccgtacctggacaagctggtcgcccgcatgc<br>cgccggtcgtcagcgaggccaccgcctacgccgccgtcttcaagttcgactg<br>gttcagcgccaccggcaccgccatcctgttcgccgccctgctgagcatcgtct<br>ggctgaagatgaagccgagcgacgccatcagcaccttcggcagcaccctga<br>aggagctggccctgccgatctacagcatcggcatggtcctggccttcgccttc<br>atcagcaactacagcggcctgagcagcaccctggccctggccctggcccac<br>accggccacgccttcaccttcttcagcccgttcctgggctggctgggcgtcttc<br>ctgaccggcagcgacaccagcagcaacgccctgttcgccgccctgcaggcc<br>accgccgcccagcagatcggcgtcagcgacctgctgctggtcgccgccaac<br>accaccggcggcgtcaccggcaagatgatcagcccgcagagcatcgccatc<br>gcctgcgccgccgtcggcctggtcggcaaggagagcgacctgttccgcttca<br>ccgtcaagcacagcctgatcttcacctgcatcgtcggcgtcatcaccaccctgc<br>aggcctacgtcctgacctggatgatcccgtga |
| SEQ ID NO: 134 | Lactate Utilization Pathway Operon | TTTGCCTCGATCGGCGGTCCTTGTGACAGGGAG<br>ATATTCCCGACGGATCCGGGGCATTCGAGCGGA<br>ACCGCCCGCCGTGGGAGTTTTTCCAGCGAGCAT<br>TCGAGAGTTTTTCAAGGCGGCTTCGAGGGGTTA<br>TTCCGTAACGCCGCCGACATGATCTGTCCAGA<br>ATCTCCGCCGCTGTTCGTAGAGCGCCGATGCAG<br>GGTCGGCATCAATCATTCTTGGAGGAGACACatg<br>aagctggccgtctacagcaccaagcagtacgacaagaagtacctgcagcag<br>gtcaacgagagcttcggcttcgagctggagttcttcgacttcctgctgaccgag<br>aagaccgccaagaccgccaacggctgcgaggccgtctgcatcttcgtcaacg<br>acgacggcagccgcccggtcctggaggagctgaagaagcacggcgtcaag |

TABLE 21-continued

Lactate Utilization Pathway Operon Codon Optimized for *M. capsulatus*

| SEQ ID NO: # | Gene Name | Nucleotide Sequence |
|---|---|---|
| | | tacatcgccctgcgctgcgccggcttcaacaacgtcgacctggacgccgcca aggagctgggcctgaaggtcgtccgcgtcccggcctacgacccggaggcc gtcgccgagcacgccatcggcatgatgatgaccctgaaccgccgcatccacc gcgcctaccagcgcacccgcgacgccaacttcagcctggagggcctgaccg gcttcaccatgtacggcaagaccgccggcgtcatcggcaccggcaagatcg gcgtcgccatgctgcgcatcctgaagggcttcggcatgcgcctgctggccttc gacccgtacccgagcgccgccgccctggagctgggcgtcgagtacgtcgac ctgccgaccctgttcagcgagagcgacgtcatcagcctgcactgcccgctga ccccggagaactaccacctgctgaacgaggccgccttcgagcagatgaaga acggcgtcatgatcgtcaacaccagccgcggcgccctgatcgacagccagg ccgccatcgaggccctgaagaaccagaagatcggcagcctgggcatggac gtctacgagaacgagcgcgacctgttcttcgaggacaagagcaacgacgtca tccaggacgacgtcttccgccgcctgagcgcctgccacaacgtcctgttcacc ggccaccaggccttcctgaccgccgaggccctgaccagcatcagccagacc accctgcagaacctgagcaacctggagaagggcgagacctgcccgaacga gctggtctgaTCATTCTTGGAGGAGACACatgaacctgtggc agcagaactacgacccggccggcaacatctggctgagcagcctgatcgcca gcctgccgatcctgttcttcttcttcgccctgatcaagctgaagctgaagggcta cgtcgccgccagctggaccgtcgccatcgccctggccgtcgccctgctgttct acaagatgccggtcgccaacgccctggccagcgtcgtctacggcttcttctac ggcctgtggccgatcgcctggatcatcatcgccgccgtcttcgtctacaagatc agcgtcaagaccggccagttcgacatcatccgcagcagcatcctgagcatca ccccggaccagcgcctgcagatgctgatcgtcggcttctgcttcggcgccttc ctggagggcgccgccggcttcggcgccccggtcgccatcaccgccgccctg ctggtcggcctgggcttcaagccgctgtacgccgccggcctgtgcctgatcgt caacaccgcccggtcgccttcggcgccatgggcatcccgatcctggtcgcc ggccaggtcaccggcatcgacagcttcgagatcggccagatggtcggccgc cagctgccgttcatgaccatcatcgtcctgttctggatcatggccatcatggacg gctggcgcggcatcaaggagacctggccggccgtcgtcgtcgccggcggc agcttcgccatcgcccagtacctgagcagcaacttcatcggcccggagctgc cggacatcatcagcagcctggtcagcctgctgtgcctgaccctgttcctgaag cgctggcagccggtccgcgtcttccgcttcggcgacctgggcgccagccag gtcgacatgaccctggcccacaccggctacaccgccggccaggtcctgcgc gcctggacccgttcctgttcctgaccgccaccgtcaccctgtggagcatccc gccgttcaaggccctgttcgccagcggcggcgccctgtacgagtgggtcatc aacatcccggtcccgtacctggacaagctggtcgcccgcatgccgccggtcg tcagcgaggccaccgcctacgccgccgtcttcaagttcgactggttcagcgcc accggcaccgccatcctgttcgccgccctgctgagcatcgtctggctgaagat gaagccgagcgacgccatcagcaccttcggcagcaccctgaaggagctggc cctgccgatctacagcatcggcatggtcctggccttcgccttcatcagcaacta cagcggcctgagcagcaccctggccctggccctggcccacaccggccacg ccttcaccHcttcagcccgttcctgggctggctgggcgtcttcctgaccggca gcgacaccagcagcaacgccctgttcgccgccctgcaggccaccgccgccc agcagatcggcgtcagcgacctgctgctggtcgccgccaacaccaccggcg gcgtcaccggcaagatgatcagcccgcagagcatcgccatcgcctgcgccg ccgtcggcctggtcggcaaggagagcgacctgttccgcttcaccgtcaagca cagcctgatcttcacctgcatcgtcggcgtcatcaccaccctgcaggcctac gtcctgacctggatgatcccgtga |

The synthetic operon is then cloned and transformed as described above. Transformation is confirmed by resistance of the cells to antibiotic selection, and gene expression is confirmed by northern blot (to confirm RNA transcription), western blot, or ELISA methods (to confirm protein expression).

Growth on Lactate as a Sole Carbon Source. Recombinant *M. capsulatus* transformed with a vector containing the synthetic operon encoding genes for lactate utilization are inoculated into 100 mL shake flasks containing 20-50 mL NMS media, 1% sodium lactate and 10 ug/mL kanamycin. The flasks are then shaken continuously while being incubated at 42° C. Growth is confirmed by monitoring optical density of the culture over time. Note that because lactate is the only carbon source provided to the cells, all cell mass produced must have been derived from lactate.

Example 9

Methylomonas Methanica Engineered to Grow on Lactate

Growth and Conjugations. The procedure for growth and conjugation of *Methylomonas methanica* was performed essentially identically to the procedures described above for *M. capsulatus*.

Introduction of Lactate Utilization Pathway. Nucleic acid sequences encoding lactate dehydrogenase D (LdhD) and a lactate permease (LctP) from *E. coli* were codon optimized for expression in *M. methanica*. The codon optimized nucleic acids encoding LdhD and LctP are synthesized as an operon (SEQ ID NO:139; see Table 22 for components of operon) under control of an hps promoter with appropriate intergenic regions (CAPITALIZED sequence) incorporating ribosome binding sequences.

TABLE 22

Lactate Utilization Pathway Operon Codon Optimized for *M. methanica*

| SEQ ID NO: # | Gene Name | Nucleotide Sequence |
|---|---|---|
| SEQ ID NO: 135 | HPS promoter | TTCGGAATCCCTGACGGGAATTGGCCCGAAG<br>AAGGCAGATGCCATCGTTCAGTATCGAAAGG<br>AACATGGGGATTTTCAGTCATTGAAGGATCTG<br>GAGAATGTCAGCGGCATTGGCGAGAAAACCC<br>TTCAGGCCAATGAAAAAGACATTCGCTTCACG<br>GATGATTTGAGCGATAAGTCATCCGCGGAAA<br>AAGGTGCGGTAGCTGTGGATAAAAAAGGCGC<br>CAGATAGTAAGCGCTAAGGATTGGGGTGCGT<br>CGCCGGTCGCGGCGGCGCTCCTCGACGGCAG<br>AGTTGGTGCCAGGTTGGCGGATGATTGATGCC<br>GAATATTACGCGACCAATTCTCGAGGCAAATG<br>AACTGTGAGCTACTGAGTTGCAGGCATTGACA<br>GCCATCCCATTTCTATCATACAGTTACGGACG<br>CATCACGAGTAGGTGATAAGCCTAGCAGATT<br>GCGGCAGTTGGCAAAATCAGCTATTACTAATA<br>ATTAAAAACTTTCGGAGCACATCAC |
| SEQ ID NO: 136 | LdhD | atgaaattggcggtctatagcaccaaacaatatgataaaaaatatttgcaaca<br>agtcaacgaaagcttcggcttcgaattggaattcttcgatttcttgttgaccga<br>aaaaaccgcgaaaaccgcgaacggctgcgaagcggtctgcatcttcgtca<br>acgatgatggcagccgccggtcttggaagaattgaaaaaacacggcgtc<br>aaatatatcgcgttgcgctgcgcgggcttcaacaacgtcgatttggatgcgg<br>cgaaagaattgggcttgaaagtcgtccgcgtcccggcgtatgatccggaag<br>cggtcgcggaacacgcgatcggcatgatgatgaccttgaaccgccgcatc<br>caccgcgcgtatcaacgcacccgcgatgcgaacttcagcttggaaggcttg<br>accggcttcaccatgtatggcaaaaccgcgggcgtcatcggcaccggcaa<br>aatcggcgtcgcgatgttgcgcatcttgaaaggcttcggcatgcgcttgttg<br>gcgttcgatccgtatccgagcgcggcggcgttggaattgggcgtcgaatat<br>gtcgatttgccgaccttgttcagcgaaagcgatgtcatcagcttgcactgccc<br>gttgaccccggaaaactatcacttgttgaacgaagcggcgttcgaacaaat<br>gaaaaacggcgtcatgatcgtcaacaccagccgcggcgcgttgatcgata<br>gccaagcggcgatcgaagcgttgaaaaaccaaaaaatcggcagcttggg<br>catggatgtctatgaaaacgaacgcgatttgttcttcgaagataaaagcaac<br>gatgtcatccaagatgatgtcttccgccgcttgagcgcgtgccacaacgtctt<br>gttcaccggccaccaagcgttcttgaccgcggaagcgttgaccagcatcag<br>ccaaaccaccttgcaaaacttgagcaacttggaaaaaggcgaaacctgcc<br>cgaacgaattggtctaa |
| SEQ ID NO: 137 | Intergenic Region | TAATAATTAAAAACTTTCGGAGCACATCAC |
| SEQ ID NO: 138 | LctP | atgaacttgtggcaacaaaactatgatccggcggcaacatctggttgagc<br>agcttgatcgcgagcttgccgatcttgttcttcttcttcgcgttgatcaaattga<br>aattgaaaggctatgtcgcggcgagctggaccgtcgcgatcgcgttggcg<br>gtcgcgttgttgttctataaaatgccggtcgcgaacgcgttggcgagcgtcg<br>tctatggcttcttctatggcttgtggccgatcgcgtggatcatcatcgcggcg<br>gtcttcgtctataaaatcagcgtcaaaaccggccaattcgatatcatccgcag<br>cagcatcttgagcatcaccccggatcaacgcttgcaaatgttgatcgtcggc<br>ttctgcttcggcgcgttcttggaaggcgcggcgggcttcggcgcgccggtc<br>gcgatcaccgcggcgttgttggtcggcttgggcttcaaaccgttgtatgcgg<br>cgggcttgtgcttgatcgtcaacaccgcgccggtcgcgttcggcgcgatgg<br>gcatcccgatcttggtcgcgggccaagtcaccggcatcgatagcttcgaaa<br>tcggccaaatggtcggccgccaattgccgttcatgaccatcatcgtcttgttc<br>tggatcatggcgatcatggatggctggcgcggcatcaaagaaacctggcc<br>ggcggtcgtcgtcgcgggcggcagcttcgcgatcgcgcaatatttgagca<br>gcaacttcatcggcccggaattgccggatatcatcagcagcttggtcagctt<br>gttgtgcttgaccttgttcttgaaacgctggcaaccggtccgcgtcttccgctt<br>cggcgatttgggcgcgagccaagtcgatatgaccttggcgcacaccggct<br>ataccgcgggccaagtcttgcgcgcgtggaccccgttcttgttcttgaccgc<br>gaccgtcaccttgtggagcatcccgccgttcaaagcgttgttcgcgagcgg<br>cggcgcgttgtatgaatgggtcatcaacatcccggtcccgtatttggataaat<br>tggtcgcgcgcatgccgccggtcgtcagcgaagcgaccgcgtatgcggc<br>ggtcttcaaattcgattggttcagcgcgaccggcaccgcgatcttgttcgcg<br>gcgttgttgagcatcgtctggtttgaaaatgaaaccgagcgatgcgatcagc<br>accttcggcagcaccttgaaagaattggcgttgccgatctatagcatcggca<br>tggtcttggcgttcgcgttcatcagcaactatagcggcttggcgcagcaccttg<br>gcgttggcgttggcgcacaccggccacgcgttcaccttcttcagcccgttct<br>tgggctggttgggcgtcttcttgaccggcagcgataccagcagcaacgcgt<br>tgttcgcggcgttgcaagcgaccgcggcgcaacaaatcggcgtcagcgat<br>ttgttgttggtcgcggcgaacaccaccggcggcggcaaatgatc<br>agcccgcaaagcatcgcgatcgcgtgcgcggcggtcggcttggtcggca<br>agaaaagcgatttgttccgcttcaccgtcaaacagcttgatcttcacctgc<br>atcgtcggcgtcatcaccaccttgcaagcgtatgtcttgacctggat<br>gatcccgtaa |

TABLE 22-continued

Lactate Utilization Pathway Operon Codon Optimized for *M. methanica*

| SEQ ID NO: # | Gene Name | Nucleotide Sequence |
|---|---|---|
| SEQ ID NO: 139 | Lactate Utilization Pathway Operon | TTCGGAATCCCTGACGGGAATTGGCCCGAAG<br>AAGGCAGATGCCATCGTTCAGTATCGAAAGG<br>AACATGGGGATTTTCAGTCATTGAAGGATCTG<br>GAGAATGTCAGCGGCATTGGCGAGAAAACCC<br>TTCAGGCCAATGAAAAAGACATTCGCTTCACG<br>GATGATTTGAGCGATAAGTCATCCGCGGAAA<br>AAGGTGCGGTAGCTGTGGATAAAAAGGCGC<br>CAGATAGTAAGCGCTAAGGATTGGGGTGCGT<br>CGCCGGTCGCGGCGGCGCTCCTCGACGGCAG<br>AGTTGGTGCCAGGTTGGCGGATGATTGATGCC<br>GAATATTACGCGACCAATTCTCGAGGCAAATG<br>AACTGTGAGCTACTGAGTTGCAGGCATTGACA<br>GCCATCCCATTTCTATCATACAGTTACGGACG<br>CATCACGAGTAGGTGATAAGCCTAGCAGATT<br>GCGGCAGTTGGCAAAATCAGCTATTACTAATA<br>ATTAAAAACTTTCGGAGCACATCACatgaaattggc<br>ggtctatagcaccaaacaatatgataaaaaatatttgcaacaagtcaacgaa<br>agcttcggcttcgaattggaattcttcgatttcttgttgaccgaaaaaaccgcg<br>aaaaccgcgaacggctgcgaagcggtctgcatcttcgtcaacgatgatgg<br>cagccgcccggtcttggaagaattgaaaaaacacggcgtcaaatatatcgc<br>gttgcgctgcgcgggcttcaacaacgtcgatttggatgcggcgaaagaatt<br>gggcttgaaagtcgtccgcgtcccggcgtatgatccggaagcggtcgcgg<br>aacacgcgatcggcatgatgatgaccttgaaccgccgcatccaccgcgcg<br>tatcaacgcacccgcgatgcgaacttcagcttggaaggcttgaccggcttc<br>accatgtatggcaaaaccgcgggcgtcatcggcaccggcaaaatcggcgt<br>cgcgatgttgcgcatcttgaaaggcttcggcatgcgcttgttggcgttcgatc<br>cgtatccgagcgcggcggcgttggaattgggcgtcgaatatgtcgatttgc<br>cgaccttgttcagcgaaagcgatgtcatcagcttgcactgcccgttgacccc<br>ggaaaactatcacttgttgaacgaagcggcgttcgaacaaatgaaaaacgg<br>cgtcatgatcgtcaacaccagccgcggcgcgttgatcgatagccaagcgg<br>cgatcgaagcgttgaaaaaccaaaaaatcggcagcttgggcatggatgtct<br>atgaaaacgaacgcgatttgttcttcgaagataaaagcaacgatgtcatcca<br>agatgatgtcttccgccgcttgagcgcgtgccacaacgtcttgttcaccggc<br>caccaagcgttcttgaccgcggaagcgttgaccagcatcagccaaaccac<br>cttgcaaaacttgagcaacttggaaaaaggcgaaacctgcccgaacgaatt<br>ggtctaaTAATAATTAAAAACTTTCGGAGCACATC<br>ACatgaacttgtggcaacaaaactatgatccggcgggcaacatctggttg<br>agcagcttgatcgcgagcttgccgatcttgttcttcttcttcgcgttgatcaaat<br>tgaaattgaaaggctatgtcgcggcgagctggaccgtcgcgatcgcgttgg<br>cggtcgcgttgttgttctataaaatgccggtcgcgaacgcgttggcgagcgt<br>cgtctatggcttcttctatggcttgtggccgatcgcgtggatcatcatcgcgg<br>cggtcttcgtctataaaatcagcgtcaaaaccggccaattcgatatcatccgc<br>agcagcatcttgagcatcaccccggatcaacgcttgcaaatgttgatcgtcg<br>gcttctgcttcggcgcgttcttggaaggcgcggcgggcttcggcgcgccg<br>gtcgcgatcaccgcggcgttgttggtcggcttgggcttcaaaccgttgtatg<br>cggcgggcttgtgcttgatcgtcaacaccgcgccggtcgcgttcggcgcg<br>atgggcatcccgatcttggtcgcgggccaagtcaccggcatcgatagcttc<br>gaaatcggccaaatggtcggccgccaattgccgttcatgaccatcatcgtct<br>tgttctggatcatggcgatcatggatggctggcgcggcatcaaagaaacct<br>ggccggcggtcgtcgtcgcgggcggcagcttcgcgatcgcgcaatatttg<br>agcagcaacttcatcggcccggaattgccggatatcatcagcagcttggtc<br>agcttgttgtgcttgaccttgttcttgaaacgctggcaaccggtccgcgtcttc<br>cgcttcggcgatttgggcgcgagccaagtcgatatgaccttggcgcacacc<br>ggctataccgcgggccaagtcttgcgcgcgttggacccgttcttgttcttga<br>ccgcgaccgtcaccttgtggagcatcccgccgttcaaagcgttgttcgcga<br>gcggcggcgcgttgtatgaatgggtcatcaacatcccggtcccgtatttgga<br>taaattggtcgcgcgcatgccgccggtcgtcagcgaagcgaccgcgtatg<br>cggcggtcttcaaattcgattggttcagcgcgaccggcaccgcgatcttgtt<br>cgcggcgttgttgagcatcgtctggttgaaaatgaaaccgagcgatgcgat<br>cagcaccttcggcagcaccttgaaagaattggcgttgccgatctatagcatc<br>ggcatggtcttggcgttcgcgttcatcagcaactatagcggcttgagcagca<br>ccttggcgttggcgttggcgcacaccggccacgcgttcaccttcttcagccc<br>gttcttgggctggtttgggcgtcttcttgaccggcagcgataccagcagcaac<br>gcgttgttcgcggcgttgcaagcgaccgcggcgaacaaatcggcgtcag<br>cgatttgttgttggtcgcggcgaacaccaccggcggcgtcaccggcaaaat<br>gatcagcccgcaaagcatcgcgatcgcgtcgcgcggcggtcggcttggtcg<br>gcaaagaaagcgatttgttccgcttcaccgtcaaacacagcttgatcttcacc<br>tgcatcgtcggcgtcatcaccaccttgcaagcgtatgtcttgacctg<br>gatgatcccgtaa |

The synthetic operon is then cloned and transformed into *M. methanica* as described above. Transformation is confirmed by resistance of the cells to antibiotic selection, and gene expression is confirmed by northern blot (to confirm RNA transcription), western blot, or ELISA methods (to confirm protein expression).

Growth on Lactate as a Sole Carbon Source. Recombinant *M. methanica* transformed with a vector containing the synthetic operon encoding genes for lactate utilization are inoculated into 100 mL shake flasks containing 20-50 mL NMS media, 1% sodium lactate and 10 ug/mL kanamycin. The flasks are then shaken continuously while being incubated at 30° C. Growth is confirmed by monitoring optical density of the culture over time. Note that because lactate is the only carbon source provided to the cells, all cell mass produced must have been derived from lactate.

The disclosure of U.S. provisional patent application Ser. No. 61/718,024 filed Oct. 24, 2012, is incorporated herein in its entirety.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A recombinant methanotrophic bacterium comprising at least one exogenous nucleic acid encoding an acetate utilization pathway component,
wherein acetate is not utilized as a carbon source by an unmodified parent methanotrophic bacterium;
wherein the encoded acetate utilization pathway component comprises an acetyl-CoA synthase and is expressed in a sufficient amount to permit growth of the recombinant methanotrophic bacterium on acetate as a primary carbon source; and
wherein the methanotrophic bacterium is selected from Methylococcus capsulatus, Methylomonas sp. 16A, Methylosinus trichosyorium, Methylosinus syorium, Methylocystis parvus, Methylomonas methanica, Methylomonas albus, Methylobacter capsulatus, Methylomonas flagellate, Methylacidiyhilum infernorum, Methylomicrobium alcaliyhilum, or Methylobacterium organophilum.

2. The recombinant methanotrophic bacterium of claim 1, further comprising at least one exogenous nucleic acid encoding an acetate transporter.

3. The recombinant methanotrophic bacterium of claim 1, wherein the parent methanotrophic bacterium is an obligate methanotrophic bacterium selected from Methylosinus trichosporium OB3b, Methylococcus capsulatus Bath, Methylomnonas sp. 16A, Methylosinus trichosporium, Methylosinus sporium, Methylomonas methanica, Methylomonas albus, Methylobacter capsulatus, Methylomonas-sp flasellata AJ-3670, Methylacidiphilum infernorum, or Methylomicrobium alcaliphilum.

4. The recombinant methanotrophic bacterium of claim 1, wherein the parent methanotrophic bacterium is facultative methanotrophic bacterium Methylobacterium organophilum.

5. The recombinant methanotrophic bacterium of claim 1, wherein the at least one exogenous nucleic acid encoding the acetyl-CoA synthase is codon optimized for the methanotrophic bacterium.

6. The recombinant methanotrophic bacterium of claim 2, wherein the exogenous nucleic acid encoding the acetate transporter has at least 80% sequence identity with a polynucleotide encoding a functionally active actP from Escherichia coli, a polynucleotide encoding a functionally active mctP from Rhizobium leguminosarum, or a polynucleotide encoding a functionally active mctC from Corynebacterium glutamicum.

7. The recombinant methanotrophic bacterium of claim 2, wherein the encoded acetate transporter comprises a polypeptide having at least 90% amino acid sequence identity with SEQ ID NO:75.

8. The recombinant methanotrophic bacterium of claim 2, wherein the exogenous nucleic acid encoding the acetate transporter comprises or consists of a polynucleotide sequence of SEQ ID NO:113, 118 or 123.

9. The recombinant methanotrophic bacterium of claim 2, wherein the exogenous nucleic acid encoding the acetate transporter and the exogenous nucleic acid encoding the acetyl-CoA synthase are codon optimized for the-host parent methanotrophic bacterium.

10. The recombinant methanotrophic bacterium of claim 9, wherein the parent methanotrophic bacterium is selected from Methylosinus trichosporium OB3b, Methylococcus capsulatus Bath, or Methylomonas methanica.

11. The recombinant methanotrophic bacterium of claim 1, wherein the exogenous nucleic acid encoding the acetyl-CoA synthase has at least 80% sequence identity with a polynucleotide encoding a functionally active acsA from Escherichia coil.

12. The recombinant methanotrophic bacterium of claim 1, wherein the exogenous nucleic acid encoding the acetyl-CoA synthase comprises or consists of a polynucleotide sequence of SEQ ID NO: 113, 116 or 121.

13. The recombinant methanotrophic bacterium of claim 1, wherein the encoded acetyl-CoA synthase comprises a polypeptide having at least 90% sequence identity with SEQ ID NO: 74.

14. The recombinant methanotrophic bacterium of claim 2, wherein the exogenous nucleic acid encoding the acetate transporter and the exogenous nucleic acid encoding the acetyl-CoA synthase are a single nucleic acid molecule.

15. The recombinant methanotrophic bacterium of claim 14, wherein the exogenous nucleic acid encoding: (a) the acetate transporter of the single nucleic acid molecule is operably linked to a mdh promoter or a hps promoter: (b) the acetyl-CoA synthase of the single nucleic acid molecule is operably linked to a mdh promoter or a hps promoter; or (c) the acetate transporter and the acetyl-CoA synthase comprise an operon in the single nucleic acid molecule, wherein the operon is operably linked to a mdh promoter or a hps promoter.

16. The recombinant methanotrophic bacterium of claim 15, wherein the mdh promoter comprises or consists of a polynucleotide sequence of SEQ ID NO: 110, and/or the hps promoter comprises or consists of a polynucleotide sequence of SEQ ID NO: 120.

17. The recombinant methanotrophic bacterium of claim 14, wherein the exogenous nucleic acid encoding the acetate transporter and the exogenous nucleic acid encoding the acetyl-CoA synthase are present on the single nucleic acid molecule as an operon.

18. The recombinant methanotrophic bacterium of claim 17, wherein the operon encoding the acetate transporter and the acetyl-CoA synthase are codon optimized for the parent methanotrophic bacterium.

19. The recombinant methanotrophic bacterium of claim 18, wherein the parent methanotrophic bacterium is Melhylosinus trichosporium OB3b, Methylococcus capsutalus Bath, or Methylomonas methanica.

20. The recombinant methanotrophic bacterium of claim 17, wherein the operon encoding the acetate transporter and the acetyl-CoA synthase comprises or consists of a polynucleotide sequence of SEQ ID NO: 114, 119 or 124.

21. A recombinant methanotrophic bacterium, comprising a methanotrophic bacterium containing at least one exogenous nucleic acid encoding an acetate utilization pathway component,
wherein acetate is not utilized as a carbon source by an unmodified parent methanotrophic bacterium;
wherein the encoded acetate utilization pathway component comprises an acetate kinase and is expressed in a sufficient amount to permit growth of the recombinant methanotrophic bacterium on acetate as a primary carbon source; and
wherein the methanotrophic bacterium is selected from Methylococcus capsulatus, Methylomonas sp. 16A, Methylosinus trichosporium, Methylosinus sporium, Methylocystis parvus, Methylomonas methanica, Methylomonas albus, Methylobacter capsulatus, Methylomonas flagellata, Methylacidiphilum infernorum, Methylomicrobium alcaliphilum, or Methylobacterium organophilum.

22. The recombinant methanotrophic bacterium of claim 21, further comprising at least one exogenous nucleic acid encoding a phosphotransacetylase.

23. The recombinant methanotrophic bacterium of claim 21, further comprising at least one exogenous nucleic acid encoding an acetate transporter.

24. The recombinant methanotrophic bacterium of claim 21, wherein the parent methanotrophic bacterium is an obligate methanotrophic bacterium selected from *Methylosinus trichosporium* OB3b, *Methylococcus capsulatus* Bath, *Methylomonas sp.* 16A, *Methylosinus trichosporium*, *Methylosinus sporium*, *Methylomonas methanica*, *Methylomonas albus*, *Methylobacter capsulatus*, *Methylomonas flagellata* AJ-3670, *Methylacidiphilum infernorum*, or *Methylomicrobium alcaliphilum*.

25. The recombinant methanotrophic bacterium of claim 21, wherein the exogenous nucleic acid encoding the acetate kinase is codon optimized for the parent methanotrophic bacterium.

26. The recombinant methanotrophic bacterium of claim 22, wherein the exogenous nucleic acid encoding the acetate kinase and the exogenous nucleic acid encoding the phosphotransacetylase are codon optimized for the parent methanotrophic bacterium.

27. The recombinant methanotrophic bacterium of claim 26, wherein the parent methanotrophic bacterium is selected from *Methylosinus trichosporium* OB3b, *Methylococcus capsulatus* Bath, or *Methylomonas methanica*.

28. The recombinant methanotrophic bacterium of claim 26, wherein the at least one exogenous nucleic acid encodes an acetate transporter, wherein the acetate transporter encoding nucleic acid is codon optimized for the parent methanotrophic bacterium.

29. The recombinant methanotrophic bacterium of claim 22, wherein the exogenous nucleic acid encoding the acetate kinase and the exogenous nucleic acid encoding the phosphotransacetylase are a single nucleic acid molecule.

30. The recombinant methanotrophic bacterium of claim 29, wherein the exogenous nucleic acid encoding: (a) the acetate kinase of the single nucleic acid molecule is operably linked to a mdh promoter or a hps promoter; (b) the phosphotransacetylase of the single nucleic acid molecule is operably linked to a mdh promoter or a hps promoter; or (c) the acetate kinase and the phosphotransacetylase comprise an operon in the single nucleic acid molecule, wherein the operon is operably linked to a mdh promoter or a hps promoter.

31. The recombinant methanotrophic bacterium of claim 24, wherein the mdh promoter comprises or consists of a polynucleotide sequence of SEQ ID NO:110, and/or the hps promoter comprises or consists of a polynucleotide sequence of SEQ ID NO:120.

32. The recombinant methanotrophic bacterium of claim 29, wherein the exogenous nucleic acid encoding the acetate kinase and the exogenous nucleic acid encoding the phosphotransacetylase are present on the single nucleic acid molecule as an operon.

33. The recombinant methanotrophic bacterium of claim 32, wherein the operon encoding the acetate kinase and the phosphotransacetylase are codon optimized for the parent methanotrophic bacterium.

34. The recombinant methanotrophic bacterium of claim 32, wherein the parent methanotrophic bacterium is selected from *Methylosinus trichosporium* OB3b, *Methylococcus capsulatus* Bath, or *Methylomonas methanica*.

* * * * *

SEQUENCE LISTING

```
<160> NUMBER OF SEQ ID NOS: 139

<210> SEQ ID NO 1
<211> LENGTH: 281
<212> TYPE: PRT
<213> ORGANISM: Escherichia coli

<400> SEQUENCE: 1

Met Ser Gln Thr Ser Thr Leu Lys Gly Gln Cys Ile Ala Glu Phe Leu
 1               5                  10                  15

Gly Thr Gly Leu Leu Ile Phe Phe Gly Val Gly Cys Val Ala Ala Leu
                20                  25                  30

Lys Val Ala Gly Ala Ser Phe Gly Gln Trp Glu Ile Ser Val Ile Trp
            35                  40                  45

Gly Leu Gly Val Ala Met Ala Ile Tyr Leu Thr Ala Gly Val Ser Gly
        50                  55                  60

Ala His Leu Asn Pro Ala Val Thr Ile Ala Leu Trp Leu Phe Ala Cys
65                  70                  75                  80

Phe Asp Lys Arg Lys Val Ile Pro Phe Ile Val Ser Gln Val Ala Gly
                85                  90                  95

Ala Phe Cys Ala Ala Ala Leu Val Tyr Gly Leu Tyr Tyr Asn Leu Phe
            100                 105                 110

Phe Asp Phe Glu Gln Thr His His Ile Val Arg Gly Ser Val Glu Ser
        115                 120                 125

Val Asp Leu Ala Gly Thr Phe Ser Thr Tyr Pro Asn Pro His Ile Asn
    130                 135                 140

Phe Val Gln Ala Phe Ala Val Glu Met Val Ile Thr Ala Ile Leu Met
145                 150                 155                 160

Gly Leu Ile Leu Ala Leu Thr Asp Asp Gly Asn Gly Val Pro Arg Gly
                165                 170                 175

Pro Leu Ala Pro Leu Leu Ile Gly Leu Leu Ile Ala Val Ile Gly Ala
            180                 185                 190

Ser Met Gly Pro Leu Thr Gly Phe Ala Met Asn Pro Ala Arg Asp Phe
        195                 200                 205

Gly Pro Lys Val Phe Ala Trp Leu Ala Gly Trp Gly Asn Val Ala Phe
    210                 215                 220

Thr Gly Gly Arg Asp Ile Pro Tyr Phe Leu Val Pro Leu Phe Gly Pro
225                 230                 235                 240
```

```
Ile Val Gly Ala Ile Val Gly Ala Phe Ala Tyr Arg Lys Leu Ile Gly
                245                 250                 255

Arg His Leu Pro Cys Asp Ile Cys Val Val Glu Glu Lys Glu Thr Thr
            260                 265                 270

Thr Pro Ser Glu Gln Lys Ala Ser Leu
        275                 280

<210> SEQ ID NO 2
<211> LENGTH: 271
<212> TYPE: PRT
<213> ORGANISM: Yersinia mollaretii

<400> SEQUENCE: 2

Met Asn Asp Ser Leu Lys Ala Gln Cys Ile Ala Glu Phe Leu Gly Thr
1               5                   10                  15

Gly Leu Phe Leu Phe Phe Gly Ile Ser Cys Leu Ala Ala Leu Lys Val
            20                  25                  30

Ala Gly Ala Ser Phe Gly Leu Trp Glu Ile Cys Ile Val Trp Gly Leu
        35                  40                  45

Gly Ile Ser Leu Ala Val Tyr Leu Thr Ala Gly Ile Ser Gly Ala His
    50                  55                  60

Leu Asn Pro Ala Ile Thr Ile Ala Leu Trp Leu Phe Ala Cys Phe Pro
65                  70                  75                  80

Gly Arg Lys Val Ile Pro Tyr Ser Ile Ala Gln Val Ala Gly Ala Phe
                85                  90                  95

Gly Gly Ala Ala Leu Ser Tyr Met Leu Tyr His Asn Leu Phe Thr Asp
            100                 105                 110

Phe Glu Thr Ala His Gln Met Val Arg Gly Ser Leu Glu Ser Leu Gln
        115                 120                 125

Leu Ala Ser Ile Phe Ser Thr Phe Pro Ser Pro Ala Ile Ser Val Trp
    130                 135                 140

Gln Ala Ala Phe Val Glu Ile Ile Thr Ser Ile Leu Met Gly Leu
145                 150                 155                 160

Ile Met Ala Leu Thr Asp Asp Gly Asn Gly Val Pro Arg Gly Ala Leu
                165                 170                 175

Gly Pro Leu Leu Ile Gly Ile Leu Val Ala Val Ile Gly Ala Ser Thr
            180                 185                 190

Gly Pro Leu Thr Gly Phe Ala Met Asn Pro Ala Arg Asp Phe Gly Pro
        195                 200                 205

Lys Leu Phe Thr Phe Phe Ala Gly Trp Gly Lys Ile Ser Met Thr Gly
    210                 215                 220

Gly Arg Asp Ile Pro Tyr Phe Ile Ile Pro Ile Val Ala Pro Ile Ile
225                 230                 235                 240

Gly Ala Cys Leu Gly Ala Ala Val Tyr Arg Phe Phe Ile Gly Lys Asn
                245                 250                 255

Leu Ala Cys Asn Thr Cys Lys Leu Glu Asp Glu Glu Ala Ala Asn
            260                 265                 270

<210> SEQ ID NO 3
<211> LENGTH: 284
<212> TYPE: PRT
<213> ORGANISM: Vibrio cholerae

<400> SEQUENCE: 3

Met Asn Gln Thr Lys Gln His Thr Leu Leu Gly Gln Cys Ile Ala Glu
1               5                   10                  15
```

```
Phe Ile Gly Thr Gly Leu Leu Ile Phe Gly Val Gly Cys Val Ala
             20                  25                  30

Ala Leu Val Leu Ala Gly Ala Gln Phe Gly Gln Trp Glu Ile Ser Ile
         35                  40                  45

Val Trp Gly Phe Gly Val Ser Ile Ala Ile Tyr Cys Thr Ala Gly Val
 50                  55                  60

Ser Gly Ala His Ile Asn Pro Ala Val Thr Ile Ala Leu Ala Ala Phe
 65                  70                  75                  80

His Gly Phe Asp Lys Ala Lys Val Leu Pro Tyr Ile Ile Ser Gln Val
             85                  90                  95

Ala Gly Ala Phe Cys Ala Ala Leu Val Tyr Ser Leu Tyr Ser Asn
            100                 105                 110

Leu Phe Thr Asp Tyr Glu Ile Ala His Asn Phe Val Arg Ser Ser Gln
            115                 120                 125

Glu Ala Leu Ala Thr Ala Gly Ile Phe Ser Thr Tyr Pro His Ala Ser
            130                 135                 140

Leu Ser Phe Met Gly Ala Met Ala Val Glu Phe Thr Ile Thr Ala Val
145                 150                 155                 160

Leu Met Phe Ala Ile Leu Ala Leu Gly Asp Glu Asn Asn Gly Ala His
                165                 170                 175

Arg Asn Ala Met Asn Pro Leu Leu Ile Gly Ile Leu Ile Ala Val Ile
            180                 185                 190

Gly Gly Ser Leu Gly Pro Leu Thr Gly Phe Ala Met Asn Pro Ala Arg
            195                 200                 205

Asp Phe Gly Pro Lys Leu Phe Ala Tyr Phe Ala Gly Trp Asp Tyr Ala
            210                 215                 220

Leu Thr Gly Ala Lys Glu Ile Pro Tyr Phe Ile Val Pro Ile Val Ala
225                 230                 235                 240

Pro Ile Leu Gly Ala Cys Phe Gly Ala Trp Ala Tyr Pro Lys Phe Ile
                245                 250                 255

Ala Ala Tyr Leu Pro Lys Thr Gly Thr Gly Cys Thr Ile Pro Asn Gln
            260                 265                 270

Cys Asp Thr Ala Glu Glu Ser Glu Glu Ala Arg Ala
            275                 280

<210> SEQ ID NO 4
<211> LENGTH: 284
<212> TYPE: PRT
<213> ORGANISM: Vibrio harveyi

<400> SEQUENCE: 4

Met Thr Thr Asn Lys His Pro Ser Leu Leu Gly Glu Cys Leu Ala Glu
  1               5                  10                  15

Phe Ile Gly Thr Gly Leu Leu Ile Phe Gly Val Gly Cys Val Ala
             20                  25                  30

Ala Leu Val Leu Thr Gly Ala Gln Phe Gly Gln Trp Glu Ile Ser Ile
         35                  40                  45

Val Trp Gly Phe Gly Val Ala Ile Ala Ile Tyr Cys Thr Ala Gly Val
 50                  55                  60

Ser Gly Ala His Ile Asn Pro Ala Val Thr Ile Ala Leu Ala Met Phe
 65                  70                  75                  80

His Gly Phe Asp Lys Ala Lys Val Val Pro Tyr Ile Ile Ala Gln Met
             85                  90                  95

Leu Gly Ala Phe Cys Ser Ala Ala Leu Val Tyr Ser Leu Tyr Ser Asn
            100                 105                 110
```

```
Leu Phe Thr Asp Tyr Glu Ile Ala His Asn Phe Val Arg Ser Ser Gln
            115                 120                 125

Asp Ala Leu Ala Thr Ala Gly Ile Phe Ser Thr Tyr Pro His Ala Ser
        130                 135                 140

Leu Ser Phe Phe Gly Ala Phe Ala Val Glu Phe Val Ile Thr Ala Val
145                 150                 155                 160

Leu Met Phe Ala Ile Leu Ala Leu Gly Asp Glu Asn Asn Gly Ala Pro
                165                 170                 175

Arg Gly Ala Met Asn Pro Leu Leu Ile Gly Ile Leu Ile Ala Val Ile
                180                 185                 190

Gly Gly Ser Leu Gly Pro Leu Thr Gly Phe Ala Met Asn Pro Ala Arg
            195                 200                 205

Asp Phe Gly Pro Lys Leu Phe Ala Tyr Phe Ala Gly Trp Asp Tyr Ala
        210                 215                 220

Leu Thr Gly Ala Arg Glu Ile Pro Tyr Phe Ile Val Pro Ile Leu Ala
225                 230                 235                 240

Pro Ile Ala Gly Ala Cys Phe Gly Gly Trp Leu Tyr Pro Lys Ala Ile
                245                 250                 255

Ala Ala Tyr Leu Pro Gln Gln Gly His Gly Cys Thr Ile Pro Asn Gln
                260                 265                 270

Cys Glu Thr Glu Glu Glu Ala Glu Gln Ala Gln Ala
            275                 280

<210> SEQ ID NO 5
<211> LENGTH: 264
<212> TYPE: PRT
<213> ORGANISM: Haemophilus influenzae

<400> SEQUENCE: 5

Met Asp Lys Ser Leu Lys Ala Asn Cys Ile Gly Glu Phe Leu Gly Thr
1               5                   10                  15

Ala Leu Leu Ile Phe Phe Gly Val Gly Cys Val Ala Ala Leu Lys Val
                20                  25                  30

Ala Gly Ala Ser Phe Gly Leu Trp Glu Ile Ser Ile Met Trp Gly Met
            35                  40                  45

Gly Val Ala Leu Ala Val Tyr Ala Thr Ala Gly Leu Ser Gly Ala His
        50                  55                  60

Leu Asn Pro Ala Val Thr Ile Ala Leu Trp Lys Phe Ala Cys Phe Asp
65                  70                  75                  80

Gly Lys Lys Val Ile Pro Tyr Ile Ile Ser Gln Met Leu Gly Ala Phe
                85                  90                  95

Phe Ala Ala Ala Leu Val Tyr Ala Leu Tyr Arg Asn Val Phe Ile Asp
                100                 105                 110

Tyr Glu Thr Ala His Asn Ile Val Arg Gly Thr Gln Glu Ser Leu Ser
            115                 120                 125

Leu Ala Gly Thr Phe Ser Thr Tyr Pro His Pro Ser Leu Ser Ile Gly
        130                 135                 140

Gly Ala Phe Ala Val Glu Phe Val Ile Thr Ala Ile Leu Met Ala Leu
145                 150                 155                 160

Ile Met Ala Leu Thr Asp Asp Gly Asn Gly Val Pro Arg Gly Pro Leu
                165                 170                 175

Ala Pro Leu Leu Ile Gly Ile Leu Ile Ala Val Ile Gly Gly Ala Met
                180                 185                 190

Gly Pro Leu Thr Gly Phe Ala Met Asn Pro Ala Arg Asp Phe Gly Pro
```

```
            195                 200                 205
Lys Phe Phe Ala Tyr Leu Ala Gly Trp Gly Glu Leu Ala Leu Thr Gly
    210                 215                 220

Gly Arg Glu Ile Pro Tyr Phe Ile Val Pro Met Val Ala Pro Val Leu
225                 230                 235                 240

Gly Ala Leu Ala Gly Ala Trp Leu Tyr Lys Lys Ala Ile Gly Gly Asn
                245                 250                 255

Leu Pro Cys Asn Cys Gly Cys Glu
            260

<210> SEQ ID NO 6
<211> LENGTH: 277
<212> TYPE: PRT
<213> ORGANISM: Erwinia pyrifoliae

<400> SEQUENCE: 6

Met Ser Tyr Ala Thr Ser Thr Leu Lys Gly Gln Cys Ile Ala Glu Phe
1               5                   10                  15

Leu Gly Thr Ala Thr Ile Ile Phe Phe Gly Ala Gly Cys Val Ala Ala
                20                  25                  30

Met Lys Val Ala Gly Ser Ser Phe Gly Gln Trp Glu Ile Ser Ile Val
            35                  40                  45

Trp Gly Leu Ala Val Ala Met Ala Val Tyr Leu Thr Ala Gly Ile Ser
        50                  55                  60

Gly Ala His Leu Asn Pro Ala Val Ser Val Ala Met Trp Leu Phe Ala
65                  70                  75                  80

Asn Phe Asp Gly Arg Lys Val Ile Pro Tyr Ala Leu Ala Gln Val Ala
                85                  90                  95

Gly Ala Phe Cys Ser Ala Ala Leu Val Tyr Gly Leu Tyr His Asn Leu
            100                 105                 110

Phe Leu Asp Tyr Glu Gln Thr His Gln Met Val Arg Gly Ser Val Glu
        115                 120                 125

Ser Leu Asp Leu Ala Gly Val Phe Ser Thr Tyr Pro Asn Pro His Ile
130                 135                 140

Ser Val Gly Gln Ala Phe Leu Val Glu Leu Thr Ile Thr Ala Ile Met
145                 150                 155                 160

Met Ala Leu Ile Met Ala Leu Thr Asp Asp Gly Asn Gly Leu Pro Arg
                165                 170                 175

Gly Pro Ile Ala Pro Leu Leu Ile Gly Leu Leu Ile Ala Thr Ile Gly
            180                 185                 190

Ala Ser Met Gly Pro Leu Thr Gly Phe Ala Leu Asn Pro Ala Arg Asp
        195                 200                 205

Phe Gly Pro Lys Leu Phe Ala Trp Val Ala Gly Trp Gly Ser Val Ala
    210                 215                 220

Phe Thr Gly Gly Arg Asp Ile Pro Tyr Phe Leu Val Pro Val Phe Gly
225                 230                 235                 240

Pro Leu Leu Gly Ala Ser Leu Gly Ala Phe Gly Tyr Arg Ala Leu Ile
                245                 250                 255

Ala Ser Asn Leu Pro Gly Glu Val Val Glu Lys His Asp Lys Pro Ala
            260                 265                 270

Ser Arg Ala Glu Gln
        275

<210> SEQ ID NO 7
<211> LENGTH: 279
```

<212> TYPE: PRT
<213> ORGANISM: Artificial Sequence
<220> FEATURE:
<223> OTHER INFORMATION: Acinetobacter sp. ATCC 27244

<400> SEQUENCE: 7

Met Ser Arg Ser Glu Pro Thr Leu Leu Gly Gln Cys Val Ala Glu Phe
1               5                   10                  15

Phe Ala Thr Ala Ile Phe Leu Ser Phe Gly Ile Gly Val Val Ala Ala
            20                  25                  30

Leu Lys Leu Ala Gly Ala Asp Leu Gly Leu Trp Glu Ile Ser Ile Val
        35                  40                  45

Trp Gly Leu Ala Val Ala Leu Ala Val Tyr Leu Ser Ala Gly Ile Ser
    50                  55                  60

Gly Ala His Leu Asn Pro Ala Val Thr Ile Ala Leu Ala Leu Phe Ala
65                  70                  75                  80

Gly Phe Asp Lys Arg Lys Val Pro Phe Tyr Ile Ile Ala Gln Val Ala
                85                  90                  95

Gly Ala Ala Thr Gly Ala Leu Met Val Tyr Gly Leu Tyr Ser Ser Leu
            100                 105                 110

Phe Leu Asp Phe Glu Gln Thr His His Met Val Arg Gly Ser Val Glu
        115                 120                 125

Ser Leu Glu Leu Ala Gly Ile Phe Ser Thr Tyr Pro His His Leu Leu
    130                 135                 140

Ser Leu Gly Gln Ala Phe Met Val Glu Met Phe Ile Thr Met Leu Leu
145                 150                 155                 160

Leu Trp Leu Ile Met Ala Ile Gly Asp Asp Ser Asn Gly Leu Pro Arg
                165                 170                 175

Gly Pro Leu Ala Pro Ile Leu Val Gly Leu Leu Val Ala Val Ile Gly
            180                 185                 190

Ala Ser Phe Gly Pro Leu Thr Gly Phe Ala Met Asn Pro Ala Arg Asp
        195                 200                 205

Phe Gly Pro Lys Ile Val Ala Tyr Phe Ser Gly Trp Gly Pro Val Ala
    210                 215                 220

Phe Thr Gly Gly Arg Asp Ile Pro Tyr Phe Ile Val Pro Ile Leu Ala
225                 230                 235                 240

Pro Ile Val Gly Ala Cys Leu Gly Val Val Gly Tyr Lys Leu Phe Phe
                245                 250                 255

Val His Phe Leu Leu Ser Asn Lys Val Glu Glu Ser Arg Ser Gly Glu
            260                 265                 270

Lys Gln Ile Ser Glu Met Gln
        275

<210> SEQ ID NO 8
<211> LENGTH: 282
<212> TYPE: PRT
<213> ORGANISM: Aeromonas hydrophila

<400> SEQUENCE: 8

Met Ser Ile Gln Arg Pro Asn Thr Leu Leu Gly Glu Cys Ile Ala Glu
1               5                   10                  15

Phe Ile Gly Thr Gly Leu Leu Ile Phe Phe Gly Val Gly Cys Val Ala
            20                  25                  30

Ala Leu Val Leu Ala Gly Ala Asn Phe Gly Gln Trp Glu Ile Ser Ile
        35                  40                  45

Thr Trp Gly Leu Gly Val Ala Ile Ala Ile Tyr Val Thr Gly Gly Ile

```
            50                  55                  60
Ser Gly Ala His Leu Asn Pro Ala Val Thr Leu Ala Leu Met Thr Phe
 65                  70                  75                  80

Cys Gly Phe Asp Lys Arg Lys Val Val Pro Tyr Ile Ile Ala Gln Val
                 85                  90                  95

Ala Gly Ala Phe Cys Phe Ala Ala Leu Val Tyr Phe Leu Tyr Gly Asn
            100                 105                 110

Leu Phe Thr Gln Trp Glu Val Thr His Asn Val Val Arg Gly Ser Val
            115                 120                 125

Glu Ser Leu Gly Ser Ala Gly Ile Phe Ser Thr Tyr Pro Asn Ala Leu
            130                 135                 140

Leu Ser Asn Met Gln Ala Phe Ala Val Glu Met Val Ile Thr Ala Val
145                 150                 155                 160

Leu Met Leu Gly Ile Met Ala Leu Gly Asp Asn Asn Asn Gly Ala Pro
                165                 170                 175

Lys Gly Phe Ala Ala Ala Leu Leu Ile Gly Ile Leu Ile Ala Val Ile
                180                 185                 190

Gly Ala Ser Leu Gly Pro Leu Thr Gly Phe Ala Met Asn Pro Ala Arg
                195                 200                 205

Asp Phe Gly Pro Lys Leu Phe Ala Phe Leu Ala Gly Trp Gly Asp Val
            210                 215                 220

Ala Met Thr Gly Gly Arg Asp Asn Pro Tyr Phe Trp Val Pro Ile Leu
225                 230                 235                 240

Gly Pro Ile Val Gly Ala Gln Ile Gly Thr Ala Leu Tyr Val Lys Val
                245                 250                 255

Leu Ala Pro Cys Val Pro Gly Asn Arg Val Ala Thr Glu Glu Ala Ala
            260                 265                 270

Lys Leu Ser Asn Lys Glu Glu Ala Ala Ala
            275                 280

<210> SEQ ID NO 9
<211> LENGTH: 264
<212> TYPE: PRT
<213> ORGANISM: Salmonella enterica

<400> SEQUENCE: 9

Met Asn Asp Ser Leu Lys Ala Gln Cys Gly Ala Glu Phe Leu Gly Thr
 1               5                  10                  15

Gly Leu Phe Leu Phe Phe Gly Ile Gly Cys Leu Ser Ala Leu Lys Val
            20                  25                  30

Ala Gly Ala Ser Leu Gly Leu Trp Glu Ile Cys Ile Ile Trp Gly Leu
            35                  40                  45

Gly Ile Ser Leu Ala Val Tyr Leu Thr Ala Gly Ile Ser Gly Gly His
            50                  55                  60

Leu Asn Pro Ala Val Thr Ile Ala Leu Trp Leu Phe Ala Cys Phe Pro
 65                  70                  75                  80

Lys Gln Lys Val Leu Pro Tyr Ile Ile Ala Gln Phe Ala Gly Ala Phe
                 85                  90                  95

Gly Gly Ala Leu Leu Ala Tyr Val Leu Tyr Ser Ser Leu Phe Thr Glu
            100                 105                 110

Phe Glu Thr Ala His His Met Val Arg Gly Ser Val Glu Ser Leu Gln
            115                 120                 125

Leu Ala Ser Ile Phe Ser Thr Tyr Pro Ala Ala Ala Leu Asn Val Trp
            130                 135                 140
```

```
Gln Ala Ala Leu Val Glu Val Val Ile Thr Ser Ile Leu Met Gly Met
145                 150                 155                 160

Ile Met Ala Leu Thr Asp Asp Gly Asn Gly Ile Pro Lys Gly Pro Leu
            165                 170                 175

Ala Pro Leu Leu Ile Gly Ile Leu Val Ala Val Ile Gly Ala Ser Thr
            180                 185                 190

Gly Pro Leu Thr Gly Phe Ala Met Asn Pro Ala Arg Asp Phe Gly Pro
            195                 200                 205

Lys Leu Phe Thr Trp Leu Ala Gly Trp Gly Asn Met Ala Met Ser Gly
            210                 215                 220

Gly Arg Glu Ile Pro Tyr Phe Ile Val Pro Ile Val Ala Pro Val Ile
225                 230                 235                 240

Gly Ala Cys Ala Gly Ala Ala Ile Tyr Arg Tyr Phe Ile Gly Lys Asn
            245                 250                 255

Leu Pro Cys Asn Arg Cys Glu Leu
            260
```

```
<210> SEQ ID NO 10
<211> LENGTH: 283
<212> TYPE: PRT
<213> ORGANISM: Pseudomonas putida

<400> SEQUENCE: 10

Met Thr Thr Ala Leu Arg Gln Pro Thr Leu Ser Ser Gln Cys Leu Ala
1               5                   10                  15

Glu Phe Leu Gly Thr Ala Leu Leu Ile Phe Phe Gly Thr Gly Cys Val
            20                  25                  30

Ala Ala Leu Lys Val Ala Gly Ala Ser Phe Gly Leu Trp Glu Ile Ser
            35                  40                  45

Ile Ile Trp Gly Val Gly Val Ser Met Ala Ile Tyr Leu Thr Ala Gly
        50                  55                  60

Ile Ser Gly Ala His Leu Asn Pro Ala Val Ser Ile Ala Leu Thr Leu
65                  70                  75                  80

Phe Ala Gly Phe Asp Lys Arg Lys Leu Pro Phe Tyr Met Leu Ala Gln
                85                  90                  95

Val Cys Gly Ala Phe Cys Gly Ala Ala Leu Val Tyr Thr Leu Tyr Ser
            100                 105                 110

Asn Leu Phe Phe Asp Phe Glu Gln Thr His Ala Met Leu Arg Gly Ser
            115                 120                 125

Glu Gly Ser Leu Glu Leu Ala Ser Val Phe Ser Thr Tyr Pro His Pro
130                 135                 140

Ser Leu Ser Thr Ser Gln Ala Phe Leu Val Glu Val Val Ile Thr Ala
145                 150                 155                 160

Ile Leu Met Ala Val Ile Met Ala Leu Thr Asp Asp Asn Asn Gly Leu
            165                 170                 175

Pro Arg Gly Ala Met Ala Pro Leu Leu Ile Gly Leu Leu Ile Ala Val
            180                 185                 190

Ile Gly Ser Ala Met Gly Pro Leu Thr Gly Phe Ala Met Asn Pro Ala
            195                 200                 205

Arg Asp Phe Gly Pro Lys Leu Met Thr Phe Leu Ala Gly Trp Gly Glu
            210                 215                 220

Ile Ala Phe Thr Gly Gly Arg Asp Ile Pro Tyr Phe Leu Val Pro Val
225                 230                 235                 240

Phe Ala Pro Ile Leu Gly Ala Cys Leu Gly Ala Ala Ser Tyr Arg Gly
            245                 250                 255
```

Leu Ile Ala Arg Asn Leu Pro Met Ala Pro Ala Ala Thr Pro Glu Thr
        260                 265                 270

Asn Asp Ile Arg Gln Gly Asp Thr Gln Ala Asn
        275                 280

<210> SEQ ID NO 11
<211> LENGTH: 265
<212> TYPE: PRT
<213> ORGANISM: Xenorhabdus nematophila

<400> SEQUENCE: 11

Met Ser Gln Thr Thr Thr Pro Thr Leu Ser Gly Gln Cys Ile Ser Glu
1               5                   10                  15

Phe Met Gly Thr Thr Leu Leu Val Phe Phe Gly Leu Gly Cys Val Ala
            20                  25                  30

Ala Ala Arg Leu Ala Gly Ala Gln Leu Gly Leu Trp Glu Ile Ser Ile
        35                  40                  45

Ile Trp Gly Phe Gly Val Ala Leu Ala Val Tyr Leu Thr Ala Gly Ile
    50                  55                  60

Ser Gly Ala His Leu Asn Pro Ala Val Thr Ile Ala Leu Cys Leu Phe
65                  70                  75                  80

Ala Asn Phe Asp Arg Lys Lys Val Leu Pro Tyr Ile Ile Ala Gln Met
                85                  90                  95

Phe Gly Gly Phe Ala Ala Ala Ala Ile Val Tyr Met Met Tyr Tyr Asn
            100                 105                 110

Leu Phe Leu Asp Tyr Glu Gln Val His Gly Ile Val Arg Gly Ser Gln
        115                 120                 125

Glu Ser Leu Phe Thr Ala Gly Val Phe Ser Thr Tyr Pro Ala Thr Gln
    130                 135                 140

Ile Ser Val Leu Gln Ala Phe Ile Val Glu Val Ile Ile Ala Ala Ile
145                 150                 155                 160

Leu Leu Cys Leu Ile Leu Ala Leu Thr Asp Asp Gly Asn Gly Ile Pro
                165                 170                 175

Lys Gly Pro Leu Ala Pro Leu Leu Ile Gly Ile Leu Ile Ala Val Ile
            180                 185                 190

Gly Gly Ser Phe Gly Pro Leu Thr Gly Phe Ala Leu Asn Pro Ala Arg
        195                 200                 205

Asp Phe Gly Pro Lys Leu Val Ala Tyr Phe Ala Gly Trp Gly Asp Ile
    210                 215                 220

Ala Leu Thr Gly Gly Arg Asp Ile Pro Tyr Cys Leu Val Pro Leu Ala
225                 230                 235                 240

Ala Pro Ile Val Gly Ala Ile Leu Gly Ala Phe Gly Tyr Arg Lys Leu
                245                 250                 255

Ile Thr Arg His Leu Pro Arg Glu Val
            260                 265

<210> SEQ ID NO 12
<211> LENGTH: 279
<212> TYPE: PRT
<213> ORGANISM: Pseudomonas aeruginosa

<400> SEQUENCE: 12

Met Thr Thr Ala Ala Pro Thr Pro Ser Leu Phe Gly Gln Cys Leu Ala
1               5                   10                  15

Glu Phe Leu Gly Thr Ala Leu Leu Ile Phe Phe Gly Thr Gly Cys Val
            20                  25                  30

Ala Ala Leu Lys Val Ala Gly Ala Ser Phe Gly Leu Trp Glu Ile Ser
            35                  40                  45

Ile Ile Trp Gly Val Gly Val Ser Met Ala Ile Tyr Leu Ser Ala Gly
 50                  55                  60

Val Ser Gly Ala His Leu Asn Pro Ala Val Ser Ile Ala Leu Trp Leu
 65                  70                  75                  80

Phe Ala Gly Phe Glu Gly Arg Lys Leu Pro Phe Tyr Ile Thr Ala Gln
                    85                  90                  95

Val Ala Gly Ala Phe Cys Ala Ala Leu Val Tyr Thr Leu Tyr Ser
                    100                 105                 110

Ser Leu Phe Ile Glu Phe Glu Gln Ala Gln Asn Ile Val Arg Gly Ser
            115                 120                 125

Gln Asp Ser Leu Ala Leu Ala Ser Val Phe Ser Thr Tyr Pro His Pro
130                 135                 140

Ala Leu Ser Val Gly Gln Ala Phe Leu Val Glu Val Ile Thr Ala
145                 150                 155                 160

Ile Leu Met Ala Val Ile Met Ala Leu Thr Asp Asp Gly Asn Gly Leu
                    165                 170                 175

Pro Arg Gly Pro Leu Ala Pro Leu Leu Ile Gly Leu Leu Ile Ala Val
                    180                 185                 190

Ile Gly Ser Ala Met Gly Pro Leu Thr Gly Phe Ala Met Asn Pro Ala
            195                 200                 205

Arg Asp Phe Gly Pro Lys Leu Met Thr Tyr Leu Ala Gly Trp Gly Pro
210                 215                 220

Ile Ala Phe Thr Gly Gly Arg Glu Ile Pro Tyr Phe Leu Val Pro Ile
225                 230                 235                 240

Phe Ala Pro Ile Leu Gly Ala Cys Leu Gly Ala Gly Tyr Arg Val
                    245                 250                 255

Leu Ile Ala Arg His Leu Pro Ser Ala Ala Pro Ala Glu Ala Glu
                    260                 265                 270

Pro Glu Lys Val Arg Ala Ser
            275

<210> SEQ ID NO 13
<211> LENGTH: 285
<212> TYPE: PRT
<213> ORGANISM: Pseudomonas syringae

<400> SEQUENCE: 13

Met Thr Ile Ala Leu Lys Gln Pro Thr Leu Thr Gly Gln Cys Val Ala
 1               5                  10                  15

Glu Phe Leu Gly Thr Ala Leu Met Ile Phe Phe Gly Thr Gly Cys Val
                    20                  25                  30

Ala Ala Leu Lys Val Ala Gly Ala Thr Phe Gly Leu Trp Glu Ile Cys
            35                  40                  45

Ile Ile Trp Gly Met Ala Val Ser Met Gly Ile Tyr Leu Ser Ala Gly
 50                  55                  60

Ile Ser Gly Ala His Leu Asn Pro Ala Val Ser Ile Ala Leu Ser Leu
 65                  70                  75                  80

Phe Ala Gly Phe Glu Lys Arg Lys Leu Pro Phe Tyr Ile Ser Ala Gln
                    85                  90                  95

Ile Ala Gly Ala Phe Cys Gly Ala Gly Leu Val Tyr Leu Leu Tyr Ile
                    100                 105                 110

Ser Leu Phe Phe Asp Phe Glu His Ala His His Ile Ile Arg Gly Ser

```
            115                 120                 125
Glu Gln Ser Leu Glu Leu Ala Ser Val Phe Ser Thr Tyr Pro Asn Pro
    130                 135                 140

Ala Ile Ser Val Gly Gln Ala Phe Leu Val Glu Val Val Ile Thr Thr
145                 150                 155                 160

Ile Leu Met Gly Val Ile Met Ala Leu Gly Asp Asp Ser Asn Gly Leu
                165                 170                 175

Pro Arg Gly Pro Leu Ala Pro Leu Leu Ile Gly Leu Leu Val Ala Val
            180                 185                 190

Ile Gly Ser Ser Met Gly Pro Leu Thr Gly Phe Ala Met Asn Pro Ala
        195                 200                 205

Arg Asp Phe Gly Pro Lys Leu Met Thr Phe Phe Ala Gly Trp Gly Glu
    210                 215                 220

Ile Ala Phe Thr Gly Gly Arg Asp Ile Pro Tyr Phe Leu Val Pro Ile
225                 230                 235                 240

Phe Ala Pro Ile Leu Gly Ala Cys Leu Gly Ala Ala Gly Tyr Arg Ala
                245                 250                 255

Leu Ile Ala Arg His Leu Pro Ser Ala Asp Pro Val Glu Asn Glu Lys
            260                 265                 270

Asn Ala Pro Val Val Arg Gly Lys Val Gln Ala Ser Ser
        275                 280                 285

<210> SEQ ID NO 14
<211> LENGTH: 281
<212> TYPE: PRT
<213> ORGANISM: Salmonella enterica

<400> SEQUENCE: 14

Met Ser Gln Thr Ser Thr Leu Lys Gly Gln Cys Ile Ala Glu Phe Leu
1               5                   10                  15

Gly Thr Gly Leu Leu Ile Phe Phe Gly Val Gly Cys Val Ala Ala Leu
                20                  25                  30

Lys Val Ala Gly Ala Thr Phe Gly Gln Trp Glu Ile Ser Val Ile Trp
            35                  40                  45

Gly Leu Gly Val Ala Met Ala Ile Tyr Leu Thr Ala Gly Val Ser Gly
        50                  55                  60

Ala His Leu Asn Pro Ala Val Thr Ile Ala Leu Trp Leu Phe Ala Cys
65                  70                  75                  80

Phe Asp Lys Arg Lys Val Val Pro Phe Ile Ile Ser Gln Val Ala Gly
                85                  90                  95

Ala Phe Cys Ala Ala Ala Leu Val Tyr Gly Leu Tyr Tyr Asn Leu Phe
            100                 105                 110

Val Asp Phe Glu Gln Thr His His Ile Val Arg Gly Ser Val Glu Ser
        115                 120                 125

Leu Asp Leu Ala Gly Ile Phe Ser Thr Tyr Pro Asn Pro His Ile Asn
    130                 135                 140

Phe Val Gln Ala Phe Ala Val Glu Met Val Ile Thr Ala Ile Leu Met
145                 150                 155                 160

Gly Leu Ile Leu Ala Leu Thr Asp Asp Gly Asn Gly Val Pro Arg Gly
                165                 170                 175

Pro Leu Ala Pro Leu Leu Ile Gly Leu Leu Ile Ala Val Ile Gly Ala
            180                 185                 190

Ser Met Gly Pro Leu Thr Gly Phe Ala Met Asn Pro Ala Arg Asp Phe
        195                 200                 205
```

```
Gly Pro Lys Met Phe Ala Gly Leu Ala Gly Trp Gly Glu Ile Ala Phe
            210                 215                 220

Thr Gly Arg Asp Ile Pro Tyr Phe Leu Val Pro Leu Phe Gly Pro
225                 230                 235                 240

Ile Val Gly Ala Ile Leu Gly Ala Phe Ala Tyr Arg Lys Phe Ile Gly
                    245                 250                 255

Arg His Leu Pro Cys Asp Thr Cys Val Val Glu Glu Lys Asp Ser Thr
                260                 265                 270

Ala Thr Thr Gln Gln Asn Ala Ser Leu
            275                 280
```

<210> SEQ ID NO 15
<211> LENGTH: 282
<212> TYPE: PRT
<213> ORGANISM: Yersinia aldovae

<400> SEQUENCE: 15

```
Met Ser Gln Thr Ala Ser Ser Thr Leu Lys Gly Gln Cys Ile Ala Glu
1               5                   10                  15

Phe Leu Gly Thr Gly Leu Leu Ile Phe Phe Gly Val Gly Cys Val Ala
                20                  25                  30

Ala Leu Lys Leu Ala Gly Ala Ser Phe Gly Gln Trp Glu Ile Ser Ile
            35                  40                  45

Ile Trp Gly Leu Gly Val Ala Met Ala Ile Tyr Leu Thr Ala Ala Ile
50                  55                  60

Ser Gly Ala His Leu Asn Pro Ala Val Thr Ile Ala Leu Trp Leu Phe
65                  70                  75                  80

Ala Cys Phe Asp Arg Arg Lys Val Ile Pro Tyr Ile Val Ala Gln Val
                85                  90                  95

Ala Gly Ala Phe Cys Ala Ala Leu Val Tyr Gly Leu Tyr Tyr Asn
            100                 105                 110

Leu Phe Val Asp Phe Glu Gln Thr His Gln Met Val Arg Gly Ser Thr
            115                 120                 125

Glu Ser Leu Asn Leu Ala Gly Ile Phe Ser Thr Tyr Pro Asn Pro His
130                 135                 140

Ile Ser Val Phe Gln Ala Phe Leu Val Glu Thr Val Ile Thr Ala Ile
145                 150                 155                 160

Leu Met Cys Leu Ile Leu Ala Leu Thr Asp Asp Gly Asn Gly Ile Pro
                165                 170                 175

Arg Gly Pro Leu Ala Pro Leu Leu Ile Gly Ile Leu Ala Val Ile
            180                 185                 190

Gly Ala Ser Met Gly Pro Leu Thr Gly Phe Ala Leu Asn Pro Ala Arg
        195                 200                 205

Asp Phe Gly Pro Lys Ala Phe Ala Tyr Leu Ala Gly Trp Gly Glu Ile
            210                 215                 220

Ala Phe Thr Gly Gly Arg Asp Ile Pro Tyr Phe Leu Val Pro Ile Phe
225                 230                 235                 240

Gly Pro Ile Val Gly Ala Leu Leu Gly Ala Phe Gly Tyr Arg Ala Leu
                245                 250                 255

Ile Gly Arg His Leu Pro Cys Asp Val Cys Val Ala Glu Glu Glu Glu
            260                 265                 270

Thr Thr Ala Thr Thr Thr Glu Arg Lys Ala
            275                 280
```

<210> SEQ ID NO 16

```
<211> LENGTH: 261
<212> TYPE: PRT
<213> ORGANISM: Mannheimia haemolytica

<400> SEQUENCE: 16

Met Ser Lys Ser Leu Arg Asn Ala Cys Ile Gly Glu Phe Ile Gly Thr
1               5                   10                  15

Gly Phe Ile Leu Phe Phe Gly Ala Gly Cys Val Ala Ala Ala Gln Val
            20                  25                  30

Ala Gly Ala Asn Phe Gly Leu Trp Glu Ile Ser Ile Trp Gly Leu
        35                  40                  45

Gly Val Ser Met Ala Ile Tyr Ile Ser Ala Gly Ile Ser Gly Ala His
50                  55                  60

Leu Asn Pro Ala Val Thr Ile Ala Leu Ala Ala Phe Tyr Gly Phe Glu
65                  70                  75                  80

Lys His Lys Ile Leu Pro Tyr Val Ile Ala Gln Val Ala Gly Ala Phe
                85                  90                  95

Cys Ser Val Ala Leu Ile Tyr Phe Met Tyr Ser Asp Leu Phe Thr Ala
            100                 105                 110

Ala Glu Ala Ala Gln Gly Ile Thr Arg Gly Glu Thr Val Gly Phe Ala
        115                 120                 125

Gly Val Phe Ser Thr Tyr Pro Asn Pro Asn Ile Thr Leu Val Thr Ala
130                 135                 140

Phe Ile Val Glu Phe Val Ile Thr Val Val Leu Met Ser Thr Ile Leu
145                 150                 155                 160

Ala Ile Gly Asp Asp Lys Asn Gly Leu Pro Asn Lys Ala Leu Ala Ala
                165                 170                 175

Leu Leu Ile Gly Leu Leu Ile Ala Val Ile Gly Gly Ala Thr Gly Pro
            180                 185                 190

Leu Thr Gly Phe Ala Met Asn Pro Ala Arg Asp Phe Gly Pro Lys Leu
        195                 200                 205

Phe Ala Tyr Leu Ala Gly Trp Gly Glu Ile Ala Leu Thr Gly Gly Lys
210                 215                 220

Glu Ile Pro Tyr Phe Ile Ile Pro Ile Val Ala Pro Ile Cys Gly Ala
225                 230                 235                 240

Leu Phe Gly Ala Trp Gly Tyr Lys Asn Leu Ile His Asn Asn Leu Pro
                245                 250                 255

Ala Asn Thr Gln Glu
            260

<210> SEQ ID NO 17
<211> LENGTH: 269
<212> TYPE: PRT
<213> ORGANISM: Escherichia coli

<400> SEQUENCE: 17

Met Asn Asp Ser Leu Lys Ala Gln Cys Val Ala Glu Phe Leu Gly Thr
1               5                   10                  15

Gly Leu Phe Leu Phe Phe Gly Ile Gly Cys Leu Cys Ala Leu Lys Leu
            20                  25                  30

Ala Gly Ala Ser Leu Gly Leu Trp Glu Ile Cys Ile Ile Trp Gly Leu
        35                  40                  45

Gly Ile Ser Leu Ala Val Tyr Leu Thr Ala Gly Ile Ser Gly Ala His
50                  55                  60

Leu Asn Pro Ala Val Thr Ile Ala Leu Trp Leu Phe Ala Ser Phe Pro
65                  70                  75                  80
```

Ala Arg Lys Val Leu Pro Phe Cys Val Ala Gln Leu Ala Gly Ala Phe
                    85                  90                  95

Gly Gly Ala Val Leu Ala Tyr Ser Leu Tyr Ser Ser Leu Phe Thr Asp
            100                 105                 110

Phe Glu Ser Ala His Asn Met Val Arg Gly Ser Ala Glu Ser Leu Gln
        115                 120                 125

Leu Ala Ser Ile Phe Ser Thr Tyr Pro Ala Ala Ile Asn Val Trp
    130                 135                 140

Gln Ala Ala Leu Val Glu Val Val Ile Thr Ser Met Leu Met Gly Leu
145                 150                 155                 160

Ile Met Ala Leu Thr Asp Asp Gly Asn Gly Val Pro Lys Gly Pro Leu
                165                 170                 175

Ala Pro Leu Leu Ile Gly Ile Leu Val Ala Val Ile Gly Ala Ser Thr
                180                 185                 190

Gly Pro Leu Thr Gly Phe Ala Met Asn Pro Ala Arg Asp Phe Gly Pro
            195                 200                 205

Lys Ile Phe Thr Trp Leu Ala Gly Trp Gly Glu Ile Ala Met Thr Gly
        210                 215                 220

Gly Arg Asn Ile Pro Tyr Phe Ile Val Pro Ile Ile Ala Pro Ile Ile
225                 230                 235                 240

Gly Ala Cys Val Gly Ala Ala Ile Tyr Arg Tyr Leu Ile Ala Lys Asn
                245                 250                 255

Leu Pro Val Asn Ser Val Thr Pro Lys Glu Ile Ser Glu
                260                 265

<210> SEQ ID NO 18
<211> LENGTH: 281
<212> TYPE: PRT
<213> ORGANISM: Enterobacter cloacae

<400> SEQUENCE: 18

Met Ser Gln Thr Ser Thr Leu Lys Gly Gln Cys Ile Ala Glu Phe Leu
 1               5                  10                  15

Gly Thr Gly Leu Leu Ile Phe Phe Gly Val Gly Cys Val Ala Ala Leu
            20                  25                  30

Lys Val Ala Gly Ala Ser Phe Gly Gln Trp Glu Ile Ser Ile Ile Trp
        35                  40                  45

Gly Leu Gly Val Ala Met Ala Ile Tyr Leu Thr Ala Gly Val Ser Gly
    50                  55                  60

Ala His Leu Asn Pro Ala Val Thr Ile Ala Leu Trp Leu Phe Ala Cys
65                  70                  75                  80

Phe Asp Gly Arg Lys Val Val Pro Phe Ile Ile Ser Gln Phe Ala Gly
                85                  90                  95

Ala Phe Cys Ala Ala Ala Leu Val Tyr Gly Leu Tyr Tyr Asn Leu Phe
            100                 105                 110

Ile Asp Phe Glu Gln Thr His His Met Val Arg Gly Ser Val Glu Ser
        115                 120                 125

Leu Asp Leu Ala Gly Ile Phe Ser Thr Tyr Pro Asn Pro His Ile Asn
    130                 135                 140

Phe Val Gln Ala Phe Ala Val Glu Met Val Ile Thr Ala Ile Leu Met
145                 150                 155                 160

Gly Val Ile Leu Ala Leu Thr Asp Asp Gly Asn Gly Ile Pro Arg Gly
                165                 170                 175

Pro Leu Ala Pro Leu Leu Ile Gly Leu Leu Ile Ala Val Ile Gly Ala

```
            180                 185                 190
Ser Met Gly Pro Leu Thr Gly Phe Ala Met Asn Pro Ala Arg Asp Ile
            195                 200                 205

Gly Pro Lys Ala Phe Ala Phe Ile Ala Gly Trp Gly Asp Val Ala Phe
        210                 215                 220

Thr Gly Gly Lys Asp Ile Pro Tyr Phe Leu Val Pro Leu Phe Ala Pro
225                 230                 235                 240

Val Val Gly Ala Ala Leu Gly Ala Phe Ser Tyr Arg Lys Leu Ile Gly
                245                 250                 255

Arg His Leu Pro Cys Asp Thr Cys Val Asp Glu Glu Lys Glu Thr Thr
                260                 265                 270

Ser Thr Ala Gln Gln Lys Ala Ser Leu
            275                 280

<210> SEQ ID NO 19
<211> LENGTH: 283
<212> TYPE: PRT
<213> ORGANISM: Pantoea  aB

<400> SEQUENCE: 19

Met Ser Gln Thr Thr Asn Thr Leu Lys Gly Gln Cys Ile Ala Glu Phe
1               5                   10                  15

Leu Gly Thr Gly Leu Ile Ile Phe Phe Gly Ala Gly Cys Val Ala Ala
            20                  25                  30

Leu Lys Leu Ala Gly Ala Ala Phe Gly Gln Trp Glu Ile Cys Ile Ile
            35                  40                  45

Trp Gly Leu Ala Val Ser Met Ala Val Tyr Leu Thr Ala Gly Val Ser
        50                  55                  60

Gly Ala His Leu Asn Pro Ala Val Thr Val Ala Leu Cys Leu Phe Ala
65                  70                  75                  80

Asn Phe Glu Gly Arg Lys Val Val Pro Tyr Ile Leu Ala Gln Ile Ala
                85                  90                  95

Gly Ala Phe Cys Ala Ala Ala Leu Val Tyr Gly Leu Tyr Tyr Ser Leu
            100                 105                 110

Phe Phe Asp Tyr Glu Gln Ser His Gln Met Val Arg Gly Thr Val Gln
        115                 120                 125

Ser Leu Asp Leu Ala Gly Ile Phe Ser Thr Tyr Pro Asn Pro His Ile
130                 135                 140

Ser Val Gly Gln Ala Phe Leu Val Glu Met Val Ile Thr Ala Val Leu
145                 150                 155                 160

Met Ala Val Ile Met Ala Leu Thr Asp Asp Gly Asn Gly Val Pro Arg
                165                 170                 175

Gly Pro Met Ala Pro Leu Leu Ile Gly Leu Leu Val Ala Val Ile Gly
            180                 185                 190

Gly Ser Met Gly Pro Leu Thr Gly Phe Ala Leu Asn Pro Ala Arg Asp
        195                 200                 205

Phe Gly Pro Lys Leu Phe Ala Phe Phe Ala Gly Trp Gly Asn Val Ala
    210                 215                 220

Phe Thr Gly Gly Lys Asp Ile Pro Tyr Phe Leu Val Pro Ile Phe Gly
225                 230                 235                 240

Pro Leu Val Gly Ala Cys Leu Gly Ala Val Gly Tyr Arg Thr Leu Ile
                245                 250                 255

Gly Arg Tyr Leu Pro Gly Ala Ala Gln Glu Pro Ser Val Pro Ala Asp
                260                 265                 270
```

```
Lys Pro Val Ala Arg Ala Gln Gln Arg Lys Ala
        275                 280

<210> SEQ ID NO 20
<211> LENGTH: 281
<212> TYPE: PRT
<213> ORGANISM: Escherichia coli

<400> SEQUENCE: 20

Met Ser Gln Thr Ser Thr Leu Lys Gly Gln Cys Ile Ala Glu Phe Leu
1               5                   10                  15

Gly Thr Gly Leu Leu Ile Phe Phe Gly Val Gly Cys Val Ala Ala Leu
            20                  25                  30

Lys Val Ala Gly Ala Ser Phe Gly Gln Trp Glu Ile Ser Val Ile Trp
        35                  40                  45

Gly Leu Gly Val Ala Met Ala Ile Tyr Leu Thr Ala Gly Val Ser Gly
    50                  55                  60

Ala His Leu Asn Pro Ala Val Thr Ile Ala Leu Trp Leu Phe Ala Cys
65                  70                  75                  80

Phe Asp Lys Arg Lys Val Ile Pro Phe Ile Val Ser Gln Val Ala Gly
                85                  90                  95

Ala Phe Cys Ala Ala Ala Leu Val Tyr Gly Leu Tyr Tyr Asn Leu Phe
            100                 105                 110

Phe Asp Phe Glu Gln Thr His His Ile Val Arg Gly Ser Val Glu Ser
        115                 120                 125

Val Asp Leu Ala Gly Thr Phe Ser Thr Tyr Pro Asn Pro His Ile Asn
    130                 135                 140

Phe Val Gln Ala Phe Ala Val Glu Met Val Ile Thr Ala Ile Leu Met
145                 150                 155                 160

Gly Leu Ile Leu Ala Leu Thr Asp Asp Gly Asn Gly Val Pro Arg Gly
                165                 170                 175

Pro Leu Ala Pro Leu Leu Ile Gly Leu Leu Ile Ala Val Ile Gly Ala
            180                 185                 190

Ser Met Gly Pro Leu Thr Gly Phe Ala Met Asn Pro Ala Arg Asp Phe
        195                 200                 205

Gly Pro Lys Val Phe Ala Trp Leu Ala Gly Trp Gly Asn Val Ala Phe
    210                 215                 220

Thr Gly Gly Arg Asp Ile Pro Tyr Phe Leu Val Pro Leu Phe Gly Pro
225                 230                 235                 240

Ile Val Gly Ala Ile Val Gly Ala Phe Ala Tyr Arg Lys Leu Ile Gly
                245                 250                 255

Arg His Leu Pro Cys Asp Ile Cys Val Val Glu Glu Lys Glu Thr Thr
            260                 265                 270

Thr Pro Ser Glu Gln Lys Ala Ser Leu
        275                 280

<210> SEQ ID NO 21
<211> LENGTH: 260
<212> TYPE: PRT
<213> ORGANISM: Actinobacillus pleuropneumoniae

<400> SEQUENCE: 21

Met Glu Arg Ser Leu Lys Gly Ala Cys Ile Ala Glu Phe Ile Gly Thr
1               5                   10                  15

Gly Leu Ile Ile Phe Phe Gly Val Gly Cys Val Ala Ala Ala Gln Leu
            20                  25                  30
```

```
Ala Gly Ala Thr Phe Gly Leu Trp Glu Ile Ser Ile Met Trp Gly Val
            35                  40                  45

Gly Val Ala Leu Ala Val Tyr Thr Thr Ala Gly Val Ser Gly Ala His
 50                  55                  60

Leu Asn Pro Ala Val Thr Val Ala Leu Trp Lys Phe Ala Cys Phe Asp
 65                  70                  75                  80

Gly Lys Lys Val Leu Pro Tyr Ile Ile Ser Gln Phe Leu Gly Ala Phe
                    85                  90                  95

Ala Ala Ala Ala Leu Val Tyr Phe Leu Tyr Lys Asp Leu Phe Ala Ala
                100                 105                 110

Thr Glu Ala Ala Lys Asn Ile Val Arg Gly Glu Gly Val Gly Leu Ala
                115                 120                 125

Gly Val Phe Ser Thr Tyr Pro His Gln His Ile Ser Val Leu Gln Ala
130                 135                 140

Phe Cys Val Glu Ala Val Ile Thr Met Ala Leu Val Ala Leu Ile Leu
145                 150                 155                 160

Ala Leu Thr Asp Asp Gly Asn Gly Val Pro Arg Gly Pro Met Ala Pro
                165                 170                 175

Leu Leu Ile Gly Leu Leu Ile Ala Ala Ile Gly Gly Ala Phe Gly Pro
                180                 185                 190

Leu Thr Gly Phe Ala Met Asn Pro Ala Arg Asp Phe Gly Pro Lys Ala
                195                 200                 205

Phe Ala Phe Leu Ala Gly Trp Gly Glu Val Ala Phe Thr Gly Ala Arg
                210                 215                 220

Asp Ile Pro Tyr Phe Leu Val Pro Leu Ile Ala Pro Ile Val Gly Gly
225                 230                 235                 240

Leu Val Gly Ala Trp Gly Tyr Arg Arg Phe Ile Gly Lys Asn Leu Pro
                245                 250                 255

Cys Asn Cys Lys
                260

<210> SEQ ID NO 22
<211> LENGTH: 502
<212> TYPE: PRT
<213> ORGANISM: Escherichia coli

<400> SEQUENCE: 22

Met Thr Glu Lys Lys Tyr Ile Val Ala Leu Asp Gln Gly Thr Thr Ser
 1               5                  10                  15

Ser Arg Ala Val Val Met Asp His Asp Ala Asn Ile Ile Ser Val Ser
                20                  25                  30

Gln Arg Glu Phe Glu Gln Ile Tyr Pro Lys Pro Gly Trp Val Glu His
            35                  40                  45

Asp Pro Met Glu Ile Trp Ala Thr Gln Ser Ser Thr Leu Val Glu Val
 50                  55                  60

Leu Ala Lys Ala Asp Ile Ser Ser Asp Gln Ile Ala Ala Ile Gly Ile
 65                  70                  75                  80

Thr Asn Gln Arg Glu Thr Thr Ile Val Trp Glu Lys Glu Thr Gly Lys
                85                  90                  95

Pro Ile Tyr Asn Ala Ile Val Trp Gln Cys Arg Arg Thr Ala Glu Ile
                100                 105                 110

Cys Glu His Leu Lys Arg Asp Gly Leu Glu Asp Tyr Ile Arg Ser Asn
                115                 120                 125

Thr Gly Leu Val Ile Asp Pro Tyr Phe Ser Gly Thr Lys Val Lys Trp
130                 135                 140
```

Ile Leu Asp His Val Glu Gly Ser Arg Glu Arg Ala Arg Arg Gly Glu
145                 150                 155                 160

Leu Leu Phe Gly Thr Val Asp Thr Trp Leu Ile Trp Lys Met Thr Gln
                165                 170                 175

Gly Arg Val His Val Thr Asp Tyr Thr Asn Ala Ser Arg Thr Met Leu
            180                 185                 190

Phe Asn Ile His Thr Leu Asp Trp Asp Asp Lys Met Leu Glu Val Leu
        195                 200                 205

Asp Ile Pro Arg Glu Met Leu Pro Glu Val Arg Arg Ser Ser Glu Val
    210                 215                 220

Tyr Gly Gln Thr Asn Ile Gly Gly Lys Gly Thr Arg Ile Pro Ile
225                 230                 235                 240

Ser Gly Ile Ala Gly Asp Gln Gln Ala Ala Leu Phe Gly Gln Leu Cys
                245                 250                 255

Val Lys Glu Gly Met Ala Lys Asn Thr Tyr Gly Thr Gly Cys Phe Met
            260                 265                 270

Leu Met Asn Thr Gly Glu Lys Ala Val Lys Ser Glu Asn Gly Leu Leu
        275                 280                 285

Thr Thr Ile Ala Cys Gly Pro Thr Gly Glu Val Asn Tyr Ala Leu Glu
    290                 295                 300

Gly Ala Val Phe Met Ala Gly Ala Ser Ile Gln Trp Leu Arg Asp Glu
305                 310                 315                 320

Met Lys Leu Ile Asn Asp Ala Tyr Asp Ser Glu Tyr Phe Ala Thr Lys
                325                 330                 335

Val Gln Asn Thr Asn Gly Val Tyr Val Pro Ala Phe Thr Gly Leu
            340                 345                 350

Gly Ala Pro Tyr Trp Asp Pro Tyr Ala Arg Gly Ala Ile Phe Gly Leu
        355                 360                 365

Thr Arg Gly Val Asn Ala Asn His Ile Ile Arg Ala Thr Leu Glu Ser
    370                 375                 380

Ile Ala Tyr Gln Thr Arg Asp Val Leu Glu Ala Met Gln Ala Asp Ser
385                 390                 395                 400

Gly Ile Arg Leu His Ala Leu Arg Val Asp Gly Gly Ala Val Ala Asn
                405                 410                 415

Asn Phe Leu Met Gln Phe Gln Ser Asp Ile Leu Gly Thr Arg Val Glu
            420                 425                 430

Arg Pro Glu Val Arg Glu Val Thr Ala Leu Gly Ala Ala Tyr Leu Ala
        435                 440                 445

Gly Leu Ala Val Gly Phe Trp Gln Asn Leu Asp Glu Leu Gln Glu Lys
    450                 455                 460

Ala Val Ile Glu Arg Glu Phe Arg Pro Gly Ile Glu Thr Thr Glu Arg
465                 470                 475                 480

Asn Tyr Arg Tyr Ala Gly Trp Lys Lys Ala Val Lys Arg Ala Met Ala
                485                 490                 495

Trp Glu Glu His Asp Glu
            500

<210> SEQ ID NO 23
<211> LENGTH: 502
<212> TYPE: PRT
<213> ORGANISM: Acinetobacter baumannii

<400> SEQUENCE: 23

Met Ser Asn Cys Pro Lys Lys Tyr Ile Val Ala Phe Asp Gln Gly Thr

```
  1               5                  10                 15
Thr Ser Ser Arg Ala Ile Val Leu Asp His Asp Ala Asn Val Val Ser
            20                  25                 30
Ile Ala Gln Arg Glu Phe Thr Gln Ile Tyr Pro Gln Pro Gly Trp Val
            35                  40                 45
Glu His Asp Pro Met Glu Ile Trp Ala Thr Gln Ser Ala Val Trp Val
 50                  55                  60
Glu Ala Leu Ala Gln Ala Gly Ile Lys Ser Glu Gln Val Ala Ala Ile
 65                  70                  75                  80
Gly Ile Thr Asn Gln Arg Glu Thr Thr Ile Val Trp Asp Lys Lys Thr
                85                  90                  95
Gly Arg Pro Ile Tyr Asn Ala Ile Val Trp Gln Ser Arg Gln Thr Thr
               100                 105                 110
Glu Ile Cys Asn Gln Leu Tyr Lys Ala Gly Trp Gln Glu Tyr Ile Arg
           115                 120                 125
Lys Thr Thr Gly Leu Val Ile Asp Pro Tyr Phe Ser Ala Thr Lys Ile
    130                 135                 140
Lys Trp Ile Leu Asp His Val Glu Gly Ser Arg Glu Arg Ala Glu Arg
145                 150                 155                 160
Gly Glu Leu Leu Phe Gly Thr Val Asp Thr Trp Leu Ile Trp Lys Leu
               165                 170                 175
Thr Asn Gly Ala Val His Val Thr Asp Phe Thr Asn Ala Ser Arg Thr
           180                 185                 190
Met Leu Phe Asp Ile Glu Lys Leu Glu Trp Asp Glu Lys Leu Leu Gln
        195                 200                 205
Ala Leu Asp Ile Pro Arg Ala Met Leu Pro Glu Val Arg Ser Ser Ser
210                 215                 220
Glu Val Tyr Gly Tyr Thr His Thr Ile Ser Gly Gln Glu Val Gly Ile
225                 230                 235                 240
Pro Ile Ala Gly Ile Ala Gly Asp Gln Gln Ala Ala Leu Phe Gly Gln
               245                 250                 255
Met Cys Val Glu Ser Gly Gln Ala Lys Asn Thr Tyr Gly Thr Gly Cys
            260                 265                 270
Phe Leu Leu Met Asn Thr Gly Lys Lys Ile Val Arg Ser Glu His Gly
         275                 280                 285
Leu Leu Thr Thr Ile Ala Cys Gly Ala Ser Gly Glu Val Asn Tyr Ala
    290                 295                 300
Leu Glu Gly Ala Val Phe Asn Gly Gly Ser Cys Val Gln Trp Leu Arg
305                 310                 315                 320
Asp Glu Leu Lys Val Ile Lys Asn Ala Lys Asp Ser Glu Leu Tyr Ala
            325                 330                 335
Thr Arg Val Lys Asp Asn Asn Gly Val Tyr Val Val Pro Ala Phe Thr
            340                 345                 350
Gly Leu Gly Ala Pro Tyr Trp Asp Pro Thr Ala Arg Gly Ala Ile Phe
         355                 360                 365
Gly Leu Thr Arg Gly Ala Ser Ile Glu His Ile Ile Arg Ala Thr Leu
    370                 375                 380
Glu Ser Ile Ala Phe Gln Thr Arg Asp Val Leu Asp Ala Met Gln Gln
385                 390                 395                 400
Asp Ala Glu Glu Glu Leu Arg Thr Leu Arg Val Asp Gly Gly Val Thr
            405                 410                 415
Glu Asn Asn Phe Leu Met Gln Phe Gln Ala Asp Ile Leu Thr Thr Pro
            420                 425                 430
```

-continued

Val Glu Arg Pro Ile Met Lys Glu Thr Thr Ala Leu Gly Ala Ala Phe
        435                 440                 445

Leu Ala Gly Leu Ala Thr Gly Phe Trp Gln Asp Leu His Glu Leu Arg
450                 455                 460

Asn Lys Ser Ala Ile Glu Lys Val Phe Glu Pro Lys Met Pro Ser Glu
465                 470                 475                 480

Gln Ala Glu Leu Ile Tyr Lys Gly Trp Leu Lys Ala Val Lys Arg Ser
                485                 490                 495

Gln Asn Trp Ala Glu Asp
            500

<210> SEQ ID NO 24
<211> LENGTH: 503
<212> TYPE: PRT
<213> ORGANISM: Pantoea Sc1

<400> SEQUENCE: 24

Met Thr Thr Thr Asp Lys Lys Tyr Ile Val Ala Leu Asp Gln Gly Thr
1               5                   10                  15

Thr Ser Ser Arg Ala Val Ile Leu Asp His Asp Ala Asn Ile Val Ala
            20                  25                  30

Val Ser Gln Arg Glu Phe Thr Gln Ile Tyr Pro Lys Ala Gly Trp Val
        35                  40                  45

Glu His Asp Pro Met Asp Ile Trp Ala Ser Gln Ser Ser Thr Leu Val
    50                  55                  60

Glu Val Leu Ala His Ala Asp Ile Arg Ser Asp Glu Ile Ala Ala Ile
65                  70                  75                  80

Gly Ile Thr Asn Gln Arg Glu Thr Ala Ile Val Trp Asp Lys Glu Thr
                85                  90                  95

Gly Lys Pro Val Tyr Asn Ala Ile Val Trp Gln Asp Pro Arg Thr Ala
            100                 105                 110

Asp Tyr Cys Asn Lys Leu Lys Lys Glu Gly Leu Glu Glu Tyr Ile Gln
        115                 120                 125

His Thr Thr Gly Leu Val Ile Asn Pro Tyr Phe Ser Gly Thr Lys Val
    130                 135                 140

Lys Trp Ile Leu Asp Asn Val Glu Gly Ala Arg Glu Arg Ala Lys Arg
145                 150                 155                 160

Gly Glu Leu Leu Phe Gly Thr Val Asp Thr Trp Leu Val Trp Lys Met
                165                 170                 175

Thr Gln Gly Arg Val His Ile Thr Asp Tyr Thr Asn Ala Ser Arg Thr
            180                 185                 190

Met Met Phe Asn Ile His Lys Leu Glu Trp Asp Gln Arg Leu Leu Asp
        195                 200                 205

Ile Leu Asp Ile Pro Arg Glu Met Leu Pro Glu Val Lys Ser Ser Ser
    210                 215                 220

Glu Val Tyr Gly Gln Thr Asn Ile Gly Gly Lys Gly Gly Thr Arg Ile
225                 230                 235                 240

Pro Ile Ala Gly Ile Ala Gly Asp Gln Gln Ala Ala Leu Tyr Gly Gln
                245                 250                 255

Leu Cys Val Gln Pro Gly Met Ala Lys Asn Thr Tyr Gly Thr Gly Cys
            260                 265                 270

Phe Met Leu Met Asn Thr Gly Thr Glu Ala Val Thr Ser Thr His Gly
        275                 280                 285

Leu Leu Thr Thr Ile Ala Cys Gly Pro Arg Gly Glu Val Asn Tyr Ala

```
                290             295             300
Leu Glu Gly Ala Val Phe Ile Gly Ala Ser Ile Gln Trp Leu Arg
305                 310             315                 320

Asp Glu Met Lys Leu Ile Ser Asp Ala Ala Asp Ser Glu Tyr Phe Ala
                325             330                 335

Met Lys Val Lys Asp Thr Asn Gly Val Tyr Met Val Pro Ala Phe Thr
                340             345             350

Gly Leu Gly Ala Pro Tyr Trp Asp Pro Tyr Ala Arg Gly Ala Ile Phe
            355             360                 365

Gly Leu Thr Arg Gly Ala Asn Ala Asn His Ile Ile Arg Ala Thr Leu
        370             375             380

Glu Ser Ile Ala Tyr Gln Thr Arg Asp Val Leu Glu Ala Met Gln Asn
385             390             395                 400

Asp Ala Asn Thr Arg Leu Gln Ala Leu Arg Val Asp Gly Gly Ala Val
                405             410             415

Ala Asn Asn Phe Leu Met Gln Phe Gln Ser Asp Ile Leu Gly Thr Arg
            420             425             430

Val Glu Arg Pro Glu Val Arg Glu Val Thr Ala Leu Gly Ser Ala Tyr
        435             440             445

Leu Ala Gly Leu Ala Val Gly Phe Trp Gln Asp Leu Asp Glu Val Arg
    450             455             460

Ala Lys Ser Val Ile Glu Arg Glu Phe Arg Pro Ser Leu Glu Thr Thr
465             470             475                 480

Glu Arg Asn Phe Arg Tyr Ala Gly Trp Lys Lys Ala Val Ala Arg Ala
                485             490             495

Gln Ala Trp Glu Glu Glu
            500

<210> SEQ ID NO 25
<211> LENGTH: 497
<212> TYPE: PRT
<213> ORGANISM: Fusobacterium nucleatum

<400> SEQUENCE: 25

Met Lys Tyr Ile Val Ala Leu Asp Gln Gly Thr Thr Ser Ser Arg Ala
1               5                   10                  15

Ile Leu Phe Asp Glu Ser Gln Asn Ile Ile Gly Val Ala Gln Lys Glu
                20                  25                  30

Phe Thr Gln Ile Tyr Pro Asn Glu Gly Trp Val Glu His Asp Pro Met
            35                  40                  45

Glu Ile Trp Ala Ser Gln Ser Gly Val Leu Ser Glu Val Ile Ala Arg
    50                  55                  60

Ala Gly Ile Ser Gln His Asp Ile Ile Ala Leu Gly Ile Thr Asn Gln
65                  70                  75                  80

Arg Glu Thr Thr Ile Val Trp Asp Lys Lys Thr Gly Lys Pro Val Tyr
                85                  90                  95

Asn Ala Ile Val Trp Gln Cys Arg Arg Thr Ala Lys Ile Cys Asp Glu
            100                 105                 110

Leu Lys Lys Ile Asp Gly Phe Ser Asp Tyr Val Lys Asp Asn Thr Gly
        115                 120                 125

Leu Leu Val Asp Ala Tyr Phe Ser Gly Thr Lys Ile Lys Trp Ile Leu
    130                 135                 140

Asp Asn Val Glu Gly Ala Arg Glu Arg Ala Glu Lys Gly Glu Leu Leu
145                 150                 155                 160
```

Phe Gly Thr Val Asp Thr Trp Leu Ile Trp Gln Leu Thr Asn Gly Lys
        165                 170                 175

Val His Ala Thr Asp Tyr Thr Asn Ala Ser Arg Thr Met Leu Tyr Asn
        180                 185                 190

Ile Lys Glu Leu Lys Trp Asp Glu Lys Ile Leu Lys Thr Leu Asn Ile
        195                 200                 205

Pro Lys Ser Met Leu Pro Glu Val Lys Asp Ser Ser Gly Thr Phe Gly
        210                 215                 220

Tyr Ala Asn Leu Gly Gly Lys Gly Gly His Arg Ile Pro Ile Ala Gly
225                 230                 235                 240

Val Ala Gly Asp Gln Gln Ser Ala Leu Phe Gly Gln Ala Cys Phe Glu
        245                 250                 255

Glu Gly Glu Ser Lys Asn Thr Tyr Gly Thr Gly Cys Phe Leu Leu Met
        260                 265                 270

Asn Thr Gly Glu Lys Phe Val Lys Ser Asn Asn Gly Leu Ile Thr Thr
        275                 280                 285

Ile Ala Ile Gly Leu Asn Gly Lys Val Gln Tyr Ala Leu Glu Gly Ser
        290                 295                 300

Val Phe Val Gly Gly Ala Ser Val Gln Trp Leu Arg Asp Glu Leu Lys
305                 310                 315                 320

Leu Ile Ser Glu Ser Arg Asp Thr Glu Tyr Phe Ala Arg Lys Val Lys
        325                 330                 335

Asp Asn Gly Gly Val Tyr Val Val Pro Ala Phe Val Gly Leu Gly Ala
        340                 345                 350

Pro Tyr Trp Asp Met Tyr Ala Arg Gly Ala Ile Leu Gly Leu Thr Arg
        355                 360                 365

Gly Ala Asn Lys Asn His Ile Ile Arg Ala Thr Leu Glu Ser Ile Ala
        370                 375                 380

Tyr Gln Thr Lys Asp Val Leu Lys Ala Met Glu Glu Asp Ser Gly Ile
385                 390                 395                 400

Lys Leu Asn Gly Leu Lys Val Asp Gly Gly Ala Ala Ala Asn Asn Phe
        405                 410                 415

Leu Met Glu Phe Gln Ala Asp Ile Leu Gly Glu Ser Val Lys Arg Pro
        420                 425                 430

Thr Val Leu Glu Thr Thr Ala Leu Gly Ala Ala Tyr Leu Ala Gly Leu
        435                 440                 445

Ala Val Gly Phe Trp Glu Asn Lys Asn Glu Ile Lys Gln Lys Trp Val
        450                 455                 460

Leu Asp Lys Glu Phe Thr Pro Asn Met Ser Lys Glu Glu Arg Asp Lys
465                 470                 475                 480

Lys Tyr Ala Gly Trp Leu Lys Ala Val Glu Arg Thr Lys Lys Trp Glu
        485                 490                 495

Glu

<210> SEQ ID NO 26
<211> LENGTH: 505
<212> TYPE: PRT
<213> ORGANISM: Pseudomonas aeruginosa

<400> SEQUENCE: 26

Met Thr Asp Lys His Asn Lys Lys Tyr Val Ala Leu Asp Gln Gly Thr
1               5                   10                  15

Thr Thr Ser Ser Arg Ala Ile Val Phe Asp Arg Asp Ala Asn Val Val
            20                  25                  30

-continued

```
Ser Gln Ala Gln Arg Glu Phe Ala Gln Phe Tyr Pro Gln Ala Gly Trp
         35                  40                  45
Val Glu His Asp Pro Met Glu Ile Trp Ala Thr Gln Ser Ser Thr Leu
 50                  55                  60
Val Glu Ala Leu Ala Gln Ala Ser Ile Glu His Asp Gln Val Ala Ala
 65                  70                  75                  80
Ile Gly Ile Thr Asn Gln Arg Glu Thr Thr Val Val Trp Asp Arg His
                 85                  90                  95
Ser Gly Arg Pro Ile His Asn Ala Ile Val Trp Gln Cys Arg Arg Ser
            100                 105                 110
Ala Ala Ile Cys Ala Gln Leu Lys Arg Asp Gly Leu Glu Asp Tyr Ile
        115                 120                 125
Arg Glu Thr Thr Gly Leu Val Thr Asp Pro Tyr Phe Ser Gly Thr Lys
    130                 135                 140
Leu Lys Trp Ile Leu Asp Asn Val Glu Gly Ala Arg Glu Arg Ala Arg
145                 150                 155                 160
Asn Gly Asp Leu Leu Phe Gly Thr Ile Asp Thr Trp Leu Ile Trp Lys
                165                 170                 175
Leu Thr Glu Gly Lys Val His Val Thr Asp Tyr Thr Asn Ala Ser Arg
            180                 185                 190
Thr Met Leu Phe Asn Ile His Ser Leu Asp Trp Asp Ala Arg Met Leu
        195                 200                 205
Glu Val Leu Asp Ile Pro Arg Ser Met Leu Pro Glu Val Arg Asn Ser
    210                 215                 220
Ser Glu Val Tyr Gly Asn Ala Arg Ile Gly Gly Val Gly Gly Gly Glu
225                 230                 235                 240
Leu Pro Ile Ala Gly Ile Ala Gly Asp Gln Gln Ala Ala Leu Phe Gly
                245                 250                 255
Gln Met Cys Val Glu Pro Gly Gln Ala Lys Asn Thr Tyr Gly Thr Gly
            260                 265                 270
Cys Phe Leu Leu Met His Thr Gly Asp Lys Ala Val Lys Ser Thr His
        275                 280                 285
Gly Leu Leu Thr Thr Ile Ala Cys Gly Pro Arg Gly Glu Val Gly Tyr
    290                 295                 300
Ala Leu Glu Gly Ala Val Phe Asn Gly Gly Ser Thr Val Gln Trp Leu
305                 310                 315                 320
Arg Asp Glu Leu Lys Val Ile Asn Asp Ser Phe Asp Ser Glu Tyr Phe
                325                 330                 335
Ala Thr Lys Val Lys Asp Ser Asn Gly Val Tyr Leu Val Pro Ala Phe
            340                 345                 350
Thr Gly Leu Gly Ala Pro Tyr Trp Asp Pro Tyr Ala Arg Gly Ala Val
        355                 360                 365
Phe Gly Leu Thr Arg Gly Val Lys Ala Asp His Leu Ile Arg Ala Thr
    370                 375                 380
Leu Glu Ser Ile Ala Tyr Gln Thr Arg Asp Val Leu Asp Ala Met Gln
385                 390                 395                 400
Arg Asp Ala Gly Glu Arg Leu Arg Ala Leu Arg Val Asp Gly Gly Ala
                405                 410                 415
Val Ala Asn Asn Phe Leu Met Gln Phe Gln Ala Asp Ile Leu Gly Thr
            420                 425                 430
Arg Val Glu Arg Pro Val Met Arg Glu Thr Thr Ala Leu Gly Ala Ala
        435                 440                 445
Tyr Leu Ala Gly Leu Ala Cys Gly Phe Trp Ser Ser Leu Asp Glu Leu
```

```
            450                 455                 460
Lys Ser Lys Ala Val Ile Glu Arg Val Phe Glu Pro Glu Cys Asp Glu
465                 470                 475                 480

Pro Arg Arg Glu Lys Leu Tyr Ala Gly Trp Lys Lys Ala Val Glu Arg
                    485                 490                 495

Thr Arg Gly Trp Asp Asp Gly Glu Leu
                500                 505

<210> SEQ ID NO 27
<211> LENGTH: 405
<212> TYPE: PRT
<213> ORGANISM: Shigella flexneri

<400> SEQUENCE: 27

Met Glu Ile Trp Ala Thr Gln Ser Ser Thr Leu Val Glu Val Leu Ala
 1               5                  10                  15

Lys Ala Asp Ile Ser Ser Asp Gln Ile Ala Ala Ile Gly Ile Thr Asn
                20                  25                  30

Gln Arg Glu Thr Thr Ile Val Trp Glu Lys Glu Thr Gly Lys Pro Ile
             35                  40                  45

Tyr Asn Ala Ile Val Trp Gln Cys Arg Arg Thr Ala Glu Ile Cys Glu
 50                  55                  60

His Leu Lys Arg Asp Gly Leu Glu Asp Tyr Ile Arg Ser Asn Thr Gly
 65                  70                  75                  80

Leu Val Ile Asp Pro Tyr Phe Ser Gly Thr Lys Val Lys Trp Ile Leu
                 85                  90                  95

Asp His Val Glu Gly Ser Arg Glu Arg Ala Arg Arg Gly Glu Leu Leu
            100                 105                 110

Phe Gly Thr Val Asp Thr Trp Leu Ile Trp Lys Met Thr Gln Gly Arg
        115                 120                 125

Val His Val Thr Asp Tyr Thr Asn Ala Ser Arg Thr Met Leu Phe Asn
    130                 135                 140

Ile His Thr Leu Asp Trp Asp Asp Lys Met Leu Glu Val Leu Asp Ile
145                 150                 155                 160

Pro Arg Glu Met Leu Pro Glu Val Arg Arg Ser Ser Glu Val Tyr Gly
                165                 170                 175

Gln Thr Asn Ile Gly Gly Lys Gly Thr Arg Ile Pro Ile Ser Gly
            180                 185                 190

Ile Ala Gly Asp Gln Gln Ala Ala Leu Phe Gly Gln Leu Cys Val Lys
        195                 200                 205

Glu Gly Met Ala Lys Asn Thr Tyr Gly Thr Gly Cys Phe Met Leu Met
    210                 215                 220

Asn Thr Gly Glu Lys Ala Val Lys Ser Glu Asn Gly Leu Leu Thr Thr
225                 230                 235                 240

Ile Ala Cys Gly Pro Thr Gly Glu Val Asn Tyr Ala Leu Glu Gly Ala
                245                 250                 255

Val Phe Met Ala Gly Ala Ser Ile Gln Trp Leu Arg Asp Glu Met Lys
            260                 265                 270

Leu Ile Asn Asp Ala Tyr Asp Ser Glu Tyr Phe Ala Thr Lys Val Gln
        275                 280                 285

Asn Thr Asn Gly Val Tyr Val Val Pro Ala Phe Thr Gly Leu Gly Ala
    290                 295                 300

Pro Tyr Trp Asp Pro Tyr Ala Arg Gly Ala Ile Phe Gly Leu Thr Arg
305                 310                 315                 320
```

```
Gly Val Asn Ala Asn His Ile Ile Arg Ala Thr Leu Glu Ser Ile Ala
            325                 330                 335

Tyr Gln Thr Arg Asp Val Leu Glu Ala Met Gln Ala Asp Ser Gly Ile
        340                 345                 350

Arg Leu His Ala Leu Arg Val Asp Gly Gly Ala Val Ala Asn Asn Phe
                355                 360                 365

Leu Met Gln Phe Gln Ser Asp Ile Leu Gly Thr Arg Val Glu Arg Pro
370                 375                 380

Glu Val Arg Glu Val Thr Ala Leu Gly Ala Ala Tyr Leu Ala Gly Leu
385                 390                 395                 400

Ala Val Gly Phe Trp
            405

<210> SEQ ID NO 28
<211> LENGTH: 494
<212> TYPE: PRT
<213> ORGANISM: Shewanella baltica

<400> SEQUENCE: 28

Met Gln Lys Lys Tyr Val Val Ala Leu Asp Gln Gly Thr Thr Ser Ser
1               5                   10                  15

Arg Ala Ile Val Phe Asp His Ala Asn Ile Val Ser Val Ser Gln
            20                  25                  30

Arg Glu Phe Thr Gln Leu Tyr Pro Asn Pro Gly Trp Val Glu His Asp
        35                  40                  45

Pro Met Glu Ile Trp Ala Ser Gln Ser Ser Val Leu Val Glu Val Leu
    50                  55                  60

Ala Arg Ala Gly Ile His Ser Asp Glu Val Ala Ala Ile Gly Ile Thr
65                  70                  75                  80

Asn Gln Arg Glu Thr Thr Val Ile Trp Glu Lys Ala Thr Gly Lys Pro
                85                  90                  95

Ile Tyr Asn Ala Ile Val Trp Gln Cys Arg Arg Ser Ser Glu Ile Cys
            100                 105                 110

Glu Gln Leu Lys Ala Gln Gly Leu Glu Glu Tyr Val Arg Glu Asn Thr
        115                 120                 125

Gly Leu Leu Leu Asp Pro Tyr Phe Ser Gly Thr Lys Ile Lys Trp Ile
    130                 135                 140

Leu Asp Asn Val Pro Asn Ala Arg Ala Gln Ala Glu Arg Gly Glu Leu
145                 150                 155                 160

Leu Phe Gly Thr Ile Asp Thr Trp Leu Val Trp Lys Leu Thr Glu Gly
                165                 170                 175

Lys Val His Val Thr Asp Pro Thr Asn Ala Ala Arg Thr Leu Leu Phe
            180                 185                 190

Asn Ile His Ser Leu Thr Trp Asp Asn Lys Leu Leu Glu Ala Leu Asp
        195                 200                 205

Ile Pro Leu Ser Leu Leu Pro Glu Val Lys Pro Ser Cys Ser Val Tyr
    210                 215                 220

Gly Thr Thr Arg Ile Ala Gly Glu Gly Ser Glu Ile Gln Val Ala Gly
225                 230                 235                 240

Met Ala Gly Asp Gln Gln Ala Ala Leu Phe Gly Gln Leu Cys Val Glu
                245                 250                 255

Pro Gly Met Ala Lys Asn Thr Tyr Gly Thr Gly Cys Phe Leu Leu Met
            260                 265                 270

Asn Thr Gly Thr Lys Ala Val Arg Ser Asn His Gly Leu Leu Thr Thr
        275                 280                 285
```

```
Val Ala Val Gly Pro Lys Gly Glu Val Asn Tyr Ala Leu Glu Gly Ser
    290                 295                 300

Val Phe Met Gly Gly Ala Thr Ile Gln Trp Leu Arg Asp Glu Leu Gly
305                 310                 315                 320

Leu Ile Arg Asp Ala Ser Asp Thr Glu Tyr Phe Ala Ser Lys Val Ala
                325                 330                 335

Asp Thr Asn Gly Val Tyr Leu Val Pro Ala Phe Val Gly Leu Gly Ala
                340                 345                 350

Pro Tyr Trp Asp Pro Asn Ala Arg Gly Ala Leu Phe Gly Leu Thr Arg
            355                 360                 365

Gly Ala Asn Arg Asn His Ile Ile Arg Ala Ala Leu Glu Ser Ile Ala
        370                 375                 380

Tyr Gln Ser Lys Asp Leu Leu Asp Ala Met Thr Lys Asp Ser Gly Val
385                 390                 395                 400

Ser Leu Lys Arg Leu Lys Val Asp Gly Ala Val Ala Asn Asp Phe
                405                 410                 415

Leu Met Gln Phe Gln Ala Asp Ile Thr Asp Val Glu Val Leu Arg Pro
                420                 425                 430

Ser Val Cys Glu Thr Thr Ala Leu Gly Ala Ala Phe Leu Ala Gly Leu
            435                 440                 445

Ala Val Gly Phe Trp Glu Ser Val Ile Glu Leu Glu His Lys Ala Cys
        450                 455                 460

Ile Asp Lys His Phe Ile Pro Asn Ile Asp Ala Glu Thr Arg Val Arg
465                 470                 475                 480

Leu Tyr Ala Gly Trp Gln Asp Ala Val Ala Arg Thr Arg Ala
                485                 490

<210> SEQ ID NO 29
<211> LENGTH: 503
<212> TYPE: PRT
<213> ORGANISM: Actinobacillus pleuropneumoniae

<400> SEQUENCE: 29

Met Thr Lys Glu Tyr Ile Ile Ala Leu Asp Gln Gly Thr Thr Ser Ser
1               5                   10                  15

Arg Ala Val Leu Leu Asp Lys Asn Ala Asn Ile Val Glu Val Ser Gln
                20                  25                  30

Arg Glu Phe Thr Gln Ile Tyr Pro Gln Val Gly Trp Val Glu His Asn
            35                  40                  45

Pro Met Glu Ile Trp Ala Thr Gln Ser Ser Thr Leu Asn Glu Val Val
        50                  55                  60

Ala Lys Ala Gly Ile Thr Ser Asp Lys Ile Ala Ala Ile Gly Ile Thr
65                  70                  75                  80

Asn Gln Arg Glu Thr Thr Ile Val Trp Glu Lys Glu Thr Gly Lys Pro
                85                  90                  95

Val Tyr Asn Ala Ile Val Trp Gln Cys Arg Arg Thr Ala Asp Ile Cys
            100                 105                 110

Ala Lys Leu Lys Glu Asp Gly His Glu Ala Tyr Ile Arg Lys Thr Thr
        115                 120                 125

Gly Leu Val Val Asp Pro Tyr Phe Ser Gly Thr Lys Val Lys Trp Ile
    130                 135                 140

Leu Asp Asn Val Glu Gly Ala Arg Glu Lys Ala Glu Arg Gly Glu Leu
145                 150                 155                 160

Leu Phe Gly Thr Val Asp Thr Trp Leu Val Trp Lys Leu Thr Gln Gly
```

165                 170                 175
Arg Val His Val Thr Asp Tyr Thr Asn Ala Ser Arg Thr Met Met Phe
            180                 185                 190

Asn Ile His Thr Lys Gln Trp Asp Asp Lys Met Leu Glu Leu Leu Asn
            195                 200                 205

Ile Pro Arg Ser Met Leu Pro Glu Val Arg Asn Ser Ser Glu Val Tyr
            210                 215                 220

Gly Glu Thr Asn Ile Gly Gly Lys Gly Gly Val Arg Ile Pro Val Ala
225                 230                 235                 240

Gly Met Ala Gly Asp Gln Gln Ala Ala Leu Tyr Gly His Leu Cys Val
            245                 250                 255

Glu Ala Gly Gln Ala Lys Asn Thr Tyr Gly Thr Gly Cys Phe Met Leu
            260                 265                 270

Met Asn Thr Gly Asn Glu Ala Val Glu Ser Lys Asn Gly Leu Leu Thr
            275                 280                 285

Thr Ile Ala Cys Asn Ala Lys Gly Glu Pro Cys Tyr Ala Leu Glu Gly
            290                 295                 300

Ser Ile Phe Met Gly Gly Ala Ser Ile Gln Trp Leu Arg Asp Glu Leu
305                 310                 315                 320

Lys Ile Val His Asp Ser Lys Asp Ser Glu Tyr Phe Ala Thr Lys Glu
            325                 330                 335

Asp Ser Thr Asn Gly Val Tyr Val Pro Ala Phe Thr Gly Leu Gly
            340                 345                 350

Ala Pro Tyr Trp Asp Pro Tyr Ala Arg Gly Ala Ile Leu Gly Leu Ser
            355                 360                 365

Arg Gly Ala Asn Arg Asn His Ile Val Arg Ala Thr Leu Glu Ser Ile
            370                 375                 380

Ala Tyr Gln Thr Arg Asp Val Leu Asp Ala Met Gln Ser Asp Ser Gly
385                 390                 395                 400

Lys His Leu Ala Thr Leu Arg Val Asp Gly Gly Ala Val Ala Asn Asn
            405                 410                 415

Phe Leu Met Gln Phe Gln Ala Asp Ile Leu Asn Ala Asn Val Glu Arg
            420                 425                 430

Pro Val Val Arg Glu Val Thr Ala Leu Gly Ala Ala Tyr Leu Ala Gly
            435                 440                 445

Leu Ala Val Gly Phe Trp Lys Asp Leu Gln Glu Leu Arg Gly Lys Ala
            450                 455                 460

Ser Ile Glu Arg Thr Phe Val Pro Asp Gly Asp Glu Ala Lys Arg Thr
465                 470                 475                 480

Arg Arg Tyr Lys Gly Trp Lys Lys Ala Val Lys Arg Ala Leu Glu Trp
            485                 490                 495

Ala Lys Glu Asp Ala Glu Glu
            500

<210> SEQ ID NO 30
<211> LENGTH: 502
<212> TYPE: PRT
<213> ORGANISM: Salmonella enterica

<400> SEQUENCE: 30

Met Thr Glu Lys Lys Tyr Ile Val Ala Leu Asp Gln Gly Thr Thr Ser
1               5                   10                  15

Ser Arg Ala Val Val Met Asp His Asp Ala Asn Ile Val Ser Val Ser
            20                  25                  30

-continued

Gln Arg Glu Phe Glu Gln Ile Tyr Pro Lys Pro Gly Trp Val Glu His
         35                  40                  45

Asp Pro Met Glu Ile Trp Ala Ser Gln Ser Ser Thr Leu Val Glu Val
 50                  55                  60

Leu Ala Lys Ala Asp Ile Ser Ser Asp Gln Ile Ala Ala Ile Gly Ile
 65                  70                  75                  80

Thr Asn Gln Arg Glu Thr Ala Ile Val Trp Glu Arg Glu Thr Gly Lys
                 85                  90                  95

Pro Ile Tyr Asn Ala Ile Val Trp Gln Cys Arg Arg Thr Ala Asp Ile
            100                 105                 110

Cys Glu Gln Leu Lys Arg Asp Gly Met Glu Asp Tyr Ile Arg Asp Asn
        115                 120                 125

Thr Gly Leu Val Val Asp Pro Tyr Phe Ser Gly Thr Lys Val Lys Trp
130                 135                 140

Ile Leu Asp His Val Glu Gly Ser Arg Glu Arg Ala Lys Arg Gly Glu
145                 150                 155                 160

Leu Leu Phe Gly Thr Val Asp Thr Trp Leu Ile Trp Lys Met Thr Gln
                165                 170                 175

Gly Arg Val His Val Thr Asp Tyr Thr Asn Ala Ser Arg Thr Met Leu
            180                 185                 190

Phe Asn Ile His Asp Leu Asp Trp Asp Asp Lys Met Leu Asp Val Leu
        195                 200                 205

Asp Ile Pro Arg Ala Met Leu Pro Gln Val Arg Lys Ser Ser Glu Val
210                 215                 220

Tyr Gly Gln Thr Asn Ile Gly Gly Lys Gly Gly Thr Arg Ile Pro Ile
225                 230                 235                 240

Ala Gly Ile Ala Gly Asp Gln Gln Ala Ala Leu Phe Gly Gln Leu Cys
                245                 250                 255

Val Lys Glu Gly Met Ala Lys Asn Thr Tyr Gly Thr Gly Cys Phe Met
            260                 265                 270

Leu Met Asn Thr Gly Glu Lys Ala Val Lys Ser Glu Asn Gly Leu Leu
        275                 280                 285

Thr Thr Ile Ala Cys Gly Pro Ser Gly Glu Val Asn Tyr Ala Leu Glu
290                 295                 300

Gly Ala Val Phe Met Ala Gly Ala Ser Ile Gln Trp Leu Arg Asp Glu
305                 310                 315                 320

Met Lys Leu Ile Ser Asp Ala Phe Asp Ser Glu Tyr Phe Ala Thr Lys
                325                 330                 335

Val Lys Asp Thr Asn Gly Val Tyr Val Val Pro Ala Phe Thr Gly Leu
            340                 345                 350

Gly Ala Pro Tyr Trp Asp Pro Tyr Ala Arg Gly Ala Ile Phe Gly Leu
        355                 360                 365

Thr Arg Gly Val Asn Ser Asn His Ile Ile Arg Ala Thr Leu Glu Ser
370                 375                 380

Ile Ala Tyr Gln Thr Arg Asp Val Leu Glu Ala Met Gln Ala Asp Ser
385                 390                 395                 400

Gly Ile Arg Leu His Ala Leu Arg Val Asp Gly Gly Ala Val Ala Asn
                405                 410                 415

Asn Phe Leu Met Gln Phe Gln Ser Asp Ile Leu Gly Thr Arg Val Glu
            420                 425                 430

Arg Pro Glu Val Arg Glu Val Thr Ala Leu Gly Ala Ala Tyr Leu Ala
        435                 440                 445

Gly Leu Ala Val Gly Tyr Trp Gln Asn Leu Asp Glu Leu Gln Glu Lys

```
                450             455             460
Ala Val Ile Glu Arg Glu Phe Arg Pro Gly Ile Glu Thr Thr Glu Arg
465                 470                 475                 480

Asn Tyr Arg Tyr Ser Gly Trp Lys Lys Ala Val Lys Arg Ala Met Ala
                485                 490                 495

Trp Glu Glu His Asp Lys
            500

<210> SEQ ID NO 31
<211> LENGTH: 504
<212> TYPE: PRT
<213> ORGANISM: Aeromonas veronii

<400> SEQUENCE: 31

Met Glu Asn Ile Met Ser Ala Glu Lys Lys Tyr Val Ala Leu Asp
  1               5                  10                  15

Gln Gly Thr Thr Ser Ser Arg Ala Ile Val Phe Asp Gln Asp Ala Asn
             20                  25                  30

Ile Val Gly Thr Ser Gln Arg Glu Phe Thr Gln His Tyr Pro Lys Ala
         35                  40                  45

Gly Trp Val Glu His Asp Pro Met Glu Ile Trp Ala Thr Gln Ser Ser
 50                  55                  60

Val Phe Thr Glu Val Leu Ala Lys Thr Gly Leu Arg Ser Glu Ile
65                  70                  75                  80

Ala Ala Ile Gly Ile Thr Asn Gln Arg Glu Thr Thr Val Val Trp Glu
                 85                  90                  95

Lys Ala Thr Gly Lys Pro Ile Tyr Asn Ala Ile Val Trp Gln Cys Arg
            100                 105                 110

Arg Thr Ala Ala Ile Cys Glu Glu Leu Lys Ala Arg Gly Leu Glu Glu
        115                 120                 125

Tyr Val Arg Glu Asn Thr Gly Leu Val Leu Asp Ala Tyr Phe Ser Gly
    130                 135                 140

Thr Lys Val Lys Trp Ile Leu Asp Asn Val Glu Gly Ala Arg Glu Lys
145                 150                 155                 160

Ala Met Asn Gly Glu Leu Leu Phe Gly Thr Ile Asp Thr Trp Leu Val
                165                 170                 175

Trp Lys Met Thr Asn Gly Glu Val His Val Thr Asp Pro Thr Asn Ala
            180                 185                 190

Ser Arg Thr Met Leu Tyr Asn Ile Arg Glu Leu Lys Trp Asp Glu Lys
        195                 200                 205

Met Leu Asp Glu Leu Gly Ile Pro Met Ser Met Leu Pro Glu Val Lys
    210                 215                 220

Pro Ser Ser Glu Val Tyr Gly Tyr Thr Thr Arg Gly Gly Gly Ser Arg
225                 230                 235                 240

Ile Pro Ile Ala Gly Ile Ala Gly Asp Gln Gln Ser Ala Leu Phe Gly
                245                 250                 255

Gln Leu Cys Phe Glu Lys Gly Met Ala Lys Asn Thr Tyr Gly Thr Gly
            260                 265                 270

Cys Phe Met Leu Met Asn Thr Gly Thr Glu Pro Val Arg Ser Ser Asn
        275                 280                 285

Gly Leu Leu Thr Thr Val Ala Ile Gly Pro Lys Gly Glu Val Asn Tyr
    290                 295                 300

Ala Leu Glu Gly Ala Val Phe Met Gly Gly Ala Thr Ile Gln Trp Leu
305                 310                 315                 320
```

```
Arg Asp Glu Leu Lys Ile Ile His Asp Ala Arg Asp Thr Asp Tyr Phe
            325                 330                 335

Ala Ser Lys Val Gly Asp Thr Asn Gly Val Tyr Leu Val Pro Ala Phe
            340                 345                 350

Val Gly Leu Gly Ala Pro Tyr Trp Asp Pro Tyr Ala Arg Gly Thr Met
            355                 360                 365

Val Gly Leu Thr Arg Gly Ala Asn Arg Asn His Ile Ile Arg Ala Ala
            370                 375                 380

Leu Glu Ser Ile Ala Tyr Gln Ser Arg Asp Val Leu Asp Ala Met Gln
385                 390                 395                 400

Gln Asp Ser Gly Ile Lys Leu Ala Ala Leu Lys Val Asp Gly Gly Ala
                405                 410                 415

Val Ala Asn Asp Phe Leu Met Gln Phe Gln Ala Asp Met Met His Thr
            420                 425                 430

Pro Val Val Arg Pro Thr Arg Ile Glu Thr Thr Ala Met Gly Ala Ala
            435                 440                 445

Phe Leu Ala Gly Leu Ala Val Gly Phe Trp Lys Ser Ser Asp Glu Leu
            450                 455                 460

Glu Asp Lys Phe Ser Val Asp Arg Glu Phe Ile Pro Gln Met Asp Arg
465                 470                 475                 480

Asp Asp Arg Ala Lys Arg Tyr Ser Gly Trp Gln Lys Ala Val Glu Arg
                485                 490                 495

Ser Arg Arg Trp Ala Glu Glu Asp
            500

<210> SEQ ID NO 32
<211> LENGTH: 507
<212> TYPE: PRT
<213> ORGANISM: Yersinia bercovieri

<400

```
Ser Arg Thr Met Met Phe Asn Ile Arg Thr Lys Glu Trp Asp Glu Arg
        195                 200                 205

Met Leu Ala Ala Leu Asn Ile Pro Arg Ala Met Leu Pro Glu Val Arg
    210                 215                 220

Pro Ser Ser Glu Val Tyr Gly Gln Thr Asn Ile Gly Gly Lys Gly Gly
225                 230                 235                 240

Thr Arg Ile Pro Ile Ala Gly Ile Ala Gly Asp Gln Ala Ala Leu
            245                 250                 255

Phe Gly Gln Leu Cys Val Gln Pro Gly Met Ala Lys Asn Thr Tyr Gly
                260                 265                 270

Thr Gly Cys Phe Leu Leu Met Asn Thr Gly Glu Glu Ala Val Gln Ser
            275                 280                 285

Asn His Gly Leu Leu Thr Thr Ile Ala Cys Gly Pro Arg Gly Glu Val
        290                 295                 300

Asn Tyr Ala Leu Glu Gly Ala Val Phe Ile Gly Gly Ala Ser Ile Gln
305                 310                 315                 320

Trp Leu Arg Asp Glu Leu Lys Leu Ile Ser Asp Ala Thr Asp Ser Glu
                325                 330                 335

Tyr Phe Ala Thr Lys Val Lys Asp Ser Asn Gly Val Tyr Val Val Pro
            340                 345                 350

Ala Phe Thr Gly Leu Gly Ala Pro Tyr Trp Asp Pro Tyr Ala Arg Gly
        355                 360                 365

Ala Ile Phe Gly Leu Thr Arg Gly Val Asn Ser Asn His Ile Ile Arg
    370                 375                 380

Ala Thr Leu Glu Ser Ile Ala Tyr Gln Thr Arg Asp Val Leu Asp Ala
385                 390                 395                 400

Met Gln Ala Asp Ser Gly Ala Arg Leu Lys Ser Leu Arg Val Asp Gly
                405                 410                 415

Gly Ala Val Ala Asn Asn Phe Leu Met Gln Phe Gln Ala Asp Ile Leu
            420                 425                 430

Gly Thr Arg Val Glu Arg Pro Ala Val Arg Glu Ser Thr Ala Leu Gly
        435                 440                 445

Ala Ala Phe Leu Ala Gly Leu Ala Thr Gly Phe Trp Asn Asp Leu Asp
    450                 455                 460

Glu Val Lys Ser Lys Ala Thr Ile Glu Arg Glu Phe Arg Pro Gly Ile
465                 470                 475                 480

Glu Thr Thr Glu Arg Asp Phe Arg Tyr Lys Gly Trp Lys Lys Ala Val
                485                 490                 495

Ala Arg Ala Gln Ala Trp Glu Glu His Glu Glu
            500                 505

<210> SEQ ID NO 33
<211> LENGTH: 501
<212> TYPE: PRT
<213> ORGANISM: Pseudomonas fluorescens

<400> SEQUENCE: 33

Met Thr Asp Leu Gln Asn Lys Asn Tyr Ile Ile Ala Leu Asp Gln Gly
1               5                   10                  15

Thr Thr Ser Ser Arg Ala Ile Ile Phe Asp Arg Asp Ala Asn Val Val
                20                  25                  30

Cys Thr Ala Gln Arg Glu Phe Val Gln His Tyr Pro Gln Ala Gly Trp
            35                  40                  45

Val Glu His Asp Pro Met Glu Ile Phe Ala Thr Gln Ser Ala Val Met
```

```
                50                  55                  60
Val Glu Ala Leu Ala Gln Ala Gly Leu His His Asp Gln Val Ala Ala
 65                  70                  75                  80

Ile Gly Ile Thr Asn Gln Arg Glu Thr Thr Val Val Trp Asp Lys Ile
                 85                  90                  95

Thr Gly Arg Pro Ile Tyr Asn Ala Ile Val Trp Gln Cys Arg Arg Ser
                100                 105                 110

Thr Glu Ile Cys Gln Gln Leu Lys Arg Asp Gly His Glu Gln Tyr Ile
                115                 120                 125

Ser Asp Thr Thr Gly Leu Val Thr Asp Pro Tyr Phe Ser Gly Thr Lys
        130                 135                 140

Leu Lys Trp Ile Leu Asp Asn Val Glu Gly Ser Arg Glu Arg Ala Arg
145                 150                 155                 160

Asn Gly Glu Leu Leu Phe Gly Thr Val Asp Ser Trp Leu Ile Trp Lys
                165                 170                 175

Phe Thr Gly Gly Lys Thr His Val Thr Asp Tyr Thr Asn Ala Ser Arg
                180                 185                 190

Thr Met Leu Phe Asn Ile His Thr Leu Glu Trp Asp Ala Lys Met Leu
        195                 200                 205

Glu Ile Leu Asp Ile Pro Arg Glu Met Leu Pro Glu Val Lys Ser Ser
210                 215                 220

Ser Gln Ile Tyr Gly Arg Thr Lys Ser Gly Ile Ala Ile Gly Gly Ile
225                 230                 235                 240

Ala Gly Asp Gln Gln Ala Ala Leu Phe Gly Gln Met Cys Val Glu Ala
                245                 250                 255

Gly Gln Ala Lys Asn Thr Tyr Gly Thr Gly Cys Phe Leu Leu Met Asn
                260                 265                 270

Thr Gly Asp Lys Ala Val Lys Ser Lys His Gly Met Leu Thr Thr Ile
                275                 280                 285

Ala Cys Gly Pro Arg Gly Glu Val Ala Tyr Ala Leu Glu Gly Ala Val
        290                 295                 300

Phe Asn Gly Gly Ser Thr Val Gln Trp Leu Arg Asp Glu Leu Lys Ile
305                 310                 315                 320

Ile Asn Asp Ala His Asp Thr Glu Tyr Phe Ala Gly Lys Val Lys Asp
                325                 330                 335

Ser Asn Gly Val Tyr Leu Val Pro Ala Phe Thr Gly Leu Gly Ala Pro
                340                 345                 350

Tyr Trp Asp Pro Tyr Ala Arg Gly Ala Leu Phe Gly Leu Thr Arg Gly
                355                 360                 365

Val Arg Val Asp His Ile Ile Arg Ala Ala Leu Glu Ser Ile Ala Tyr
        370                 375                 380

Gln Thr Arg Asp Val Leu Asp Ala Met Gln Gln Asp Ser Gly Glu Arg
385                 390                 395                 400

Leu Lys Ala Leu Arg Val Asp Gly Gly Ala Val Ala Asn Asn Phe Leu
                405                 410                 415

Met Gln Phe Gln Ala Asp Ile Leu Gly Thr Gln Val Glu Arg Pro Gln
                420                 425                 430

Met Arg Glu Thr Thr Ala Leu Gly Ala Ala Tyr Leu Ala Gly Leu Ala
        435                 440                 445

Cys Gly Phe Trp Gly Ser Leu Asp Glu Leu Arg Gly Lys Ala Val Ile
        450                 455                 460

Glu Arg Glu Phe Glu Pro Gln Leu Asp Glu Ala Ala Lys Glu Lys Leu
465                 470                 475                 480
```

```
Tyr Ala Gly Trp Gln Lys Ala Val Ser Arg Thr Arg Asp Trp Glu Pro
                485                 490                 495

His Glu Gly Ala Glu
            500

<210> SEQ ID NO 34
<211> LENGTH: 502
<212> TYPE: PRT
<213> ORGANISM: Serratia AS12

<400> SEQUENCE: 34

Met Thr Val Glu Lys Lys Tyr Ile Val Ala Leu Asp Gln Gly Thr Thr
  1               5                  10                  15

Ser Ser Arg Ala Val Val Leu Asp His Asp Ala Asn Ile Val Ala Val
                 20                  25                  30

Ser Gln Arg Glu Phe Thr Gln Ile Tyr Pro Lys Ala Gly Trp Val Glu
             35                  40                  45

His Asp Pro Met Glu Ile Trp Ser Ser Gln Ser Ser Thr Leu Val Glu
         50                  55                  60

Val Leu Ala Lys Ala Asp Ile Asn Ser Asp Gln Ile Ala Gly Ile Gly
 65                  70                  75                  80

Ile Thr Asn Gln Arg Glu Thr Thr Ile Val Trp Glu Lys Glu Thr Gly
                 85                  90                  95

Lys Pro Ile Tyr Asn Ala Ile Val Trp Gln Cys Arg Arg Thr Ala Asp
            100                 105                 110

Ile Cys Glu Lys Leu Lys Arg Asp Gly Leu Glu Glu Tyr Ile Arg His
        115                 120                 125

Asn Thr Gly Leu Val Val Asp Pro Tyr Phe Ser Gly Thr Lys Val Lys
130                 135                 140

Trp Ile Leu Asp Asn Val Glu Gly Ala Arg Glu Arg Ala Lys Arg Gly
145                 150                 155                 160

Glu Leu Leu Phe Gly Thr Val Asp Thr Trp Leu Val Trp Lys Met Thr
                165                 170                 175

Gln Gly Arg Val His Val Thr Asp Tyr Thr Asn Ala Ser Arg Thr Met
            180                 185                 190

Met Phe Asn Ile His Glu Leu Asp Trp Asp Asp Arg Met Leu Glu Ala
        195                 200                 205

Leu Asp Ile Pro Arg Val Met Leu Pro Lys Val Arg Pro Ser Ser Glu
210                 215                 220

Val Tyr Gly Gln Thr Asn Ile Gly Gly Lys Gly Gly Thr Arg Ile Pro
225                 230                 235                 240

Ile Ala Gly Ile Ala Gly Asp Gln Gln Ala Ala Leu Tyr Gly Gln Leu
                245                 250                 255

Cys Val Gln Pro Gly Met Ala Lys Asn Thr Tyr Gly Thr Gly Cys Phe
            260                 265                 270

Leu Leu Met Asn Thr Gly Lys Glu Ala Val Arg Ser Asn His Gly Leu
        275                 280                 285

Leu Thr Thr Ile Ala Cys Gly Pro Arg Gly Glu Val Asn Tyr Ala Leu
    290                 295                 300

Glu Gly Ala Val Phe Ile Gly Gly Ala Ser Ile Gln Trp Leu Arg Asp
305                 310                 315                 320

Glu Leu Lys Leu Ile Ser Asp Ala Ala Asp Ser Glu Tyr Phe Ala Thr
                325                 330                 335

Lys Val Lys Asp Ser Asn Gly Val Tyr Val Val Pro Ala Phe Thr Gly
```

```
                     340                 345                 350
Leu Gly Ala Pro Tyr Trp Asp Pro Tyr Ala Arg Gly Ala Ile Phe Gly
                355                 360                 365

Leu Thr Arg Gly Ala Asn Ser Asn His Ile Ile Arg Ala Thr Leu Glu
            370                 375                 380

Ser Ile Ala Tyr Gln Thr Arg Asp Val Leu Asp Ala Met Gln Ala Asp
385                 390                 395                 400

Ser Asn Thr Arg Leu Gln Ser Leu Arg Val Asp Gly Ala Val Ala
                405                 410                 415

Asn Asn Phe Leu Met Gln Phe Gln Ser Asp Ile Leu Gly Thr Arg Val
            420                 425                 430

Glu Arg Pro Glu Val Arg Glu Ser Thr Ala Leu Gly Ala Ala Phe Leu
                435                 440                 445

Ala Gly Leu Ala Ile Gly Tyr Trp Asn Asp Leu Asp Glu Val Lys Ser
            450                 455                 460

Lys Ala Val Ile Glu Arg Glu Phe Arg Pro Ser Ile Glu Thr Thr Glu
465                 470                 475                 480

Arg Asn Phe Arg Tyr Ser Gly Trp Lys Lys Ala Val Ala Arg Ala Gln
                485                 490                 495

Ala Trp Glu Asp His Asp
            500

<210> SEQ ID NO 35
<211> LENGTH: 504
<212> TYPE: PRT
<213> ORGANISM: Vibrio fischeri

<400> SEQUENCE: 35

Met Thr Glu Gln Lys Tyr Ile Val Ala Leu Asp Gln Gly Thr Thr Ser
1               5                   10                  15

Ser Arg Ala Val Ile Leu Asp His Asp Ala Asn Ile Val Ser Val Ser
                20                  25                  30

Gln Arg Glu Phe Thr Gln Ile Tyr Pro Glu Ala Gly Trp Val Glu His
            35                  40                  45

Asp Pro Leu Glu Ile Tyr Ala Thr Gln Ser Ser Thr Leu Val Glu Thr
        50                  55                  60

Leu Ala Lys Ala Gly Ile Arg Ser Asp Gln Ile Ala Gly Ile Gly Ile
65                  70                  75                  80

Thr Asn Gln Arg Glu Thr Thr Ile Val Trp Asn Lys Glu Thr Gly Lys
                85                  90                  95

Pro Val Tyr Asn Ala Ile Val Trp Gln Cys Arg Arg Thr Ala Asp Thr
            100                 105                 110

Cys Glu Lys Leu Lys Glu Ala Gly Leu Glu Glu Tyr Ile Arg Glu Asn
        115                 120                 125

Thr Gly Leu Val Val Asp Pro Tyr Phe Ser Gly Thr Lys Ile Lys Trp
    130                 135                 140

Ile Leu Asp Asn Val Glu Gly Ala Arg Glu Asp Ala Glu Ala Gly Lys
145                 150                 155                 160

Leu Leu Phe Gly Thr Val Asp Thr Trp Leu Val Trp Lys Met Thr Gln
                165                 170                 175

Gly Arg Val His Val Thr Asp Tyr Thr Asn Ala Ser Arg Thr Met Val
            180                 185                 190

Phe Asn Ile Asn Thr Leu Gln Trp Asp Glu Lys Leu Leu Lys Glu Leu
        195                 200                 205
```

Asp Ile Pro Leu Ser Met Met Pro Glu Val Lys Ser Ser Glu Val
210             215                 220

Tyr Gly Glu Thr Asn Ile Gly Gly Lys Gly Gly Thr Arg Ile Pro Ile
225                 230                 235                 240

Ala Gly Ile Ala Gly Asp Gln Gln Ala Leu Tyr Gly Gln Met Cys
            245                 250                 255

Val Glu Gln Gly Gln Ala Lys Asn Thr Tyr Gly Thr Gly Cys Phe Leu
        260                 265                 270

Leu Met Asn Thr Gly Lys Glu Lys Val Thr Ser Arg Asn Gly Leu Leu
            275                 280                 285

Thr Thr Leu Ala Cys Gly Pro Arg Gly Glu Ala Ser Tyr Ala Leu Glu
290                 295                 300

Gly Ala Val Phe Met Gly Gly Ala Ser Ile Gln Trp Leu Arg Asp Glu
305                 310                 315                 320

Met Lys Leu Leu Ala Asp Ala Lys Asp Ser Glu Tyr Phe Ala Thr Lys
                325                 330                 335

Val Asp Thr Ser Asn Gly Val Tyr Val Val Pro Ala Phe Thr Gly Leu
            340                 345                 350

Gly Ala Pro Tyr Trp Asp Ala Tyr Ala Arg Gly Thr Ile Val Gly Leu
        355                 360                 365

Thr Arg Gly Cys Gly Ser Asn His Ile Ile Arg Ala Thr Leu Glu Ser
370                 375                 380

Ile Ala Tyr Gln Thr Arg Asp Val Ile Asp Ala Met Gln Ala Asp Ser
385                 390                 395                 400

Gly Ile Lys Leu Ser Ala Leu Arg Val Asp Gly Gly Ala Val Ala Asn
                405                 410                 415

Asn Phe Leu Met Gln Phe Gln Ser Asp Val Leu Asp Val Ala Val His
            420                 425                 430

Arg Pro Lys Val Thr Glu Val Thr Ala Leu Gly Ala Ala Tyr Leu Ala
        435                 440                 445

Gly Leu Ala Val Gly Phe Trp Asn Gly Leu Asp Glu Leu Ala Asp Lys
450                 455                 460

Ala Val Ile Asp Arg Ser Phe Glu Pro His His Asp Glu Glu Lys Arg
465                 470                 475                 480

Asn Gln Arg Tyr Arg Gly Trp Lys Arg Ala Val Lys Cys Ala Gln Ser
                485                 490                 495

Trp Ala Glu Leu His Asp Glu Glu
            500

<210> SEQ ID NO 36
<211> LENGTH: 503
<212> TYPE: PRT
<213> ORGANISM: Haemophilus haemolyticus

<400> SEQUENCE: 36

Met Thr Asp Lys Lys Tyr Ile Ile Ala Leu Asp Gln Gly Thr Thr Ser
1               5                   10                  15

Ser Arg Ala Val Leu Leu Asp His Asn Ala Asn Val Val Glu Ile Ala
            20                  25                  30

Gln Arg Glu Phe Thr Gln Ile Tyr Pro Arg Ala Gly Trp Val Glu His
        35                  40                  45

Asn Pro Met Glu Ile Trp Ala Thr Gln Ser Ser Thr Leu Asn Glu Val
    50                  55                  60

Val Ala Lys Ala Gly Ile Thr Ser Asp Glu Ile Ala Ala Ile Gly Ile
65                  70                  75                  80

-continued

```
Thr Asn Gln Arg Glu Thr Thr Ile Val Trp Glu Lys Ala Thr Gly Thr
                 85                  90                  95
Pro Val Tyr Asn Ala Ile Val Trp Gln Cys Arg Arg Thr Ala Asp Ile
            100                 105                 110
Thr Asp Lys Leu Lys Ala Asp Gly His Glu Glu Tyr Ile Arg Asn Thr
        115                 120                 125
Thr Gly Leu Val Val Asp Pro Tyr Phe Ser Gly Thr Lys Val Lys Trp
    130                 135                 140
Ile Leu Asp Asn Val Glu Gly Ala Arg Glu Lys Ala Glu Arg Gly Glu
145                 150                 155                 160
Leu Leu Phe Gly Thr Val Asp Thr Trp Leu Val Trp Lys Leu Thr Gln
                165                 170                 175
Gly Arg Val His Val Thr Asp Tyr Thr Asn Ala Ser Arg Thr Met Leu
            180                 185                 190
Phe Asn Ile His Thr Lys Gln Trp Asp Asp Lys Met Leu Glu Ile Leu
        195                 200                 205
Asn Ile Pro Arg Ser Met Leu Pro Glu Val Arg Asn Ser Ser Glu Ile
    210                 215                 220
Tyr Gly Gln Thr Asn Ile Gly Gly Lys Gly Val Arg Ile Pro Val
225                 230                 235                 240
Ala Gly Ile Ala Gly Asp Gln Gln Ala Ala Leu Tyr Gly His Leu Cys
                245                 250                 255
Val His Ala Gly Gln Ala Lys Asn Thr Tyr Gly Thr Gly Cys Phe Met
            260                 265                 270
Leu Leu His Thr Gly Asn Lys Ala Ile Thr Ser Lys Asn Gly Leu Leu
        275                 280                 285
Thr Thr Ile Ala Cys Asn Ala Lys Gly Glu Pro Glu Tyr Ala Leu Glu
    290                 295                 300
Gly Ser Val Phe Ile Ala Gly Ala Ser Ile Gln Trp Leu Arg Asp Glu
305                 310                 315                 320
Leu Lys Ile Val His Asp Ser Phe Asp Ser Glu Tyr Phe Ala Gln Lys
                325                 330                 335
Val Thr Asp Ser Asn Gly Val Tyr Val Val Pro Ala Phe Thr Gly Leu
            340                 345                 350
Gly Ala Pro Tyr Trp Asp Pro Tyr Ala Arg Gly Ala Ile Phe Gly Leu
        355                 360                 365
Ser Arg Gly Ala Asn Arg Asn His Ile Val Arg Ala Thr Leu Glu Ser
    370                 375                 380
Ile Ala Tyr Gln Thr Arg Asp Val Leu Glu Ala Met Gln Ser Asp Ser
385                 390                 395                 400
Gly Glu Arg Leu Gln Tyr Leu Arg Val Asp Gly Gly Ala Thr Asn Asn
                405                 410                 415
Asn Phe Leu Met Gln Phe Gln Ala Asp Ile Leu Asp Val Asn Val Glu
            420                 425                 430
Arg Pro Val Val Lys Glu Val Thr Ala Leu Gly Ala Ala Tyr Leu Ala
        435                 440                 445
Gly Leu Ala Thr Gly Phe Trp Lys Asp Leu Asp Glu Leu Arg Asp Lys
    450                 455                 460
Ala Arg Val Glu Arg Thr Phe Ser Pro Asp Ser Asp Asn Glu Lys Arg
465                 470                 475                 480
Glu Arg Arg Tyr Lys Gly Trp Lys Lys Ala Val Lys Arg Ser Leu Glu
                485                 490                 495
```

```
Trp Ala Lys Glu Asp Glu Glu
            500

<210> SEQ ID NO 37
<211> LENGTH: 505
<212> TYPE: PRT
<213> ORGANISM: Vibrio harveyi

<400> SEQUENCE: 37

Met Thr Glu Gln Lys Tyr Ile Val Ala Leu Asp Gln Gly Thr Thr Ser
 1               5                  10                  15

Ser Arg Ala Val Ile Leu Asp His Asp Ala Asn Ile Val Ser Val Ala
             20                  25                  30

Gln Arg Glu Phe Thr Gln Ile Tyr Pro Glu Ala Gly Trp Val Glu His
         35                  40                  45

Asp Pro Met Glu Ile Trp Ala Thr Gln Ser Ser Thr Leu Val Glu Ala
     50                  55                  60

Leu Ala Lys Thr Gly Ile Arg Ser Asp Gln Leu Ala Gly Ile Gly Ile
 65                  70                  75                  80

Thr Asn Gln Arg Glu Thr Thr Ile Val Trp Asn Lys Glu Thr Gly Lys
                 85                  90                  95

Pro Val Tyr Asn Ala Ile Val Trp Gln Cys Arg Arg Thr Ala Asp Ile
            100                 105                 110

Cys Glu Glu Leu Lys Ala Arg Gly Leu Glu Asp Tyr Val Arg Asp Asn
        115                 120                 125

Thr Gly Leu Val Leu Asp Pro Tyr Phe Ser Gly Thr Lys Val Lys Trp
    130                 135                 140

Ile Leu Asp Asn Val Glu Gly Ala Arg Glu Asp Ala Glu Ala Gly Lys
145                 150                 155                 160

Leu Leu Phe Gly Thr Val Asp Thr Trp Leu Val Trp Lys Met Thr Gln
                165                 170                 175

Gly Arg Val His Val Thr Asp Tyr Thr Asn Ala Ser Arg Thr Met Leu
            180                 185                 190

Phe Asn Ile Asn Asp Leu Cys Trp Asp Gln Lys Met Leu Asp Glu Met
        195                 200                 205

Gly Ile Pro Ala Ser Met Met Pro Glu Val Lys Arg Ser Ser Glu Ile
    210                 215                 220

Tyr Gly Gln Thr Asn Ile Gly Gly Lys Gly Thr Arg Ile Pro Ile
225                 230                 235                 240

Ala Gly Ile Ala Gly Asp Gln Gln Ala Ala Leu Tyr Gly Gln Met Cys
                245                 250                 255

Val Glu Ala Gly Gln Ala Lys Asn Thr Tyr Gly Thr Gly Cys Phe Leu
            260                 265                 270

Leu Met Asn Thr Gly Gln Glu Lys Val Thr Ser Lys Asn Gly Leu Leu
        275                 280                 285

Thr Thr Leu Ala Cys Gly Pro Lys Gly Glu Pro Ala Tyr Ala Leu Glu
    290                 295                 300

Gly Ala Val Phe Met Gly Gly Ala Ser Ile Gln Trp Leu Arg Asp Glu
305                 310                 315                 320

Met Lys Ile Leu Ala Gly Ala Glu Asp Ser Glu Tyr Phe Ala Thr Lys
                325                 330                 335

Val Asp Thr Ser Asn Gly Val Tyr Val Val Pro Ala Phe Thr Gly Leu
            340                 345                 350

Gly Ala Pro Tyr Trp Asp Ala Tyr Ala Arg Gly Thr Ile Val Gly Leu
        355                 360                 365
```

```
Thr Arg Gly Val Asn Ser Asn His Ile Ile Arg Ala Thr Leu Glu Gly
            370                 375                 380

Ile Ala Tyr Gln Thr Arg Asp Val Leu Asp Ala Met Gln Ala Asp Ser
385                 390                 395                 400

Gly Ile Lys Leu Ala Asn Leu Arg Val Asp Gly Gly Ala Val Ala Asn
                405                 410                 415

Asn Phe Leu Met Gln Phe Gln Ser Asp Val Leu Asn Thr Glu Val His
                420                 425                 430

Arg Pro Gln Val Thr Glu Val Thr Ala Leu Gly Ala Ala Tyr Leu Ala
                435                 440                 445

Gly Leu Ala Val Gly Phe Trp Asn Ser Ile Asp Glu Leu Gln Asp Lys
            450                 455                 460

Ala Val Leu Asp Arg Thr Phe Glu Pro His Asp Asp Glu Glu Lys Arg
465                 470                 475                 480

Asn Arg Arg Tyr Lys Gly Trp Lys Arg Ala Val Lys Cys Ala Gln Thr
                485                 490                 495

Trp Ser Glu Leu His Asp Glu Asp
            500                 505

<210> SEQ ID NO 38
<211> LENGTH: 505
<212> TYPE: PRT
<213> ORGANISM: Vibrio cholerae

<400> SEQUENCE: 38

Met Thr Glu Gln Lys Tyr Val Val Ala Leu Asp Gln Gly Thr Thr Ser
1               5                   10                  15

Ser Arg Ala Val Val Leu Asp His Asp Ala Asn Ile Val Ser Val Ser
                20                  25                  30

Gln Arg Glu Phe Thr Gln Ile Tyr Pro Gln Ala Gly Trp Val Glu His
            35                  40                  45

Asp Pro Met Glu Ile Tyr Ala Thr Gln Ser Ser Thr Leu Val Glu Ala
50                  55                  60

Leu Gly Lys Ala Gly Ile Arg Ser Asp Glu Val Ala Ala Ile Gly Ile
65                  70                  75                  80

Thr Asn Gln Arg Glu Thr Thr Val Val Trp Asn Lys Glu Thr Gly Lys
                85                  90                  95

Pro Val Tyr Asn Ala Ile Val Trp Gln Cys Arg Arg Thr Ala Ala Ile
                100                 105                 110

Cys Glu Glu Leu Lys Ala Arg Gly Leu Glu Ser Tyr Ile Arg Asp Asn
            115                 120                 125

Thr Gly Leu Val Leu Asp Pro Tyr Phe Ser Gly Thr Lys Ile Lys Trp
130                 135                 140

Ile Leu Asp Asn Val Glu Gly Ala Arg Glu Gln Ala Glu Ala Gly Gln
145                 150                 155                 160

Leu Leu Phe Gly Thr Val Asp Thr Trp Leu Val Trp Lys Met Thr Gln
                165                 170                 175

Gly Arg Val His Val Thr Asp Tyr Thr Asn Ala Ser Arg Thr Met Leu
            180                 185                 190

Phe Asn Ile Asn Thr Leu Gln Trp Asp Glu Lys Ile Leu Ala Glu Phe
        195                 200                 205

Asn Ile Pro Leu Ser Met Met Pro Glu Val Lys Lys Ser Ser Glu Val
        210                 215                 220

Tyr Gly Gln Thr Asn Ile Gly Gly Lys Gly Gly Thr Arg Ile Pro Ile
```

```
                225                 230                 235                 240
Ala Gly Ile Ala Gly Asp Gln Gln Ala Leu Tyr Gly Gln Met Cys
                    245                 250                 255

Val Gln Ala Gly Gln Ala Lys Asn Thr Tyr Gly Thr Gly Cys Phe Leu
                260                 265                 270

Leu Met Asn Thr Gly Gln Glu Lys Val Thr Ser His Asn Gly Leu Leu
                275                 280                 285

Thr Thr Leu Ala Cys Gly Pro Arg Gly Glu Pro Ala Tyr Ala Leu Glu
                290                 295                 300

Gly Ala Val Phe Met Gly Gly Ala Ser Ile Gln Trp Leu Arg Asp Glu
305                 310                 315                 320

Leu Lys Leu Ile Ser Asp Ala Arg Asp Ser Glu Tyr Phe Ala Thr Lys
                    325                 330                 335

Val Asp Thr Ser Asn Gly Val Tyr Val Pro Ala Phe Thr Gly Leu
                340                 345                 350

Gly Ala Pro Tyr Trp Asp Ala Tyr Ala Arg Gly Thr Ile Val Gly Leu
                355                 360                 365

Thr Arg Gly Val Asn Ser Asn His Ile Ile Arg Ala Thr Leu Glu Ser
                370                 375                 380

Ile Ala Tyr Gln Thr Arg Asp Val Leu Asp Ala Met Gln Ala Asp Ser
385                 390                 395                 400

Gly Ile Lys Leu Ser Ala Leu Arg Val Asp Gly Gly Ala Val Ala Asn
                    405                 410                 415

Asn Phe Leu Met Gln Phe Gln Ala Asp Val Leu Asp Thr Glu Val His
                420                 425                 430

Arg Pro Lys Val Thr Glu Val Thr Ala Leu Gly Ala Ala Tyr Leu Ala
                435                 440                 445

Gly Leu Ala Val Gly Phe Trp Asp Gly Leu Glu Glu Leu Gln Gly Lys
                450                 455                 460

Ala Glu Ile Asp Arg Ser Phe Lys Pro His His Asp Glu Glu Lys Arg
465                 470                 475                 480

Gln Arg Arg Tyr Lys Gly Trp Lys Arg Ala Val Lys Cys Ala Gln Ala
                    485                 490                 495

Trp Ala Val Leu His Asn Glu Glu Glu
                500                 505

<210> SEQ ID NO 39
<211> LENGTH: 499
<212> TYPE: PRT
<213> ORGANISM: Pseudomonas putida

<400> SEQUENCE: 39

Met Thr Asp Thr Gln Asp Lys Asn Tyr Ile Ile Ala Leu Asp Gln Gly
1               5                   10                  15

Thr Thr Ser Ser Arg Ala Ile Ile Phe Asp Arg Asp Ala Asn Val Val
                20                  25                  30

Gly Thr Ser Gln Arg Glu Phe Ala Gln His Tyr Pro Gln Ala Gly Trp
            35                  40                  45

Val Glu His Asp Pro Met Glu Ile Phe Ala Thr Gln Ser Ala Thr Met
        50                  55                  60

Val Glu Ala Leu Ala Gln Ala Gly Ile Ser His Ala Gln Val Ala Ala
65                  70                  75                  80

Leu Gly Ile Thr Asn Gln Arg Glu Thr Thr Val Val Trp Asp Lys Glu
                85                  90                  95
```

```
Thr Gly Arg Pro Val Tyr Asn Ala Ile Val Trp Gln Cys Arg Arg Ser
            100                 105                 110

Thr Glu Ile Cys Ala Gln Leu Lys Arg Asp Gly His Glu Gly Tyr Ile
        115                 120                 125

Arg Glu Thr Thr Gly Leu Val Thr Asp Pro Tyr Phe Ser Gly Thr Lys
    130                 135                 140

Leu Lys Trp Ile Leu Asp Asn Val Glu Gly Ala Arg Glu Arg Ala Glu
145                 150                 155                 160

Arg Gly Glu Leu Leu Phe Gly Thr Ile Asp Thr Trp Leu Ile Trp Lys
                165                 170                 175

Phe Ser Gly Gly Lys Val His Val Thr Asp Tyr Thr Asn Ala Ser Arg
            180                 185                 190

Thr Leu Met Phe Asn Ile His Ser Leu Gln Trp Asp Asp Lys Leu Leu
        195                 200                 205

Glu Ile Leu Gly Ile Pro Arg Gln Met Leu Pro Glu Val Arg Pro Ser
    210                 215                 220

Ser Glu Val Tyr Gly His Thr Lys Ser Gly Ile Ala Ile Ala Gly Ile
225                 230                 235                 240

Ala Gly Asp Gln Gln Ser Ala Leu Phe Gly Gln Met Cys Val Glu Pro
                245                 250                 255

Gly Gln Ala Lys Asn Thr Tyr Gly Thr Gly Cys Phe Leu Leu Met Asn
            260                 265                 270

Thr Gly Asp Gln Ala Val Lys Ser Ser His Gly Leu Leu Thr Thr Ile
        275                 280                 285

Ala Cys Gly Pro Arg Gly Glu Val Ala Tyr Ala Leu Glu Gly Ala Val
    290                 295                 300

Phe Asn Gly Gly Ser Thr Val Gln Trp Leu Arg Asp Glu Leu Lys Ile
305                 310                 315                 320

Val Asn Asp Ala Leu Asp Thr Glu Tyr Phe Ala Ser Lys Val Lys Asp
                325                 330                 335

Ser Asn Gly Val Tyr Leu Val Pro Ala Phe Thr Gly Leu Gly Ala Pro
            340                 345                 350

Tyr Trp Asp Pro Tyr Ala Arg Gly Ala Leu Phe Gly Leu Thr Arg Gly
        355                 360                 365

Val Lys Val Asp His Ile Ile Arg Ala Ala Leu Glu Ser Ile Ala Tyr
    370                 375                 380

Gln Thr Arg Asp Val Leu Asp Ala Met Gln Gln Asp Cys Gly Gln Arg
385                 390                 395                 400

Leu Ser Glu Leu Arg Val Asp Gly Gly Ala Val Ala Asn Asn Phe Leu
                405                 410                 415

Met Gln Phe Gln Ala Asp Ile Leu Gly Thr Cys Val Glu Arg Pro Lys
            420                 425                 430

Met Arg Glu Thr Thr Ala Leu Gly Ala Ala Tyr Leu Ala Gly Leu Ala
        435                 440                 445

Cys Gly Phe Trp Ser Gly Leu Asp Glu Leu Arg Asp Lys Ala Ile Ile
    450                 455                 460

Glu Arg Glu Phe Ser Pro Gln Leu Asp Glu Thr Gln Lys Glu Lys Leu
465                 470                 475                 480

Tyr Ala Gly Trp Lys Lys Ala Val Asp Arg Thr Arg Asp Trp Glu Asp
                485                 490                 495

His Glu Ala

<210> SEQ ID NO 40
```

```
<211> LENGTH: 503
<212> TYPE: PRT
<213> ORGANISM: Pectobacterium carotovorum

<400> SEQUENCE: 40

Met Asn Pro Glu Lys Lys Tyr Ile Val Ala Leu Asp Gln Gly Thr Thr
1               5                   10                  15

Ser Ser Arg Ala Ile Val Leu Asp His Asp Ala Asn Ile Val Ser Val
            20                  25                  30

Ser Gln Arg Glu Phe Thr Gln Ile Tyr Pro Lys Ala Gly Trp Val Glu
        35                  40                  45

His Asp Pro Met Glu Ile Trp Ala Ser Gln Ser Ser Thr Leu Val Glu
50                  55                  60

Val Leu Ala Lys Ala Asp Ile Ser Ser Asp Glu Val Ala Gly Ile Gly
65                  70                  75                  80

Ile Thr Asn Gln Arg Glu Thr Thr Val Val Trp Glu Lys Glu Ser Gly
                85                  90                  95

Lys Pro Ile Tyr Asn Ala Ile Val Trp Gln Cys Arg Arg Thr Ala Asp
            100                 105                 110

Ile Cys Glu Lys Leu Lys Lys Asp Gly Leu Glu Glu Tyr Val Arg Asn
        115                 120                 125

Thr Thr Gly Leu Val Val Asp Pro Tyr Phe Ser Gly Thr Lys Val Lys
130                 135                 140

Trp Ile Leu Asp His Val Glu Gly Ser Arg Glu Arg Ala Lys Arg Gly
145                 150                 155                 160

Glu Leu Leu Phe Gly Thr Ile Asp Thr Trp Leu Ile Trp Lys Met Thr
                165                 170                 175

Gln Gly Arg Val His Val Thr Asp Tyr Thr Asn Ala Ser Arg Thr Met
            180                 185                 190

Leu Phe Asn Ile His Thr Leu Glu Trp Asp Thr Arg Met Leu Glu Ala
        195                 200                 205

Leu Asp Ile Pro Arg Glu Met Leu Pro Glu Val Arg Ala Ser Ser Glu
210                 215                 220

Val Tyr Gly Gln Thr Asn Ile Gly Gly Lys Gly Gly Thr Arg Ile Pro
225                 230                 235                 240

Ile Ala Gly Ile Ala Gly Asp Gln Gln Ala Ala Leu Tyr Gly Gln Leu
                245                 250                 255

Cys Val Asn Pro Gly Gln Ala Lys Asn Thr Tyr Gly Thr Gly Cys Phe
            260                 265                 270

Leu Leu Met Asn Thr Gly Lys Glu Ala Val Leu Ser Lys His Gly Leu
        275                 280                 285

Leu Thr Thr Ile Ala Cys Gly Pro Arg Gly Glu Val Asn Tyr Ala Leu
290                 295                 300

Glu Gly Ser Val Phe Val Gly Ala Ser Ile Gln Trp Leu Arg Asp
305                 310                 315                 320

Glu Leu Lys Leu Ile Gly Asp Ser Met Asp Ser Glu Tyr Phe Ala Thr
                325                 330                 335

Lys Val Lys Asp Thr Asn Gly Val Tyr Val Val Pro Ala Phe Thr Gly
            340                 345                 350

Leu Gly Ala Pro Tyr Trp Asp Pro Tyr Ala Arg Gly Ala Ile Phe Gly
        355                 360                 365

Leu Thr Arg Gly Val Asn Ala Asn His Ile Ile Arg Ala Thr Leu Glu
370                 375                 380

Ser Ile Ala Phe Gln Thr Arg Asp Val Leu Asp Ala Met Gln Ala Asp
```

```
385                 390                 395                 400
Ala Asp Thr Arg Leu Lys Ala Leu Arg Val Asp Gly Ala Val Ala
                405                 410                 415

Asn Asn Phe Leu Met Gln Phe Gln Ser Asp Ile Leu Gly Thr Arg Val
                420                 425                 430

Glu Arg Pro Glu Val Arg Glu Ser Thr Ala Leu Gly Ala Ala Phe Leu
                435                 440                 445

Ala Gly Leu Ala Thr Gly Phe Trp Asn Asp Leu Asp Glu Val Lys Ser
        450                 455                 460

Lys Ala Thr Ile Glu Arg Glu Phe Arg Pro Ser Ile Glu Thr Val Glu
465                 470                 475                 480

Arg Asn Tyr Arg Tyr Ser Gly Trp Gln Lys Ala Val Ala Arg Ala Arg
                485                 490                 495

Asn Trp Glu Asp His Asp Ala
                500

<210> SEQ ID NO 41
<211> LENGTH: 501
<212> TYPE: PRT
<213> ORGANISM: Pseudomonas syringae

<400> SEQUENCE: 41

Met Thr Asp Thr Gln Asn Lys Asn Tyr Ile Ile Ala Leu Asp Gln Gly
1               5                   10                  15

Thr Thr Ser Ser Arg Ala Ile Ile Phe Asp Arg Asp Ala Asn Val Val
                20                  25                  30

Ser Thr Ala Gln Ser Glu Phe Val Gln His Tyr Pro Gln Ala Gly Trp
            35                  40                  45

Val Glu His Asp Pro Met Glu Ile Phe Ala Thr Gln Thr Ala Cys Met
        50                  55                  60

Thr Lys Ala Leu Ala Gln Ala Asp Leu His His Asn Gln Ile Ala Ala
65                  70                  75                  80

Ile Gly Ile Thr Asn Gln Arg Glu Thr Thr Val Ile Trp Glu Arg Asp
                85                  90                  95

Thr Gly Arg Pro Ile Tyr Asn Ala Ile Val Trp Gln Cys Arg Arg Ser
                100                 105                 110

Thr Glu Ile Cys Gln Gln Leu Lys Arg Asp Gly Leu Glu Glu Tyr Ile
                115                 120                 125

Lys Asp Thr Thr Gly Leu Val Ile Asp Pro Tyr Phe Ser Gly Ser Lys
        130                 135                 140

Val Lys Trp Ile Leu Asp Asn Val Glu Gly Ser Arg Glu Arg Ala Arg
145                 150                 155                 160

Lys Gly Glu Leu Met Phe Gly Thr Ile Asp Thr Trp Leu Ile Trp Lys
                165                 170                 175

Phe Thr Gly Gly Lys Val His Val Thr Asp Tyr Thr Asn Ala Ser Arg
                180                 185                 190

Thr Met Leu Phe Asn Ile His Thr Leu Glu Trp Asp Gln Arg Met Leu
            195                 200                 205

Asp Val Leu Asp Ile Pro Arg Glu Ile Leu Pro Glu Val Lys Ala Ser
        210                 215                 220

Ser Glu Val Tyr Gly His Ser Lys Ser Gly Ile Pro Ile Ala Gly Ile
225                 230                 235                 240

Ala Gly Asp Gln Gln Ala Ala Leu Phe Gly Gln Met Cys Val Glu Pro
                245                 250                 255
```

Gly Gln Ala Lys Asn Thr Tyr Gly Thr Gly Cys Phe Leu Leu Met Asn
            260                 265                 270

Thr Gly Lys Lys Ala Val Lys Ser Ala His Gly Met Leu Thr Thr Ile
            275                 280                 285

Gly Cys Gly Pro Arg Gly Glu Val Ala Tyr Ala Leu Glu Gly Ala Val
            290                 295                 300

Phe Asn Gly Gly Ser Thr Val Gln Trp Leu Arg Asp Glu Leu Lys Leu
305                 310                 315                 320

Ile Asn Asp Ala Leu Asp Thr Glu Tyr Phe Ala Ser Lys Val Lys Asp
                325                 330                 335

Ser Asn Gly Val Tyr Leu Val Pro Ala Phe Thr Gly Leu Gly Ala Pro
            340                 345                 350

Tyr Trp Asp Pro Tyr Ala Arg Gly Ala Leu Phe Gly Leu Thr Arg Gly
            355                 360                 365

Val Lys Val Asp His Ile Ile Arg Ala Ala Leu Glu Ser Ile Ala Tyr
            370                 375                 380

Gln Thr Arg Asp Val Leu Asp Ala Met Gln Gln Asp Ser Gly Glu Arg
385                 390                 395                 400

Leu Lys Ser Leu Arg Val Asp Gly Gly Ala Val Ala Asn Asn Phe Leu
                405                 410                 415

Met Gln Phe Gln Ala Asp Ile Leu Gly Thr His Val Glu Arg Pro Gln
            420                 425                 430

Met Arg Glu Thr Thr Ala Leu Gly Ala Ala Phe Leu Ala Gly Leu Ala
            435                 440                 445

Ile Gly Phe Trp Ser Ser Leu Asp Glu Leu Arg Asn Lys Ala Val Ile
            450                 455                 460

Glu Arg Val Phe Glu Pro Ser Cys Glu Ala His Arg Glu Lys Leu
465                 470                 475                 480

Tyr Ala Gly Trp Gln Lys Ala Val Ala Arg Thr Arg Asp Trp Glu Pro
            485                 490                 495

His Glu Asn Glu Glu
            500

<210> SEQ ID NO 42
<211> LENGTH: 504
<212> TYPE: PRT
<213> ORGANISM: Artificial Sequence
<220> FEATURE:
<223> OTHER INFORMATION: Acinetobacter sp. ATCC 27244

<400> SEQUENCE: 42

Met Ile Ser Thr Asp Ser Gln Lys Lys Tyr Val Val Ala Phe Asp Gln
1               5                   10                  15

Gly Thr Thr Ser Ser Arg Ala Ile Val Leu Asp His Asp Ala Asn Val
            20                  25                  30

Ile Thr Ile Ala Gln Arg Glu Phe Thr Gln Ile Tyr Pro Gln Pro Gly
            35                  40                  45

Trp Val Glu His Asp Pro Met Glu Ile Trp Ala Thr Gln Ser Ala Val
            50                  55                  60

Trp Val Glu Ala Leu Ala Gln Ala Ser Ile Ser Ser Asp Glu Ile Ala
65                  70                  75                  80

Ala Ile Gly Ile Thr Asn Gln Arg Glu Thr Thr Val Ile Trp Asp Lys
                85                  90                  95

Lys Thr Gly Lys Pro Ile Tyr Asn Ala Ile Val Trp Gln Ser Arg Gln
            100                 105                 110

Ser Asn Glu Ile Cys Asn Gln Leu Arg Gln Asn Gly Trp Gln Asp Tyr
            115                 120                 125

Val Arg Lys Val Thr Gly Leu Val Ile Asp Pro Tyr Phe Ser Ala Thr
        130                 135                 140

Lys Ile Lys Trp Ile Leu Asp Arg Val Glu Gly Ser Arg Glu Arg Ala
145                 150                 155                 160

Glu Arg Gly Glu Leu Leu Phe Gly Thr Ile Asp Thr Trp Leu Ile Trp
                165                 170                 175

Lys Leu Thr Asn Gly Gln Val His Val Thr Asp Tyr Thr Asn Ala Ser
            180                 185                 190

Arg Thr Met Leu Phe Asn Ile Glu Thr Leu Gln Trp Asp Asp Lys Leu
        195                 200                 205

Leu Glu Ala Leu Asp Ile Pro Lys Ala Met Leu Pro Glu Val Arg Ser
210                 215                 220

Ser Ser Glu Val Tyr Gly Tyr Thr His Thr Ile Ser Gly Gln Glu Ile
225                 230                 235                 240

Gly Ile Pro Ile Ala Gly Ile Ala Gly Asp Gln Gln Ala Ala Leu Phe
                245                 250                 255

Gly Gln Met Cys Val Glu Val Gly Gln Ala Lys Asn Thr Tyr Gly Thr
            260                 265                 270

Gly Cys Phe Leu Leu Met Asn Thr Gly Glu Arg Met Val Gln Ser Asp
        275                 280                 285

His Gly Leu Leu Thr Thr Ile Ala Cys Gly Ala Lys Gly Glu Val Asn
        290                 295                 300

Tyr Ala Leu Glu Gly Ala Val Phe Asn Gly Gly Ser Cys Val Gln Trp
305                 310                 315                 320

Leu Arg Asp Glu Leu Lys Ala Ile Asn Asp Ser His Asp Ser Glu Tyr
                325                 330                 335

Tyr Ala Thr Lys Val Lys Asp Ser Asn Gly Val Tyr Val Val Pro Ala
            340                 345                 350

Phe Thr Gly Leu Gly Ala Pro Tyr Trp Asp Pro Thr Ala Arg Gly Ala
        355                 360                 365

Ile Leu Gly Ile Thr Arg Gly Val Ser Ile Glu His Ile Ile Arg Ala
370                 375                 380

Thr Leu Glu Ser Ile Ala Tyr Gln Thr Arg Asp Val Leu Asp Ala Met
385                 390                 395                 400

Gln Gln Asp Ser Gly Glu Lys Leu Arg Thr Leu Arg Val Asp Gly Gly
                405                 410                 415

Val Thr Ala Asn Asn Phe Leu Met Gln Phe Gln Ala Asp Ile Leu Ser
            420                 425                 430

Thr Ser Val Glu Arg Pro Ala Met Lys Glu Thr Thr Gly Met Gly Ala
        435                 440                 445

Ala Phe Leu Ala Gly Leu Ala Val Gly Phe Trp Ser Asp Leu Asn Glu
450                 455                 460

Leu Lys Arg Arg Met Thr Ile Glu Asn Thr Phe Thr Pro Ala Cys Thr
465                 470                 475                 480

Gln Glu Glu Thr Glu Lys Leu Tyr Thr Gly Trp Leu Lys Ala Val Gly
                485                 490                 495

Arg Thr Arg Asp Trp Ala Glu Asp
            500

<210> SEQ ID NO 43
<211> LENGTH: 501
<212> TYPE: PRT

<213> ORGANISM: Escherichia coli

<400> SEQUENCE: 43

Met Glu Thr Lys Asp Leu Ile Val Ile Gly Gly Ile Asn Gly Ala
1               5                   10                  15

Gly Ile Ala Ala Asp Ala Ala Gly Arg Gly Leu Ser Val Leu Met Leu
            20                  25                  30

Glu Ala Gln Asp Leu Ala Cys Ala Thr Ser Ser Ala Ser Ser Lys Leu
        35                  40                  45

Ile His Gly Gly Leu Arg Tyr Leu Glu His Tyr Glu Phe Arg Leu Val
    50                  55                  60

Ser Glu Ala Leu Ala Glu Arg Glu Val Leu Leu Lys Met Ala Pro His
65                  70                  75                  80

Ile Ala Phe Pro Met Arg Phe Arg Leu Pro His Arg Pro His Leu Arg
                85                  90                  95

Pro Ala Trp Met Ile Arg Ile Gly Leu Phe Met Tyr Asp His Leu Gly
            100                 105                 110

Lys Arg Thr Ser Leu Pro Gly Ser Thr Gly Leu Arg Phe Gly Ala Asn
        115                 120                 125

Ser Val Leu Lys Pro Glu Ile Lys Arg Gly Phe Glu Tyr Ser Asp Cys
    130                 135                 140

Trp Val Asp Asp Ala Arg Leu Val Leu Ala Asn Ala Gln Met Val Val
145                 150                 155                 160

Arg Lys Gly Gly Glu Val Leu Thr Arg Thr Arg Ala Thr Ser Ala Arg
                165                 170                 175

Arg Glu Asn Gly Leu Trp Ile Val Glu Ala Glu Asp Ile Asp Thr Gly
            180                 185                 190

Lys Lys Tyr Ser Trp Gln Ala Arg Gly Leu Val Asn Ala Thr Gly Pro
        195                 200                 205

Trp Val Lys Gln Phe Phe Asp Asp Gly Met His Leu Pro Ser Pro Tyr
    210                 215                 220

Gly Ile Arg Leu Ile Lys Gly Ser His Ile Val Pro Arg Val His
225                 230                 235                 240

Thr Gln Lys Gln Ala Tyr Ile Leu Gln Asn Glu Asp Lys Arg Ile Val
                245                 250                 255

Phe Val Ile Pro Trp Met Asp Glu Phe Ser Ile Ile Gly Thr Thr Asp
            260                 265                 270

Val Glu Tyr Lys Gly Asp Pro Lys Ala Val Lys Ile Glu Glu Ser Glu
        275                 280                 285

Ile Asn Tyr Leu Leu Asn Val Tyr Asn Thr His Phe Lys Lys Gln Leu
    290                 295                 300

Ser Arg Asp Asp Ile Val Trp Thr Tyr Ser Gly Val Arg Pro Leu Cys
305                 310                 315                 320

Asp Asp Glu Ser Asp Ser Pro Gln Ala Ile Thr Arg Asp Tyr Thr Leu
                325                 330                 335

Asp Ile His Asp Glu Asn Gly Lys Ala Pro Leu Leu Ser Val Phe Gly
            340                 345                 350

Gly Lys Leu Thr Thr Tyr Arg Lys Leu Ala Glu His Ala Leu Glu Lys
        355                 360                 365

Leu Thr Pro Tyr Tyr Gln Gly Ile Gly Pro Ala Trp Thr Lys Glu Ser
    370                 375                 380

Val Leu Pro Gly Gly Ala Ile Glu Gly Asp Arg Asp Asp Tyr Ala Ala
385                 390                 395                 400

Arg Leu Arg Arg Arg Tyr Pro Phe Leu Thr Glu Ser Leu Ala Arg His
                405                 410                 415

Tyr Ala Arg Thr Tyr Gly Ser Asn Ser Glu Leu Leu Gly Asn Ala
            420                 425                 430

Gly Thr Val Ser Asp Leu Gly Glu Asp Phe Gly His Glu Phe Tyr Glu
                435                 440                 445

Ala Glu Leu Lys Tyr Leu Val Asp His Glu Trp Val Arg Arg Ala Asp
450                 455                 460

Asp Ala Leu Trp Arg Arg Thr Lys Gln Gly Met Trp Leu Asn Ala Asp
465                 470                 475                 480

Gln Gln Ser Arg Val Ser Gln Trp Leu Val Glu Tyr Thr Gln Gln Arg
                485                 490                 495

Leu Ser Leu Ala Ser
            500

<210> SEQ ID NO 44
<211> LENGTH: 512
<212> TYPE: PRT
<213> ORGANISM: Photobacterium profundum

<400> SEQUENCE: 44

Met Thr Ala Glu Asn Thr Gln Ile Leu Asp Leu Ile Val Val Gly Gly
1               5                   10                  15

Gly Ile Asn Gly Ala Gly Ile Ala Ala Asp Ala Ala Gly Arg Gly Leu
                20                  25                  30

Thr Val Gly Leu Tyr Glu Ala Asp Asp Phe Ala Ser Ala Thr Ser Ser
            35                  40                  45

Ala Ser Ser Lys Leu Ile His Gly Gly Leu Arg Tyr Leu Glu His Tyr
50                  55                  60

Glu Phe Arg Leu Val Gly Glu Ala Leu Ala Arg Glu Val Leu Leu
65                  70                  75                  80

Lys Lys Ile Pro His Ile Ala Arg Pro Met Arg Phe Arg Leu Pro His
                85                  90                  95

Arg Pro His Leu Arg Pro Ala Trp Met Ile Arg Ala Gly Leu Phe Met
            100                 105                 110

Tyr Asp Asn Leu Gly Lys Arg Thr Thr Leu Pro Ala Ser His Gly Leu
        115                 120                 125

Lys Phe Gly Gln Asp Ser Val Leu Ile Pro Glu Ile Thr Lys Gly Phe
    130                 135                 140

Glu Tyr Ser Asp Cys Trp Val Asp Asp Ala Arg Leu Val Ile Leu Asn
145                 150                 155                 160

Ala Met Glu Val Ala Glu Lys Gly Gly Asp Val Arg Asn Arg Cys Arg
                165                 170                 175

Val Glu Lys Ala Val Arg Glu Gly Glu Phe Trp Leu Val Thr Ile Arg
            180                 185                 190

Asp Val Gln Thr Asn Glu Ile Phe Val Arg Lys Ser Arg Ala Leu Val
        195                 200                 205

Asn Ala Ala Gly Pro Trp Val Lys Ala Phe Phe Asp Asn Ser Met Glu
    210                 215                 220

Glu Val Ser Pro Arg Asn Ile Arg Leu Ile Lys Gly Ser His Ile Val
225                 230                 235                 240

Val Pro Arg Ala His Asp Glu Pro Gln Ala Tyr Ile Leu Gln Asn Glu
                245                 250                 255

Asp Asn Arg Ile Val Phe Val Ile Pro Tyr Leu Asp Arg Phe Ser Ile
            260                 265                 270

```
Ile Gly Thr Thr Asp Val Glu Tyr Asn Gly Asp Pro Arg Asn Val Ala
            275                 280                 285

Ile Asp Ser Glu Ile Asp Tyr Leu Leu Lys Ala Tyr Asn Ala Asn
290                 295                 300

Phe Val Lys Lys Leu Asp Arg Thr Asp Val Val Trp Thr Tyr Ser Gly
305                 310                 315                 320

Val Arg Pro Leu Cys Asp Asp Glu Ser Asp Ser Pro Gln Ala Ile Thr
                325                 330                 335

Arg Asp Tyr Thr Leu Glu Leu Glu Gln Gln Ala Asn Lys Ala Pro Leu
            340                 345                 350

Leu Ser Ile Phe Gly Gly Lys Leu Thr Thr Tyr Arg Lys Leu Ala Glu
            355                 360                 365

Ala Ala Met Thr Lys Leu Ser Pro Phe Phe Ser Asn Met Gly Pro Ser
370                 375                 380

Trp Thr Ala Asp Ser Tyr Leu Pro Gly Gly Glu Ala Asn Phe Ser Ile
385                 390                 395                 400

Pro Gln Leu Ala Lys Lys Leu Gln Gln Gln His Ala Trp Leu Ser Ala
                405                 410                 415

Phe Thr Cys Glu Arg Met Ala Thr Asn Tyr Gly Asn Arg Ala Val Arg
            420                 425                 430

Leu Leu Glu Gly Val Asn Gly Glu Ala Asp Met Gly Lys His Phe Gly
            435                 440                 445

Glu Gly Leu Tyr Ala Arg Glu Leu Asp Tyr Met Ile Glu Gln Glu Phe
        450                 455                 460

Ala Gln Asn Glu Ile Asp Ala Leu Trp Arg Arg Ser Lys Leu Gly Leu
465                 470                 475                 480

Tyr Leu Asn Asp Glu Gln Ile Ala Ala Val Ala Gln Tyr Ile Thr Asp
                485                 490                 495

Lys Ala Leu Ser Ile Glu Ala Lys Lys Ser Glu Ala Asn Val Ala Ala
            500                 505                 510

<210> SEQ ID NO 45
<211> LENGTH: 504
<212> TYPE: PRT
<213> ORGANISM: Yersinia enterocolitica

<400> SEQUENCE: 45

Met Glu Thr Lys Asp Leu Ile Val Ile Gly Gly Ile Asn Gly Ala
1               5                   10                  15

Gly Ile Ala Ala Asp Ala Ala Gly Arg Gly Leu Ser Val Leu Leu Leu
            20                  25                  30

Glu Ala Gln Asp Leu Ala Cys Ala Thr Ser Ser Ala Ser Ser Lys Leu
        35                  40                  45

Ile His Gly Gly Leu Arg Tyr Leu Glu His Tyr Glu Phe Arg Leu Val
    50                  55                  60

Ser Glu Ala Leu Ala Glu Arg Glu Val Leu Leu Lys Leu Ala Pro His
65                  70                  75                  80

Ile Ala Phe Pro Met Arg Phe Arg Leu Pro His Gln Pro His Leu Arg
                85                  90                  95

Pro Ala Trp Met Ile Arg Thr Gly Leu Phe Leu Tyr Asp His Leu Gly
            100                 105                 110

Lys Arg Thr Ser Leu Pro Ala Ser Lys Gly Leu Arg Phe Gly Pro Glu
        115                 120                 125

Ser Val Leu Lys Pro Glu Leu Val Arg Gly Phe Glu Tyr Ser Asp Cys
```

```
            130                 135                 140
Trp Val Asp Asp Ala Arg Leu Val Leu Asn Ala Gln Glu Val
145                 150                 155                 160

Glu Arg Gly Gly Glu Val Arg Thr Arg Thr Lys Val Thr Arg Ala Trp
                165                 170                 175

Arg Glu Gln Gly Leu Trp Met Val Glu Ala Val Asp Ala Asn Thr Gly
            180                 185                 190

Lys Thr Phe Thr Trp Arg Ala Lys Gly Leu Val Asn Ala Thr Gly Pro
                195                 200                 205

Trp Val Lys Gln Phe Phe Asp Asp Gly Leu Lys Leu Lys Ser Pro Tyr
210                 215                 220

Gly Ile Arg Leu Ile Lys Gly Ser His Ile Val Pro Arg Val His
225                 230                 235                 240

Asn Gln Pro Gln Ala Tyr Ile Leu Gln Asn Glu Asp His Arg Ile Val
                245                 250                 255

Phe Val Ile Pro Trp Leu Asp Glu Tyr Ser Ile Ile Gly Thr Thr Asp
                260                 265                 270

Val Glu Tyr His Gly Asp Pro Lys Asp Val Lys Ile Asp Asp Gln Glu
            275                 280                 285

Ile Asp Tyr Leu Leu Lys Val Tyr Asn Asp His Phe Lys Lys Gln Leu
290                 295                 300

Gly Arg Asp Asp Ile Val Trp Thr Tyr Ser Gly Val Arg Pro Leu Cys
305                 310                 315                 320

Asp Asp Glu Ser Asp Ser Pro Gln Ala Val Thr Arg Asp Tyr Thr Leu
                325                 330                 335

Asp Val Ala Asp Glu Gly Gly Lys Ala Pro Leu Leu Ser Val Phe Gly
            340                 345                 350

Gly Lys Leu Thr Thr Tyr Arg Lys Leu Ala Glu His Ala Leu Glu Lys
                355                 360                 365

Leu Ser Gly Tyr Tyr Pro Asn Val Gly Pro Ala Trp Thr Lys Thr Gly
370                 375                 380

Ser Leu Pro Gly Gly Asp Ile Gly Gly Ser Arg Asp Asn Tyr Thr Val
385                 390                 395                 400

Gln Leu Arg His Arg Tyr Asn Trp Leu Pro Glu Gly Leu Ala Arg Arg
                405                 410                 415

Tyr Thr Thr Tyr Gly Ser His Ser Glu Leu Ile Leu Ala Asp Ala
            420                 425                 430

Thr Ser Ile Glu Ser Leu Gly Glu His Phe Gly His Gly Leu Tyr Glu
                435                 440                 445

Ala Glu Leu Arg Tyr Leu Val Glu Lys Glu Trp Val Glu Leu Asp
450                 455                 460

Asp Ala Ile Trp Arg Arg Thr Lys Leu Gly Met Thr Leu Asp Asp Val
465                 470                 475                 480

Gln Lys Gln Arg Val Ala Glu Trp Leu Ala Gln Val Gln Ala Glu Lys
                485                 490                 495

Gln Gln Thr Leu Ser Leu Val Ser
            500
```

<210> SEQ ID NO 46
<211> LENGTH: 502
<212> TYPE: PRT
<213> ORGANISM: Enterobacter cloacae

<400> SEQUENCE: 46

-continued

```
Met Glu Thr Lys Asp Leu Ile Val Ile Gly Gly Ile Asn Gly Ala
 1               5                  10                  15
Gly Ile Ala Val Asp Ala Ala Gly Arg Gly Leu Ser Val Leu Met Leu
                20                  25                  30
Glu Ala Asn Asp Leu Ala Cys Ala Thr Ser Ser Ala Ser Ser Lys Leu
                35                  40                  45
Ile His Gly Gly Leu Arg Tyr Leu Glu His Tyr Glu Phe Arg Leu Val
    50                  55                  60
Ser Glu Ala Leu Ala Glu Arg Glu Val Leu Leu Lys Met Ala Pro His
 65                 70                  75                  80
Leu Ala Ile Pro Met Arg Phe Arg Leu Pro His Arg Pro His Leu Arg
                85                  90                  95
Pro Ala Trp Met Ile Arg Ile Gly Leu Phe Met Tyr Asp His Leu Gly
                100                 105                 110
Lys Arg Thr Ser Leu Pro Gly Ser Thr Gly Leu Arg Phe Gly Ser Glu
                115                 120                 125
Ser Val Leu Lys Pro Glu Ile Val Arg Gly Phe Glu Tyr Ser Asp Cys
                130                 135                 140
Trp Val Asp Asp Ala Arg Leu Val Leu Ala Asn Ala Gln Met Val Glu
145                 150                 155                 160
Lys Lys Gly Gly Glu Val Lys Thr Arg Thr Arg Ala Thr Ala Ala Arg
                165                 170                 175
Arg Glu Asn Gly Leu Trp Ile Val Glu Ala Glu Asp Val Asp Thr Gly
                180                 185                 190
Glu Lys Phe Ser Trp Lys Ala Arg Gly Leu Val Asn Ala Thr Gly Pro
                195                 200                 205
Trp Val Lys Gln Phe Phe Asp Asp Gly Met His Leu Pro Ser Pro Tyr
210                 215                 220
Gly Ile Arg Leu Ile Lys Gly Ser His Ile Val Pro Arg Val His
225                 230                 235                 240
Thr Gln Lys Gln Ala Tyr Ile Leu Gln Asn Glu Asp Lys Arg Ile Val
                245                 250                 255
Phe Val Ile Pro Trp Met Asp Glu Phe Ser Ile Ile Gly Thr Thr Asp
                260                 265                 270
Val Glu Tyr Lys Gly Asp Pro Lys Asn Val Glu Ile Asp Glu Ser Glu
                275                 280                 285
Val Ser Tyr Leu Leu Lys Val Tyr Asn Ala His Phe Lys Lys Gln Leu
                290                 295                 300
Ala Arg Asp Asp Val Val Trp Thr Tyr Ser Gly Val Arg Pro Leu Cys
305                 310                 315                 320
Asp Asp Glu Ser Asp Ser Pro Gln Ala Ile Thr Arg Asp Tyr Thr Leu
                325                 330                 335
Asp Ile His Asp Val Asp Gly Gln Ala Pro Leu Leu Ser Val Phe Gly
                340                 345                 350
Gly Lys Leu Thr Thr Tyr Arg Lys Leu Ala Glu His Ala Leu Glu Lys
                355                 360                 365
Leu Ala Pro Tyr Tyr Lys Gly Ile Gly Pro Ala Trp Thr Lys Gly Ala
                370                 375                 380
Val Leu Pro Gly Gly Asp Ile Gly Asp Asn Arg Asp Asp Tyr Ala Ala
385                 390                 395                 400
Lys Leu Arg Arg Arg Phe Pro Phe Ile Thr Glu Gly Met Ala Arg His
                405                 410                 415
Tyr Ala Arg Thr Tyr Gly Ser Asn Thr Glu Leu Phe Leu Gly Glu Ala
```

-continued

```
                420                 425                 430
Lys Glu Ile Ala Asp Leu Gly Glu His Phe Gly His Glu Leu Tyr Glu
            435                 440                 445

Ala Glu Leu Arg Tyr Leu Val Glu His Glu Trp Val Arg Arg Leu Asp
        450                 455                 460

Asp Ala Ile Trp Arg Arg Thr Lys Glu Gly Met Trp Leu Asn Ala Glu
465                 470                 475                 480

Gln Gln Ser Arg Val Ala Gln Trp Leu Gln Gln His Ala Gly Lys Arg
            485                 490                 495

Glu Leu Ser Leu Ala Ser
            500

<210> SEQ ID NO 47
<211> LENGTH: 494
<212> TYPE: PRT
<213> ORGANISM: Pseudomonas aeruginosa

<400> SEQUENCE: 47

Met Val Gly Gly Gly Ile Asn Gly Val Gly Ile Ala Ala Asp Ala Ala
1               5                   10                  15

Gly Arg Gly Leu Ser Val Phe Leu Cys Glu Gln His Asp Leu Ala Gln
            20                  25                  30

His Thr Ser Ser Ala Ser Ser Lys Leu Ile His Gly Gly Leu Arg Tyr
        35                  40                  45

Leu Glu His Tyr Glu Phe Arg Leu Val Arg Glu Ala Leu Ala Glu Arg
    50                  55                  60

Glu Val Leu Leu Ala Lys Ala Pro His Ile Val Lys Pro Leu Arg Phe
65                  70                  75                  80

Val Leu Pro His Arg Pro His Leu Arg Pro Ala Trp Met Ile Arg Ala
            85                  90                  95

Gly Leu Phe Leu Tyr Asp His Leu Gly Lys Arg Glu Lys Leu Pro Ala
        100                 105                 110

Ser Arg Gly Leu Arg Phe Thr Gly Ser Ser Pro Leu Lys Ala Glu Ile
    115                 120                 125

Arg Arg Gly Phe Glu Tyr Ser Asp Cys Ala Val Asp Asp Ala Arg Leu
130                 135                 140

Val Val Leu Asn Ala Ile Ser Ala Arg Glu His Gly Ala His Val His
145                 150                 155                 160

Thr Arg Thr Arg Cys Val Ser Ala Arg Ser Lys Gly Leu Trp His
            165                 170                 175

Leu His Leu Glu Arg Ser Asp Gly Ser Leu Tyr Ser Ile Arg Ala Arg
        180                 185                 190

Ala Leu Val Asn Ala Ala Gly Pro Trp Val Ala Arg Phe Ile Gln Asp
    195                 200                 205

Asp Leu Lys Gln Lys Ser Pro Tyr Gly Ile Arg Leu Ile Gln Gly Ser
210                 215                 220

His Ile Ile Val Pro Lys Leu Tyr Glu Gly Glu His Ala Tyr Ile Leu
225                 230                 235                 240

Gln Asn Glu Asp Arg Arg Ile Val Phe Ala Ile Pro Tyr Leu Asp Arg
            245                 250                 255

Phe Thr Met Ile Gly Thr Thr Asp Arg Glu Tyr Gln Gly Asp Pro Ala
        260                 265                 270

Lys Val Ala Ile Ser Glu Glu Glu Thr Ala Tyr Leu Leu Gln Val Val
    275                 280                 285
```

```
Asn Ala His Phe Lys Gln Gln Leu Ala Ala Ala Asp Ile Leu His Ser
    290                 295                 300

Phe Ala Gly Val Arg Pro Leu Cys Asp Asp Glu Ser Asp Glu Pro Ser
305                 310                 315                 320

Ala Ile Thr Arg Asp Tyr Thr Leu Ser Leu Ser Ala Gly Asn Gly Glu
                325                 330                 335

Pro Pro Leu Leu Ser Val Phe Gly Gly Lys Leu Thr Thr Tyr Arg Lys
                340                 345                 350

Leu Ala Glu Ser Ala Leu Thr Gln Leu Gln Pro Phe Phe Ala Asn Leu
                355                 360                 365

Gly Pro Ala Trp Thr Ala Lys Ala Pro Leu Pro Gly Gly Glu Gln Met
370                 375                 380

Gln Ser Val Glu Ala Leu Thr Glu Gln Leu Ala Asn Arg Tyr Ala Trp
385                 390                 395                 400

Leu Asp Arg Glu Leu Ala Leu Arg Trp Ala Arg Thr Tyr Gly Thr Arg
                405                 410                 415

Val Trp Arg Leu Leu Asp Gly Val Asn Gly Glu Ala Asp Leu Gly Glu
                420                 425                 430

His Leu Gly Gly Gly Leu Tyr Ala Arg Glu Val Asp Tyr Leu Cys Lys
                435                 440                 445

His Glu Trp Ala Gln Asp Ala Glu Asp Ile Leu Trp Arg Arg Ser Lys
450                 455                 460

Leu Gly Leu Phe Leu Ser Pro Ser Gln Gln Val Arg Leu Gly Gln Tyr
465                 470                 475                 480

Leu Gln Ser Glu His Pro His Arg Pro Arg Val His Ala Ala
                485                 490

<210> SEQ ID NO 48
<211> LENGTH: 512
<212> TYPE: PRT
<213> ORGANISM: Pseudomonas fluorescens

<400> SEQUENCE: 48

Met Asn Pro Ser Thr Leu Pro Ala Pro Pro Leu Ala Glu Val Tyr Asp
1               5                   10                  15

Val Ala Val Ile Gly Gly Gly Ile Asn Gly Val Gly Ile Ala Ala Asp
                20                  25                  30

Ala Ala Gly Arg Gly Leu Ser Val Phe Leu Cys Glu Lys Asp Asp Leu
                35                  40                  45

Ala Ser His Thr Ser Ser Ala Ser Ser Lys Leu Ile His Gly Gly Leu
                50                  55                  60

Arg Tyr Leu Glu His Tyr Glu Phe Arg Leu Val Arg Glu Ala Leu Ala
65                  70                  75                  80

Glu Arg Glu Val Leu Leu Asp Lys Ala Pro His Ile Val Lys Gln Met
                85                  90                  95

Arg Phe Val Leu Pro His Arg Pro His Leu Arg Pro Ala Trp Met Ile
                100                 105                 110

Arg Ala Gly Leu Phe Leu Tyr Asp His Leu Gly Lys Arg Glu Lys Leu
                115                 120                 125

Ala Gly Ser Lys Ser Leu Lys Phe Gly Ala Asp Ser Pro Leu Lys Ser
                130                 135                 140

Glu Ile Thr Arg Gly Phe Glu Tyr Ser Asp Cys Trp Val Asp Asp Ala
145                 150                 155                 160

Arg Leu Val Val Leu Asn Ala Met Ala Ala Arg Glu Lys Gly Ala His
                165                 170                 175
```

```
Ile His Thr Gln Thr Arg Cys Val Ser Ala His Arg Ser Asn Gly Leu
            180                 185                 190

Trp Glu Met Asn Met Glu Arg Ala Asp Gly Ser Leu Phe Ser Ile Arg
            195                 200                 205

Ala Arg Ala Leu Val Asn Ala Ala Gly Pro Trp Val Ala Lys Phe Ile
210                 215                 220

Lys Asp Asp Leu Lys Leu Asp Ser Pro Tyr Gly Ile Arg Leu Ile Gln
225                 230                 235                 240

Gly Ser His Leu Ile Val Pro Arg Leu Tyr Glu Gly Ala His Ala His
                245                 250                 255

Ile Leu Gln Asn Glu Asp Gln Arg Ile Val Phe Thr Ile Pro Tyr Leu
            260                 265                 270

Asn His Leu Thr Ile Ile Gly Thr Thr Asp Arg Glu Tyr Thr Gly Asp
            275                 280                 285

Pro Ala Ala Val Ala Ile Thr Glu Gly Glu Thr Asp Tyr Met Leu Lys
        290                 295                 300

Val Val Asn Ala His Phe Lys Lys Gln Leu Ser Arg Asp Asp Ile Val
305                 310                 315                 320

His Thr Tyr Ser Gly Val Arg Pro Leu Cys Asn Asp Glu Ser Asp Asn
                325                 330                 335

Pro Ser Ala Ile Thr Arg Asp Tyr Thr Leu Ala Leu Ser Gly Gly Thr
            340                 345                 350

Gly Glu Ala Pro Ile Leu Ser Val Phe Gly Gly Lys Leu Thr Thr Tyr
            355                 360                 365

Arg Lys Leu Ala Glu Ser Ala Met Ala Gln Leu Ala Pro Tyr Phe Thr
370                 375                 380

Gln Met Arg Pro Ser Trp Thr Ala Thr Ala Ser Leu Pro Gly Gly Glu
385                 390                 395                 400

Asp Met Thr Thr Pro Glu Ala Leu Ala Asp Ala Ile Arg Ala Lys Phe
                405                 410                 415

Asp Trp Val Pro Ser Glu Ile Ala Arg Arg Trp Ser Thr Thr Tyr Gly
            420                 425                 430

Ser Arg Thr Trp Arg Leu Leu Glu Gly Val Gln Thr Leu Ala Asp Leu
        435                 440                 445

Gly Asp His Leu Gly Gly Gly Leu Tyr Ser Arg Glu Val Asp Tyr Leu
450                 455                 460

Cys Ala Glu Glu Trp Val Thr Gln Pro Gln Asp Val Leu Trp Arg Arg
465                 470                 475                 480

Thr Lys Leu Gly Leu Phe Thr Thr Glu Gln Glu Gln Glu Asn Leu Gln
                485                 490                 495

Arg Tyr Leu Ser Lys Val Glu Gln Asn Arg Ser Lys Ile Glu Ala Ala
            500                 505                 510

<210> SEQ ID NO 49
<211> LENGTH: 513
<212> TYPE: PRT
<213> ORGANISM: Vibrio vulnificus

<400> SEQUENCE: 49

Met Lys Asn Asn Ser Ser Thr Pro Thr Ser Thr Leu Asp Ile Leu Val
  1               5                  10                  15

Val Gly Gly Gly Ile Asn Gly Ala Gly Ile Ala Ala Asp Ala Ala Gly
            20                  25                  30

Arg Gly Leu Ser Val Ala Leu Phe Glu Ala Lys Asp Phe Ala Ser Ala
```

```
            35                  40                  45
Thr Ser Ser Ala Ser Ser Lys Leu Ile His Gly Gly Leu Arg Tyr Leu
 50                  55                  60
Glu His Tyr Glu Phe Arg Leu Val Ser Glu Ala Leu Ala Glu Arg Glu
 65                  70                  75                  80
Val Leu Ile Lys Lys Ala Pro His Ile Ala Phe Pro Met Arg Phe Arg
                 85                  90                  95
Leu Pro His Arg Ser Tyr Leu Arg Pro Ala Trp Met Ile Arg Cys Gly
                100                 105                 110
Leu Phe Leu Tyr Asp His Leu Gly Lys Arg Thr Thr Leu Pro Ser Ser
                115                 120                 125
His Lys Val Asn Leu Ala Glu Thr Gly Leu Leu Lys Glu Met Lys
   130                 135                 140
Ile Gly Phe Glu Tyr Ser Asp Cys Trp Val Asp Ala Arg Leu Thr
145                 150                 155                 160
Leu Leu Asn Ala Ile Ser Ala Lys Arg Asn Gly Ala Glu Val Arg Asn
                165                 170                 175
Tyr Cys Lys Val Ser Lys Ala Glu Arg Val Asp Gly Leu Trp Lys Val
                180                 185                 190
Thr Ile Glu Asp Gln Gln Asn Gly Glu Gln Phe Val Arg Tyr Ala Lys
                195                 200                 205
Ala Leu Val Asn Ala Ala Gly Pro Trp Val Lys Gln Phe Tyr Asp Asp
   210                 215                 220
Ser Leu Asp Gly Pro Ser Pro Arg Asn Ile Arg Leu Ile Lys Gly Ser
225                 230                 235                 240
His Ile Val Val Pro Arg Val His Pro Asp Pro Gln Ala Tyr Ile Leu
                245                 250                 255
Gln Asn Asn Asp Gly Arg Ile Val Phe Val Ile Pro Tyr Leu Asp Lys
                260                 265                 270
Phe Ser Ile Val Gly Thr Thr Asp Val Glu Tyr Thr Gly Asp Pro Arg
   275                 280                 285
His Val Ala Ile Ser Glu Gln Glu Val Asp Tyr Leu Ile Asp Ile Val
   290                 295                 300
Asn Gln His Phe Val His Gln Leu Ser Lys Gln Asp Val Val Trp Thr
305                 310                 315                 320
Tyr Ser Gly Val Arg Pro Leu Cys Asp Asp Glu Ser Asp Ser Pro Gln
                325                 330                 335
Ala Ile Thr Arg Asp Tyr Thr Ile Glu Leu Glu Gln Glu Leu Asp Gln
                340                 345                 350
Ala Pro Leu Leu Ser Ile Phe Gly Gly Lys Leu Thr Thr Tyr Arg Lys
                355                 360                 365
Leu Ala Glu Ser Ala Met Arg Lys Leu Ala Pro Tyr Phe Asp His Met
   370                 375                 380
Gly Thr Pro Trp Thr Ala Gln Gln Thr Leu Pro Gly Gly Asp Phe Ser
385                 390                 395                 400
Cys Thr Arg Glu Gln Leu Ala His Ala Leu Arg Gln Gln Tyr Pro Trp
                405                 410                 415
Leu Ser Ala Thr Leu Ala Tyr Tyr Val Cys Gln Tyr Gly Ser Asp
                420                 425                 430
Ala Arg Gln Leu Leu Ala Gly Ala Glu Glu Val Ser Ala Met Gly Ile
                435                 440                 445
Glu Leu Ala Pro Glu Val Tyr Gln Arg Glu Leu Asp Tyr Leu Met Ala
   450                 455                 460
```

```
His Glu Phe Ala Gln Cys Ser Glu Asp Ile Leu Trp Arg Arg Thr Lys
465                 470                 475                 480

Leu Gly Leu Tyr Leu Thr Pro Glu Gln Val Gln Ser Val Glu Asn Tyr
            485                 490                 495

Ile Ala Lys Lys His Thr Thr Ala Gln Ser Pro Gln Leu Gln Gln Ala
            500                 505                 510

Ser

<210> SEQ ID NO 50
<211> LENGTH: 502
<212> TYPE: PRT
<213> ORGANISM: Serratia odorifera

<400> SEQUENCE: 50

Met Glu Thr Lys Asp Leu Ile Val Ile Gly Gly Gly Ile Asn Gly Ala
1               5                   10                  15

Gly Ile Ala Ala Asp Ala Ala Gly Arg Gly Leu Ser Val Leu Leu Leu
            20                  25                  30

Glu Ala Gln Asp Leu Ala Cys Ala Thr Ser Ser Ala Ser Ser Lys Leu
        35                  40                  45

Ile His Gly Gly Leu Arg Tyr Leu Glu His Tyr Glu Phe Arg Leu Val
    50                  55                  60

Ser Glu Ala Leu Ala Glu Arg Glu Val Leu Leu Lys Leu Ala Pro His
65                  70                  75                  80

Ile Ala Phe Pro Met Arg Phe Arg Leu Pro His Gln Pro His Leu Arg
                85                  90                  95

Pro Ala Trp Met Ile Arg Ile Gly Leu Phe Leu Tyr Asp His Leu Gly
            100                 105                 110

Lys Arg Thr Ser Leu Pro Gly Ser Lys Ser Leu Arg Phe Gly Pro Glu
        115                 120                 125

Ser Val Leu Lys Pro Glu Leu Lys Arg Gly Phe Glu Tyr Ser Asp Cys
    130                 135                 140

Trp Val Asp Asp Ala Arg Leu Val Val Leu Asn Ala Gln Glu Val Glu
145                 150                 155                 160

Lys Arg Gly Gly Glu Val Arg Thr Arg Thr Lys Val Thr Arg Ala Trp
                165                 170                 175

Arg Glu Asn Gly Leu Trp Met Val Glu Ala Val Asp Val Asp Ser Gly
            180                 185                 190

Lys Thr Phe Thr Trp Arg Ala Lys Gly Leu Val Asn Ala Thr Gly Pro
        195                 200                 205

Trp Val Lys His Phe Phe Asp Asp Gly Leu Lys Leu Lys Ser Pro Tyr
    210                 215                 220

Gly Ile Arg Leu Ile Lys Gly Ser His Ile Val Val Pro Arg Ala His
225                 230                 235                 240

Asn Gln Pro Gln Ser Tyr Ile Leu Gln Asn Glu Asp His Arg Ile Val
                245                 250                 255

Phe Val Ile Pro Trp Asn Asp Glu Phe Ser Ile Ile Gly Thr Thr Asp
            260                 265                 270

Val Glu Tyr His Gly Asp Pro Lys Asp Val Lys Ile Asp Asp Asn Glu
        275                 280                 285

Ile Asp Tyr Leu Leu Lys Val Tyr Asn Asp His Phe Lys Lys Gln Leu
    290                 295                 300

Gly Arg Asp Asp Ile Val Trp Thr Tyr Ser Gly Val Arg Pro Leu Cys
305                 310                 315                 320
```

```
Asp Asp Glu Ser Asp Ser Pro Gln Ala Val Thr Arg Asp Tyr Thr Leu
                325                 330                 335

Asp Val His Asp Glu Gln Gly Lys Ala Pro Leu Leu Ser Val Phe Gly
            340                 345                 350

Gly Lys Leu Thr Thr Tyr Arg Lys Leu Ala Glu His Ala Met Glu Lys
        355                 360                 365

Leu Ala His Tyr Tyr Pro Gly Cys Gly Pro Ala Trp Thr Lys Asn Gly
    370                 375                 380

Ser Leu Pro Gly Gly Asp Ile Gly Gly Asp Arg Asp Ser Tyr Ala Ala
385                 390                 395                 400

Lys Leu Arg Arg Glu His Gly Trp Leu Pro Glu Ser Leu Ala Arg Arg
                405                 410                 415

Tyr Ala Arg Thr Tyr Gly Ser His Ser Glu Leu Ile Leu Ala Asn Ala
            420                 425                 430

Asn Gly Leu Ser Asp Leu Gly Glu Glu Phe Gly His Gly Leu Tyr Glu
        435                 440                 445

Ala Glu Leu Arg Tyr Leu Val Glu Lys Glu Trp Val Val Glu Leu Glu
    450                 455                 460

Asp Ala Ile Trp Arg Arg Thr Lys Leu Gly Met Trp Leu Asp Asp Ala
465                 470                 475                 480

Gln Gln Ala Arg Val Lys Ala Trp Leu Ala Gln His Thr Lys Thr Lys
                485                 490                 495

Thr Leu Ser Leu Ala Ser
            500

<210> SEQ ID NO 51
<211> LENGTH: 511
<212> TYPE: PRT
<213> ORGANISM: Pseudomonas stutzeri

<400> SEQUENCE: 51

Met Pro His Ile Ala Gln Pro Val Ser Glu Leu Tyr Asp Ile Ala Val
1               5                   10                  15

Ile Gly Gly Gly Ile Asn Gly Val Gly Ile Ala Ala Asp Ala Ala Gly
            20                  25                  30

Arg Gly Leu Ser Val Phe Leu Cys Glu Arg Asp Asp Leu Ala Ser His
        35                  40                  45

Thr Ser Ser Ala Ser Ser Lys Leu Ile His Gly Gly Leu Arg Tyr Leu
    50                  55                  60

Glu His Tyr Glu Phe Arg Leu Val Arg Glu Ala Leu Ala Glu Arg Glu
65                  70                  75                  80

Val Leu Leu Ala Lys Ala Pro His Ile Val Lys Pro Met Arg Phe Val
                85                  90                  95

Leu Pro His Arg Pro His Leu Arg Pro Ala Trp Met Ile Arg Ala Gly
            100                 105                 110

Leu Phe Leu Tyr Asp His Leu Gly Met Arg Lys Lys Leu Pro Ala Ser
        115                 120                 125

Gln Gly Leu Arg Phe Gly Ser Glu Ser Pro Leu Lys Pro Ala Ile Thr
    130                 135                 140

Arg Gly Phe Glu Tyr Ser Asp Cys Trp Val Asp Asp Ala Arg Leu Val
145                 150                 155                 160

Val Leu Asn Ala Met Ala Ala Arg Glu Lys Gly Ala His Ile His Thr
                165                 170                 175

Arg Thr Leu Cys Leu Ser Ala Lys Arg Ala Gly Gly Ile Trp His Val
```

```
            180                 185                 190
Glu Leu Gln Arg Glu Asp Gly Ser Arg Phe Ser Leu Arg Ala Lys Ala
            195                 200                 205

Leu Val Asn Ala Ala Gly Pro Trp Val Ala Gln Phe Ile Gly Glu Arg
        210                 215                 220

Leu Gln Gln Arg Ser Pro Tyr Gly Ile Arg Leu Ile Gln Gly Ser His
225                 230                 235                 240

Ile Ile Val Pro Arg Leu Tyr Glu Gly Gln Ala Tyr Ile Met Gln
                245                 250                 255

Asn Glu Asp Arg Arg Ile Val Phe Ala Ile Pro Tyr Leu Asp Arg Tyr
                260                 265                 270

Thr Met Ile Gly Thr Thr Asp Arg Glu Tyr His Gly Asp Pro Ala Gln
            275                 280                 285

Val Ser Ile Thr Glu Gln Glu Ile Ala Tyr Val Leu Gly Val Ala Asn
        290                 295                 300

Thr His Phe Arg Lys Gln Leu Glu Pro Arg Asp Ile Val His Thr Phe
305                 310                 315                 320

Ala Gly Val Arg Pro Leu Cys Asp Asp Glu Ser Asp Asn Pro Ser Ala
                325                 330                 335

Val Thr Arg Asp Tyr Thr Leu Ser Leu Val Ala Glu Lys Gln Ala
                340                 345                 350

Pro Leu Leu Ser Val Phe Gly Gly Lys Leu Thr Thr Tyr Arg Lys Leu
            355                 360                 365

Ala Glu Ser Ala Met Ala Gln Leu Lys Pro Phe Phe Pro Gly Met Gly
        370                 375                 380

Asp Ser Trp Thr Ala Asp Ala Ala Leu Pro Gly Gly Glu Asp Met Gly
385                 390                 395                 400

Thr Pro Glu Ala Leu Ala Glu Ala Leu Val Ala His Val Gln Gly Leu
                405                 410                 415

Glu Leu Pro Leu Ala Lys Arg Trp Ala Thr Leu Tyr Gly Asn Arg Val
            420                 425                 430

Trp Arg Met Leu Gly Asp Ala Arg Ser Leu Asp Ala Leu Gly Glu Asp
        435                 440                 445

Leu Gly Gln Gln Leu Tyr Ala Gln Glu Val Glu Tyr Leu Cys Arg Asp
        450                 455                 460

Glu Trp Ala Met Gln Pro Asp Asp Ile Leu Trp Arg Arg Thr Lys Leu
465                 470                 475                 480

Gly Leu Ala Phe Ser Glu Pro Glu Lys Ser Arg Leu Ala Arg Tyr Leu
                485                 490                 495

Ala Glu Arg Pro Ala Ala Glu Ser Thr His Ser Ser Asp Ala Ala
                500                 505                 510

<210> SEQ ID NO 52
<211> LENGTH: 501
<212> TYPE: PRT
<213> ORGANISM: Escherichia coli

<400> SEQUENCE: 52

Met Glu Thr Lys Asp Leu Ile Val Ile Gly Gly Gly Ile Asn Gly Ala
1               5                   10                  15

Gly Ile Ala Ala Asp Ala Ala Gly Arg Gly Leu Ser Val Leu Met Leu
            20                  25                  30

Glu Ala Gln Asp Leu Ala Cys Ala Thr Ser Ser Ala Ser Ser Lys Leu
        35                  40                  45
```

Ile His Gly Gly Leu Arg Tyr Leu Glu His Tyr Glu Phe Arg Leu Val
50              55                  60

Ser Glu Ala Leu Ala Glu Arg Glu Val Leu Leu Lys Met Ala Pro His
65              70                  75                  80

Ile Ala Phe Pro Met Arg Phe Arg Leu Pro His Arg Pro His Leu Arg
            85                  90                  95

Pro Ala Trp Met Ile Arg Ile Gly Leu Phe Met Tyr Asp His Leu Gly
            100                 105                 110

Lys Arg Thr Ser Leu Pro Gly Ser Thr Gly Leu Arg Phe Gly Ala Asn
            115                 120                 125

Ser Val Leu Lys Pro Glu Ile Lys Arg Gly Phe Glu Tyr Ser Asp Cys
130                 135                 140

Trp Val Asp Asp Ala Arg Leu Val Leu Ala Asn Ala Gln Met Val Val
145                 150                 155                 160

Arg Lys Gly Gly Glu Val Leu Thr Arg Thr Arg Ala Thr Ser Ala Arg
                165                 170                 175

Arg Glu Asn Gly Leu Trp Ile Val Glu Ala Glu Asp Ile Asp Thr Gly
                180                 185                 190

Lys Lys Tyr Thr Trp Gln Ala Arg Gly Leu Val Asn Ala Thr Gly Pro
            195                 200                 205

Trp Val Lys Gln Phe Phe Asp Asp Gly Met His Leu Pro Ser Pro Tyr
210                 215                 220

Gly Ile Arg Leu Ile Lys Gly Ser His Ile Val Pro Arg Val His
225                 230                 235                 240

Thr Gln Lys Gln Ala Tyr Ile Leu Gln Asn Glu Asp Lys Arg Ile Val
            245                 250                 255

Phe Val Ile Pro Trp Met Asp Glu Phe Ser Ile Ile Gly Thr Thr Asp
            260                 265                 270

Val Glu Tyr Lys Gly Asp Pro Lys Ala Val Lys Ile Glu Glu Ser Glu
            275                 280                 285

Ile Asn Tyr Leu Leu Lys Val Tyr Asn Thr His Phe Lys Lys Gln Leu
            290                 295                 300

Ser Arg Asp Asp Ile Val Trp Thr Tyr Ser Gly Val Arg Pro Leu Cys
305                 310                 315                 320

Asp Asp Glu Ser Asp Ser Pro Gln Ala Ile Thr Arg Asp Tyr Thr Leu
                325                 330                 335

Asp Ile His Asp Glu Asn Gly Lys Ala Pro Leu Leu Ser Val Phe Gly
            340                 345                 350

Gly Lys Leu Thr Thr Tyr Arg Lys Leu Ala Glu His Ala Leu Glu Lys
            355                 360                 365

Leu Thr Pro Tyr Tyr Gln Gly Ile Gly Pro Ala Trp Thr Lys Glu Ser
370                 375                 380

Val Leu Pro Gly Gly Ala Ile Glu Gly Asp Arg Asp Asp Tyr Ala Ala
385                 390                 395                 400

Arg Leu Arg Arg Arg Tyr Pro Phe Leu Thr Glu Ser Leu Ala Arg His
            405                 410                 415

Tyr Ala Arg Thr Tyr Gly Ser Asn Ser Glu Leu Leu Leu Gly Asn Ala
            420                 425                 430

Gly Ala Ile Ser Asp Leu Gly Glu Asp Phe Gly His Glu Phe Tyr Glu
            435                 440                 445

Ala Glu Leu Lys Tyr Leu Val Asp His Glu Trp Val Arg Arg Ala Asp
450                 455                 460

Asp Ala Leu Trp Arg Arg Thr Lys Gln Gly Met Trp Leu Asn Ala Asp

```
                465                 470                 475                 480
Gln Gln Ser Arg Val Ser Gln Trp Leu Val Glu Tyr Thr Gln Gln Lys
                    485                 490                 495

Leu Ser Leu Ala Ser
                500

<210> SEQ ID NO 53
<211> LENGTH: 503
<212> TYPE: PRT
<213> ORGANISM: Rahnella Y9602

<400> SEQUENCE: 53

Met Glu Thr Lys Asp Leu Ile Val Ile Gly Gly Ile Asn Gly Thr
  1               5                  10                  15

Gly Ile Ala Val Asp Ala Ala Gly Arg Gly Leu Ser Val Leu Leu Leu
                 20                  25                  30

Glu Ala Gln Asp Leu Ala Cys Ala Thr Ser Ser Ala Ser Ser Lys Leu
             35                  40                  45

Ile His Gly Gly Leu Arg Tyr Leu Glu His Tyr Glu Phe Arg Leu Val
         50                  55                  60

Ser Glu Ala Leu Ala Glu Arg Glu Val Leu Leu Lys Met Ala Pro His
 65                  70                  75                  80

Ile Ala Phe Pro Met Arg Phe Arg Leu Pro His Gln Pro His Leu Arg
                 85                  90                  95

Pro Ala Trp Met Ile Arg Ala Gly Leu Phe Leu Tyr Asp His Leu Gly
                100                 105                 110

Lys Arg Thr Ser Leu Pro Ala Ser Lys Gly Leu Lys Phe Gly Ser Glu
            115                 120                 125

Ser Val Leu Lys Pro Glu Leu Thr Lys Gly Phe Glu Tyr Ser Asp Cys
    130                 135                 140

Trp Val Asp Asp Ala Arg Leu Val Val Asn Ala Gln Glu Val Glu
145                 150                 155                 160

Glu Arg Gly Gly Glu Val Arg Thr Arg Thr Arg Val Thr Arg Ala Trp
                165                 170                 175

Arg Glu Asp Gly Met Trp Met Val Glu Ala Glu Asp Ile Asp Thr Gly
            180                 185                 190

Lys Thr Phe Thr Trp Arg Ala Lys Gly Leu Val Asn Ala Thr Gly Pro
    195                 200                 205

Trp Val Lys His Phe Phe Asp Asp Gly Leu Lys Leu Lys Ser Pro Tyr
210                 215                 220

Gly Ile Arg Leu Ile Lys Gly Ser His Ile Val Pro Arg Ala His
225                 230                 235                 240

Asn Gln Pro Gln Ala Tyr Ile Leu Gln Asn Glu Asp His Arg Ile Val
                245                 250                 255

Phe Val Ile Pro Trp Met Asp Glu Phe Ser Ile Ile Gly Thr Thr Asp
            260                 265                 270

Val Glu Tyr His Gly Asp Pro Lys Asp Val Lys Ile Asp Lys Glu
    275                 280                 285

Ile Gly Tyr Leu Leu Lys Val Tyr Asn Asp His Phe Lys Lys Gln Leu
    290                 295                 300

Thr Thr Glu Asp Ile Val Trp Thr Tyr Ser Gly Val Arg Pro Leu Cys
305                 310                 315                 320

Asp Asp Glu Ser Asp Ser Pro Gln Ala Val Thr Arg Asp Tyr Thr Leu
                325                 330                 335
```

```
Asp Val His Asp Gln Asp Gly Lys Ala Pro Leu Leu Ser Val Phe Gly
            340                 345                 350

Gly Lys Leu Thr Thr Tyr Arg Lys Leu Ala Glu His Ala Leu Glu Lys
        355                 360                 365

Leu Val Lys Tyr Tyr Pro Lys Ala Gly Pro Ala Trp Thr Lys Thr Ala
        370                 375                 380

Val Leu Pro Gly Gly Lys Leu Asn Gly Asp Arg Asp Thr Tyr Ser Ala
385                 390                 395                 400

Asn Leu Arg Ser Arg Phe Lys Trp Leu Pro Glu Ser Leu Ala Arg Arg
                405                 410                 415

Tyr Ala Arg Thr Tyr Gly Ser Gln Thr Glu Leu Phe Leu Asn Asp Ala
            420                 425                 430

Thr Ser Leu Glu Ser Leu Gly Glu Asp Phe Gly His Gly Phe Tyr Glu
        435                 440                 445

Ala Glu Leu Arg Tyr Leu Val Glu Lys Glu Trp Val Ser Gln Leu Asp
    450                 455                 460

Asp Ala Ile Trp Arg Arg Thr Lys Leu Gly Met Trp Leu Asp Lys Thr
465                 470                 475                 480

Gln Gln Gln Arg Val Ala Glu Trp Leu Glu Thr His Lys Gln Lys
                485                 490                 495

Lys His Leu Ser Leu Ala Ser
            500

<210> SEQ ID NO 54
<211> LENGTH: 500
<212> TYPE: PRT
<213> ORGANISM: Providencia rustigianii

<400> SEQUENCE: 54

Met Glu Thr Lys Asp Leu Ile Val Ile Gly Gly Ile Asn Gly Ala
1               5                   10                  15

Gly Ile Ala Ala Asp Ala Ala Gly Arg Gly Leu Ser Val Leu Leu Leu
            20                  25                  30

Glu Ala Gln Asp Leu Ala Ser Ala Thr Ser Ser Ala Ser Ser Lys Leu
        35                  40                  45

Ile His Gly Gly Leu Arg Tyr Leu Glu His Tyr Glu Phe Arg Leu Val
    50                  55                  60

Ser Glu Ala Leu Ala Glu Arg Glu Val Leu Leu Arg Leu Ala Pro His
65                  70                  75                  80

Ile Ala Phe Pro Met Arg Phe Arg Leu Pro His Gln Pro His Leu Arg
                85                  90                  95

Pro Ala Trp Met Ile Arg Ile Gly Leu Phe Leu Tyr Asp His Leu Gly
            100                 105                 110

Lys Arg Val Ser Leu Pro Ser Ser Lys Ser Leu Lys Phe Asn Gln Asn
        115                 120                 125

Ser Val Leu Lys Pro Glu Leu Thr Lys Gly Phe Glu Tyr Ser Asp Cys
    130                 135                 140

Trp Val Asp Asp Ala Arg Leu Val Val Leu Asn Ala Gln Glu Val Val
145                 150                 155                 160

Arg Lys Asn Gly Glu Val Arg Thr Arg Thr Lys Val Thr Arg Ala Tyr
                165                 170                 175

Arg Glu Asn Gly Leu Trp Val Val Glu Ala Gln Asp Leu Arg Thr Gly
            180                 185                 190

Glu Thr His Thr Trp Lys Ala Lys Gly Leu Val Asn Ala Thr Gly Pro
        195                 200                 205
```

```
Trp Val Lys Glu Phe Phe Asp Asp Gly Leu Lys Leu Lys Ser Pro Tyr
    210                 215                 220

Gly Ile Arg Leu Ile Lys Gly Ser His Ile Val Pro Arg Ala His
225                 230                 235                 240

Asp Glu Pro Gln Ala Tyr Ile Leu Gln Asn Glu Asp Asn Arg Ile Val
                245                 250                 255

Phe Val Ile Pro Trp Met Asp Glu Phe Ser Ile Ile Gly Thr Thr Asp
                260                 265                 270

Val Glu Tyr Asn Gly Asp Pro Lys Asp Val Lys Ile Asp Glu Asn Glu
            275                 280                 285

Val Asn Tyr Leu Leu Lys Val Tyr Asn Asp His Phe Lys Lys Gln Leu
        290                 295                 300

Thr Lys Gln Asp Val Val Trp Asp Tyr Ser Gly Val Arg Pro Leu Cys
305                 310                 315                 320

Asp Asp Glu Ser Asp Ser Pro Gln Ala Ile Thr Arg Asp Tyr Thr Leu
                325                 330                 335

Asp Ile His Asp Glu Glu Gly Lys Ala Pro Leu Leu Ser Val Phe Gly
            340                 345                 350

Gly Lys Leu Thr Thr Tyr Arg Lys Leu Ala Glu Ala Ala Val Gly Lys
        355                 360                 365

Leu Ala Ala Tyr Tyr Pro His Ala Ser Gly Pro Trp Thr Lys Asn Gly
    370                 375                 380

Gln Leu Pro Gly Gly Asp Ile Glu Gly Cys Asp Arg Asp Gly Tyr Ala
385                 390                 395                 400

Arg Val Leu Arg Gln His Tyr Gln Trp Leu Pro Glu Gly Leu Ala Leu
                405                 410                 415

Arg Tyr Ala Arg Thr Tyr Gly Ser Asn Ser Lys Leu Ile Leu Ala Gly
            420                 425                 430

Ala Asn Ser Leu Ala Asp Leu Gly Glu Ala Phe Gly Ala Asn Val Tyr
        435                 440                 445

Glu Ala Glu Leu Arg Tyr Leu Val Glu Asn Glu Trp Val Val Glu Leu
    450                 455                 460

Asp Asp Ala Ile Trp Arg Arg Thr Lys Leu Gly Met Trp Leu Asn Asp
465                 470                 475                 480

Ser Glu Lys Gln Arg Ile Ala Gln Trp Leu Ala Glu His Thr Lys Val
                485                 490                 495

Ala Val Thr Ala
            500

<210> SEQ ID NO 55
<211> LENGTH: 502
<212> TYPE: PRT
<213> ORGANISM: Klebsiella pneumoniae

<400> SEQUENCE: 55

Met Glu Thr Lys Asp Leu Ile Val Ile Gly Gly Gly Ile Asn Gly Ala
1               5                   10                  15

Gly Ile Ala Ala Asp Ala Ala Gly Arg Gly Leu Ser Val Leu Met Leu
            20                  25                  30

Glu Ala Arg Asp Leu Ala Cys Ala Thr Ser Ser Ala Ser Ser Lys Leu
        35                  40                  45

Ile His Gly Gly Leu Arg Tyr Leu Glu His Tyr Glu Phe Arg Leu Val
    50                  55                  60

Ser Glu Ala Leu Ala Glu Arg Glu Val Leu Leu Lys Met Ala Pro His
```

```
            65                  70                  75                  80
Ile Ala Phe Pro Met Arg Phe Arg Leu Pro His Arg Pro His Leu Arg
                    85                  90                  95
Pro Ala Trp Met Ile Arg Ile Gly Leu Phe Met Tyr Asp His Leu Gly
                   100                 105                 110
Lys Arg Thr Ser Leu Pro Gly Ser Thr Gly Leu Arg Phe Gly Ala Glu
                   115                 120                 125
Ser Val Leu Lys Pro Glu Ile Val Arg Gly Phe Glu Tyr Ser Asp Cys
                   130                 135                 140
Trp Val Asp Asp Ala Arg Leu Val Leu Ala Asn Ala Gln Met Val Val
145                 150                 155                 160
Arg Lys Gly Gly Glu Val Arg Thr Arg Thr Arg Ala Ile Ser Ala Lys
                   165                 170                 175
Arg Glu Asn Gly Leu Trp Val Val Glu Ala Glu Asp Ile Asp Ser Gly
                   180                 185                 190
Glu Lys Phe Thr Trp Lys Ala Arg Gly Leu Val Asn Ala Thr Gly Pro
                   195                 200                 205
Trp Val Lys Gln Phe Phe Asp Glu Gly Met His Leu Arg Ser Pro Tyr
210                 215                 220
Gly Ile Arg Leu Ile Lys Gly Ser His Ile Val Pro Arg Val His
225                 230                 235                 240
Thr Gln Lys Gln Ala Tyr Ile Leu Gln Asn Glu Asp Lys Arg Ile Val
                   245                 250                 255
Phe Val Ile Pro Trp Met Asp Glu Phe Ser Ile Ile Gly Thr Thr Asp
                   260                 265                 270
Val Glu Tyr Lys Gly Asp Pro Lys Ala Val Ala Ile Asp Asp Lys Glu
                   275                 280                 285
Ile Asn Tyr Leu Leu Asn Val Tyr Asn Ala His Phe Lys Lys Thr Leu
                   290                 295                 300
Ser Arg Asp Asp Ile Val Trp Thr Tyr Ser Gly Val Arg Pro Leu Cys
305                 310                 315                 320
Asp Asp Glu Ser Asp Ser Pro Gln Ala Ile Thr Arg Asp Tyr Thr Leu
                   325                 330                 335
Asp Ile His Asp Glu Asn Gly Gln Ala Pro Leu Leu Ser Val Phe Gly
                   340                 345                 350
Gly Lys Leu Thr Thr Tyr Arg Lys Leu Ala Glu His Ala Leu Glu Lys
                   355                 360                 365
Leu Thr Pro Tyr Tyr Lys Gly Ile Gly Pro Ala Trp Thr Lys Thr Ala
                   370                 375                 380
Val Leu Pro Gly Gly Asp Ile Gly Gly Asp Arg Asp Asp Tyr Ala Ala
385                 390                 395                 400
Lys Leu Arg Arg Arg Phe Pro Phe Ile Ser Glu Ser Leu Ala Arg His
                   405                 410                 415
Tyr Ala Arg Thr Tyr Gly Ser Asn Ser Glu Trp Ile Leu Lys Glu Ala
                   420                 425                 430
Ser Ala Leu Ser Asp Leu Gly Glu Asp Phe Gly His Glu Phe Tyr Glu
                   435                 440                 445
Ala Glu Leu Lys Tyr Leu Val Glu His Glu Trp Val Arg Ser Leu Asp
                   450                 455                 460
Asp Ala Ile Trp Arg Arg Thr Lys Gln Gly Met Trp Leu Asn Ala Glu
465                 470                 475                 480
Gln Gln Ala Arg Ile Ser Glu Trp Leu Ala Gln His Ala Gly Lys Ser
                   485                 490                 495
```

Glu Leu Ser Leu Ala Ser
            500

<210> SEQ ID NO 56
<211> LENGTH: 501
<212> TYPE: PRT
<213> ORGANISM: Pantoea ananatis

<400> SEQUENCE: 56

Met Glu Thr Lys Asp Leu Ile Val Ile Gly Gly Ile Asn Gly Ala
 1               5                  10                  15

Gly Ile Ala Ala Asp Ala Gly Arg Gly Leu Ser Val Leu Met Leu
                20                  25                  30

Glu Ala Arg Asp Leu Ala Cys Ala Thr Ser Ser Ala Ser Lys Leu
            35                  40                  45

Ile His Gly Gly Leu Arg Tyr Leu Glu His Tyr Glu Phe Arg Leu
        50                  55                  60

Ser Glu Ala Leu Ala Glu Arg Glu Val Leu Leu Lys Met Ala Pro His
65                  70                  75                  80

Ile Ala Phe Pro Met Arg Phe Arg Leu Pro His Arg Pro His Leu Arg
                85                  90                  95

Pro Ala Trp Met Ile Arg Thr Gly Leu Phe Met Tyr Asp His Leu Gly
                100                 105                 110

Lys Arg Thr Ser Leu Pro Gly Ser Lys Ser Leu Ser Phe Gly Ala Glu
            115                 120                 125

Ser Ala Leu Lys Pro Glu Ile Lys Arg Gly Phe Glu Tyr Ser Asp Cys
130                 135                 140

Trp Val Asp Asp Ala Arg Met Val Val Leu Asn Ala Gln Glu Val Val
145                 150                 155                 160

Lys His Gly Gly Glu Val Arg Thr Arg Thr Arg Val Thr Arg Ala Trp
                165                 170                 175

Arg Glu Asn Gly Leu Trp Met Val Glu Ala Glu Asp Ile Asp Ser Gly
                180                 185                 190

Lys Thr Phe Thr Trp Gln Ala Lys Gly Leu Val Asn Ala Ala Gly Pro
            195                 200                 205

Trp Val Lys Gln Phe Phe Asp Asp Gly Leu Glu Leu Lys Ser Pro Tyr
210                 215                 220

Gly Ile Arg Leu Ile Lys Gly Ser His Ile Val Pro Arg Val His
225                 230                 235                 240

Asn Glu Lys Gln Ala Tyr Ile Leu Gln Asn Glu Asp Asn Arg Ile Val
                245                 250                 255

Phe Val Ile Pro Trp Met Asp Glu Phe Ser Ile Ile Gly Thr Thr Asp
                260                 265                 270

Val Glu Tyr Lys Gly Asp Pro Lys Asn Val Ala Ile Asp Asp Asn Glu
            275                 280                 285

Ile Asp Tyr Ile Leu Lys Val Tyr Asn Gly His Phe Lys Lys Gln Leu
        290                 295                 300

Thr Pro Asp Asp Ile Val Trp Thr Tyr Ser Gly Val Arg Pro Leu Cys
305                 310                 315                 320

Asp Asp Glu Ser Asp Ser Pro Gln Ala Ile Thr Arg Asp Tyr Thr Leu
                325                 330                 335

Asp Val Arg Asp Asp Asn Gly Gln Thr Pro Leu Leu Ser Val Phe Gly
                340                 345                 350

Gly Lys Leu Thr Thr Tyr Arg Lys Leu Ala Glu His Ala Leu Glu Lys

-continued

```
                355                 360                 365
Leu Ser Lys Tyr Tyr Pro Asp Ala Gly Ala Ala Trp Thr Lys Asn Cys
    370                 375                 380

Val Leu Pro Gly Gly Asn Ile Ser Gly Ser Ser Asp Asp Tyr Ala Ala
385                 390                 395                 400

Ser Leu Arg Arg Arg Tyr Pro Phe Ile Thr Glu Asn Met Ala Arg His
                405                 410                 415

Tyr Ala Arg Thr Tyr Gly Ser Ser Thr Glu Val Leu Leu Lys Asp Ala
            420                 425                 430

Thr Ser Leu Glu Asp Leu Gly Glu Asn Phe Gly His Glu Phe Tyr Glu
        435                 440                 445

Ala Glu Leu Arg Tyr Leu Val Gln His Glu Trp Val Arg Glu Val Asp
    450                 455                 460

Asp Ala Ile Trp Arg Arg Thr Lys Gln Gly Met Trp Leu Asn Glu Ala
465                 470                 475                 480

Gln Gln Ala Arg Ile Ala Glu Trp Leu Ala Ala Lys Ala Lys Pro Thr
                485                 490                 495

Leu Ser Leu Ala Ser
            500

<210> SEQ ID NO 57
<211> LENGTH: 502
<212> TYPE: PRT
<213> ORGANISM: Salmonella enterica

<400> SEQUENCE: 57

Met Glu Thr Lys Asp Leu Ile Val Ile Gly Gly Ile Asn Gly Ala
1               5                   10                  15

Gly Ile Ala Ala Asp Ala Ala Gly Arg Gly Leu Ser Val Leu Met Leu
            20                  25                  30

Glu Ala Gln Asp Leu Ala Cys Ala Thr Ser Ser Ala Ser Ser Lys Leu
        35                  40                  45

Ile His Gly Gly Leu Arg Tyr Leu Glu His Tyr Glu Phe Arg Leu Val
    50                  55                  60

Ser Glu Ala Leu Ala Glu Arg Glu Val Leu Leu Lys Met Ala Pro His
65                  70                  75                  80

Ile Ala Phe Pro Met Arg Phe Arg Leu Pro His Arg Pro His Leu Arg
                85                  90                  95

Pro Ala Trp Met Ile Arg Ile Gly Leu Phe Met Tyr Asp His Leu Gly
            100                 105                 110

Lys Arg Thr Ser Leu Pro Gly Ser Thr Gly Val Arg Phe Gly Ala Asp
        115                 120                 125

Ser Val Leu Lys Pro Glu Ile Val Arg Gly Phe Glu Tyr Ser Asp Cys
    130                 135                 140

Trp Val Asp Asp Ala Arg Leu Val Leu Ala Asn Ala Gln Met Val Val
145                 150                 155                 160

Arg Lys Gly Gly Glu Val Leu Thr Arg Thr Arg Ala Thr Ala Ala Arg
                165                 170                 175

Arg Glu Asn Gly Leu Trp Ile Val Glu Ala Glu Asp Ile Asp Thr Gly
            180                 185                 190

Lys Lys Tyr Val Trp Gln Ala Arg Gly Leu Val Asn Ala Thr Gly Pro
        195                 200                 205

Trp Val Lys Gln Phe Phe Asp Glu Gly Met His Leu Pro Ser Pro Tyr
    210                 215                 220
```

Gly Ile Arg Leu Ile Lys Gly Ser His Ile Val Pro Arg Val His
225                 230                 235                 240

Asn Gln Lys Gln Ala Tyr Ile Leu Gln Asn Glu Asp Lys Arg Ile Val
            245                 250                 255

Phe Val Ile Pro Trp Met Glu Glu Phe Ser Ile Ile Gly Thr Thr Asp
            260                 265                 270

Val Glu Tyr Lys Gly Asp Pro Lys Ala Val Lys Ile Glu Glu Ser Glu
            275                 280                 285

Ile Asn Tyr Leu Leu Lys Val Tyr Asn Ala His Phe Gln Lys Gln Leu
290                 295                 300

Gly Arg Asp Asp Ile Val Trp Thr Tyr Ser Gly Val Arg Pro Leu Cys
305                 310                 315                 320

Asp Asp Glu Ser Asp Ser Pro Gln Ala Ile Thr Arg Asp Tyr Thr Leu
            325                 330                 335

Asp Ile His Asp Glu Asn Gly Lys Ala Pro Leu Leu Ser Val Phe Gly
            340                 345                 350

Gly Lys Leu Thr Thr Tyr Arg Lys Leu Ala Glu His Ala Met Glu Lys
            355                 360                 365

Leu Ala Ser Tyr Tyr Pro Gly Ile Gly Pro Ala Trp Thr Lys Thr Cys
370                 375                 380

Val Leu Pro Gly Gly Asp Ile Asp Gly Ser Arg Glu Asp Tyr Ala Ala
385                 390                 395                 400

Lys Leu Arg Arg Arg Tyr Pro Phe Leu Thr Glu Ser Leu Ala Arg His
            405                 410                 415

Tyr Ser Arg Thr Tyr Gly Ser Asn Thr Glu Trp Ile Leu Gly Glu Ala
            420                 425                 430

Thr Ser Leu Leu Asp Leu Gly Glu Asp Phe Gly His Glu Phe Tyr Glu
            435                 440                 445

Ala Glu Leu Lys Tyr Leu Val Asp His Glu Trp Val Arg Arg Thr Glu
450                 455                 460

Asp Ala Ile Trp Arg Arg Thr Lys Glu Gly Met Trp Leu Thr Ala Glu
465                 470                 475                 480

Gln Gln Ser Arg Ile Thr Gln Trp Leu Ala Ala Tyr Val Glu Lys His
            485                 490                 495

Gln Leu Ser Leu Ala Ser
            500

<210> SEQ ID NO 58
<211> LENGTH: 499
<212> TYPE: PRT
<213> ORGANISM: Dickeya dadantii

<400> SEQUENCE: 58

Met Lys Thr Gln Asp Leu Ile Val Ile Gly Gly Ile Asn Gly Thr
1               5                   10                  15

Gly Ile Ala Ala Asp Ala Ala Gly Arg Gly Leu Ser Val Leu Leu Leu
            20                  25                  30

Glu Ala Gln Asp Leu Ala Cys Ala Thr Ser Ser Ala Ser Ser Lys Leu
        35                  40                  45

Ile His Gly Gly Leu Arg Tyr Leu Glu His Tyr Glu Phe Arg Leu Val
    50                  55                  60

Gly Glu Ala Leu Ser Glu Arg Glu Val Leu Lys Met Ala Pro His
65                  70                  75                  80

Ile Ile Phe Pro Met Arg Phe Arg Leu Pro His Gln Pro His Leu Arg
                85                  90                  95

```
Pro Ala Trp Met Ile Arg Ala Gly Leu Phe Met Tyr Asp His Leu Gly
            100                 105                 110

Lys Arg Val Ser Leu Pro Ser His Gly Leu Arg Phe Gly Arg Glu
            115                 120                 125

Ser Val Leu Lys Pro Glu Leu Thr Arg Gly Phe Glu Tyr Ser Asp Cys
130                 135                 140

Trp Val Asp Asp Ala Arg Leu Val Val Leu Asn Ala Gln Glu Val Val
145                 150                 155                 160

Arg Arg Gly Gly Glu Val Lys Thr Arg Met Lys Val Thr Arg Ala His
                165                 170                 175

Arg Glu Asn Gly Leu Trp Ile Val Glu Ala Asp Thr Leu Ser Gly
            180                 185                 190

Glu Thr His Arg Trp Gln Ala Lys Gly Leu Val Asn Ala Thr Gly Pro
            195                 200                 205

Trp Val Arg Gln Phe Phe Asp Asp Gly Leu Ala Leu Pro Ser Pro Tyr
            210                 215                 220

Gly Ile Arg Leu Ile Lys Gly Ser His Ile Val Pro Arg Val His
225                 230                 235                 240

Gln Glu Glu Gln Ala Tyr Ile Leu Gln Asn Lys Asp Asn Arg Ile Val
                245                 250                 255

Phe Val Ile Pro Trp Gln Asp Glu Phe Ser Ile Ile Gly Thr Thr Asp
            260                 265                 270

Val Glu Tyr His Gly Asp Pro His Gln Val Lys Ile Asp Asp Asn Glu
            275                 280                 285

Ile Arg Tyr Leu Leu Asp Val Tyr Asn Asp His Phe Lys Lys Gln Leu
            290                 295                 300

Thr Arg Asp Asp Ile Val Trp Thr Tyr Ser Gly Val Arg Pro Leu Cys
305                 310                 315                 320

Asp Asp Glu Ser Asp Ser Pro Gln Ala Ile Thr Arg Asp Tyr Thr Leu
                325                 330                 335

Ser Val Ala Asp Glu Asn Gly Lys Ala Pro Leu Leu Ser Val Phe Gly
            340                 345                 350

Gly Lys Leu Thr Thr Tyr Arg Lys Leu Ala His Ala Leu Glu Lys
            355                 360                 365

Leu Val Lys Tyr Tyr Pro Gln Ala Gly Gln Ala Trp Thr Arg Asn Ala
370                 375                 380

Ile Leu Pro Gly Gly Asp Ile Ser Gly Ser Arg Glu Asp Tyr Ala Ala
385                 390                 395                 400

Thr Leu Arg Arg Arg Tyr Asn Leu Pro Glu Ala Leu Ala Arg Tyr
            405                 410                 415

Ser Arg Thr Tyr Gly Ser Gln Ser Glu Lys Ile Leu Gly Asn Ala Gln
            420                 425                 430

Ser Leu Ser Asp Leu Gly Glu His Phe Gly His Asn Leu Tyr Glu Ala
            435                 440                 445

Glu Leu Arg Tyr Leu Val Glu His Glu Trp Val Val Thr Leu Glu Asp
            450                 455                 460

Ala Ile Trp Arg Arg Thr Lys Leu Gly Met Trp Leu Asp Asp Ala Gln
465                 470                 475                 480

Arg Gln Arg Val Ala Asp Trp Leu Val Ser Tyr Arg Ser Gln Leu Ala
                485                 490                 495

Lys Ala Gly
```

<210> SEQ ID NO 59
<211> LENGTH: 519
<212> TYPE: PRT
<213> ORGANISM: Vibrio parahaemolyticus

<400> SEQUENCE: 59

```
Met Ser Ile Gln Lys Asn Thr Ser Thr Thr Ser Ser Thr Leu Leu
 1               5                  10                  15

Asp Leu Ile Val Ile Gly Gly Ile Asn Gly Ala Gly Ile Ala Ala
             20                  25                  30

Asp Ala Ala Gly Arg Gly Leu Ser Val Gly Leu Tyr Glu Ala Asn Asp
         35                  40                  45

Phe Ala Ser Ala Thr Ser Ser Ala Ser Ser Lys Leu Ile His Gly Gly
     50                  55                  60

Leu Arg Tyr Leu Glu His Tyr Glu Phe Arg Leu Val Ser Glu Ala Leu
 65                  70                  75                  80

Ala Glu Arg Glu Val Ile Leu Arg Lys Ala Pro His Val Ala Leu Pro
                 85                  90                  95

Met Arg Phe Arg Leu Pro His Arg Pro Phe Leu Arg Pro Ala Trp Met
            100                 105                 110

Ile Arg Cys Gly Leu Phe Leu Tyr Asp Asn Leu Gly Lys Arg Thr Thr
        115                 120                 125

Leu Pro Gly Ser Lys Thr Val Asn Leu Ala Lys Ser Gly Leu Leu Lys
130                 135                 140

Pro Glu Met Lys Thr Gly Phe Glu Tyr Ser Asp Cys Trp Val Asp Asp
145                 150                 155                 160

Ala Arg Leu Val Leu Leu Asn Val Met Ala Arg Glu Asn His Ala
                165                 170                 175

Glu Val Arg Asn Tyr Cys Arg Val Glu Lys Ala His Arg Glu Asn Gly
            180                 185                 190

Val Trp His Val Thr Ile His Asp Val Thr Thr Asp Gln Arg Phe Glu
        195                 200                 205

Arg Lys Ala Lys Ala Leu Val Asn Ala Ala Gly Pro Trp Val Lys Gln
    210                 215                 220

Phe Phe Asp Glu Gly Leu Glu Gln Thr Ser Pro Arg Asn Ile Arg Leu
225                 230                 235                 240

Ile Lys Gly Ser His Ile Val Val Pro Arg Ile His Asn Glu Pro Gln
                245                 250                 255

Ala Tyr Ile Leu Gln Asn Lys Asp Asn Arg Ile Val Phe Met Ile Pro
            260                 265                 270

Tyr Leu Asp Lys Phe Ser Ile Ile Gly Thr Thr Asp Val Glu Tyr Lys
        275                 280                 285

Gly Asp Pro Arg Glu Val Ala Ile Ser Asp Glu Val Asp Tyr Leu
    290                 295                 300

Ile Asp Ile Val Asn Gln His Phe Val His Gln Leu Thr Arg Glu Asp
305                 310                 315                 320

Val Val Trp Thr Tyr Ser Gly Val Arg Pro Leu Cys Asp Asp Glu Ser
                325                 330                 335

Asp Ser Pro Gln Ala Ile Thr Arg Asp Tyr Thr Leu Glu Leu Asp Ala
            340                 345                 350

Glu Tyr Asp Gln Ala Pro Leu Leu Ser Val Phe Gly Gly Lys Leu Thr
        355                 360                 365

Thr Tyr Arg Lys Leu Gly Glu Ala Ala Met Lys Lys Leu Glu Pro Tyr
    370                 375                 380
```

```
Leu Pro Gln Met Gly Gly Asn Trp Thr Ala Asn Gln Thr Leu Pro Gly
385                 390                 395                 400

Gly Asn Phe Ser Cys Thr Arg Glu Gln Leu Ala Lys Gln Ile His Ala
            405                 410                 415

Lys Tyr Ser Trp Ala Pro Gln Ala Leu Ile Leu Arg Tyr Val Thr Gln
            420                 425                 430

Phe Gly Thr Gln Thr Trp Asp Leu Met Glu Gly Ala Ser Ser Glu Ala
            435                 440                 445

Asp Leu Gly Gln Ala Phe Ser Glu Gln Ala Gly Gly Val Tyr Gln Arg
            450                 455                 460

Glu Ile Asp Tyr Leu Met Asn His Glu Met Ala Leu Thr Asp Glu Asp
465                 470                 475                 480

Ile Leu Trp Arg Arg Thr Lys Leu Gly Leu Tyr Met Asn Asp Glu Glu
            485                 490                 495

Lys Gln Ala Leu Ala Asp Tyr Leu Lys Glu Lys Leu Gln Gln Lys Val
            500                 505                 510

Val Asn Leu Ser Gln Val Ser
            515

<210> SEQ ID NO 60
<211> LENGTH: 502
<212> TYPE: PRT
<213> ORGANISM: Edwardsiella tarda

<400> SEQUENCE: 60

Met Asp Ile Lys Asp Val Ile Val Gly Gly Gly Ile Asn Gly Ala
1               5                   10                  15

Gly Ile Ala Ala Asp Ala Ala Gly Arg Gly Leu Ser Val Leu Met Leu
                20                  25                  30

Glu Ala Arg Asp Leu Ala Cys Ala Thr Ser Ser Ala Ser Ser Lys Leu
            35                  40                  45

Ile His Gly Gly Leu Arg Tyr Leu Glu His Tyr Glu Phe Arg Leu Val
        50                  55                  60

Ser Glu Ala Leu Ala Glu Arg Glu Val Leu Leu Lys Met Ala Pro His
65              70                  75                  80

Ile Ala Phe Pro Leu Arg Phe Arg Leu Pro His Gln Pro His Leu Arg
                85                  90                  95

Pro Ala Trp Met Ile Arg Ala Gly Leu Phe Leu Tyr Asp His Leu Gly
                100                 105                 110

Lys Arg Thr Ser Leu Pro Gly Ser Cys Ala Leu Arg Phe Gly Ala Gly
            115                 120                 125

Ser Val Leu Lys Pro Ser Leu Thr Arg Gly Phe Glu Tyr Ser Asp Cys
        130                 135                 140

Trp Val Asp Asp Ala Arg Leu Val Val Leu Asn Ala Met Ala Val Val
145                 150                 155                 160

Glu Arg Gly Gly Glu Val Arg Thr Arg Thr Glu Val Thr Arg Ala Trp
                165                 170                 175

Arg Glu Glu Gly Ile Trp Val Glu Ala Arg Asp Ile Asp Ser Gly
            180                 185                 190

Glu Thr Leu Thr Trp Arg Ala Arg Gly Leu Val Asn Ala Thr Gly Pro
            195                 200                 205

Trp Val Lys Gln Leu Phe Asp Asp Gly Leu Gln Leu Lys Ser Pro Tyr
        210                 215                 220

Gly Ile Arg Leu Ile Lys Gly Ser His Ile Val Val Pro Arg Val His
225                 230                 235                 240
```

```
Asp Gln Pro Gln Ala Tyr Ile Leu Gln Asn Glu Asp Gln Arg Ile Val
                245                 250                 255

Phe Val Ile Pro Trp Leu Asp Ala Phe Ser Ile Ile Gly Thr Thr Asp
            260                 265                 270

Val Glu Tyr His Gly Asp Pro Arg Ala Val Gln Ile Asp Glu Gly Glu
        275                 280                 285

Ile Asp Tyr Leu Leu Gln Val Tyr Asn Ser His Phe Val Arg Gln Leu
    290                 295                 300

Asn Arg Gln Asp Ile Val Trp Thr Tyr Ser Gly Val Arg Pro Leu Cys
305                 310                 315                 320

Asp Asp Glu Ser Asp Ser Pro Gln Ala Ile Thr Arg Asp Tyr Thr Leu
                325                 330                 335

Asp Ile His Asp Arg Asp Gly Ala Ala Pro Leu Leu Ser Val Phe Gly
            340                 345                 350

Gly Lys Leu Thr Thr Tyr Arg Lys Leu Ala Glu His Ala Leu Glu Lys
        355                 360                 365

Leu Arg Pro Tyr Tyr Pro His Cys Gly Asp Ala Trp Thr Lys Gly Ala
    370                 375                 380

Val Leu Pro Gly Gly Glu Met Gly Cys Asp Arg Asp Ser Tyr Ala Ala
385                 390                 395                 400

Ala Leu Arg Gln Arg His Asp Trp Leu Pro Gln Ala Leu Ala Arg Arg
                405                 410                 415

Tyr Ala His Thr Tyr Gly Ala Arg Ser Glu Arg Leu Ile Gly Ser Ala
            420                 425                 430

Ala Ser Leu Ala Asp Leu Gly Glu His Phe Gly His Gly Leu Tyr Ala
        435                 440                 445

Ala Glu Leu Asp Tyr Leu Ala Gly His Glu Trp Val Thr Thr Ala Glu
    450                 455                 460

Asp Ala Leu Trp Arg Arg Thr Lys Leu Gly Met Trp Leu Asp Asp Ala
465                 470                 475                 480

Gln Arg Gln Arg Val Ala Glu Trp Leu Ala Ala His Arg Pro Ala Ala
                485                 490                 495

Glu Thr Ser Ser Pro Ser
            500

<210> SEQ ID NO 61
<211> LENGTH: 501
<212> TYPE: PRT
<213> ORGANISM: Erwinia amylovora

<400> SEQUENCE: 61

Met Glu Thr Lys Asp Leu Ile Val Ile Gly

```
                100                 105                 110
Lys Arg Thr Ser Leu Pro Gly Ser Lys Ser Val Arg Phe Gly Ser Asp
            115                 120                 125
Ser Val Leu Lys Pro Glu Ile Val Arg Gly Phe Glu Tyr Ser Asp Cys
            130                 135                 140
Trp Val Asp Asp Ala Arg Leu Val Val Leu Asn Ala Gln Gln Val Glu
145                 150                 155                 160
Lys Arg Gly Gly Glu Val Arg Thr Arg Thr Arg Val Thr Arg Ala Trp
                165                 170                 175
Arg Glu Asn Gly Leu Trp Thr Val Glu Ala Glu Asp Ile Asp Ser Gly
            180                 185                 190
Lys Thr Leu Thr Trp Arg Ala Lys Gly Leu Val Asn Ala Ala Gly Pro
            195                 200                 205
Trp Val Lys Gln Leu Phe Asp Asp Gly Leu Lys Leu Lys Ser Pro Tyr
            210                 215                 220
Gly Ile Arg Leu Ile Lys Gly Ser His Ile Val Val Pro Arg Val Gly
225                 230                 235                 240
Thr Gln Lys Gln Ala Tyr Ile Leu Gln Asn Glu Asp Ser Arg Ile Val
                245                 250                 255
Phe Val Ile Pro Trp Met Asp Glu Phe Ser Ile Ile Gly Thr Thr Asp
                260                 265                 270
Val Glu Tyr Lys Gly Asp Ala His Asp Val Lys Ile Asp Asp Asn Glu
                275                 280                 285
Ile Asp Tyr Leu Leu Lys Val Phe Asn Ala His Phe Lys Gln Asp Leu
            290                 295                 300
Ala Arg Asp Asp Ile Val Trp Ser Tyr Ser Gly Val Arg Pro Leu Cys
305                 310                 315                 320
Asp Asp Glu Ser Asp Ser Pro Gln Ala Ile Thr Arg Asp Tyr Thr Leu
                325                 330                 335
Asp Val His Asp Asp Gly Gln Ala Pro Leu Leu Ser Val Phe Gly
            340                 345                 350
Gly Lys Leu Thr Thr Tyr Arg Lys Leu Ala Glu His Ala Met Glu Lys
            355                 360                 365
Leu Ser Lys Tyr Tyr Pro Gln Ala Gly Ala Ala Trp Thr Lys Ser Cys
            370                 375                 380
Val Leu Pro Gly Gly Asn Phe Ala Gly Thr Arg Asp Glu Tyr Ala Val
385                 390                 395                 400
Ser Leu Arg Arg Arg Phe Pro Phe Ile Ser Val Glu Leu Ala Arg His
                405                 410                 415
Tyr Ala Arg Thr Tyr Gly Ser Asn Ser Glu Gln Leu Leu Lys Gly Ala
            420                 425                 430
Thr Ser Leu Ala Asp Leu Gly Glu Leu Phe Gly His His Phe Tyr Glu
            435                 440                 445
Ala Glu Leu Arg Tyr Leu Val Glu Asn Glu Trp Val Arg Ala Thr Asp
            450                 455                 460
Asp Ala Leu Trp Arg Arg Thr Lys Glu Gly Met Trp Leu Asn Gln Gln
465                 470                 475                 480
Gln Gln Ala Arg Val Gly Glu Trp Leu Ala Gln His Ala Lys Pro Leu
                485                 490                 495
Leu Ser Leu Ala Ser
            500

<210> SEQ ID NO 62
```

```
<211> LENGTH: 514
<212> TYPE: PRT
<213> ORGANISM: Photobacterium SKA34

<400> SEQUENCE: 62
```

| | | | | | | | | | | | | | | |
|---|---|---|---|---|---|---|---|---|---|---|---|---|---|---|
| Met | Asp | Ile | Thr | Lys | Asn | Asn | Ser | Ala | Thr | Pro | Leu | Leu | Asp | Ile | Ile |
| 1 | | | | 5 | | | | | 10 | | | | | 15 | |
| Val | Ile | Gly | Gly | Gly | Ile | Asn | Gly | Ala | Gly | Ile | Ala | Ala | Asp | Ala | Ala |
| | | | 20 | | | | | 25 | | | | | 30 | | |
| Gly | Arg | Gly | Leu | Asn | Val | Ala | Leu | Tyr | Glu | Ala | Asn | Asp | Phe | Ala | Ser |
| | | 35 | | | | | 40 | | | | | 45 | | | |
| Ala | Thr | Ser | Ser | Ala | Ser | Ser | Lys | Leu | Ile | His | Gly | Gly | Leu | Arg | Tyr |
| | 50 | | | | | 55 | | | | | 60 | | | | |
| Leu | Glu | His | Tyr | Glu | Phe | Arg | Leu | Val | Ser | Glu | Ala | Leu | Ala | Glu | Arg |
| 65 | | | | | 70 | | | | | 75 | | | | | 80 |
| Glu | Val | Ile | Leu | Lys | Lys | Ala | Pro | His | Val | Ala | Glu | Pro | Met | Arg | Phe |
| | | | | 85 | | | | | 90 | | | | | 95 | |
| Arg | Leu | Pro | His | Arg | Pro | Phe | Leu | Arg | Pro | Ala | Trp | Met | Ile | Arg | Cys |
| | | | 100 | | | | | 105 | | | | | 110 | | |
| Gly | Leu | Phe | Leu | Tyr | Asp | Asn | Leu | Gly | Lys | Arg | Thr | Thr | Leu | Pro | Ala |
| | | 115 | | | | | 120 | | | | | 125 | | | |
| Ser | Lys | Lys | Ile | Asn | Leu | Ala | Gln | Ser | Gly | Leu | Leu | Lys | Pro | Glu | Met |
| | 130 | | | | | 135 | | | | | 140 | | | | |
| Lys | Val | Gly | Phe | Glu | Tyr | Ser | Asp | Cys | Trp | Val | Asp | Asp | Ala | Arg | Leu |
| 145 | | | | | 150 | | | | | 155 | | | | | 160 |
| Val | Leu | Leu | Asn | Ile | Met | Ala | Ile | Glu | Glu | Asn | Gly | Gly | Glu | Val | Ala |
| | | | | 165 | | | | | 170 | | | | | 175 | |
| Asn | Tyr | Cys | Lys | Val | Glu | Asn | Ala | Val | Arg | Glu | Gly | Asp | Ile | Trp | Arg |
| | | | 180 | | | | | 185 | | | | | 190 | | |
| Val | Thr | Met | Val | Asp | Gln | Arg | Thr | Gly | Glu | His | Phe | Glu | Arg | Arg | Thr |
| | | 195 | | | | | 200 | | | | | 205 | | | |
| Lys | Ala | Leu | Val | Asn | Ala | Ala | Gly | Pro | Trp | Val | Lys | Gln | Phe | Phe | Asp |
| | 210 | | | | | 215 | | | | | 220 | | | | |
| Asn | Gly | Leu | Glu | Thr | Pro | Ser | Pro | Arg | Asn | Ile | Arg | Leu | Ile | Lys | Gly |
| 225 | | | | | 230 | | | | | 235 | | | | | 240 |
| Ser | His | Ile | Val | Val | Pro | Lys | Ile | His | Asn | Glu | Gln | Ala | Tyr | Ile |
| | | | | 245 | | | | | 250 | | | | | 255 |
| Leu | Gln | Asn | Lys | Asp | Asn | Arg | Ile | Val | Phe | Val | Ile | Pro | Tyr | Leu | Asp |
| | | | 260 | | | | | 265 | | | | | 270 | | |
| Asp | Phe | Ser | Ile | Ile | Gly | Thr | Thr | Asp | Leu | Glu | Tyr | Lys | Gly | Asp | Pro |
| | | 275 | | | | | 280 | | | | | 285 | | | |
| Arg | His | Val | Ala | Ile | Asp | Glu | Thr | Glu | Ile | Asp | Tyr | Leu | Ile | Asp | Ile |
| | 290 | | | | | 295 | | | | | 300 | | | | |
| Val | Asn | Gln | His | Phe | Val | Asp | Gln | Leu | Gly | Arg | Glu | Asp | Val | Val | Trp |
| 305 | | | | | 310 | | | | | 315 | | | | | 320 |
| Thr | Phe | Ser | Gly | Val | Arg | Pro | Leu | Cys | Asp | Asp | Glu | Ser | Asn | Ser | Pro |
| | | | | 325 | | | | | 330 | | | | | 335 | |
| Gln | Ala | Ile | Thr | Arg | Asp | Tyr | Thr | Leu | Glu | Leu | Glu | Gln | Glu | Leu | Asp |
| | | | 340 | | | | | 345 | | | | | 350 | | |
| Gln | Ala | Pro | Leu | Leu | Ser | Ile | Phe | Gly | Gly | Lys | Leu | Thr | Thr | Tyr | Arg |
| | | 355 | | | | | 360 | | | | | 365 | | | |
| Lys | Leu | Ser | Glu | Ser | Ala | Met | Lys | His | Leu | Glu | Pro | Phe | Phe | Pro | Gln |
| | 370 | | | | | 375 | | | | | 380 | | | | |
| Met | Gly | Lys | Ser | Trp | Thr | Ala | Asn | Gln | Ala | Leu | Pro | Gly | Gly | Asn | Phe |

```
            385                 390                 395                 400
Ser Cys Ser Arg Lys Gln Leu Ala Glu Ser Leu Gln Ser Arg Tyr Pro
                    405                 410                 415

Trp Leu Ser Asp Lys Gln Ala Leu Arg Tyr Val Lys Gln Phe Gly Ser
                    420                 425                 430

Tyr Cys Tyr Lys Met Leu Ala Asp Val Thr Cys Ile Asp Asp Met Gly
                    435                 440                 445

Ile Gln Phe Ala Asp Ala Val Tyr Gln Lys Glu Ile Asp Tyr Val Ile
    450                 455                 460

Ala His Glu His Val Lys Thr Val Glu Asp Phe Leu Trp Arg Arg Thr
465                 470                 475                 480

Lys Leu Gly Leu Tyr Leu Thr Asp Glu Gln Gln Leu Gln Val Lys Glu
                    485                 490                 495

Tyr Ile Asp Ala Asn Ala Pro Ser Asn Asn Ile Val Ser Phe His Lys
                500                 505                 510

Val Gly

<210> SEQ ID NO 63
<211> LENGTH: 499
<212> TYPE: PRT
<213> ORGANISM: Pectobacterium carotovorum

<400> SEQUENCE: 63

Met Glu Thr Lys Asp Leu Ile Val Ile Gly Gly Ile Asn Gly Ala
  1               5                  10                  15

Gly Ile Ala Ala Asp Ala Ala Gly Arg Gly Leu Ser Val Leu Leu Leu
                20                  25                  30

Glu Ala Gln Asp Leu Ala Cys Ala Thr Ser Ser Ala Ser Ser Lys Leu
            35                  40                  45

Ile His Gly Gly Leu Arg Tyr Leu Glu His Tyr Glu Phe Arg Leu Val
    50                  55                  60

Ser Glu Ala Leu Ser Glu Arg Glu Thr Leu Leu Lys Met Ala Pro His
65                  70                  75                  80

Ile Ile Phe Pro Met Arg Phe Arg Leu Pro His Gln Pro His Leu Arg
                85                  90                  95

Pro Ala Trp Met Ile Arg Ile Gly Leu Phe Met Tyr Asp Asn Ile Gly
                100                 105                 110

Lys Arg Val Ser Leu Pro Ala Ser Lys Gly Leu Lys Phe Gly Ala Asp
            115                 120                 125

Ser Val Leu Lys Pro Glu Leu Lys Gln Gly Phe Glu Tyr Ser Asp Cys
    130                 135                 140

Trp Val Asp Asp Ala Arg Leu Val Val Leu Asn Ala Gln Glu Val Thr
145                 150                 155                 160

Lys Arg Gly Gly Glu Val Arg Thr Arg Thr Lys Val Thr Arg Ala Arg
                165                 170                 175

Arg Glu Gln Gly Val Trp Ile Val Asp Ala Val Asp Ser Leu Thr Gly
            180                 185                 190

Glu Thr Phe Thr Trp Arg Ala Lys Gly Leu Val Asn Ala Thr Gly Pro
    195                 200                 205

Trp Val Lys Glu Phe Phe Asp Asp Gly Leu Gln Leu Lys Ser Pro Tyr
210                 215                 220

Gly Ile Arg Leu Ile Lys Gly Ser His Ile Val Val Pro Lys Val His
225                 230                 235                 240

Asn Gln Pro Gln Ala Tyr Ile Leu Gln Asn Lys Asp His Arg Ile Val
```

```
                    245                 250                 255
        Phe Val Ile Pro Trp Gln Asp Asp Tyr Ser Ile Ile Gly Thr Thr Asp
                        260                 265                 270

Val Glu Tyr Lys Gly Asn Pro His Asp Val Lys Ile Asp Asp Asn Glu
                    275                 280                 285

Val Gly Tyr Leu Leu Asp Val Tyr Asn Asp His Phe Lys Gln Gln Leu
                    290                 295                 300

Thr Arg Asp Asp Ile Val Trp Thr Tyr Ser Gly Val Arg Pro Leu Cys
        305                 310                 315                 320

Asp Asp Glu Ser Asp Ser Pro Gln Ala Ile Thr Arg Asp Tyr Thr Leu
                        325                 330                 335

Ser Val Asp Asp Asn Gly Gln Ala Pro Leu Leu Ser Val Phe Gly
                        340                 345                 350

Gly Lys Leu Thr Thr Tyr Arg Lys Leu Ala Glu His Ala Leu Asp Lys
                        355                 360                 365

Leu His Lys Tyr Tyr Pro Gln Ala Gly Lys Ala Trp Thr Lys Gly Ala
                    370                 375                 380

Val Leu Pro Gly Gly Asp Ile Ala Gly Thr Arg Asp Asp Tyr Ala Ala
        385                 390                 395                 400

Ala Leu Arg Arg Arg Phe Asn Leu Pro Glu Ser Leu Thr Arg Tyr
                        405                 410                 415

Ser Arg Thr Tyr Gly Ser Asn Ser Glu Leu Ile Leu Ala Asn Val Lys
                        420                 425                 430

Gly Leu Ser Asp Leu Gly Glu Asp Phe Gly His Asp Leu Tyr Glu Ala
                        435                 440                 445

Glu Leu Arg Tyr Leu Val Glu Lys Glu Trp Ala Val Met Leu Asp Asp
                    450                 455                 460

Val Ile Trp Arg Arg Thr Lys Leu Gly Met Arg Phe Asp Ala Gln
        465                 470                 475                 480

Lys Gln Arg Ile Ser Asp Trp Leu Ala Asn His Tyr Gln Gln Met Ala
                        485                 490                 495

Lys Ala Gly

<210> SEQ ID NO 64
<211> LENGTH: 831
<212> TYPE: PRT
<213> ORGANISM: Escherichia coli

<400> SEQUENCE: 64

Met Leu Thr Ile Gln Phe Leu Cys Pro Leu Pro Asn Gly Leu His Ala
        1               5                   10                  15

Arg Pro Ala Trp Glu Leu Lys Glu Gln Cys Ser Gln Trp Gln Ser Glu
                        20                  25                  30

Ile Thr Phe Ile Asn His Arg Gln Asn Ala Lys Ala Asp Ala Lys Ser
                    35                  40                  45

Ser Leu Ala Leu Ile Gly Thr Gly Thr Leu Phe Asn Asp Ser Cys Ser
                50                  55                  60

Leu Asn Ile Ser Gly Ser Asp Glu Glu Gln Ala Arg Arg Val Leu Glu
        65                  70                  75                  80

Glu Tyr Ile Gln Val Arg Phe Ile Asp Ser Asp Ser Val Gln Pro Thr
                        85                  90                  95

Gln Ala Glu Leu Thr Ala His Pro Leu Pro Arg Ser Leu Ser Arg Leu
                    100                 105                 110

Asn Pro Asp Leu Leu Tyr Gly Asn Val Leu Ala Ser Gly Val Gly Val
```

```
            115                 120                 125
Gly Thr Leu Thr Leu Leu Gln Ser Asp Ser Leu Asp Ser Tyr Arg Ala
    130                 135                 140

Ile Pro Ala Ser Ala Gln Asp Ser Thr Arg Leu Glu His Ser Leu Ala
145                 150                 155                 160

Thr Leu Ala Glu Gln Leu Asn Gln Gln Leu Arg Glu Arg Asp Gly Glu
                165                 170                 175

Ser Lys Thr Ile Leu Ser Ala His Leu Ser Leu Ile Gln Asp Asp Glu
            180                 185                 190

Phe Ala Gly Asn Ile Arg Arg Leu Met Thr Glu Gln His Gln Gly Leu
        195                 200                 205

Gly Ala Ala Ile Ile Ser Asn Met Glu Gln Val Cys Ala Lys Leu Ser
    210                 215                 220

Ala Ser Ala Ser Asp Tyr Leu Arg Glu Arg Val Ser Asp Ile Arg Asp
225                 230                 235                 240

Ile Ser Glu Gln Leu Leu His Ile Thr Trp Pro Glu Leu Lys Pro Arg
                245                 250                 255

Asn Lys Leu Val Leu Glu Lys Pro Thr Ile Leu Val Ala Glu Asp Leu
            260                 265                 270

Thr Pro Ser Gln Phe Leu Ser Leu Asp Leu Lys Asn Leu Ala Gly Met
        275                 280                 285

Ile Leu Glu Lys Thr Gly Arg Thr Ser His Thr Leu Ile Leu Ala Arg
    290                 295                 300

Ala Ser Ala Ile Pro Val Leu Ser Gly Leu Pro Leu Asp Ala Ile Ala
305                 310                 315                 320

Arg Tyr Ala Gly Gln Pro Ala Val Leu Asp Ala Gln Cys Gly Val Leu
                325                 330                 335

Ala Ile Asn Pro Asn Asp Ala Val Ser Gly Tyr Tyr Gln Val Ala Gln
            340                 345                 350

Thr Leu Ala Asp Lys Arg Gln Lys Gln Gln Ala Gln Ala Ala Ala Gln
        355                 360                 365

Leu Ala Tyr Ser Arg Asp Asn Lys Arg Ile Asp Ile Ala Ala Asn Ile
    370                 375                 380

Gly Thr Ala Leu Glu Ala Pro Gly Ala Phe Ala Asn Gly Ala Glu Gly
385                 390                 395                 400

Val Gly Leu Phe Arg Thr Glu Met Leu Tyr Met Asp Arg Asp Ser Ala
                405                 410                 415

Pro Asp Glu Gln Glu Gln Phe Glu Ala Tyr Gln Gln Val Leu Leu Ala
            420                 425                 430

Ala Gly Asp Lys Pro Ile Ile Phe Arg Thr Met Asp Ile Gly Gly Asp
        435                 440                 445

Lys Ser Ile Pro Tyr Leu Asn Ile Pro Gln Glu Glu Asn Pro Phe Leu
    450                 455                 460

Gly Tyr Arg Ala Val Arg Ile Tyr Pro Glu Phe Ala Gly Leu Phe Arg
465                 470                 475                 480

Thr Gln Leu Arg Ala Ile Leu Arg Ala Ala Ser Phe Gly Asn Ala Gln
                485                 490                 495

Leu Met Ile Pro Met Val His Ser Leu Asp Gln Ile Leu Trp Val Lys
            500                 505                 510

Gly Glu Ile Gln Lys Ala Ile Val Glu Leu Lys Arg Asp Gly Leu Arg
        515                 520                 525

His Ala Glu Thr Ile Thr Leu Gly Ile Met Val Glu Val Pro Ser Val
    530                 535                 540
```

Cys Tyr Ile Ile Asp His Phe Cys Asp Glu Val Asp Phe Phe Ser Ile
545                 550                 555                 560

Gly Ser Asn Asp Met Thr Gln Tyr Leu Tyr Ala Val Asp Arg Asn Asn
                565                 570                 575

Pro Arg Val Ser Pro Leu Tyr Asn Pro Ile Thr Pro Ser Phe Leu Arg
            580                 585                 590

Met Leu Gln Gln Ile Val Thr Thr Ala His Gln Arg Gly Lys Trp Val
        595                 600                 605

Gly Ile Cys Gly Glu Leu Gly Gly Glu Ser Arg Tyr Leu Pro Leu Leu
    610                 615                 620

Leu Gly Leu Gly Leu Asp Glu Leu Ser Met Ser Ser Pro Arg Ile Pro
625                 630                 635                 640

Ala Val Lys Ser Gln Leu Arg Gln Leu Asp Ser Glu Ala Cys Arg Glu
                645                 650                 655

Leu Ala Arg Gln Ala Cys Glu Cys Arg Ser Ala Gln Glu Ile Glu Ala
            660                 665                 670

Leu Leu Thr Ala Phe Thr Pro Glu Glu Asp Val Arg Pro Leu Leu Ala
        675                 680                 685

Leu Glu Asn Ile Phe Val Asp Gln Asp Phe Ser Asn Lys Glu Gln Ala
    690                 695                 700

Ile Gln Phe Leu Cys Gly Asn Leu Gly Val Asn Gly Arg Thr Glu His
705                 710                 715                 720

Pro Phe Glu Leu Glu Glu Asp Val Trp Gln Arg Glu Ile Val Thr
                725                 730                 735

Thr Gly Val Gly Phe Gly Val Ala Ile Pro His Thr Lys Ser Gln Trp
            740                 745                 750

Ile Arg His Ser Ser Ile Ser Ile Ala Arg Leu Ala Lys Pro Ile Gly
        755                 760                 765

Trp Gln Ser Glu Met Gly Glu Val Glu Leu Val Ile Met Leu Thr Leu
    770                 775                 780

Gly Ala Asn Glu Gly Met Asn His Val Lys Val Phe Ser Gln Leu Ala
785                 790                 795                 800

Arg Lys Leu Val Asn Lys Asn Phe Arg Gln Ser Leu Phe Ala Ala Gln
                805                 810                 815

Asp Ala Gln Ser Ile Leu Thr Leu Leu Glu Thr Glu Leu Thr Phe
            820                 825                 830

<210> SEQ ID NO 65
<211> LENGTH: 833
<212> TYPE: PRT
<213> ORGANISM: Escherichia coli

<400> SEQUENCE: 65

Met Ala Leu Ile Val Glu Phe Ile Cys Glu Leu Pro Asn Gly Val His
1               5                   10                  15

Ala Arg Pro Ala Ser His Val Glu Thr Leu Cys Asn Thr Phe Ser Ser
                20                  25                  30

Gln Ile Glu Trp His Asn Leu Arg Thr Asp Arg Lys Gly Asn Ala Lys
            35                  40                  45

Ser Ala Leu Ala Leu Ile Gly Thr Asp Thr Leu Ala Gly Asp Asn Cys
        50                  55                  60

Gln Leu Leu Ile Ser Gly Ala Asp Glu Gln Glu Ala His Gln Arg Leu
65                  70                  75                  80

Ser Gln Trp Leu Arg Asp Glu Phe Pro His Cys Asp Ala Pro Leu Ala

```
                         85                  90                  95
        Glu Val Lys Ser Asp Glu Leu Glu Pro Leu Val Ser Leu Thr Asn
                        100                 105                 110
        Leu Asn Pro Gln Ile Ile Arg Ala Arg Thr Val Cys Ser Gly Ser Ala
                        115                 120                 125
        Gly Gly Ile Leu Thr Pro Ile Ser Ser Leu Asp Leu Asn Ala Leu Gly
                        130                 135                 140
        Asn Leu Pro Ala Ala Lys Gly Val Asp Ala Glu Gln Ser Ala Leu Glu
        145                 150                 155                 160
        Asn Gly Leu Thr Leu Val Leu Lys Asn Ile Glu Phe Arg Leu Leu Asp
                        165                 170                 175
        Ser Asp Gly Ala Thr Ser Ala Ile Leu Glu Ala His Arg Ser Leu Ala
                        180                 185                 190
        Gly Asp Thr Ser Leu Arg Glu His Leu Leu Ala Gly Val Ser Ala Gly
                        195                 200                 205
        Leu Ser Cys Ala Glu Ala Ile Val Ala Ser Ala Asn His Phe Cys Glu
                        210                 215                 220
        Glu Phe Ser Arg Ser Ser Ser Tyr Leu Gln Glu Arg Ala Leu Asp
        225                 230                 235                 240
        Val Arg Asp Val Cys Phe Gln Leu Leu Gln Gln Ile Tyr Gly Glu Gln
                        245                 250                 255
        Arg Phe Pro Ala Pro Gly Lys Leu Thr Gln Pro Ala Ile Cys Met Ala
                        260                 265                 270
        Asp Glu Leu Thr Pro Ser Gln Phe Leu Glu Leu Asp Lys Asn His Leu
                        275                 280                 285
        Lys Gly Leu Leu Leu Lys Ser Gly Gly Thr Thr Ser His Thr Val Ile
                        290                 295                 300
        Leu Ala Arg Ser Phe Asn Ile Pro Thr Leu Val Gly Val Asp Ile Asp
        305                 310                 315                 320
        Ala Leu Thr Pro Trp Gln Gln Thr Ile Tyr Ile Asp Gly Asn Ala
                        325                 330                 335
        Gly Ala Ile Val Val Glu Pro Gly Glu Ala Val Ala Arg Tyr Tyr Gln
                        340                 345                 350
        Gln Glu Ala Arg Val Gln Asp Ala Leu Arg Glu Gln Arg Val Trp
                        355                 360                 365
        Leu Thr Gln Gln Ala Arg Thr Ala Asp Gly Ile Arg Ile Glu Ile Ala
        370                 375                 380
        Ala Asn Ile Ala His Ser Val Glu Ala Gln Ala Ala Phe Gly Asn Gly
        385                 390                 395                 400
        Ala Glu Gly Val Gly Leu Phe Arg Thr Glu Met Leu Tyr Met Asp Arg
                        405                 410                 415
        Thr Ser Ala Pro Gly Glu Ser Glu Leu Tyr Asn Ile Phe Cys Gln Ala
                        420                 425                 430
        Leu Glu Ser Ala Asn Gly Arg Ser Ile Val Arg Thr Met Asp Ile
                        435                 440                 445
        Gly Gly Asp Lys Pro Val Asp Tyr Leu Asn Ile Pro Ala Glu Ala Asn
        450                 455                 460
        Pro Phe Leu Gly Tyr Arg Ala Val Arg Ile Tyr Glu Glu Tyr Ala Ser
        465                 470                 475                 480
        Leu Phe Thr Thr Gln Leu Arg Ser Ile Leu Arg Ala Ser Ala His Gly
                        485                 490                 495
        Ser Leu Lys Ile Met Ile Pro Met Ile Ser Ser Met Glu Glu Ile Leu
                        500                 505                 510
```

-continued

Trp Val Lys Glu Lys Leu Ala Glu Ala Lys Gln Gln Leu Arg Asn Glu
    515                 520                 525

His Ile Pro Phe Asp Glu Lys Ile Gln Leu Gly Ile Met Leu Glu Val
    530                 535                 540

Pro Ser Val Met Phe Ile Ile Asp Gln Cys Cys Glu Glu Ile Asp Phe
545                 550                 555                 560

Phe Ser Ile Gly Ser Asn Asp Leu Thr Gln Tyr Leu Leu Ala Val Asp
                565                 570                 575

Arg Asp Asn Ala Lys Val Thr Arg His Tyr Asn Ser Leu Asn Pro Ala
                580                 585                 590

Phe Leu Arg Ala Leu Asp Tyr Ala Val Gln Ala Val His Arg Gln Gly
            595                 600                 605

Lys Trp Ile Gly Leu Cys Gly Glu Leu Gly Ala Lys Gly Ser Val Leu
            610                 615                 620

Pro Leu Val Gly Leu Gly Leu Asp Glu Leu Ser Met Ser Ala Pro
625                 630                 635                 640

Ser Ile Pro Ala Ala Lys Ala Arg Met Ala Gln Leu Asp Ser Arg Glu
                645                 650                 655

Cys Arg Lys Leu Leu Asn Gln Ala Met Ala Cys Arg Thr Ser Leu Glu
            660                 665                 670

Val Glu His Leu Leu Ala Gln Phe Arg Met Thr Gln Gln Asp Ala Pro
            675                 680                 685

Leu Val Thr Ala Glu Cys Ile Thr Leu Glu Ser Asp Trp Arg Ser Lys
            690                 695                 700

Glu Glu Val Leu Lys Gly Met Thr Asp Asn Leu Leu Leu Ala Gly Arg
705                 710                 715                 720

Cys Arg Tyr Pro Arg Lys Leu Glu Ala Asp Leu Trp Ala Arg Glu Ala
                725                 730                 735

Val Phe Ser Thr Gly Leu Gly Phe Ser Phe Ala Ile Pro His Ser Lys
            740                 745                 750

Ser Glu His Ile Glu Gln Ser Thr Ile Ser Val Ala Arg Leu Gln Ala
            755                 760                 765

Pro Val Arg Trp Gly Asp Glu Ala Gln Phe Ile Ile Met Leu Thr
            770                 775                 780

Leu Asn Lys His Ala Ala Gly Asp Gln His Met Arg Ile Phe Ser Arg
785                 790                 795                 800

Leu Ala Arg Arg Ile Met His Glu Glu Phe Arg Asn Ala Leu Val Asn
                805                 810                 815

Ala Ala Ser Ala Asp Ala Ile Ala Ser Leu Leu Gln His Glu Leu Glu
            820                 825                 830

Leu

<210> SEQ ID NO 66
<211> LENGTH: 477
<212> TYPE: PRT
<213> ORGANISM: Escherichia coli

<400> SEQUENCE: 66

Met Phe Lys Asn Ala Phe Ala Asn Leu Gln Lys Val Gly Lys Ser Leu
1               5                   10                  15

Met Leu Pro Val Ser Val Leu Pro Ile Ala Gly Ile Leu Leu Gly Val
            20                  25                  30

Gly Ser Ala Asn Phe Ser Trp Leu Pro Ala Val Val Ser His Val Met
        35                  40                  45

```
Ala Glu Ala Gly Gly Ser Val Phe Ala Asn Met Pro Leu Ile Phe Ala
     50                  55                  60

Ile Gly Val Ala Leu Gly Phe Thr Asn Asn Asp Gly Val Ser Ala Leu
 65                  70                  75                  80

Ala Ala Val Val Ala Tyr Gly Ile Met Val Lys Thr Met Ala Val Val
                 85                  90                  95

Ala Pro Leu Val Leu His Leu Pro Ala Glu Glu Ile Ala Ser Lys His
            100                 105                 110

Leu Ala Asp Thr Gly Val Leu Gly Ile Ile Ser Gly Ala Ile Ala
            115                 120                 125

Ala Tyr Met Phe Asn Arg Phe Tyr Arg Ile Lys Leu Pro Glu Tyr Leu
        130                 135                 140

Gly Phe Phe Ala Gly Lys Arg Phe Val Pro Ile Ile Ser Gly Leu Ala
145                 150                 155                 160

Ala Ile Phe Thr Gly Val Val Leu Ser Phe Ile Trp Pro Pro Ile Gly
            165                 170                 175

Ser Ala Ile Gln Thr Phe Ser Gln Trp Ala Ala Tyr Gln Asn Pro Val
            180                 185                 190

Val Ala Phe Gly Ile Tyr Gly Phe Ile Glu Arg Cys Leu Val Pro Phe
        195                 200                 205

Gly Leu His His Ile Trp Asn Val Pro Phe Gln Met Gln Ile Gly Glu
    210                 215                 220

Tyr Thr Asn Ala Ala Gly Gln Val Phe His Gly Asp Ile Pro Arg Tyr
225                 230                 235                 240

Met Ala Gly Asp Pro Thr Ala Gly Lys Leu Ser Gly Phe Leu Phe
                245                 250                 255

Lys Met Tyr Gly Leu Pro Ala Ala Ala Ile Ala Ile Trp His Ser Ala
            260                 265                 270

Lys Pro Glu Asn Arg Ala Lys Val Gly Gly Ile Met Ile Ser Ala Ala
            275                 280                 285

Leu Thr Ser Phe Leu Thr Gly Ile Thr Glu Pro Ile Glu Phe Ser Phe
        290                 295                 300

Met Phe Val Ala Pro Ile Leu Tyr Ile Ile His Ala Ile Leu Ala Gly
305                 310                 315                 320

Leu Ala Phe Pro Ile Cys Ile Leu Leu Gly Met Arg Asp Gly Thr Ser
                325                 330                 335

Phe Ser His Gly Leu Ile Asp Phe Ile Val Leu Ser Gly Asn Ser Ser
            340                 345                 350

Lys Leu Trp Leu Phe Pro Ile Val Gly Ile Gly Tyr Ala Ile Val Tyr
        355                 360                 365

Tyr Thr Ile Phe Arg Val Leu Ile Lys Ala Leu Asp Leu Lys Thr Pro
    370                 375                 380

Gly Arg Glu Asp Ala Thr Glu Asp Ala Lys Ala Thr Gly Thr Ser Glu
385                 390                 395                 400

Met Ala Pro Ala Leu Val Ala Ala Phe Gly Gly Lys Glu Asn Ile Thr
                405                 410                 415

Asn Leu Asp Ala Cys Ile Thr Arg Leu Arg Val Ser Val Ala Asp Val
            420                 425                 430

Ser Lys Val Asp Gln Ala Gly Leu Lys Lys Leu Gly Ala Ala Gly Val
        435                 440                 445

Val Val Ala Gly Ser Gly Val Gln Ala Ile Phe Gly Thr Lys Ser Asp
    450                 455                 460
```

Asn Leu Lys Thr Glu Met Asp Glu Tyr Ile Arg Asn His
465                 470                 475

<210> SEQ ID NO 67
<211> LENGTH: 530
<212> TYPE: PRT
<213> ORGANISM: Escherichia coli

<400> SEQUENCE: 67

Met Thr Ala Lys Thr Ala Pro Lys Val Thr Leu Trp Glu Phe Phe Gln
1               5                   10                  15

Gln Leu Gly Lys Thr Phe Met Leu Pro Val Ala Leu Leu Ser Phe Cys
            20                  25                  30

Gly Ile Met Leu Gly Ile Gly Ser Ser Leu Ser Ser His Asp Val Ile
        35                  40                  45

Thr Leu Ile Pro Val Leu Gly Asn Pro Val Leu Gln Ala Ile Phe Thr
    50                  55                  60

Trp Met Ser Lys Ile Gly Ser Phe Ala Phe Ser Phe Leu Pro Val Met
65                  70                  75                  80

Phe Cys Ile Ala Ile Pro Leu Gly Leu Ala Arg Glu Asn Lys Gly Val
                85                  90                  95

Ala Ala Phe Ala Gly Phe Ile Gly Tyr Ala Val Met Asn Leu Ala Val
            100                 105                 110

Asn Phe Trp Leu Thr Asn Lys Gly Ile Leu Pro Thr Thr Asp Ala Ala
        115                 120                 125

Val Leu Lys Ala Asn Asn Ile Gln Ser Ile Leu Gly Ile Gln Ser Ile
    130                 135                 140

Asp Thr Gly Ile Leu Gly Ala Val Ile Ala Gly Ile Ile Val Trp Met
145                 150                 155                 160

Leu His Glu Arg Phe His Asn Ile Arg Leu Pro Asp Ala Leu Ala Phe
                165                 170                 175

Phe Gly Gly Thr Arg Phe Val Pro Ile Ile Ser Ser Leu Val Met Gly
            180                 185                 190

Leu Val Gly Leu Val Ile Pro Leu Val Trp Pro Ile Phe Ala Met Gly
        195                 200                 205

Ile Ser Gly Leu Gly His Met Ile Asn Ser Ala Gly Asp Phe Gly Pro
    210                 215                 220

Met Leu Phe Gly Thr Gly Glu Arg Leu Leu Pro Phe Gly Leu His His
225                 230                 235                 240

His Ile Leu Val Ala Leu Ile Arg Phe Thr Asp Ala Gly Gly Thr Gln
                245                 250                 255

Glu Val Cys Gly Gln Thr Val Ser Gly Ala Leu Thr Ile Phe Gln Ala
            260                 265                 270

Gln Leu Ser Cys Pro Thr Thr His Gly Phe Ser Glu Ser Ala Thr Arg
        275                 280                 285

Phe Leu Ser Gln Gly Lys Met Pro Ala Phe Leu Gly Gly Leu Pro Gly
    290                 295                 300

Ala Ala Leu Ala Met Tyr His Cys Ala Arg Pro Glu Asn Arg His Lys
305                 310                 315                 320

Ile Lys Gly Leu Leu Ile Ser Gly Leu Ile Ala Cys Val Val Gly Gly
                325                 330                 335

Thr Thr Glu Pro Leu Glu Phe Leu Phe Leu Phe Val Ala Pro Val Leu
            340                 345                 350

Tyr Val Ile His Ala Leu Leu Thr Gly Leu Gly Phe Thr Val Met Ser
        355                 360                 365

Val Leu Gly Val Thr Ile Gly Asn Thr Asp Gly Asn Ile Ile Asp Phe
    370                 375                 380

Val Val Phe Gly Ile Leu His Gly Leu Ser Thr Lys Trp Tyr Met Val
385                 390                 395                 400

Pro Val Val Ala Ala Ile Trp Phe Val Val Tyr Tyr Val Ile Phe Arg
                405                 410                 415

Phe Ala Ile Thr Arg Phe Asn Leu Lys Thr Pro Gly Arg Asp Ser Glu
                420                 425                 430

Val Ala Ser Ser Ile Glu Lys Ala Val Ala Gly Ala Pro Gly Lys Ser
                435                 440                 445

Gly Tyr Asn Val Pro Ala Ile Leu Glu Ala Leu Gly Gly Ala Asp Asn
            450                 455                 460

Ile Val Ser Leu Asp Asn Cys Ile Thr Arg Leu Arg Leu Ser Val Lys
465                 470                 475                 480

Asp Met Ser Leu Val Asn Val Gln Ala Leu Lys Asp Asn Arg Ala Ile
                485                 490                 495

Gly Val Val Gln Leu Asn Gln His Asn Leu Gln Val Val Ile Gly Pro
            500                 505                 510

Gln Val Gln Ser Val Lys Asp Glu Met Ala Gly Leu Met His Thr Val
        515                 520                 525

Gln Ala
    530

<210> SEQ ID NO 68
<211> LENGTH: 589
<212> TYPE: PRT
<213> ORGANISM: Prochlorococcus marinus

<400> SEQUENCE: 68

Met Ala Ala Ile Asp Trp Ile Ile Leu Val Gly Tyr Leu Ala Ile Thr
1               5                   10                  15

Leu Val Ile Gly Leu Trp Leu Ser Arg Arg Asn Arg Ser Glu Asp Asp
                20                  25                  30

Tyr Phe Val Ala Gly Arg Arg Leu Ser Gly Trp Leu Ala Gly Ala Ser
            35                  40                  45

Met Ala Ala Thr Thr Phe Ser Ile Asp Thr Pro Leu Tyr Val Ala Gly
        50                  55                  60

Leu Val Gly Thr Arg Gly Leu Ala Gly Asn Trp Glu Trp Trp Ser Phe
65                  70                  75                  80

Gly Leu Ala His Val Ala Met Ala Val Val Phe Ala Pro Leu Trp Arg
                85                  90                  95

Arg Ser Gly Val Leu Thr Asp Ala Ala Phe Thr Glu Leu Arg Tyr Gly
            100                 105                 110

Gly Ala Pro Ala Ala Trp Leu Arg Gly Ile Lys Ala Phe Leu Leu Ala
        115                 120                 125

Leu Pro Val Asn Cys Ile Gly Ile Gly Tyr Ala Phe Leu Ala Met Arg
    130                 135                 140

Lys Val Val Glu Ala Leu Gly Ile Val Ser Gly Ser Pro Val Ala Val
145                 150                 155                 160

Leu Gly Gly Thr Pro Asp Thr Val Val Leu Ala Val Val Ala Val
                165                 170                 175

Met Val Leu Val Tyr Thr Val Ala Gly Gly Leu Trp Ala Val Val Ile
            180                 185                 190

Thr Asp Phe Val Gln Leu Leu Leu Ala Leu Leu Gly Ala Val Ala Val

```
              195                 200                 205
Ala Trp Ala Ala Val His Ala Ala Gly Gly Met Asp Ala Met Leu Asp
210                 215                 220

Gln Leu Arg Gly Leu Glu Arg Pro Glu Leu Leu Ala Ile Val Pro Trp
225                 230                 235                 240

Gln Trp Asn Gly Asp Gly Phe Asp Trp Ile Gly Gly Ala Glu Ile Ser
                245                 250                 255

Val Ala Thr Phe Leu Ser Tyr Leu Thr Val Gln Trp Trp Ser Phe Arg
                260                 265                 270

Arg Ser Asp Gly Gly Glu Phe Ile Gln Arg Met Leu Ala Thr Arg
            275                 280                 285

Asp Glu Arg Gln Ala Gln Leu Ala Gly Trp Val Phe Leu Val Val Asn
290                 295                 300

Tyr Leu Val Arg Ser Trp Leu Trp Val Val Ala Leu Ala Ala Leu
305                 310                 315                 320

Val Leu Leu Pro Ala Gln Ala Asp Trp Glu Leu Ser Tyr Pro Thr Leu
                325                 330                 335

Ala Val Thr Tyr Leu Pro Pro Val Val Leu Gly Leu Val Val Ser
                340                 345                 350

Leu Val Ala Ala Phe Met Ser Thr Val Ser Thr Ala Val Asn Trp Gly
                355                 360                 365

Ala Ser Tyr Leu Thr His Asp Leu Tyr Gln Arg Phe Ile Arg Pro Asp
370                 375                 380

Ala Asp Gln Arg Glu Leu Leu Val Gly Gln Phe Thr Ser Val Leu
385                 390                 395                 400

Leu Leu Val Leu Gly Val Ile Thr Ala Leu Ile Ser Asp Ser Ile Gly
                405                 410                 415

Thr Val Phe Arg Leu Val Ile Ala Ile Gly Thr Gly Pro Gly Val Val
                420                 425                 430

Leu Val Leu Arg Trp Phe Trp Trp Arg Ile Asn Ala Ala Ala Glu Leu
                435                 440                 445

Ala Ala Met Val Cys Gly Phe Val Val Gly Leu Cys Thr Ser Val Val
450                 455                 460

Pro Leu Val Thr Ile Pro Asp Tyr Gly Thr Arg Leu Met Ile Thr Thr
465                 470                 475                 480

Ala Ile Thr Ala Val Trp Val Val Met Leu Val Thr Pro Pro
                485                 490                 495

Glu Ser Pro Gln Val Leu Glu Arg Phe Val Asn Gln Val Gln Pro Pro
                500                 505                 510

Gly Pro Gly Trp Ser Arg Leu Arg Gln Arg Leu Asp Ile Thr Pro Val
                515                 520                 525

Asp Ser Leu Val Ser Leu Cys Leu Arg Phe Ile Leu Ser Val Gly Val
530                 535                 540

Leu Phe Gly Gly Leu Leu Gly Thr Gly Ala Phe Leu Leu His Gln Gln
545                 550                 555                 560

Leu Gly Gly Trp Ile Gly Leu Val Val Thr Val Val Cys Val Leu Pro
                565                 570                 575

Leu Thr Arg Gly Trp Leu Arg Ser Arg Met Gly Val Ala
                580                 585

<210> SEQ ID NO 69
<211> LENGTH: 464
<212> TYPE: PRT
<213> ORGANISM: Lysinibacillus sphaericus
```

<400> SEQUENCE: 69

Met Ala Gly Lys Gly Thr Gly Leu Phe Ala Leu Thr Ala Thr Leu Val
1               5                   10                  15

Ala Ala Glu Phe Asn Thr Ala Thr Leu Ile Gly Gly Ala Ser Val Ala
            20                  25                  30

Tyr Leu Phe Gly Thr Val Gly Met Trp Tyr Thr Ser Leu Ile Phe Ile
                35                  40                  45

Ala Val Phe Leu Ala Tyr Ala Phe Thr Val Ala Lys Lys Tyr Arg Lys
    50                  55                  60

Leu Asn Ile Ser Thr Ile Ser Gln Phe Phe Asp Lys Arg Phe Lys Asn
65                  70                  75                  80

Glu Lys Tyr Ser Glu Leu Ile Arg Phe Met Ser Ala Ile Ile Thr Leu
                85                  90                  95

Phe Tyr Thr Trp Leu Ala Pro Ala Ser Tyr Leu Ala Gly Leu Ala Val
                100                 105                 110

Ile Gly Ser Val Leu Leu Gly Val Asp Pro Val Ile Phe Ser Ile Thr
            115                 120                 125

Ile Val Val Ile Cys Leu Ile Leu Ser Ile Thr Gly Gly Leu Leu Thr
130                 135                 140

Ala Ile Gly Ile Asp Val Val Ala Phe Ile Met Ile Met Ile Gly Ile
145                 150                 155                 160

Pro Thr Ile Leu Phe Ile Gly Ile Ser Ala Ala Gly Gly Phe Gly Ser
                165                 170                 175

Leu Ser Gln Val Tyr Glu Pro Lys Leu Leu Ser Leu Ala Pro Val Trp
            180                 185                 190

Asp Thr Glu Val Asn Phe Pro Ile Ala Leu Thr Trp Gly Leu Gln Ile
            195                 200                 205

Leu Phe Leu Tyr Ile Ala Ala Pro Trp Tyr Gly Gln Arg Ile Phe Ser
210                 215                 220

Ala Lys Asn Glu Lys Val Ala Tyr Thr Ala Met Leu Trp Asn Thr Phe
225                 230                 235                 240

Phe Ile Val Val Leu Tyr Gly Met Val Val Leu Ala Thr Met Phe Ser
                245                 250                 255

Lys Val Val Phe Pro Ser Leu Asp Lys Pro Glu Glu Ala Leu Pro Leu
            260                 265                 270

Leu Ile Ala Thr Gln Ser Asn Ser Leu Val Gln Gly Leu Leu Leu Val
            275                 280                 285

Thr Leu Leu Leu Val Gly Val Ser Thr Leu Ile Ala Val Trp Asn Ser
290                 295                 300

Ala Val Ser Ile Ile Val Asn Asp Val Val Arg Arg Tyr Phe Leu Lys
305                 310                 315                 320

Asn Lys Gly Asp Arg Gln Phe Ile Ile Ala Ser Arg Ile Cys Phe Val
                325                 330                 335

Ile Ile Ala Ala Ser Thr Leu Ile Phe Gly Ile Val Phe Ile Gly Asn
            340                 345                 350

Ile Gln Asn Ser Leu Leu Phe Leu Ser Thr Phe Thr Gly Ile Val Ala
            355                 360                 365

Ile Pro Ile Leu Ile Ser Leu Tyr Trp Lys Lys Tyr Asn Ser Leu Gly
            370                 375                 380

Ala Leu Ser Ser Met Ile Ser Gly Leu Ala Tyr Ser Gly Ile Ala Ile
385                 390                 395                 400

Thr Leu Ser Phe Pro Ile Tyr Phe Ile Ser Pro Ile Ala Val Ile Val

```
                   405                 410                 415
Ala Thr Ile Val Gly Ile Ile Val Ser Leu Ala Thr Ser Lys Asn His
            420                 425                 430

Val Thr Asp Asn Gln Glu Phe Tyr Glu Leu Ile Glu Ser Pro Leu Glu
            435                 440                 445

Leu Glu Ser His Glu Thr Glu Ser Val Leu Ile Pro Lys Glu Ser Asn
            450                 455                 460

<210> SEQ ID NO 70
<211> LENGTH: 602
<212> TYPE: PRT
<213> ORGANISM: Rhodopirellula baltica

<400> SEQUENCE: 70

Met Ala Leu Ser Tyr Val Asp Tyr Ala Ile Ile Ala Phe Phe Val
 1               5                  10                  15

Ile Thr Thr Ser Ile Gly Leu Phe Ala Ser Arg Arg Ala Gly Lys Ser
            20                  25                  30

Phe Ala Glu Tyr Phe Leu Ala Gly Gly Gln Met Ser Trp Trp Met Leu
            35                  40                  45

Gly Ile Ser Met Val Ala Thr Thr Phe Ala Ala Asp Thr Pro Asn Leu
        50                  55                  60

Val Thr Gly Ile Val Arg Arg Asp Gly Val Ser Gly Asn Trp Val Trp
65                  70                  75                  80

Trp Ala Phe Leu Leu Thr Gly Leu Leu Thr Val Phe Val Tyr Ala Arg
                85                  90                  95

Leu Trp Lys Arg Ser Gly Val Ser Thr Asp Leu Glu Phe Tyr Glu Leu
            100                 105                 110

Arg Tyr Ser Gly Lys Thr Ala Gly Phe Leu Arg Gly Phe Arg Ala Ile
            115                 120                 125

Tyr Leu Gly Val Ile Phe Asn Cys Leu Val Met Ala Asn Val Ile Leu
        130                 135                 140

Ala Gly Ile Lys Leu Gly Gly Val Leu Val Gly Ala Thr Pro Ile Gln
145                 150                 155                 160

Val Val Leu Val Thr Gly Thr Ile Thr Val Ile Tyr Thr Leu Leu Gly
                165                 170                 175

Gly Leu Arg Gly Val Ile Leu Thr Asp Cys Phe Gln Phe Ile Val Ala
            180                 185                 190

Met Phe Gly Ala Ile Ala Ala Ala Tyr Val Val Cys Asn Leu Pro Glu
            195                 200                 205

Val Gly Gly Phe Ser Asn Leu Leu Gln His Glu Glu Val Arg Ser Lys
        210                 215                 220

Thr Ala Leu Leu Pro Asp Phe Ser Asp Met Asp Ala Leu Ile Pro Leu
225                 230                 235                 240

Met Ile Ile Pro Phe Ala Val Gln Trp Trp Ser Gly Trp Tyr Pro Gly
                245                 250                 255

Ser Glu Pro Gly Gly Gly Tyr Val Ala Gln Arg Met Leu Gly Ala
            260                 265                 270

Arg Ser Glu Lys Asp Ala Thr Leu Ala Thr Leu Leu Phe Gln Ala Thr
            275                 280                 285

His Tyr Ala Leu Arg Pro Trp Pro Trp Ile Ile Val Ala Leu Ala Ser
        290                 295                 300

Ile Val Val Phe Pro Asn Leu Glu Ser Ile Gln Val Ala Phe Pro Asp
305                 310                 315                 320
```

```
Ile Asp Pro Gln Ile Val Gln Asp Asp Leu Ala Tyr Pro Ala Met Leu
            325                 330                 335

Thr Phe Leu Pro Ser Gly Leu Leu Gly Ile Val Ile Ala Ser Leu Ile
        340                 345                 350

Ala Ala Phe Met Ser Thr Ile Ser Thr His Leu Asn Trp Gly Ala Ser
                355                 360                 365

Tyr Ile Ala His Asp Phe Tyr Arg Arg Phe Val Asn Pro Asp Ala Thr
    370                 375                 380

Glu Gln Arg Leu Val Ala Thr Gly Arg Trp Ala Thr Val Gly Leu Met
385                 390                 395                 400

Ile Val Ala Gly Ala Val Ala Leu Thr Leu Glu Ser Ala Met Glu Ser
                405                 410                 415

Phe Gly Ile Ile Leu Gln Ile Gly Ala Gly Thr Gly Leu Ile Tyr Ile
                420                 425                 430

Leu Arg Trp Phe Trp Trp Arg Ile Asn Ala Phe Thr Glu Ile Thr Gly
            435                 440                 445

Met Ala Val Ser Leu Ala Ile Ala Met Phe Phe Lys Phe Gly Tyr Ser
        450                 455                 460

His Thr Gly Leu Pro Glu Leu Asn Ser Trp Gln Gln Leu Leu Thr Gly
465                 470                 475                 480

Val Val Ile Thr Thr Val Ser Trp Met Leu Val Thr Phe Leu Ser Pro
                485                 490                 495

Pro Thr Asp Arg Glu Thr Leu Lys Arg Phe Val Thr Lys Ile Arg Pro
                500                 505                 510

Gly Gly Ala Gly Trp Lys Ser Ile Arg Asp Glu Leu Ala Asp Ser Gly
            515                 520                 525

Ile His Val Ala Thr Gly Asp Ser Ile Thr Ala Gly Leu Lys Ala Met
        530                 535                 540

Met Ala Ser Thr Phe Leu Val Tyr Ser Ala Leu Phe Ser Thr Gly Tyr
545                 550                 555                 560

Leu Leu Tyr Gln Ser Trp Leu Cys Leu Ala Val Ser Leu Ser Val Cys
                565                 570                 575

Val Ala Ser Ala Ile Ala Leu Trp Lys Thr Trp Pro Ser Leu Gln Ile
            580                 585                 590

Asp Gly Pro Ala Arg Ala Ser Asp Gln Ser
        595                 600

<210> SEQ ID NO 71
<211> LENGTH: 399
<212> TYPE: PRT
<213> ORGANISM: Pseudomonas fluorescens

<400> SEQUENCE: 71

Met Glu Val Val His Trp Trp Thr Ser Gly Gly Glu Lys Ala Ala Val
 1               5                  10                  15

Asp Val Leu Lys Ala Gln Val Glu Lys Asp Gly Phe Thr Trp Lys Asp
            20                  25                  30

Gly Ala Val Ala Gly Gly Gly Ser Thr Ala Met Thr Val Leu Lys
        35                  40                  45

Ser Arg Ala Val Ala Gly Asn Pro Pro Gly Val Ala Gln Ile Lys Gly
    50                  55                  60

Pro Asp Ile Gln Glu Trp Ala Ser Thr Gly Leu Leu Asp Ser Asp Val
65                  70                  75                  80

Leu Lys Asp Val Ala Lys Ala Glu Lys Trp Asp Ser Leu Leu Asp Lys
                85                  90                  95
```

```
Lys Val Ser Asp Thr Val Lys Tyr Glu Gly Asp Tyr Val Ala Val Pro
            100                 105                 110

Val Asn Ile His Arg Val Asn Trp Leu Trp Ile Asn Pro Glu Val Phe
            115                 120                 125

Lys Lys Ala Gly Ile Thr Lys Asn Pro Thr Thr Leu Glu Glu Phe Tyr
130                 135                 140

Ala Ala Gly Asp Lys Leu Lys Ala Ala Gly Phe Ile Pro Leu Ala His
145                 150                 155                 160

Gly Gly Gln Pro Trp Gln Asp Ser Thr Val Phe Glu Ala Val Val Leu
                165                 170                 175

Ser Val Met Gly Ala Asp Gly Tyr Lys Lys Ala Leu Val Asp Leu Asp
            180                 185                 190

Asn Lys Ala Leu Thr Gly Pro Glu Met Val Lys Ala Leu Thr Glu Leu
            195                 200                 205

Lys Lys Val Ala Thr Tyr Met Asp Ala Asp Gly Lys Gly Gln Asp Trp
210                 215                 220

Asn Leu Glu Ala Ala Lys Val Ile Asn Gly Lys Ala Gly Met Gln Ile
225                 230                 235                 240

Met Gly Asp Trp Ala Lys Ser Glu Trp Thr Ala Ala Lys Lys Val Ala
                245                 250                 255

Gly Lys Asp Tyr Glu Cys Val Ala Phe Pro Gly Thr Asp Lys Ala Phe
            260                 265                 270

Thr Tyr Asn Ile Asp Ser Leu Ala Val Phe Lys Gln Lys Asp Ala Gly
            275                 280                 285

Thr Ala Ala Gly Gln Gln Asp Ile Ala Lys Val Val Leu Gly Glu Asn
290                 295                 300

Phe Gln Lys Val Phe Ser Ile Asn Lys Gly Ser Ile Pro Val Arg Asn
305                 310                 315                 320

Asp Met Leu Gly Asp Met Ala Lys Tyr Gly Phe Asp Ser Cys Ala Gln
                325                 330                 335

Thr Ala Ala Lys Asp Phe Leu Thr Asp Ala Lys Ser Gly Gly Leu Gln
            340                 345                 350

Pro Ser Met Ala His Asn Met Ala Thr Thr Leu Ala Val Gln Gly Ala
            355                 360                 365

Phe Phe Asp Val Val Thr Asn Tyr Ile Asn Asp Pro Lys Ala Asp Pro
370                 375                 380

Ala Asp Ala Ala Lys Lys Leu Gly Ala Ala Val Gln Ser Ala Lys
385                 390                 395

<210> SEQ ID NO 72
<211> LENGTH: 321
<212> TYPE: PRT
<213> ORGANISM: Escherichia coli DH1

<400> SEQUENCE: 72

Met Thr Lys Tyr Ala Leu Val Gly Asp Val Gly Gly Thr Asn Ala Arg
  1               5                  10                  15

Leu Ala Leu Cys Asp Ile Ala Ser Gly Glu Ile Ser Gln Ala Lys Thr
            20                  25                  30

Tyr Ser Gly Leu Asp Tyr Pro Ser Leu Glu Ala Val Ile Arg Val Tyr
        35                  40                  45

Leu Glu Glu His Lys Val Glu Val Lys Asp Gly Cys Ile Ala Ile Ala
    50                  55                  60

Cys Pro Ile Thr Gly Asp Trp Val Ala Met Thr Asn His Thr Trp Ala
```

Phe Ser Ile Ala Glu Met Lys Lys Asn Leu Gly Phe Ser His Leu Glu
65                  70                  75                  80

Ile Ile Asn Asp Phe Thr Ala Val Ser Met Ala Ile Pro Met Leu Lys
            85                  90                  95

Lys Glu His Leu Ile Gln Phe Gly Ala Glu Pro Val Glu Gly Lys
            100                 105                 110

Pro Ile Ala Val Tyr Gly Ala Gly Thr Gly Leu Gly Val Ala His Leu
        130                 135                 140

Val His Val Asp Lys Arg Trp Val Ser Leu Pro Gly Glu Gly His
145                 150                 155                 160

Val Asp Phe Ala Pro Asn Ser Glu Glu Ala Ile Ile Leu Glu Ile
                165                 170                 175

Leu Arg Ala Glu Ile Gly His Val Ser Ala Glu Arg Val Leu Ser Gly
            180                 185                 190

Pro Gly Leu Val Asn Leu Tyr Arg Ala Ile Val Lys Ala Asp Asn Arg
        195                 200                 205

Leu Pro Glu Asn Leu Lys Pro Lys Asp Ile Thr Glu Arg Ala Leu Ala
210                 215                 220

Asp Ser Cys Thr Asp Cys Arg Arg Ala Leu Ser Leu Phe Cys Val Ile
225                 230                 235                 240

Met Gly Arg Phe Gly Gly Asn Leu Ala Leu Asn Leu Gly Thr Phe Gly
            245                 250                 255

Gly Val Phe Ile Ala Gly Gly Ile Val Pro Arg Phe Leu Glu Phe Phe
        260                 265                 270

Lys Ala Ser Gly Phe Arg Ala Ala Phe Glu Asp Lys Gly Arg Phe Lys
        275                 280                 285

Glu Tyr Val His Asp Ile Pro Val Tyr Leu Ile Val His Asp Asn Pro
        290                 295                 300

Gly Leu Leu Gly Ser Gly Ala His Leu Arg Gln Thr Leu Gly His Ile
305                 310                 315                 320

Leu

<210> SEQ ID NO 73
<211> LENGTH: 500
<212> TYPE: PRT
<213> ORGANISM: Saccharomyces cerevisiae

<400> SEQUENCE: 73

Met Ser Phe Asp Asp Leu His Lys Ala Thr Glu Arg Ala Val Ile Gln
1               5                   10                  15

Ala Val Asp Gln Ile Cys Asp Asp Phe Glu Val Thr Pro Glu Lys Leu
            20                  25                  30

Asp Glu Leu Thr Ala Tyr Phe Ile Glu Gln Met Glu Lys Gly Leu Ala
        35                  40                  45

Pro Pro Lys Glu Gly His Thr Leu Ala Ser Asp Lys Gly Leu Pro Met
    50                  55                  60

Ile Pro Ala Phe Val Thr Gly Ser Pro Asn Gly Thr Glu Arg Gly Val
65                  70                  75                  80

Leu Leu Ala Ala Asp Leu Gly Gly Thr Asn Phe Arg Ile Cys Ser Val
                85                  90                  95

Asn Leu His Gly Asp His Thr Phe Ser Met Glu Gln Met Lys Ser Lys
            100                 105                 110

Ile Pro Asp Asp Leu Leu Asp Asp Glu Asn Val Thr Ser Asp Asp Leu

```
            115                 120                 125
Phe Gly Phe Leu Ala Arg Arg Thr Leu Ala Phe Met Lys Lys Tyr His
        130                 135                 140

Pro Asp Glu Leu Ala Lys Gly Lys Asp Ala Lys Pro Met Lys Leu Gly
145                 150                 155                 160

Phe Thr Phe Ser Tyr Pro Val Asp Gln Thr Ser Leu Asn Ser Gly Thr
                165                 170                 175

Leu Ile Arg Trp Thr Lys Gly Phe Arg Ile Ala Asp Thr Val Gly Lys
            180                 185                 190

Asp Val Val Gln Leu Tyr Gln Glu Gln Leu Ser Ala Gln Gly Met Pro
        195                 200                 205

Met Ile Lys Val Val Ala Leu Thr Asn Asp Thr Val Gly Thr Tyr Leu
    210                 215                 220

Ser His Cys Tyr Thr Ser Asp Asn Thr Asp Ser Met Thr Ser Gly Glu
225                 230                 235                 240

Ile Ser Glu Pro Val Ile Gly Cys Ile Phe Gly Thr Gly Thr Asn Gly
                245                 250                 255

Cys Tyr Met Glu Glu Ile Asn Lys Ile Thr Lys Leu Pro Gln Glu Leu
            260                 265                 270

Arg Asp Lys Leu Ile Lys Glu Gly Lys Thr His Met Ile Ile Asn Val
        275                 280                 285

Glu Trp Gly Ser Phe Asp Asn Glu Leu Lys His Leu Pro Thr Thr Lys
    290                 295                 300

Tyr Asp Val Val Ile Asp Gln Lys Leu Ser Thr Asn Pro Gly Phe His
305                 310                 315                 320

Leu Phe Glu Lys Arg Val Ser Gly Met Phe Leu Gly Glu Val Leu Arg
                325                 330                 335

Asn Ile Leu Val Asp Leu His Ser Gln Gly Leu Leu Leu Gln Gln Tyr
            340                 345                 350

Arg Ser Lys Glu Gln Leu Pro Arg His Leu Thr Thr Pro Phe Gln Leu
        355                 360                 365

Ser Ser Glu Val Leu Ser His Ile Glu Ile Asp Asp Ser Thr Gly Leu
    370                 375                 380

Arg Glu Thr Glu Leu Ser Leu Leu Gln Ser Leu Arg Leu Pro Thr Thr
385                 390                 395                 400

Pro Thr Glu Arg Val Gln Ile Gln Lys Leu Val Arg Ala Ile Ser Arg
                405                 410                 415

Arg Ser Ala Tyr Leu Ala Ala Val Pro Leu Ala Ala Ile Leu Ile Lys
            420                 425                 430

Thr Asn Ala Leu Asn Lys Arg Tyr His Gly Glu Val Glu Ile Gly Cys
        435                 440                 445

Asp Gly Ser Val Val Glu Tyr Tyr Pro Gly Phe Arg Ser Met Leu Arg
    450                 455                 460

His Ala Leu Ala Leu Ser Pro Leu Gly Ala Glu Gly Glu Arg Lys Val
465                 470                 475                 480

His Leu Lys Ile Ala Lys Asp Gly Ser Gly Val Gly Ala Ala Leu Cys
                485                 490                 495

Ala Leu Val Ala
            500

<210> SEQ ID NO 74
<211> LENGTH: 652
<212> TYPE: PRT
<213> ORGANISM: Escherichia coli
```

<400> SEQUENCE: 74

```
Met Ser Gln Ile His Lys His Thr Ile Pro Ala Asn Ile Ala Asp Arg
 1               5                  10                  15

Cys Leu Ile Asn Pro Gln Gln Tyr Glu Ala Met Tyr Gln Gln Ser Ile
                20                  25                  30

Asn Val Pro Asp Thr Phe Trp Gly Glu Gln Gly Lys Ile Leu Asp Trp
            35                  40                  45

Ile Lys Pro Tyr Gln Lys Val Lys Asn Thr Ser Phe Ala Pro Gly Asn
 50                  55                  60

Val Ser Ile Lys Trp Tyr Glu Asp Gly Thr Leu Asn Leu Ala Ala Asn
 65                  70                  75                  80

Cys Leu Asp Arg His Leu Gln Glu Asn Gly Asp Arg Thr Ala Ile Ile
                85                  90                  95

Trp Glu Gly Asp Asp Ala Ser Gln Ser Lys His Ile Ser Tyr Lys Glu
            100                 105                 110

Leu His Arg Asp Val Cys Arg Phe Ala Asn Thr Leu Leu Glu Leu Gly
        115                 120                 125

Ile Lys Lys Gly Asp Val Val Ala Ile Tyr Met Pro Met Val Pro Glu
130                 135                 140

Ala Ala Val Ala Met Leu Ala Cys Ala Arg Ile Gly Ala Val His Ser
145                 150                 155                 160

Val Ile Phe Gly Gly Phe Ser Pro Glu Ala Val Ala Gly Arg Ile Ile
                165                 170                 175

Asp Ser Asn Ser Arg Leu Val Ile Thr Ser Asp Glu Gly Val Arg Ala
            180                 185                 190

Gly Arg Ser Ile Pro Leu Lys Lys Asn Val Asp Asp Ala Leu Lys Asn
        195                 200                 205

Pro Asn Val Thr Ser Val Glu His Val Val Leu Lys Arg Thr Gly
210                 215                 220

Gly Lys Ile Asp Trp Gln Glu Gly Arg Asp Leu Trp Trp His Asp Leu
225                 230                 235                 240

Val Glu Gln Ala Ser Asp Gln His Gln Ala Glu Glu Met Asn Ala Glu
                245                 250                 255

Asp Pro Leu Phe Ile Leu Tyr Thr Ser Gly Ser Thr Gly Lys Pro Lys
            260                 265                 270

Gly Val Leu His Thr Thr Gly Gly Tyr Leu Val Tyr Ala Ala Leu Thr
        275                 280                 285

Phe Lys Tyr Val Phe Asp Tyr His Pro Gly Asp Ile Tyr Trp Cys Thr
290                 295                 300

Ala Asp Val Gly Trp Val Thr Gly His Ser Tyr Leu Leu Tyr Gly Pro
305                 310                 315                 320

Leu Ala Cys Gly Ala Thr Thr Leu Met Phe Glu Gly Val Pro Asn Trp
                325                 330                 335

Pro Thr Pro Ala Arg Met Ala Gln Val Val Asp Lys His Gln Val Asn
            340                 345                 350

Ile Leu Tyr Thr Ala Pro Thr Ala Ile Arg Ala Leu Met Ala Glu Gly
        355                 360                 365

Asp Lys Ala Ile Glu Gly Thr Asp Arg Ser Ser Leu Arg Ile Leu Gly
370                 375                 380

Ser Val Gly Glu Pro Ile Asn Pro Glu Ala Trp Glu Trp Tyr Trp Lys
385                 390                 395                 400

Lys Ile Gly Asn Glu Lys Cys Pro Val Val Asp Thr Trp Trp Gln Thr
```

```
            405                 410                 415
Glu Thr Gly Gly Phe Met Ile Thr Pro Leu Pro Gly Ala Thr Glu Leu
            420                 425                 430

Lys Ala Gly Ser Ala Thr Arg Pro Phe Phe Gly Val Gln Pro Ala Leu
            435                 440                 445

Val Asp Asn Glu Gly Asn Pro Leu Glu Gly Ala Thr Glu Gly Ser Leu
450                 455                 460

Val Ile Thr Asp Ser Trp Pro Gly Gln Ala Arg Thr Leu Phe Gly Asp
465                 470                 475                 480

His Glu Arg Phe Glu Gln Thr Tyr Phe Ser Thr Phe Lys Asn Met Tyr
                485                 490                 495

Phe Ser Gly Asp Gly Ala Arg Arg Asp Glu Asp Gly Tyr Tyr Trp Ile
            500                 505                 510

Thr Gly Arg Val Asp Asp Val Leu Asn Val Ser Gly His Arg Leu Gly
            515                 520                 525

Thr Ala Glu Ile Glu Ser Ala Leu Val Ala His Pro Lys Ile Ala Glu
            530                 535                 540

Ala Ala Val Val Gly Ile Pro His Asn Ile Lys Gly Gln Ala Ile Tyr
545                 550                 555                 560

Ala Tyr Val Thr Leu Asn His Gly Glu Glu Pro Ser Pro Glu Leu Tyr
                565                 570                 575

Ala Glu Val Arg Asn Trp Val Arg Lys Glu Ile Gly Pro Leu Ala Thr
            580                 585                 590

Pro Asp Val Leu His Trp Thr Asp Ser Leu Pro Lys Thr Arg Ser Gly
            595                 600                 605

Lys Ile Met Arg Arg Ile Leu Arg Lys Ile Ala Ala Gly Asp Thr Ser
            610                 615                 620

Asn Leu Gly Asp Thr Ser Thr Leu Ala Asp Pro Gly Val Val Glu Lys
625                 630                 635                 640

Leu Leu Glu Glu Lys Gln Ala Ile Ala Met Pro Ser
                645                 650

<210> SEQ ID NO 75
<211> LENGTH: 549
<212> TYPE: PRT
<213> ORGANISM: Escherichia coli

<400> SEQUENCE: 75

Met Lys Arg Val Leu Thr Ala Leu Ala Ala Thr Leu Pro Phe Ala Ala
1               5                   10                  15

Asn Ala Ala Asp Ala Ile Ser Gly Ala Val Glu Arg Gln Pro Thr Asn
            20                  25                  30

Trp Gln Ala Ile Ile Met Phe Leu Ile Phe Val Val Phe Thr Leu Gly
            35                  40                  45

Ile Thr Tyr Trp Ala Ser Lys Arg Val Arg Ser Arg Ser Asp Tyr Tyr
        50                  55                  60

Thr Ala Gly Gly Asn Ile Thr Gly Phe Gln Asn Gly Leu Ala Ile Ala
65                  70                  75                  80

Gly Asp Tyr Met Ser Ala Ala Ser Phe Leu Gly Ile Ser Ala Leu Val
                85                  90                  95

Phe Thr Ser Gly Tyr Asp Gly Leu Ile Tyr Ser Leu Gly Phe Leu Val
            100                 105                 110

Gly Trp Pro Ile Ile Leu Phe Leu Ile Ala Glu Arg Leu Arg Asn Leu
            115                 120                 125
```

```
Gly Arg Tyr Thr Phe Ala Asp Val Ala Ser Tyr Arg Leu Lys Gln Gly
    130                 135                 140

Pro Ile Arg Ile Leu Ser Ala Cys Gly Ser Leu Val Val Ala Leu
145                 150                 155                 160

Tyr Leu Ile Ala Gln Met Val Gly Ala Gly Lys Leu Ile Glu Leu Leu
                165                 170                 175

Phe Gly Leu Asn Tyr His Ile Ala Val Val Leu Val Gly Val Leu Met
                180                 185                 190

Met Met Tyr Val Leu Phe Gly Gly Met Leu Ala Thr Thr Trp Val Gln
        195                 200                 205

Ile Ile Lys Ala Val Leu Leu Leu Phe Gly Ala Ser Phe Met Ala Phe
    210                 215                 220

Met Val Met Lys His Val Gly Phe Ser Phe Asn Asn Leu Phe Ser Glu
225                 230                 235                 240

Ala Met Ala Val His Pro Lys Gly Val Asp Ile Met Lys Pro Gly Gly
                245                 250                 255

Leu Val Lys Asp Pro Ile Ser Ala Leu Ser Leu Gly Leu Gly Leu Met
            260                 265                 270

Phe Gly Thr Ala Gly Leu Pro His Ile Leu Met Arg Phe Phe Thr Val
        275                 280                 285

Ser Asp Ala Arg Glu Ala Arg Lys Ser Val Phe Tyr Ala Thr Gly Phe
290                 295                 300

Met Gly Tyr Phe Tyr Ile Leu Thr Phe Ile Ile Gly Phe Gly Ala Ile
305                 310                 315                 320

Met Leu Val Gly Ala Asn Pro Glu Tyr Lys Asp Ala Ala Gly His Leu
                325                 330                 335

Ile Gly Gly Asn Asn Met Ala Ala Val His Leu Ala Asn Ala Val Gly
            340                 345                 350

Gly Asn Leu Phe Leu Gly Phe Ile Ser Ala Val Ala Phe Ala Thr Ile
        355                 360                 365

Leu Ala Val Val Ala Gly Leu Thr Leu Ala Gly Ala Ser Ala Val Ser
370                 375                 380

His Asp Leu Tyr Ala Asn Val Phe Lys Lys Gly Ala Thr Glu Arg Glu
385                 390                 395                 400

Glu Leu Arg Val Ser Lys Ile Thr Val Leu Ile Leu Gly Val Ile Ala
                405                 410                 415

Ile Ile Leu Gly Val Leu Phe Glu Asn Gln Asn Ile Ala Phe Met Val
            420                 425                 430

Gly Leu Ala Phe Ala Ile Ala Ala Ser Cys Asn Phe Pro Ile Ile Leu
        435                 440                 445

Leu Ser Met Tyr Trp Ser Lys Leu Thr Thr Arg Gly Ala Met Met Gly
    450                 455                 460

Gly Trp Leu Gly Leu Ile Thr Ala Val Val Leu Met Ile Leu Gly Pro
465                 470                 475                 480

Thr Ile Trp Val Gln Ile Leu Gly His Glu Lys Ala Ile Phe Pro Tyr
                485                 490                 495

Glu Tyr Pro Ala Leu Phe Ser Ile Thr Val Ala Phe Leu Gly Ile Trp
            500                 505                 510

Phe Phe Ser Ala Thr Asp Asn Ser Ala Glu Gly Ala Arg Glu Arg Glu
        515                 520                 525

Leu Phe Arg Ala Gln Phe Ile Arg Ser Gln Thr Gly Phe Gly Val Glu
530                 535                 540

Gln Gly Arg Ala His
```

<210> SEQ ID NO 76
<211> LENGTH: 329
<212> TYPE: PRT
<213> ORGANISM: Escherichia coli

<400> SEQUENCE: 76

Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
            20                  25                  30

Leu Leu Thr Glu Lys Thr Ala Lys Thr Ala Asn Gly Cys Glu Ala Val
        35                  40                  45

Cys Ile Phe Val Asn Asp Asp Gly Ser Arg Pro Val Leu Glu Glu Leu
    50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
            100                 105                 110

Met Met Thr Leu Asn Arg Arg Ile His Arg Ala Tyr Gln Arg Thr Arg
        115                 120                 125

Asp Ala Asn Phe Ser Leu Glu Gly Leu Thr Gly Phe Thr Met Tyr Gly
    130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Glu Gln Met Lys
    210                 215                 220

Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Asp Val Phe Arg Arg Leu Ser Ala Cys His
        275                 280                 285

Asn Val Leu Phe Thr Gly His Gln Ala Phe Leu Thr Ala Glu Ala Leu
    290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325

<210> SEQ ID NO 77
<211> LENGTH: 532
<212> TYPE: PRT
<213> ORGANISM: Staphylococcus aureus

```
<400> SEQUENCE: 77

Met Leu Val Asn Thr Phe Asn Pro Phe Asp Asn Leu Leu Ser Ser
 1               5                  10                  15

Leu Ile Ala Ala Ile Pro Ile Val Leu Phe Leu Leu Cys Leu Thr Val
                20                  25                  30

Phe Lys Met Lys Gly Ile Tyr Ala Ala Ile Thr Thr Leu Val Val Thr
             35                  40                  45

Leu Leu Ile Ala Ile Pro Phe Phe Lys Leu Pro Val Gly Ile Ala Ser
         50                  55                  60

Gly Ala Val Val Glu Gly Phe Phe Gln Gly Ile Ile Pro Ile Gly Tyr
 65                  70                  75                  80

Ile Val Met Met Ala Val Leu Leu Tyr Lys Ile Thr Val Glu Ser Gly
                 85                  90                  95

Gln Phe Leu Thr Ile Gln Asp Ser Ile Thr Asn Ile Ser Gln Asp Gln
            100                 105                 110

Arg Ile Gln Val Leu Leu Ile Gly Phe Ala Phe Asn Ala Phe Leu Glu
        115                 120                 125

Gly Ala Ala Gly Phe Gly Val Pro Ile Ala Ile Cys Ala Leu Leu Leu
130                 135                 140

Thr Gln Leu Gly Phe Asn Pro Leu Lys Ala Ala Met Leu Cys Leu Val
145                 150                 155                 160

Ala Asn Ala Ala Ser Gly Ala Phe Gly Ala Ile Gly Ile Pro Val Gly
                165                 170                 175

Val Val Glu Thr Leu Lys Leu Pro Gly Asp Val Ser Val Leu Gly Val
            180                 185                 190

Ser Gln Ser Ala Thr Leu Thr Leu Ala Ile Ile Asn Phe Ile Ile Pro
        195                 200                 205

Phe Leu Leu Ile Phe Ile Ile Asp Gly Phe Arg Gly Val Lys Glu Thr
    210                 215                 220

Leu Pro Ala Ile Leu Val Val Ser Ile Thr Tyr Thr Leu Thr Gln Gly
225                 230                 235                 240

Leu Leu Thr Val Phe Ser Gly Pro Glu Leu Ala Asp Ile Ile Pro Pro
                245                 250                 255

Leu Leu Thr Met Leu Ala Leu Ala Val Phe Ser Lys Lys Phe Gln Pro
            260                 265                 270

Lys His Ile Tyr Arg Val Asn Lys Asp Glu Glu Ile Glu Pro Ala Lys
        275                 280                 285

Ala His Ser Ala Lys Ala Val Leu His Ala Trp Ser Pro Phe Ile Val
    290                 295                 300

Leu Thr Val Ile Val Met Ile Trp Ser Ala Pro Phe Phe Lys Asn Leu
305                 310                 315                 320

Phe Leu Pro Asn Gly Ala Leu Ser Ser Leu Val Phe Lys Phe Asn Leu
                325                 330                 335

Pro Gly Thr Val Ser Glu Val Thr His Lys Pro Leu Val Leu Thr Leu
            340                 345                 350

Asn Ile Ile Gly Gln Thr Gly Thr Ala Ile Leu Leu Thr Ile Ile Ile
        355                 360                 365

Thr Ile Leu Met Ser Lys Lys Val Asn Phe Lys Asp Ala Gly Arg Leu
    370                 375                 380

Phe Gly Val Thr Phe Lys Glu Leu Trp Leu Pro Val Leu Thr Ile Cys
385                 390                 395                 400

Phe Ile Leu Ala Ile Ser Lys Ile Thr Thr Tyr Gly Gly Leu Ser Ala
                405                 410                 415
```

```
Ala Met Gly Gln Gly Ile Ala Lys Ala Gly Asn Val Phe Pro Val Leu
        420                 425                 430

Ser Pro Ile Leu Gly Trp Ile Gly Val Phe Met Thr Gly Ser Val Val
        435                 440                 445

Asn Asn Asn Ser Leu Phe Ala Pro Ile Gln Ala Ser Val Ala Gln Gln
450                 455                 460

Ile Gly Thr Ser Gly Ser Leu Leu Val Ser Ala Asn Thr Val Gly Gly
465                 470                 475                 480

Val Ala Ala Lys Leu Ile Ser Pro Gln Ser Ile Ala Ile Ala Thr Ala
            485                 490                 495

Ala Val Lys Gln Val Gly Lys Glu Ser Glu Leu Leu Lys Met Thr Leu
        500                 505                 510

Lys Tyr Ser Val Cys Leu Leu Ile Phe Ile Cys Ile Trp Thr Phe Ile
        515                 520                 525

Leu Ser Leu Leu
    530

<210> SEQ ID NO 78
<211> LENGTH: 551
<212> TYPE: PRT
<213> ORGANISM: Escherichia coli

<400> SEQUENCE: 78

Met Asn Leu Trp Gln Gln Asn Tyr Asp Pro Ala Gly Asn Ile Trp Leu
1               5                   10                  15

Ser Ser Leu Ile Ala Ser Leu Pro Ile Leu Phe Phe Phe Phe Ala Leu
            20                  25                  30

Ile Lys Leu Lys Leu Lys Gly Tyr Val Ala Ala Ser Trp Thr Val Ala
        35                  40                  45

Ile Ala Leu Ala Val Ala Leu Leu Phe Tyr Lys Met Pro Val Ala Asn
    50                  55                  60

Ala Leu Ala Ser Val Val Tyr Gly Phe Phe Tyr Gly Leu Trp Pro Ile
65                  70                  75                  80

Ala Trp Ile Ile Ile Ala Ala Val Phe Val Tyr Lys Ile Ser Val Lys
                85                  90                  95

Thr Gly Gln Phe Asp Ile Ile Arg Ser Ser Ile Leu Ser Ile Thr Pro
            100                 105                 110

Asp Gln Arg Leu Gln Met Leu Ile Val Gly Phe Cys Phe Gly Ala Phe
        115                 120                 125

Leu Glu Gly Ala Ala Gly Phe Gly Ala Pro Val Ala Ile Thr Ala Ala
    130                 135                 140

Leu Leu Val Gly Leu Gly Phe Lys Pro Leu Tyr Ala Ala Gly Leu Cys
145                 150                 155                 160

Leu Ile Val Asn Thr Ala Pro Val Ala Phe Gly Ala Met Gly Ile Pro
                165                 170                 175

Ile Leu Val Ala Gly Gln Val Thr Gly Ile Asp Ser Phe Glu Ile Gly
            180                 185                 190

Gln Met Val Gly Arg Gln Leu Pro Phe Met Thr Ile Ile Val Leu Phe
        195                 200                 205

Trp Ile Met Ala Ile Met Asp Gly Trp Arg Gly Ile Lys Glu Thr Trp
    210                 215                 220

Pro Ala Val Val Val Ala Gly Gly Ser Phe Ala Ile Ala Gln Tyr Leu
225                 230                 235                 240

Ser Ser Asn Phe Ile Gly Pro Glu Leu Pro Asp Ile Ile Ser Ser Leu
```

```
                245                 250                 255
Val Ser Leu Leu Cys Leu Thr Leu Phe Leu Lys Arg Trp Gln Pro Val
            260                 265                 270

Arg Val Phe Arg Phe Gly Asp Leu Gly Ala Ser Gln Val Asp Met Thr
        275                 280                 285

Leu Ala His Thr Gly Tyr Thr Ala Gly Gln Val Leu Arg Ala Trp Thr
    290                 295                 300

Pro Phe Leu Phe Leu Thr Ala Thr Val Thr Leu Trp Ser Ile Pro Pro
305                 310                 315                 320

Phe Lys Ala Leu Phe Ala Ser Gly Ala Leu Tyr Glu Trp Val Ile
            325                 330                 335

Asn Ile Pro Val Pro Tyr Leu Asp Lys Leu Val Ala Arg Met Pro Pro
            340                 345                 350

Val Val Ser Glu Ala Thr Ala Tyr Ala Ala Val Phe Lys Phe Asp Trp
            355                 360                 365

Phe Ser Ala Thr Gly Thr Ala Ile Leu Phe Ala Ala Leu Leu Ser Ile
    370                 375                 380

Val Trp Leu Lys Met Lys Pro Ser Asp Ala Ile Ser Thr Phe Gly Ser
385                 390                 395                 400

Thr Leu Lys Glu Leu Ala Leu Pro Ile Tyr Ser Ile Gly Met Val Leu
                405                 410                 415

Ala Phe Ala Phe Ile Ser Asn Tyr Ser Gly Leu Ser Ser Thr Leu Ala
            420                 425                 430

Leu Ala Leu Ala His Thr Gly His Ala Phe Thr Phe Phe Ser Pro Phe
        435                 440                 445

Leu Gly Trp Leu Gly Val Phe Leu Thr Gly Ser Asp Thr Ser Ser Asn
    450                 455                 460

Ala Leu Phe Ala Ala Leu Gln Ala Thr Ala Gln Gln Ile Gly Val
465                 470                 475                 480

Ser Asp Leu Leu Leu Val Ala Ala Asn Thr Thr Gly Gly Val Thr Gly
                485                 490                 495

Lys Met Ile Ser Pro Gln Ser Ile Ala Ile Ala Cys Ala Ala Val Gly
            500                 505                 510

Leu Val Gly Lys Glu Ser Asp Leu Phe Arg Phe Thr Val Lys His Ser
        515                 520                 525

Leu Ile Phe Thr Cys Ile Val Gly Val Ile Thr Thr Leu Gln Ala Tyr
    530                 535                 540

Val Leu Thr Trp Met Ile Pro
545                 550

<210> SEQ ID NO 79
<211> LENGTH: 566
<212> TYPE: PRT
<213> ORGANISM: Escherichia coli

<400> SEQUENCE: 79

Met Ala Ile Ala Ile Gly Leu Asp Phe Gly Ser Asp Ser Val Arg Ala
 1               5                  10                  15

Leu Ala Val Asp Cys Ala Ser Gly Glu Glu Ile Ala Thr Ser Val Glu
            20                  25                  30

Trp Tyr Pro Arg Trp Gln Lys Gly Gln Phe Cys Asp Ala Pro Asn Asn
        35                  40                  45

Gln Phe Arg His His Pro Arg Asp Tyr Ile Glu Ser Met Glu Ala Ala
    50                  55                  60
```

```
Leu Lys Thr Val Leu Ala Glu Leu Ser Val Glu Gln Arg Ala Ala Val
 65                  70                  75                  80

Val Gly Ile Gly Val Asp Ser Thr Gly Ser Thr Pro Ala Pro Ile Asp
                 85                  90                  95

Ala Asp Gly Asn Val Leu Ala Leu Arg Pro Glu Phe Ala Glu Asn Pro
            100                 105                 110

Asn Ala Met Phe Val Leu Trp Lys Asp His Thr Ala Val Glu Arg Ser
        115                 120                 125

Glu Glu Ile Thr Arg Leu Cys His Ala Pro Gly Asn Val Asp Tyr Ser
130                 135                 140

Arg Tyr Ile Gly Gly Ile Tyr Ser Ser Glu Trp Phe Trp Ala Lys Ile
145                 150                 155                 160

Leu His Val Thr Arg Gln Asp Ser Ala Val Ala Gln Ser Ala Ala Ser
                165                 170                 175

Trp Ile Glu Leu Cys Asp Trp Val Pro Ala Leu Leu Ser Gly Thr Thr
            180                 185                 190

Arg Pro Gln Asp Ile Arg Arg Gly Arg Cys Ser Ala Gly His Lys Ser
        195                 200                 205

Leu Trp His Glu Ser Trp Gly Gly Leu Pro Pro Ala Ser Phe Phe Asp
210                 215                 220

Glu Leu Asp Pro Ile Leu Asn Arg His Leu Pro Ser Pro Leu Phe Thr
225                 230                 235                 240

Asp Thr Trp Thr Ala Asp Ile Pro Val Gly Thr Leu Cys Pro Glu Trp
                245                 250                 255

Ala Gln Arg Leu Gly Leu Pro Glu Ser Val Val Ile Ser Gly Gly Ala
            260                 265                 270

Phe Asp Cys His Met Gly Ala Val Gly Ala Gly Ala Gln Pro Asn Ala
        275                 280                 285

Leu Val Lys Val Ile Gly Thr Ser Thr Cys Asp Ile Leu Ile Ala Asp
290                 295                 300

Lys Gln Ser Val Gly Glu Arg Ala Val Lys Gly Ile Cys Gly Gln Val
305                 310                 315                 320

Asp Gly Ser Val Val Pro Gly Phe Ile Gly Leu Glu Ala Gly Gln Ser
                325                 330                 335

Ala Phe Gly Asp Ile Tyr Ala Trp Phe Gly Arg Val Leu Ser Trp Pro
            340                 345                 350

Leu Glu Gln Leu Ala Ala Gln His Pro Glu Leu Lys Ala Gln Ile Asn
        355                 360                 365

Ala Ser Gln Lys Gln Leu Leu Pro Ala Leu Thr Glu Ala Trp Ala Lys
370                 375                 380

Asn Pro Ser Leu Asp His Leu Pro Val Val Leu Asp Trp Phe Asn Gly
385                 390                 395                 400

Arg Arg Ser Pro Asn Ala Asn Gln Arg Leu Lys Gly Val Ile Thr Asp
                405                 410                 415

Leu Asn Leu Ala Thr Asp Ala Pro Leu Leu Phe Gly Gly Leu Ile Ala
            420                 425                 430

Ala Thr Ala Phe Gly Ala Arg Ala Ile Met Glu Cys Phe Thr Asp Gln
        435                 440                 445

Gly Ile Ala Val Asn Asn Val Met Ala Leu Gly Gly Ile Ala Arg Lys
450                 455                 460

Asn Gln Val Ile Met Gln Ala Cys Cys Asp Val Leu Asn Arg Pro Leu
465                 470                 475                 480

Gln Ile Val Ala Ser Asp Gln Cys Cys Ala Leu Gly Ala Ala Ile Phe
```

```
                        485                 490                 495
Ala Ala Val Ala Ala Lys Val His Ala Asp Ile Pro Ser Ala Gln Gln
                500                 505                 510
Lys Met Ala Ser Ala Val Glu Lys Thr Leu Gln Pro Arg Ser Glu Gln
            515                 520                 525
Ala Gln Arg Phe Glu Gln Leu Tyr Arg Arg Tyr Gln Gln Trp Ala Met
        530                 535                 540
Ser Ala Glu Gln His Tyr Leu Pro Thr Ser Ala Pro Ala Gln Ala Ala
545                 550                 555                 560
Gln Ala Val Ala Thr Leu
                565

<210> SEQ ID NO 80
<211> LENGTH: 500
<212> TYPE: PRT
<213> ORGANISM: Escherichia coli

<400> SEQUENCE: 80

Met Thr Ile Phe Asp Asn Tyr Glu Val Trp Phe Val Ile Gly Ser Gln
 1               5                  10                  15

His Leu Tyr Gly Pro Glu Thr Leu Arg Gln Val Thr Gln His Ala Glu
            20                  25                  30

His Val Val Asn Ala Leu Asn Thr Glu Ala Lys Leu Pro Cys Lys Leu
        35                  40                  45

Val Leu Lys Pro Leu Gly Thr Thr Pro Asp Glu Ile Thr Ala Ile Cys
    50                  55                  60

Arg Asp Ala Asn Tyr Asp Arg Cys Ala Gly Leu Val Val Trp Leu
65                  70                  75                  80

His Thr Phe Ser Pro Ala Lys Met Trp Ile Asn Gly Leu Thr Met Leu
                85                  90                  95

Asn Lys Pro Leu Leu Gln Phe His Thr Gln Phe Asn Ala Ala Leu Pro
            100                 105                 110

Trp Asp Ser Ile Asp Met Asp Phe Met Asn Leu Asn Gln Thr Ala His
        115                 120                 125

Gly Gly Arg Glu Phe Gly Phe Ile Gly Ala Arg Met Arg Gln Gln His
    130                 135                 140

Ala Val Val Thr Gly His Trp Gln Asp Lys Gln Ala His Glu Arg Ile
145                 150                 155                 160

Gly Ser Trp Met Arg Gln Ala Val Ser Lys Gln Asp Thr Arg His Leu
                165                 170                 175

Lys Val Cys Arg Phe Gly Asp Asn Met Arg Glu Val Ala Val Thr Asp
            180                 185                 190

Gly Asp Lys Val Ala Ala Gln Ile Lys Phe Gly Phe Ser Val Asn Thr
        195                 200                 205

Trp Ala Val Gly Asp Leu Val Gln Val Val Asn Ser Ile Ser Asp Gly
    210                 215                 220

Asp Val Asn Ala Leu Val Asp Glu Tyr Glu Ser Cys Tyr Thr Met Thr
225                 230                 235                 240

Pro Ala Thr Gln Ile His Gly Lys Lys Arg Gln Asn Val Leu Glu Ala
                245                 250                 255

Ala Arg Ile Glu Leu Gly Met Lys Arg Phe Leu Glu Gln Gly Gly Phe
            260                 265                 270

His Ala Phe Thr Thr Thr Phe Glu Asp Leu His Gly Leu Lys Gln Leu
        275                 280                 285
```

-continued

```
Pro Gly Leu Ala Val Gln Arg Leu Met Gln Gln Tyr Gly Phe Ala
    290                 295                 300
Gly Glu Gly Asp Trp Lys Thr Ala Ala Leu Leu Arg Ile Met Lys Val
305                 310                 315                 320
Met Ser Thr Gly Leu Gln Gly Gly Thr Ser Phe Met Glu Asp Tyr Thr
                325                 330                 335
Tyr His Phe Glu Lys Gly Asn Asp Leu Val Leu Gly Ser His Met Leu
                340                 345                 350
Glu Val Cys Pro Ser Ile Ala Ala Glu Glu Lys Pro Ile Leu Asp Val
            355                 360                 365
Gln His Leu Gly Ile Gly Gly Lys Asp Asp Pro Ala Arg Leu Ile Phe
    370                 375                 380
Asn Thr Gln Thr Gly Pro Ala Ile Val Ala Ser Leu Ile Asp Leu Gly
385                 390                 395                 400
Asp Arg Tyr Arg Leu Leu Val Asn Cys Ile Asp Thr Val Lys Thr Pro
                405                 410                 415
His Ser Leu Pro Lys Leu Pro Val Ala Asn Ala Leu Trp Lys Ala Gln
                420                 425                 430
Pro Asp Leu Pro Thr Ala Ser Glu Ala Trp Ile Leu Ala Gly Gly Ala
            435                 440                 445
His His Thr Val Phe Ser His Ala Leu Asn Leu Asn Asp Met Arg Gln
    450                 455                 460
Phe Ala Glu Met His Asp Ile Glu Ile Thr Val Ile Asp Asn Asp Thr
465                 470                 475                 480
Arg Leu Pro Ala Phe Lys Asp Ala Leu Arg Trp Asn Glu Val Tyr Tyr
                485                 490                 495
Gly Phe Arg Arg
            500

<210> SEQ ID NO 81
<211> LENGTH: 231
<212> TYPE: PRT
<213> ORGANISM: Escherichia coli

<400> SEQUENCE: 81

Met Leu Glu Asp Leu Lys Arg Gln Val Leu Glu Ala Asn Leu Ala Leu
1               5                   10                  15
Pro Lys His Asn Leu Val Thr Leu Thr Trp Gly Asn Val Ser Ala Val
                20                  25                  30
Asp Arg Glu Arg Gly Val Phe Val Ile Lys Pro Ser Gly Val Asp Tyr
            35                  40                  45
Ser Val Met Thr Ala Asp Asp Met Val Val Ser Ile Glu Thr Gly
    50                  55                  60
Glu Val Val Glu Gly Thr Lys Lys Pro Ser Ser Asp Thr Pro Thr His
65                  70                  75                  80
Arg Leu Leu Tyr Gln Ala Phe Pro Ser Ile Gly Gly Ile Val His Thr
                85                  90                  95
His Ser Arg His Ala Thr Ile Trp Ala Gln Ala Gly Gln Ser Ile Pro
                100                 105                 110
Ala Thr Gly Thr Thr His Ala Asp Tyr Phe Tyr Gly Thr Ile Pro Cys
            115                 120                 125
Thr Arg Lys Met Thr Asp Ala Glu Ile Asn Gly Glu Tyr Glu Trp Glu
    130                 135                 140
Thr Gly Asn Val Ile Val Glu Thr Phe Glu Lys Gln Gly Ile Asp Ala
145                 150                 155                 160
```

```
Ala Gln Met Pro Gly Val Leu Val His Ser His Gly Pro Phe Ala Trp
            165                 170                 175

Gly Lys Asn Ala Glu Asp Ala Val His Asn Ala Ile Val Leu Glu Glu
            180                 185                 190

Val Ala Tyr Met Gly Ile Phe Cys Arg Gln Leu Ala Pro Gln Leu Pro
            195                 200                 205

Asp Met Gln Gln Thr Leu Leu Asp Lys His Tyr Leu Arg Lys His Gly
            210                 215                 220

Ala Lys Ala Tyr Tyr Gly Gln
225                 230

<210> SEQ ID NO 82
<211> LENGTH: 472
<212> TYPE: PRT
<213> ORGANISM: Escherichia coli

<400> SEQUENCE: 82

Met Val Thr Ile Asn Thr Glu Ser Ala Leu Thr Pro Arg Ser Leu Arg
  1               5                  10                  15

Asp Thr Arg Arg Met Asn Met Phe Val Ser Val Ala Ala Ala Val Ala
             20                  25                  30

Gly Leu Leu Phe Gly Leu Asp Ile Gly Val Ile Ala Gly Ala Leu Pro
         35                  40                  45

Phe Ile Thr Asp His Phe Val Leu Thr Ser Arg Leu Gln Glu Trp Val
 50                  55                  60

Val Ser Ser Met Met Leu Gly Ala Ala Ile Gly Ala Leu Phe Asn Gly
 65                  70                  75                  80

Trp Leu Ser Phe Arg Leu Gly Arg Lys Tyr Ser Leu Met Ala Gly Ala
             85                  90                  95

Ile Leu Phe Val Leu Gly Ser Ile Gly Ser Ala Phe Ala Thr Ser Val
            100                 105                 110

Glu Met Leu Ile Ala Ala Arg Val Val Leu Gly Ile Ala Val Gly Ile
            115                 120                 125

Ala Ser Tyr Thr Ala Pro Leu Tyr Leu Ser Glu Met Ala Ser Glu Asn
        130                 135                 140

Val Arg Gly Lys Met Ile Ser Met Tyr Gln Leu Met Val Thr Leu Gly
145                 150                 155                 160

Ile Val Leu Ala Phe Leu Ser Asp Thr Ala Phe Ser Tyr Ser Gly Asn
                165                 170                 175

Trp Arg Ala Met Leu Gly Val Leu Ala Leu Pro Ala Val Leu Leu Ile
            180                 185                 190

Ile Leu Val Val Phe Leu Pro Asn Ser Pro Arg Trp Leu Ala Glu Lys
            195                 200                 205

Gly Arg His Ile Glu Ala Glu Glu Val Leu Arg Met Leu Arg Asp Thr
        210                 215                 220

Ser Glu Lys Ala Arg Glu Glu Leu Asn Glu Ile Arg Glu Ser Leu Lys
225                 230                 235                 240

Leu Lys Gln Gly Gly Trp Ala Leu Phe Lys Ile Asn Arg Asn Val Arg
                245                 250                 255

Arg Ala Val Phe Leu Gly Met Leu Leu Gln Ala Met Gln Gln Phe Thr
            260                 265                 270

Gly Met Asn Ile Ile Met Tyr Tyr Ala Pro Arg Ile Phe Lys Met Ala
            275                 280                 285

Gly Phe Thr Thr Thr Glu Gln Gln Met Ile Ala Thr Leu Val Val Gly
```

```
            290                 295                 300
Leu Thr Phe Met Phe Ala Thr Phe Ile Ala Val Phe Thr Val Asp Lys
305                 310                 315                 320

Ala Gly Arg Lys Pro Ala Leu Lys Ile Gly Phe Ser Val Met Ala Leu
                325                 330                 335

Gly Thr Leu Val Leu Gly Tyr Cys Leu Met Gln Phe Asp Asn Gly Thr
                340                 345                 350

Ala Ser Ser Gly Leu Ser Trp Leu Ser Val Gly Met Thr Met Met Cys
            355                 360                 365

Ile Ala Gly Tyr Ala Met Ser Ala Ala Pro Val Val Trp Ile Leu Cys
        370                 375                 380

Ser Glu Ile Gln Pro Leu Lys Cys Arg Asp Phe Gly Ile Thr Cys Ser
385                 390                 395                 400

Thr Thr Thr Asn Trp Val Ser Asn Met Ile Ile Gly Ala Thr Phe Leu
                405                 410                 415

Thr Leu Leu Asp Ser Ile Gly Ala Ala Gly Thr Phe Trp Leu Tyr Thr
                420                 425                 430

Ala Leu Asn Ile Ala Phe Val Gly Ile Thr Phe Trp Leu Ile Pro Glu
            435                 440                 445

Thr Lys Asn Val Thr Leu Glu His Ile Glu Arg Lys Leu Met Ala Gly
        450                 455                 460

Glu Lys Leu Arg Asn Ile Gly Val
465                 470
```

<210> SEQ ID NO 83
<211> LENGTH: 329
<212> TYPE: PRT
<213> ORGANISM: Escherichia coli

<400> SEQUENCE: 83

```
Met His Lys Phe Thr Lys Ala Leu Ala Ala Ile Gly Leu Ala Ala Val
1               5                   10                  15

Met Ser Gln Ser Ala Met Ala Glu Asn Leu Lys Leu Gly Phe Leu Val
                20                  25                  30

Lys Gln Pro Glu Glu Pro Trp Phe Gln Thr Glu Trp Lys Phe Ala Asp
                35                  40                  45

Lys Ala Gly Lys Asp Leu Gly Phe Glu Val Ile Lys Ile Ala Val Pro
            50                  55                  60

Asp Gly Glu Lys Thr Leu Asn Ala Ile Asp Ser Leu Ala Ala Ser Gly
65                  70                  75                  80

Ala Lys Gly Phe Val Ile Cys Thr Pro Asp Pro Lys Leu Gly Ser Ala
                85                  90                  95

Ile Val Ala Lys Ala Arg Gly Tyr Asp Met Lys Val Ile Ala Val Asp
                100                 105                 110

Asp Gln Phe Val Asn Ala Lys Gly Lys Pro Met Asp Thr Val Pro Leu
            115                 120                 125

Val Met Met Ala Ala Thr Lys Ile Gly Glu Arg Gln Gly Gln Glu Leu
130                 135                 140

Tyr Lys Glu Met Gln Lys Arg Gly Trp Asp Val Lys Glu Ser Ala Val
145                 150                 155                 160

Met Ala Ile Thr Ala Asn Glu Leu Asp Thr Ala Arg Arg Arg Thr Thr
                165                 170                 175

Gly Ser Met Asp Ala Leu Lys Ala Ala Gly Phe Pro Glu Lys Gln Ile
                180                 185                 190
```

```
Tyr Gln Val Pro Thr Lys Ser Asn Asp Ile Pro Gly Ala Phe Asp Ala
            195                 200                 205
Ala Asn Ser Met Leu Val Gln His Pro Glu Val Lys His Trp Leu Ile
        210                 215                 220
Val Gly Met Asn Asp Ser Thr Val Leu Gly Val Arg Ala Thr Glu
225                 230                 235                 240
Gly Gln Gly Phe Lys Ala Ala Asp Ile Ile Gly Ile Gly Ile Asn Gly
                245                 250                 255
Val Asp Ala Val Ser Glu Leu Ser Lys Ala Gln Ala Thr Gly Phe Tyr
            260                 265                 270
Gly Ser Leu Leu Pro Ser Pro Asp Val His Gly Tyr Lys Ser Ser Glu
        275                 280                 285
Met Leu Tyr Asn Trp Val Ala Lys Asp Val Glu Pro Pro Lys Phe Thr
    290                 295                 300
Glu Val Thr Asp Val Val Leu Ile Thr Arg Asp Asn Phe Lys Glu Glu
305                 310                 315                 320
Leu Glu Lys Lys Gly Leu Gly Gly Lys
                325

<210> SEQ ID NO 84
<211> LENGTH: 504
<212> TYPE: PRT
<213> ORGANISM: Escherichia coli

<400> SEQUENCE: 84

Met Gln Gln Ser Thr Pro Tyr Leu Ser Phe Arg Gly Ile Gly Lys Thr
1               5                   10                  15
Phe Pro Gly Val Lys Ala Leu Thr Asp Ile Ser Phe Asp Cys Tyr Ala
                20                  25                  30
Gly Gln Val His Ala Leu Met Gly Glu Asn Gly Ala Gly Lys Ser Thr
            35                  40                  45
Leu Leu Lys Ile Leu Ser Gly Asn Tyr Ala Pro Thr Thr Gly Ser Val
        50                  55                  60
Val Ile Asn Gly Gln Glu Met Ser Phe Ser Asp Thr Thr Ala Ala Leu
65                  70                  75                  80
Asn Ala Gly Val Ala Ile Ile Tyr Gln Glu Leu His Leu Val Pro Glu
                85                  90                  95
Met Thr Val Ala Glu Asn Ile Tyr Leu Gly Gln Leu Pro His Lys Gly
            100                 105                 110
Gly Ile Val Asn Arg Ser Leu Leu Asn Tyr Glu Ala Gly Leu Gln Leu
        115                 120                 125
Lys His Leu Gly Met Asp Ile Asp Pro Asp Thr Pro Leu Lys Tyr Leu
    130                 135                 140
Ser Ile Gly Gln Trp Gln Met Val Glu Ile Ala Lys Ala Leu Ala Arg
145                 150                 155                 160
Asn Ala Lys Ile Ile Ala Phe Asp Glu Pro Thr Ser Ser Leu Ser Ala
                165                 170                 175
Arg Glu Ile Asp Asn Leu Phe Arg Val Ile Arg Glu Leu Arg Lys Glu
            180                 185                 190
Gly Arg Val Ile Leu Tyr Val Ser His Arg Met Glu Glu Ile Phe Ala
        195                 200                 205
Leu Ser Asp Ala Ile Thr Val Phe Lys Asp Gly Arg Tyr Val Lys Thr
    210                 215                 220
Phe Thr Asp Met Gln Gln Val Asp His Asp Ala Leu Val Gln Ala Met
225                 230                 235                 240
```

```
Val Gly Arg Asp Ile Gly Asp Ile Tyr Gly Trp Gln Pro Arg Ser Tyr
                245                 250                 255

Gly Glu Glu Arg Leu Arg Leu Asp Ala Val Lys Ala Pro Gly Val Arg
            260                 265                 270

Thr Pro Ile Ser Leu Ala Val Arg Ser Gly Glu Ile Val Gly Leu Phe
        275                 280                 285

Gly Leu Val Gly Ala Gly Arg Ser Glu Leu Met Lys Gly Met Phe Gly
    290                 295                 300

Gly Thr Gln Ile Thr Ala Gly Gln Val Tyr Ile Asp Gln Gln Pro Ile
305                 310                 315                 320

Asp Ile Arg Lys Pro Ser His Ala Ile Ala Gly Met Met Leu Cys
                325                 330                 335

Pro Glu Asp Arg Lys Ala Glu Gly Ile Ile Pro Val His Ser Val Arg
                340                 345                 350

Asp Asn Ile Asn Ile Ser Ala Arg Arg Lys His Val Leu Gly Gly Cys
            355                 360                 365

Val Ile Asn Asn Gly Trp Glu Glu Asn Ala Asp His His Ile Arg
        370                 375                 380

Ser Leu Asn Ile Lys Thr Pro Gly Ala Glu Gln Leu Ile Met Asn Leu
385                 390                 395                 400

Ser Gly Gly Asn Gln Gln Lys Ala Ile Leu Gly Arg Trp Leu Ser Glu
                405                 410                 415

Glu Met Lys Val Ile Leu Leu Asp Glu Pro Thr Arg Gly Ile Asp Val
                420                 425                 430

Gly Ala Lys His Glu Ile Tyr Asn Val Ile Tyr Ala Leu Ala Ala Gln
                435                 440                 445

Gly Val Ala Val Leu Phe Ala Ser Ser Asp Leu Pro Glu Val Leu Gly
    450                 455                 460

Val Ala Asp Arg Ile Val Val Met Arg Glu Gly Glu Ile Ala Gly Glu
465                 470                 475                 480

Leu Leu His Glu Gln Ala Asp Glu Arg Gln Ala Leu Ser Leu Ala Met
                485                 490                 495

Pro Lys Val Ser Gln Ala Val Ala
            500

<210> SEQ ID NO 85
<211> LENGTH: 328
<212> TYPE: PRT
<213> ORGANISM: Escherichia coli

<400> SEQUENCE: 85

Met Ser Ser Val Ser Thr Ser Gly Ser Gly Ala Pro Lys Ser Ser Phe
1               5                   10                  15

Ser Phe Gly Arg Ile Trp Asp Gln Tyr Gly Met Leu Val Val Phe Ala
            20                  25                  30

Val Leu Phe Ile Ala Cys Ala Ile Phe Val Pro Asn Phe Ala Thr Phe
        35                  40                  45

Ile Asn Met Lys Gly Leu Gly Leu Ala Ile Ser Met Ser Gly Met Val
    50                  55                  60

Ala Cys Gly Met Leu Phe Cys Leu Ala Ser Gly Asp Phe Asp Leu Ser
65                  70                  75                  80

Val Ala Ser Val Ile Ala Cys Ala Gly Val Thr Thr Ala Val Val Ile
                85                  90                  95

Asn Leu Thr Glu Ser Leu Trp Ile Gly Val Ala Ala Gly Leu Leu Leu
```

```
            100                 105                 110
Gly Val Leu Cys Gly Leu Val Asn Gly Phe Ile Ala Lys Leu Lys
        115                 120                 125

Ile Asn Ala Leu Ile Thr Thr Leu Ala Thr Met Gln Ile Val Arg Gly
    130                 135                 140

Leu Ala Tyr Ile Ile Ser Asp Gly Lys Ala Val Gly Ile Glu Asp Glu
145                 150                 155                 160

Ser Phe Phe Ala Leu Gly Tyr Ala Asn Trp Phe Gly Leu Pro Ala Pro
                165                 170                 175

Ile Trp Leu Thr Val Ala Cys Leu Ile Ile Phe Gly Leu Leu Leu Asn
            180                 185                 190

Lys Thr Thr Phe Gly Arg Asn Thr Leu Ala Ile Gly Gly Asn Glu Glu
        195                 200                 205

Ala Ala Arg Leu Ala Gly Val Pro Val Arg Thr Lys Ile Ile Ile
    210                 215                 220

Phe Val Leu Ser Gly Leu Val Ser Ala Ile Ala Gly Ile Ile Leu Ala
225                 230                 235                 240

Ser Arg Met Thr Ser Gly Gln Pro Met Thr Ser Ile Gly Tyr Glu Leu
                245                 250                 255

Ile Val Ile Ser Ala Cys Val Leu Gly Val Ser Leu Lys Gly Gly
            260                 265                 270

Ile Gly Lys Ile Ser Tyr Val Val Ala Gly Ile Leu Ile Leu Gly Thr
        275                 280                 285

Val Glu Asn Ala Met Asn Leu Leu Asn Ile Ser Pro Phe Ala Gln Tyr
    290                 295                 300

Val Val Arg Gly Leu Ile Leu Ala Ala Val Ile Phe Asp Arg Tyr
305                 310                 315                 320

Lys Gln Lys Ala Lys Arg Thr Val
                325

<210> SEQ ID NO 86
<211> LENGTH: 487
<212> TYPE: PRT
<213> ORGANISM: Escherichia coli

<400> SEQUENCE: 86

Met Ser Leu Ala Lys Asp Asn Ile Trp Lys Leu Leu Ala Pro Leu Val
1               5                   10                  15

Val Met Gly Val Met Phe Leu Ile Pro Val Pro Asp Gly Met Pro Pro
                20                  25                  30

Gln Ala Trp His Tyr Phe Ala Val Phe Val Ala Met Ile Val Gly Met
            35                  40                  45

Ile Leu Glu Pro Ile Pro Ala Thr Ala Ile Ser Phe Ile Ala Val Thr
    50                  55                  60

Ile Cys Val Ile Gly Ser Asn Tyr Leu Leu Phe Asp Ala Lys Glu Leu
65                  70                  75                  80

Ala Asp Pro Ala Phe Asn Ala Gln Lys Gln Ala Leu Lys Trp Gly Leu
                85                  90                  95

Ala Gly Phe Ser Ser Thr Thr Val Trp Leu Val Phe Gly Ala Phe Ile
            100                 105                 110

Phe Ala Leu Gly Tyr Glu Val Ser Gly Leu Gly Arg Arg Ile Ala Leu
        115                 120                 125

Phe Leu Val Lys Phe Met Gly Lys Arg Thr Leu Thr Leu Gly Tyr Ala
    130                 135                 140
```

```
Ile Val Ile Ile Asp Ile Leu Leu Ala Pro Phe Thr Pro Ser Asn Thr
145                 150                 155                 160

Ala Arg Thr Gly Gly Thr Val Phe Pro Val Ile Lys Asn Leu Pro Pro
                165                 170                 175

Leu Phe Lys Ser Phe Pro Asn Asp Pro Ser Ala Arg Arg Ile Gly Gly
            180                 185                 190

Tyr Leu Met Trp Met Met Val Ile Ser Thr Ser Leu Ser Ser Ser Met
        195                 200                 205

Phe Val Thr Gly Ala Ala Pro Asn Val Leu Gly Leu Glu Phe Val Ser
    210                 215                 220

Lys Ile Ala Gly Ile Gln Ile Ser Trp Leu Gln Trp Phe Leu Cys Phe
225                 230                 235                 240

Leu Pro Val Gly Val Ile Leu Ile Ile Ala Pro Trp Leu Ser Tyr
                245                 250                 255

Val Leu Tyr Lys Pro Glu Ile Thr His Ser Glu Val Ala Thr Trp
                260                 265                 270

Ala Gly Asp Glu Leu Lys Thr Met Gly Ala Leu Thr Arg Arg Glu Trp
            275                 280                 285

Thr Leu Ile Gly Leu Val Leu Leu Ser Leu Gly Leu Trp Val Phe Gly
            290                 295                 300

Ser Glu Val Ile Asn Ala Thr Ala Val Gly Leu Leu Ala Val Ser Leu
305                 310                 315                 320

Met Leu Ala Leu His Val Pro Trp Lys Asp Ile Thr Arg Tyr Asn
                325                 330                 335

Ser Ala Trp Asn Thr Leu Val Asn Leu Ala Thr Leu Val Met Ala
                340                 345                 350

Asn Gly Leu Thr Arg Ser Gly Phe Ile Asp Trp Phe Ala Gly Thr Met
            355                 360                 365

Ser Thr His Leu Glu Gly Phe Ser Pro Asn Ala Thr Val Ile Val Leu
            370                 375                 380

Val Leu Val Phe Tyr Phe Ala His Tyr Leu Phe Ala Ser Leu Ser Ala
385                 390                 395                 400

His Thr Ala Thr Met Leu Pro Val Ile Leu Ala Val Gly Lys Gly Ile
                405                 410                 415

Pro Gly Val Pro Met Glu Gln Leu Cys Ile Leu Leu Val Leu Ser Ile
            420                 425                 430

Gly Ile Met Gly Cys Leu Thr Pro Tyr Ala Thr Gly Pro Gly Val Ile
                435                 440                 445

Ile Tyr Gly Cys Gly Tyr Val Lys Ser Lys Asp Tyr Trp Arg Leu Gly
            450                 455                 460

Ala Ile Phe Gly Val Ile Tyr Ile Ser Met Leu Leu Val Gly Trp
465                 470                 475                 480

Pro Ile Leu Ala Met Trp Asn
                485
```

<210> SEQ ID NO 87
<211> LENGTH: 610
<212> TYPE: PRT
<213> ORGANISM: Escherichia coli

<400> SEQUENCE: 87

```
Met Asn Gly Glu Leu Ile Trp Val Leu Ser Leu Leu Ala Val Ala Ile
1               5                   10                  15

Val Leu Phe Ala Thr Gly Arg Val Arg Met Asp Ala Val Ala Leu Phe
                20                  25                  30
```

-continued

```
Val Ile Val Ala Phe Ala Leu Ser Gly Thr Leu Thr Val Pro Glu Val
        35                  40                  45

Phe Ser Gly Phe Ser Asp Pro Asn Val Val Leu Ile Ala Ala Leu Phe
 50                  55                  60

Ile Ile Gly Asp Gly Leu Val Arg Thr Gly Val Ala Thr Val Met Gly
 65                  70                  75                  80

Thr Trp Leu Val Lys Val Ala Gly Asn Ser Glu Ile Lys Met Leu Val
                 85                  90                  95

Leu Leu Met Leu Thr Val Ala Gly Leu Gly Ala Phe Met Ser Ser Thr
                100                 105                 110

Gly Val Val Ala Ile Phe Ile Pro Val Val Leu Ser Val Ala Met Arg
                115                 120                 125

Met Gln Thr Ser Pro Ser Arg Leu Met Met Pro Leu Ser Phe Ala Gly
        130                 135                 140

Leu Ile Ser Gly Met Met Thr Leu Val Ala Thr Pro Pro Asn Leu Val
145                 150                 155                 160

Val Asn Ser Glu Leu Leu Arg Glu Gly Tyr His Gly Phe Ser Phe Phe
                165                 170                 175

Ser Val Thr Pro Ile Gly Leu Val Val Leu Val Leu Gly Ile Leu Tyr
                180                 185                 190

Met Leu Val Met Arg Phe Met Leu Lys Gly Asp Thr Gln Thr Pro Gln
        195                 200                 205

Arg Glu Gly Trp Thr Arg Arg Thr Phe Arg Asp Leu Ile Arg Glu Tyr
        210                 215                 220

Arg Leu Thr Gly Arg Ala Arg Arg Leu Ala Ile Arg Pro Gly Ser Pro
225                 230                 235                 240

Met Ile Gly Gln Arg Leu Asp Asp Leu Lys Leu Arg Glu Arg Tyr Gly
                245                 250                 255

Ala Asn Val Ile Gly Val Glu Arg Trp Arg Arg Phe Arg Arg Val Ile
                260                 265                 270

Val Asn Val Asn Gly Val Ser Glu Phe Arg Ala Arg Asp Val Leu Leu
        275                 280                 285

Ile Asp Met Ser Ala Ala Asp Val Asp Leu Arg Gln Phe Cys Ser Glu
        290                 295                 300

Gln Leu Leu Glu Pro Met Val Leu Arg Gly Glu Tyr Phe Ser Asp Gln
305                 310                 315                 320

Ala Leu Asp Val Gly Met Ala Glu Ile Ser Leu Ile Pro Glu Ser Glu
                325                 330                 335

Leu Ile Gly Lys Ser Val Arg Glu Ile Gly Phe Arg Thr Arg Tyr Gly
                340                 345                 350

Leu Asn Val Val Gly Leu Lys Arg Asn Gly Val Ala Leu Glu Gly Ser
        355                 360                 365

Leu Ala Asp Glu Pro Leu Leu Leu Gly Asp Ile Ile Leu Val Val Gly
        370                 375                 380

Asn Trp Lys Leu Ile Gly Met Leu Ala Lys Gln Gly Arg Asp Phe Val
385                 390                 395                 400

Ala Leu Asn Leu Pro Glu Glu Val Ser Glu Ala Ser Pro Ala His Ser
                405                 410                 415

Gln Ala Pro His Ala Ile Phe Cys Leu Val Leu Met Val Ala Leu Met
        420                 425                 430

Leu Thr Asp Glu Ile Pro Asn Pro Val Ala Ala Ile Ile Ala Cys Leu
        435                 440                 445
```

```
Leu Met Gly Lys Phe Arg Cys Ile Asp Ala Glu Ser Ala Tyr Lys Ser
    450                 455                 460
Ile His Trp Pro Ser Ile Ile Leu Ile Val Gly Met Met Pro Phe Ala
465                 470                 475                 480
Val Ala Leu Gln Lys Thr Gly Val Ala Leu Ala Val Lys Gly Leu
                485                 490                 495
Met Asp Ile Gly Gly Gly Tyr Gly Pro His Met Met Leu Gly Cys Leu
                500                 505                 510
Phe Val Leu Ser Ala Val Ile Gly Leu Phe Ile Ser Asn Thr Ala Thr
                515                 520                 525
Ala Val Leu Met Ala Pro Ile Ala Leu Ala Ala Lys Thr Met Gly
    530                 535                 540
Val Ser Pro Tyr Pro Phe Ala Met Val Val Ala Met Ala Ala Ser Ala
545                 550                 555                 560
Ala Phe Met Thr Pro Val Ser Ser Pro Val Asn Thr Leu Val Leu Gly
                565                 570                 575
Pro Gly Asn Tyr Ser Phe Ser Asp Phe Val Lys Leu Gly Val Pro Phe
                580                 585                 590
Thr Ile Ile Val Met Ala Val Cys Val Val Met Ile Pro Met Leu Phe
                595                 600                 605
Pro Phe
    610

<210> SEQ ID NO 88
<211> LENGTH: 432
<212> TYPE: PRT
<213> ORGANISM: Bacillus amyloliquefaciens

<400> SEQUENCE: 88

Met Leu Ala Ile Leu Gly Phe Leu Met Met Leu Val Phe Met Val Leu
  1                5                  10                  15
Ile Met Thr Lys Arg Leu Ser Val Leu Thr Ala Leu Val Leu Thr Pro
                20                  25                  30
Ile Val Phe Ala Leu Phe Ala Gly Phe Ser Phe Asn Arg Val Gly Glu
                35                  40                  45
Met Met Ile Ser Gly Ile Glu Gln Val Ala Pro Ile Ala Val Met Ile
    50                  55                  60
Met Phe Ala Ile Leu Tyr Phe Gly Ile Met Ile Asp Thr Gly Leu Phe
65                  70                  75                  80
Asp Pro Met Val Ser Arg Ile Leu Lys Leu Val Lys Gly Asp Pro Leu
                85                  90                  95
Lys Ile Val Val Gly Thr Ala Val Leu Thr Met Leu Val Ala Leu Asp
                100                 105                 110
Gly Asp Gly Ser Thr Thr Tyr Met Ile Thr Thr Ser Ala Met Leu Pro
                115                 120                 125
Leu Tyr Ile Met Leu Gly Ile Arg Pro Ile Ile Leu Ala Gly Ile Ala
    130                 135                 140
Gly Val Gly Met Gly Ile Met Asn Thr Ile Pro Trp Gly Gly Ala Thr
145                 150                 155                 160
Pro Arg Ala Ala Ser Ala Leu Gly Val Asp Pro Ala Glu Leu Thr Gly
                165                 170                 175
Pro Met Leu Pro Val Ile Ala Ser Gly Met Val Cys Met Ile Val Val
                180                 185                 190
Ala Tyr Val Leu Gly Arg Met Glu Arg Lys Arg Leu Gly Val Ile Glu
                195                 200                 205
```

```
Leu Lys Gln Pro Ser His Thr Asn Glu Thr Ala Ala Ala Glu Asp
    210                 215                 220

Glu Trp Arg Arg Pro Lys Leu Trp Trp Phe Asn Leu Leu Thr Leu
225                 230                 235                 240

Ser Leu Val Gly Phe Leu Val Ser Gly Lys Val Asn Leu Thr Val Leu
            245                 250                 255

Phe Ile Ile Ala Phe Cys Ile Ala Leu Ile Val Asn Tyr Pro Lys Leu
            260                 265                 270

Asn Asp Gln Arg Glu Arg Ile Ser Ala His Ser Ser Asn Val Leu Ala
        275                 280                 285

Ile Gly Ser Met Ile Phe Ala Ala Gly Val Phe Thr Gly Ile Leu Thr
        290                 295                 300

Gly Thr Lys Met Val Asp Glu Met Ala Ile Ser Leu Val Ser Leu Ile
305                 310                 315                 320

Pro Glu Gln Met Gly Gly Phe Ile Pro Ala Ile Val Ala Leu Thr Ser
            325                 330                 335

Gly Ile Phe Thr Phe Leu Met Pro Asn Asp Ala Tyr Phe Tyr Gly Val
            340                 345                 350

Leu Pro Ile Leu Ser Glu Thr Ala Val Ala Tyr Gly Val Asp Lys Val
        355                 360                 365

Glu Ile Ala Arg Ala Ser Ile Ile Gly Gln Pro Ile His Met Leu Ser
370                 375                 380

Pro Leu Val Pro Ser Thr His Leu Leu Val Gly Leu Ala Gly Val Thr
385                 390                 395                 400

Ile Asp Glu His Gln Lys Phe Ala Met Lys Trp Ala Val Leu Ala Val
            405                 410                 415

Ile Val Met Thr Ala Phe Ala Leu Ile Ile Gly Ala Ile Thr Ile Phe
            420                 425                 430

<210> SEQ ID NO 89
<211> LENGTH: 229
<212> TYPE: DNA
<213> ORGANISM: Artificial Sequence
<220> FEATURE:
<223> OTHER INFORMATION: MDH promoter

<400> SEQUENCE: 89
tttgcctcga tcggcggtcc ttgtgacagg gagatattcc cgacggatcc ggggcattcg      60
agcggaaccg cccgccgtgg gagttttcc agcgagcatt cgagagtttt tcaaggcggc     120
ttcgaggggt tattccgtaa cgccgccgac atgatctgtc ccagaatctc cgccgctgtt    180
cgtagagcgc cgatgcaggg tcggcatcaa tcattcttgg aggagacac               229

<210> SEQ ID NO 90
<211> LENGTH: 1506
<212> TYPE: DNA
<213> ORGANISM: Artificial Sequence
<220> FEATURE:
<223> OTHER INFORMATION: codon optimized GlpK

<400> SEQUENCE: 90
atgaccgaga agaagtatat cgtcgcgctg gaccagggca ccacctcgtc gcgcgcggtc      60
gtcatggacc atgacgcgaa catcatctcg gtctcgcagc gcgagttcga gcagatctat    120
ccgaagccgg gctgggtcga gcatgacccg atggagatct gggcgaccca gtcgtcgacc    180
ctggtcgagg tcctggcgaa ggcggacatc tcgtcggacc agatcgcggc gatcggcatc    240
```

```
accaaccagc gcgagaccac catcgtctgg gagaaggaga ccggcaagcc gatctataac      300
gcgatcgtct ggcagtgccg ccgcaccgcg gagatctgcg agcatctgaa gcgcgacggc      360
ctggaggact atatccgctc gaacaccggc ctggtcatcg acccgtattt ctcgggcacc      420
aaggtcaagt ggatcctgga ccatgtcgag ggctcgcgcg agcgcgcgcg ccgcggcgag      480
ctgctgttcg gcaccgtcga cacctggctg atctggaaga tgacccaggg ccgcgtccat      540
gtcaccgact ataccaacgc gtcgcgcacc atgctgttca acatccatac cctggactgg      600
gacgacaaga tgctggaggt cctggacatc ccgcgcgaga tgctgccgga ggtccgccgc      660
tcgtcggagg tctatggcca gaccaacatc ggcggcaagg cggcacccg catcccgatc       720
tcgggcatcg cgggcgacca gcaggcggcg ctgttcggcc agctgtgcgt caaggagggc      780
atggcgaaga acacctatgg caccggctgc ttcatgctga tgaacaccgg cgagaaggcg      840
gtcaagtcgg agaacggcct gctgaccacc atcgcgtgcg gcccgaccgg cgaggtcaac      900
tatgcgctgg agggcgcggt cttcatggcg gcgcgtcga tccagtggct gcgcgacgag       960
atgaagctga tcaacgacgc gtatgactcg gagtatttcg cgaccaaggt ccagaacacc     1020
aacggcgtct atgtcgtccc ggcgttcacc ggcctgggcg cgccgtattg ggacccgtat     1080
gcgcgcggcg cgatcttcgg cctgaccgc ggcgtcaacg cgaaccatat catccgcgcg       1140
accctggagt cgatcgcgta tcagacccgc gacgtcctgg aggcgatgca ggcggactcg     1200
ggcatccgcc tgcatgcgct gcgcgtcgac ggcggcgcgg tcgcgaacaa cttcctgatg     1260
cagttccagt cggacatcct gggcacccgc gtcgagcgcc cggaggtccg gaggtcacc      1320
gcgctgggcg cggcgtatct ggcgggcctg gcggtcggct tctggcagaa cctggacgag     1380
ctgcaggaga aggcggtcat cgagcgcgag ttccgcccgg gcatcgagac caccgagcgc     1440
aactatcgct atgcgggctg gaagaaggcg gtcaagcgcg cgatggcgtg ggaggagcat     1500
gactga                                                               1506

<210> SEQ ID NO 91
<211> LENGTH: 19
<212> TYPE: DNA
<213> ORGANISM: Artificial Sequence
<220> FEATURE:
<223> OTHER INFORMATION: Intergenic region

<400> SEQUENCE: 91
tcattcttgg aggagacac                                                    19

<210> SEQ ID NO 92
<211> LENGTH: 1506
<212> TYPE: DNA
<213> ORGANISM: Artificial Sequence
<220> FEATURE:
<223> OTHER INFORMATION: codon optimized GlpD

<400> SEQUENCE: 92
atggagacca aggacctgat cgtcatcggc ggcggcatca acggcgcggg catcgcggcg       60
gacgcggcgg gccgcggcct gtcggtcctg atgctggagg cgcaggacct ggcgtgcgcg      120
acctcgtcgg cgtcgtcgaa gctgatccat ggcggcctgc gctatctgga gcattatgag      180
ttccgcctgg tctcggaggc gctggcggag cgcgaggtcc tgctgaagat ggcgccgcat      240
atcgcgttcc cgatgcgctt ccgcctgccg catcgcccgc atctgcgccc ggcgtggatg      300
atccgcatcg gcctgttcat gtatgaccat ctgggcaagc gcacctcgct gccgggctcg      360
accggcctgc gcttcggcgc gaactcggtc ctgaagccgg agatcaagcg cggcttcgag      420
```

```
tattcggact gctgggtcga cgacgcgcgc ctggtcctgg cgaacgcgca gatggtcgtc    480
cgcaagggcg gcgaggtcct gacccgcacc cgcgcgacct cggcgcgccg cgagaacggc    540
ctgtggatcg tcgaggcgga ggacatcgac accggcaaga agtattcgtg gcaggcgcgc    600
ggcctggtca acgcgaccgg cccgtgggtc aagcagttct tcgacgacgg catgcatctg    660
ccgtcgccgt atggcatccg cctgatcaag ggctcgcata tcgtcgtccc gcgcgtccat    720
acccagaagc aggcgtatat cctgcagaac gaggacaagc gcatcgtctt cgtcatcccg    780
tggatggacg agttctcgat catcggcacc accgacgtcg agtataaggg cgacccgaag    840
gcggtcaaga tcgaggagtc ggagatcaac tatctgctga cgtctataa cacccatttc    900 aagaagcagc tgtcgcgcga cgacatcgtc tggacctatt cgggcgtccg cccgctgtgc    960
gacgacgagt cggactcgcc gcaggcgatc acccgcgact ataccctgga catccatgac   1020
gagaacggca aggcgccgct gctgtcggtc ttcggcggca agctgaccac ctatcgcaag   1080
ctggcggagc atgcgctgga gaagctgacc ccgtattatc agggcatcgg ccggcgtgg    1140 accaaggagt cggtcctgcc gggcggcgcg atcgagggcg accgcgacga ctatgcggcg   1200
cgcctgcgcc gccgctatcc gttcctgacc gagtcgctgg cgcgccatta tgcgcgcacc   1260
tatggctcga actcggagct gctgctgggc aacgcgggca ccgtctcgga cctgggcgag   1320
gacttcggcc atgagttcta tgaggcgag ctgaagtatc tggtcgacca tgagtgggtc    1380
cgccgcgcgg acgacgcgct gtggcgccgc accaagcagg gcatgtggct gaacgcggac   1440
cagcagtcgc gcgtctcgca gtggctggtc gagtatacc agcagcgcct gtcgctggcg    1500
tcgtga                                                             1506

<210> SEQ ID NO 93
<211> LENGTH: 19
<212> TYPE: DNA
<213> ORGANISM: Artificial Sequence
<220> FEATURE:
<223> OTHER INFORMATION: Intergenic region

<400> SEQUENCE: 93
tcattcttgg aggagacac                                                 19

<210> SEQ ID NO 94
<211> LENGTH: 846
<212> TYPE: DNA
<213> ORGANISM: Artificial Sequence
<220> FEATURE:
<223> OTHER INFORMATION: codon optimized GlpF

<400> SEQUENCE: 94
atgtcgcaga cctcgaccct gaagggccag tgcatcgcgg agttcctggg caccggcctg     60
ctgatcttct tcggcgtcgg ctgcgtcgcg gcgctgaagg tcgcgggcgc gtcgttcggc    120
cagtgggaga tctcggtcat ctgggggcctg gcgtcgcga tggcgatcta tctgaccgcg    180
ggcgtctcgg gcgcgcatct gaacccggcg gtcaccatcg cgctgtggct gttcgcgtgc    240
ttcgacaagc gcaaggtcat cccgttcatc gtctcgcagg tcgcgggcgc gttctgcgcg    300
gcggcgctgg tctatggcct gtattataac ctgttcttcg acttcgagca gacccatcat    360
atcgtccgcg gctcggtcga gtcggtcgac ctggcggcca ccttctcgac ctatccgaac    420
ccgcatatca acttcgtcca ggcgttcgcg gtcgagatgg tcatcaccgc gatcctgatg    480
ggcctgatcc tggcgctgac cgacgacggc aacggcgtcc cgcgcggccc gctggcgccg    540
```

```
ctgctgatcg gcctgctgat cgcggtcatc ggcgcgtcga tgggcccgct gaccggcttc    600
gcgatgaacc cggcgcgcga cttcggcccg aaggtcttcg cgtggctggc gggctggggc    660
aacgtcgcgt tcaccggcgg ccgcgacatc ccgtatttcc tggtcccgct gttcggcccg    720
atcgtcggcg cgatcgtcgg cgcgttcgcg tatcgcaagc tgatcggccg ccatctgccg    780
tgcgacatct gcgtcgtcga ggagaaggag accaccaccc cgtcggagca gaaggcgtcg    840
ctgtga    846

<210> SEQ ID NO 95
<211> LENGTH: 4125
<212> TYPE: DNA
<213> ORGANISM: Artificial Sequence
<220> FEATURE:
<223> OTHER INFORMATION: Glycerol Utilization Pathway  Operon

<400> SEQUENCE: 95
tttgcctcga tcggcggtcc ttgtgacagg gagatattcc cgacggatcc ggggcattcg     60
agcggaaccg cccgccgtgg gagttttttcc agcgagcatt cgagagtttt tcaaggcggc    120
ttcgaggggt tattccgtaa cgccgccgac atgatctgtc ccagaatctc cgccgctgtt    180
cgtagagcgc cgatgcaggg tcggcatcaa tcattcttgg aggagacaca tgaccgagaa    240
gaagtatatc gtcgcgctgg accagggcac cacctcgtcg cgcgcggtcg tcatggacca    300
tgacgcgaac atcatctcgg tctcgcagcg cgagttcgag cagatctatc gaagccgggc    360
ctgggtcgag catgacccga tggagatctg ggcgacccag tcgtcgaccc tggtcgaggt    420
cctggcgaag gcggacatct cgtcggacca gatcgcggcg atcggcatca ccaaccagcg    480
cgagaccacc atcgtctggg agaaggagac cggcaagccg atctataacg cgatcgtctg    540
gcagtgccgc cgcaccgcgg agatctgcga gcatctgaag cgcgacggcc tggaggacta    600
tatccgctcg aacaccggcc tggtcatcga cccgtatttc tcgggcacca aggtcaagtg    660
gatcctggac catgtcgagg gctcgcgcga gcgcgcgcgc cgcggcgagc tgctgttcgg    720
caccgtcgac acctggctga tctggaagat gacccagggc cgcgtccatg tcaccgacta    780
taccaacgcg tcgcgcacca tgctgttcaa catccatacc ctggactggg acgacaagat    840
gctggaggtc ctggacatcc cgcgcgagat gctgccggag gtccgccgct cgtcggaggt    900
ctatggccag accaacatcg gcggcaaggg cggcacccgc atcccgatct cgggcatcgc    960
gggcgaccag caggcggcgc tgttcggcca gctgtgcgtc aaggagggca tggcgaagaa   1020
cacctatggc accggctgct tcatgctgat gaacaccggc gagaaggcgg tcaagtcgga   1080
gaacggcctg ctgaccacca tcgcgtgcgg cccgaccggc gaggtcaact atgcgctgga   1140
gggcgcggtc ttcatggcgg gcgcgtcgat ccagtggctg cgcgacgaga tgaagctgat   1200
caacgacgcg tatgactcgg agtatttcgc gaccaaggtc cagaacacca acggcgtcta   1260
tgtcgtcccg gcgttcaccg gcctgggcgc gccgtattgg acccgtatgc gcgcggcgc   1320 gatcttcggc ctgaccccgc gcgtcaacgc gaaccatatc atccgcgcga ccctggagtc   1380
gatcgcgtat cagacccgcg acgtcctgga ggcgatgcag gcggactcgg catccgcct   1440 gcatgcgctg cgcgtcgacg gcggcgcggt cgcgaacaac ttcctgatgc agttccagtc   1500
ggacatcctg ggcacccgcg tcgagcgccc ggaggtccgc gaggtcaccg cgctgggcgc   1560
ggcgtatctg gcgggcctgg cggtcggctt ctgcagaac ctggacgagc tgcaggagaa   1620
ggcggtcatc gagcgcgagt tccgcccggg catcgagacc accgagcgca actatcgcta   1680
tgcgggctgg aagaaggcgg tcaagcgcgc gatggcgtgg gaggagcatg actgatcatt   1740
```

```
cttggaggag acacatggag accaaggacc tgatcgtcat cggcggcggc atcaacggcg   1800
cgggcatcgc ggcggacgcg gcgggccgcg gcctgtcggt cctgatgctg gaggcgcagg   1860
acctggcgtg cgcgacctcg tcggcgtcgt cgaagctgat ccatggcggc ctgcgctatc   1920
tggagcatta tgagttccgc ctggtctcgg aggcgctggc ggagcgcgag gtcctgctga   1980
agatggcgcc gcatatcgcg ttcccgatgc gcttccgcct gccgcatcgc ccgcatctgc   2040
gcccggcgtg gatgatccgc atcggcctgt tcatgtatga ccatctgggc aagcgcacct   2100
cgctgccggg ctcgaccggc ctgcgcttcg gcgcgaactc ggtcctgaag ccggagatca   2160
agcgcggctt cgagtattcg gactgctggg tcgacgacgc gcgcctggtc ctggcgaacg   2220
cgcagatggt cgtccgcaag ggcggcgagg tcctgacccg caccgcgcg acctcggcgc   2280
gccgcgagaa cggcctgtgg atcgtcgagg cggaggacat cgacaccggc aagaagtatt   2340
cgtggcaggc gcgcggcctg gtcaacgcga ccggcccgtg ggtcaagcag ttcttcgacg   2400
acggcatgca tctgccgtcg ccgtatggca tcgcctgat caagggctcg catatcgtcg   2460
tcccgcgcgt ccataccag aagcaggcgt atatcctgca gaacgaggac aagcgcatcg   2520
tcttcgtcat cccgtggatg gacgagttct cgatcatcgg caccaccgac gtcgagtata   2580
agggcgaccc gaaggcggtc aagatcgagg agtcggagat caactatctg ctgaacgtct   2640
ataacaccca tttcaagaag cagctgtcgc gcgacgacat cgtctggacc tattcgggcg   2700
tccgcccgct gtgcgacgac gagtcggact cgccgcaggc gatcacccgc gactataccc   2760
tggacatcca tgacgagaac ggcaaggcgc gctgctgtc ggtcttcggc ggcaagctga   2820
ccacctatcg caagctggcg gagcatgcgc tggagaagct gaccccgtat tatcagggca   2880
tcggcccggc gtggaccaag gagtcggtcc tgccgggcgg cgcgatcgag ggcgaccgcg   2940
acgactatgc ggcgcgcctg cgccgccgct atccgttcct gaccgagtcg ctggcgcgcc   3000
attatgcgcg cacctatggc tcgaactcgg agctgctgct gggcaacgcg ggcaccgtct   3060
cggacctggg cgaggacttc ggccatgagt tctatgaggc ggagctgaag tatctggtcg   3120
accatgagtg ggtccgccgc gcggacgacg cgctgtggcg ccgcaccaag cagggcatgt   3180
ggctgaacgc ggaccagcag tcgcgcgtct cgcagtggcg ggtcgagtat acccagcagc   3240
gcctgtcgct ggcgtcgtga tcattcttgg aggagacaca tgtcgcagac ctcgaccctg   3300
aagggccagt gcatcgcgga gttcctgggc accggcctgc tgatcttctt cggcgtcggc   3360
tgcgtcgcgg cgctgaaggt cgcgggcgcg tcgttcggcc agtgggagat ctcggtcatc   3420
tggggcctgg gcgtcgcgat ggcgatctat ctgaccgcgg gcgtctcggg cgcgcatctg   3480
aacccggcgg tcaccatcgc gctgtggctg ttcgcgtgct tcgacaagcg caaggtcatc   3540
ccgttcatcg tctcgcaggt cgcgggcgcg ttctgcgcgg cggcgctggt ctatggcctg   3600
tattataacc tgttcttcga cttcgagcag acccatcata tcgtccgcgg ctcggtcgag   3660
tcggtcgacc tggcgggcac cttctcgacc tatccgaacc gcatatcaa cttcgtccag   3720
gcgttcgcgg tcgagatggt catcaccgcg atcctgatgg gcctgatcct ggcgctgacc   3780
gacgacggca acggcgtccc gcgcggcccc ctggcgccgc tgctgatcgg cctgctgatc   3840
gcggtcatcg gcgcgtcgat gggcccgctg accggcttcg cgatgaaccc ggcgcgcgac   3900
ttcggcccga aggtcttcgc gtggctggcg ggctggggca acgtcgcgtt caccggcggc   3960
cgcgacatcc gtatttcct ggtcccgctg ttcggcccga tcgtcggcgc gatcgtcggc   4020
gcgttcgcgt atcgcaagct gatcggccgc catctgccgt gcgacatctg cgtcgtcgag   4080
```
gagaaggaga ccaccacccc gtcggagcag aaggcgtcgc tgtga                     4125

<210> SEQ ID NO 96
<211> LENGTH: 229
<212> TYPE: DNA
<213> ORGANISM: Artificial Sequence
<220> FEATURE:
<223> OTHER INFORMATION: MDH promoter

<400> SEQUENCE: 96
tttgcctcga tcggcggtcc ttgtgacagg gagatattcc cgacggatcc ggggcattcg     60
agcggaaccg cccgccgtgg gagttttttcc agcgagcatt cgagagtttt tcaaggcggc    120
ttcgaggggt tattccgtaa cgccgccgac atgatctgtc ccagaatctc cgccgctgtt    180
cgtagagcgc cgatgcaggg tcggcatcaa tcattcttgg aggagacac                229

<210> SEQ ID NO 97
<211> LENGTH: 1509
<212> TYPE: DNA
<213> ORGANISM: Artificial Sequence
<220> FEATURE:
<223> OTHER INFORMATION: codon optimized GlpK

<400> SEQUENCE: 97
atgaccgaga agaagtacat cgtcgccctg accagggca ccaccagcag ccgcgccgtc      60
gtcatggacc acgacgccaa catcatcagc gtcagccagc gcgagttcga gcagatctac    120
ccgaagccgg gctgggtcga gcacgacccg atggagatct gggccaccca gagcagcacc    180
ctggtcgagg tcctggccaa ggccgacatc agcagcgacc agatcgccgc catcggcatc    240
accaaccagc gcgagaccac catcgtctgg gagaaggaga ccggcaagcc gatctacaac    300
gccatcgtct ggcagtgccg ccgcaccgcc gagatctgcg agcacctgaa gcgcgacggc    360
ctggaggact acatccgcag caacaccggc ctggtcatcg acccgtactt cagcggcacc    420
aaggtcaagt ggatcctgga ccacgtcgag ggcagccgcg agcgcgcccg ccgcggcgag    480
ctgctgttcg gcaccgtcga cacctggctg atctggaaga tgacccaggg ccgcgtccac    540
gtcaccgact acaccaacgc cagccgcacc atgctgttca acatccacac cctggactgg    600
gacgacaaga tgctggaggt cctggacatc ccgcgcgaga tgctgccgga ggtccgccgc    660
agcagcgagg tctacggcca gaccaacatc ggcggcaagg gcggcacccg catcccgatc    720
agcggcatcg ccggcgacca gcaggccgcc ctgttcggcc agctgtgcgt caaggagggc    780
atggccaaga acacctacgg caccggctgc ttcatgctga tgaacaccgg cgagaaggcc    840
gtcaagagcg agaacggcct gctgaccacc atcgcctgcg gcccgaccgg cgaggtcaac    900
tacgccctgg agggcgccgt cttcatggcc ggcgccagca tccagtggct cgcgacgag    960
atgaagctga tcaacgacgc ctacgacagc gagtacttcg ccaccaaggt ccagaacacc   1020
aacggcgtct acgtcgtccc ggccttcacc ggcctgggcg cccgtactg gacccgtac   1080
gcccgcggcg ccatcttcgg cctgacccgc ggcgtcaacg ccaaccacat catccgcgcc   1140
accctggaga gcatcgccta ccagacccgc gacgtcctgg aggccatgca ggccgacagc   1200
ggcatccgcc tgcacgccct gcgcgtcgac ggcggcgccg tcgccaacaa cttcctgatg   1260
cagttccaga gcgacatcct gggcacccgc gtcgagcgcc cggaggtccg cgaggtcacc   1320
gccctgggcg ccgcctacct ggccggcctg gccgtcggct tctggcagaa cctggacgag   1380
ctgcaggaga aggccgtcat cgagcgcgag ttcgcccggg gcatcgagac caccgagcgc   1440
aactaccgct acgccggctg gaagaaggcc gtcaagcgcg ccatggcctg ggaggagcac   1500

```
gacgagtga                                                                 1509

<210> SEQ ID NO 98
<211> LENGTH: 19
<212> TYPE: DNA
<213> ORGANISM: Artificial Sequence
<220> FEATURE:
<223> OTHER INFORMATION: Intergenic region

<400> SEQUENCE: 98
tcattcttgg aggagacac                                                        19

<210> SEQ ID NO 99
<211> LENGTH: 1506
<212> TYPE: DNA
<213> ORGANISM: Artificial Sequence
<220> FEATURE:
<223> OTHER INFORMATION: codon optimized GlpD

<400> SEQUENCE: 99
atggagacca aggacctgat cgtcatcggc ggcggcatca acggcgccgg catcgccgcc           60
gacgccgccg gccgcggcct gagcgtcctg atgctggagg cccaggacct ggcctgcgcc          120
accagcagcg ccagcagcaa gctgatccac ggcggcctgc gctacctgga gcactacgag          180
ttccgcctgg tcagcgaggc cctggccgag cgcgaggtcc tgctgaagat ggccccgcac          240
atcgccttcc cgatgcgctt ccgcctgccg caccgcccgc acctgcgccc ggcctggatg          300
atccgcatcg gcctgttcat gtacgaccac ctgggcaagc gcaccagcct gccgggcagc          360
accggcctgc gcttcggcgc caacagcgtc ctgaagccgg agatcaagcg cggcttcgag          420
tacagcgact gctgggtcga cgacgcccgc ctggtcctgg ccaacgccca gatggtcgtc          480
cgcaagggcg gcgaggtcct gacccgcacc cgcgccacca cgcccgccg cgagaacggc           540 ctgtggatcg tcgaggccga ggacatcgac accggcaaga agtacagctg gcaggcccgc          600
ggcctggtca cgccaccgg cccgtggtc aagcagttct cgacgacgg catgcacctg            660 ccgagcccgt acggcatccg cctgatcaag ggcagccaca tcgtcgtccc gcgcgtccac          720
acccagaagc aggcctacat cctgcagaac gaggacaagc gcatcgtctt cgtcatcccg          780
tggatggacg agttcagcat catcggcacc accgacgtcg agtacaaggg cgacccgaag          840
gccgtcaaga tcgaggagag cgagatcaac tacctgctga cgtctacaa cacccacttc          900 aagaagcagc tgagccgcga cgacatcgtc tggacctaca gcggcgtccg cccgctgtgc          960
gacgacgaga gcgacagccc gcaggccatc acccgcgact acaccctgga catccacgac         1020
gagaacggca aggccccgct gctgagcgtc ttcgcggca agctgaccac ctaccgcaag          1080
ctggccgagc acgccctgga gaagctgacc ccgtactacc agggcatcgg cccggcctgg         1140
accaaggaga gcgtcctgcc gggcggcgcc atcgagggcg accgcgacga ctacgccgcc         1200
cgcctgcgcc gccgctaccc gttcctgacc gagagcctgg cccgccacta cgcccgcacc         1260
tacggcagca acagcgagct gctgctgggc aacgccggca ccgtcagcga cctgggcgag         1320
gacttcggcc acgagttcta cgaggccgag ctgaagtacc tggtcgacca cgagtgggtc         1380
cgccgcgccg acgacgccct gtggcgccgc accaagcagg gcatgtggct gaacgccgac         1440
cagcagagcc gcgtcagcca gtggctggtc gagtacaccc agcagcgcct gagcctggcc         1500
agctga                                                                    1506

<210> SEQ ID NO 100
```

```
<211> LENGTH: 19
<212> TYPE: DNA
<213> ORGANISM: Artificial Sequence
<220> FEATURE:
<223> OTHER INFORMATION: Intergenic region

<400> SEQUENCE: 100
tcattcttgg aggagacac                                           19

<210> SEQ ID NO 101
<211> LENGTH: 846
<212> TYPE: DNA
<213> ORGANISM: Artificial Sequence
<220> FEATURE:
<223> OTHER INFORMATION: codon optimized GlpF

<400> SEQUENCE: 101
atgagccaga ccagcaccct gaagggccag tgcatcgccg agttcctggg caccggcctg    60
ctgatcttct tcggcgtcgg ctgcgtcgcc gccctgaagg tcgccggcgc cagcttcggc   120
cagtgggaga tcagcgtcat ctggggcctg ggcgtcgcca tggccatcta cctgaccgcc   180
ggcgtcagcg gcgcccacct gaacccggcc gtcaccatcg ccctgtggct gttcgcctgc   240
ttcgacaagc gcaaggtcat cccgttcatc gtcagccagg tcgccggcgc cttctgcgcc   300
gccgccctgg tctacggcct gtactacaac ctgttcttcg acttcgagca gacccaccac   360
atcgtccgcg gcagcgtcga gcgtcgac ctggccggca cctcagcac ctacccgaac   420 ccgcacatca acttcgtcca ggccttcgcc gtcgagatgg tcatcaccgc catcctgatg   480
ggcctgatcc tggccctgac cgacgacggc aacggcgtcc cgcgcggccc gctggccccg   540
ctgctgatcg gcctgctgat cgccgtcatc ggcgccagca tgggcccgct gaccggcttc   600
gccatgaacc cggccgcga cttcggcccg aaggtcttcg cctggctggc cggctggggc   660
aacgtcgcct tcaccggcgg ccgcgacatc ccgtacttcc tggtcccgct gttcggcccg   720
atcgtcggcg ccatcgtcgg cgccttcgcc taccgcaagc tgatcggccg ccacctgccg   780
tgcgacatct gcgtcgtcga ggagaaggag accaccaccc cgagcgagca aaggccagc   840 ctgtga                                                              846

<210> SEQ ID NO 102
<211> LENGTH: 4128
<212> TYPE: DNA
<213> ORGANISM: Artificial Sequence
<220> FEATURE:
<223> OTHER INFORMATION: Glycerol Utilization Pathway Operon

<400> SEQUENCE: 102
tttgcctcga tcggcggtcc ttgtgacagg gagatattcc cgacggatcc ggggcattcg    60
agcggaaccg cccgccgtgg gagttttcc agcgagcatt cgagagtttt tcaaggcggc   120
ttcgaggggt tattccgtaa cgccgccgac atgatctgtc ccagaatctc cgccgctgtt   180
cgtagagcgc cgatgcaggg tcggcatcaa tcattcttgg aggagacaca tgaccgagaa   240
gaagtacatc gtcgccctgg accagggcac caccagcagc cgcgccgtcg tcatggacca   300
cgacgccaac atcatcagcg tcagccagcg cgagttcgag cagatctacc cgaagccggg   360
ctgggtcgag cacgacccga tggagatctg gccacccag agcagcaccc tggtcgaggt   420
cctggccaag gccgacatca gcagcgacca gatcgccgcc atcggcatca ccaaccagcg   480
cgagaccacc atcgtctggg agaaggagac cggcaagccg atctacaacg ccatcgtctg   540
gcagtgccgc cgcaccgccg agatctgcga gcacctgaag gcgacggcc tggaggacta   600
```

-continued

```
catccgcagc aacaccggcc tggtcatcga cccgtacttc agcggcacca aggtcaagtg    660
gatcctggac cacgtcgagg gcagccgcga gcgcgcccgc cgcggcgagc tgctgttcgg    720
caccgtcgac acctggctga tctggaagat gacccagggc cgcgtccacg tcaccgacta    780
caccaacgcc agccgcacca tgctgttcaa catccacacc ctggactggg acgacaagat    840
gctggaggtc ctggacatcc cgcgcgagat gctgccggag gtccgccgca gcagcgaggt    900
ctacggccag accaacatcg gcggcaaggg cggcacccgc atcccgatca gcggcatcgc    960
cggcgaccag caggccgccc tgttcggcca gctgtgcgtc aaggagggca tggccaagaa   1020
cacctacggc accggctgct tcatgctgat gaacaccggc gagaaggccg tcaagagcga   1080
gaacggcctg ctgaccacca tcgcctgcgg cccgaccggc gaggtcaact acgccctgga   1140
gggcgccgtc ttcatggccg cgccagcat ccagtggctg cgcgacgaga tgaagctgat   1200
caacgacgcc tacgacagcg agtacttcgc caccaaggtc cagaacacca cggcgtcta   1260 cgtcgtcccg gccttcaccg gcctgggcgc cccgtactgg gacccgtacg cccgcggcgc   1320
catcttcggc ctgacccgcg gcgtcaacgc caaccacatc atccgcgcca cctggagag   1380 catcgcctac cagacccgcg acgtcctgga ggccatgcag gccgacagcg gcatccgcct   1440
gcacgccctg cgcgtcgacg gcggcgccgt cgccaacaac ttcctgatgc agttccagag   1500
cgacatcctg gcacccgcg tcgagcgccc ggaggtccgc gaggtcaccg ccctgggcgc   1560
cgcctacctg gccggcctgg ccgtcggctt ctggcagaac ctggacgagc tgcaggagaa   1620
ggccgtcatc gagcgcgagt tccgcccggg catcgagacc accgagcgca actaccgcta   1680
cgccggctgg aagaaggccg tcaagcgcgc catggcctgg gaggagcacg acgagtgatc   1740
attcttggag gagacacatg gagaccaagg acctgatcgt catcggcggc ggcatcaacg   1800
gcgccggcat cgccgccgac gccgccggcc gcggcctgag cgtcctgatg ctggaggccc   1860
aggacctggc ctgcgccacc agcagcgcca gcagcaagct gatccacggc ggcctgcgct   1920
acctggagca ctacgagttc cgcctggtca gcgaggccct ggccgagcgc gaggtcctgc   1980
tgaagatggc cccgcacatc gccttcccga tgcgcttccg cctgccgcac cgcccgcacc   2040
tgcgcccggc ctgatgatc cgcatcggcc tgttcatgta cgaccacctg ggcaagcgca   2100
ccagcctgcc gggcagcacc ggcctgcgct tcggcgccaa cagcgtcctg aagccggaga   2160
tcaagcgcgg cttcgagtac agcgactgct gggtcgacga cgcccgcctg gtcctggcca   2220
acgcccagat ggtcgtccgc aagggcggcg aggtcctgac ccgcacccgc gccaccagcg   2280
cccgccgcga aacggcctg tggatcgtcg aggccgagga catcgacacc ggcaagaagt   2340
acagctggca ggcccgcggc ctggtcaacg ccaccggccc gtgggtcaag cagttcttcg   2400
acgacggcat gcacctgccg agcccgtacg gcatccgcct gatcaagggc agccacatcg   2460
tcgtcccgcg cgtccacacc cagaagcagg cctacatcct gcagaacgag acaagcgca   2520 tcgtcttcgt catcccgtgg atggacgagt tcagcatcat cggcaccacc gacgtcgagt   2580
acaagggcga cccgaaggcc gtcaagatcg aggagagcga gatcaactac ctgctgaacg   2640
tctacaacac ccacttcaag aagcagctga gccgcgacga catcgtctgg acctacagcg   2700
gcgtccgccc gctgtgcgac gacgagagcg acagcccgca ggccatcacc cgcgactaca   2760
ccctggacat ccacgacgag aacggcaagg cccgctgct gagcgtcttc ggcggcaagc   2820
tgaccaccta ccgcaagctg gccgagcacg ccctggagaa gctgacccgg tactaccagg   2880
gcatcggccc ggcctggacc aaggagagcg tcctgccggg cggcgccatc gagggcgacc   2940
```

```
gcgacgacta cgccgcccgc ctgcgccgcc gctacccgtt cctgaccgag agcctggccc    3000
gccactacgc ccgcacctac ggcagcaaca gcgagctgct gctgggcaac gccggcaccg    3060
tcagcgacct gggcgaggac ttcggccacg agttctacga ggccgagctg aagtacctgg    3120
tcgaccacga gtgggtccgc cgcgccacga acgccctgtg gcgccgcacc aagcagggca    3180
tgtggctgaa cgccgaccag cagagccgcg tcagccagtg gctggtcgag tacacccagc    3240
agcgcctgag cctggccagc tgatcattct tggaggagac acatgagcca gaccagcacc    3300
ctgaagggcc agtgcatcgc cgagttcctg ggcaccggcc tgctgatctt cttcggcgtc    3360
ggctgcgtcg ccgccctgaa ggtcgccggc gccagcttcg ccagtgggga gatcagcgtc    3420
atctggggcc tgggcgtcgc catggccatc tacctgaccg ccggcgtcag cggcgcccac    3480
ctgaacccgg ccgtcaccat cgccctgtgg ctgttcgcct gcttcgacaa gcgcaaggtc    3540
atcccgttca tcgtcagcca ggtcgccggc gccttctgcg ccgccgccct ggtctacggc    3600
ctgtactaca acctgttctt cgacttcgag cagacccacc acatcgtccg ggcagcgtc     3660 gagagcgtcg acctggccgg caccttcagc acctacccga accgcacat caacttcgtc     3720 caggccttcg ccgtcgagat ggtcatcacc gccatcctga tgggcctgat cctggccctg    3780
accgacgacg gcaacggcgt cccgcgcggc ccgctgcccc gctgctgat cggcctgctg     3840 atcgccgtca tcggcgccag catgggcccg ctgaccggct tcgccatgaa cccggcccgc    3900
gacttcggcc cgaaggtctt cgcctggctg gccggctggg gcaacgtcgc cttcaccggc    3960
ggccgcgaca tcccgtactt cctggtcccg ctgttcggcc cgatcgtcgg cgccatcgtc    4020
ggcgccttcg cctaccgcaa gctgatcggc cgccacctgc cgtgcgacat ctgcgtcgtc    4080
gaggagaagg agaccaccac cccgagcgag cagaaggcca gcctgtga                4128
```

<210> SEQ ID NO 103
<211> LENGTH: 497
<212> TYPE: DNA
<213> ORGANISM: Artificial Sequence
<220> FEATURE:
<223> OTHER INFORMATION: HPS promoter

<400> SEQUENCE: 103

```
ttcggaatcc ctgacgggaa ttggcccgaa gaaggcagat gccatcgttc agtatcgaaa      60
ggaacatggg gattttcagt cattgaagga tctggagaat gtcagcggca ttggcgagaa     120 aaccctttcag gccaatgaaa aagacattcg cttcacggat gatttgagcg ataagtcatc    180
cgcggaaaaa ggtgcggtag ctgtggataa aaaaggcgcc agatagtaag cgctaaggat    240
tggggtgcgt cgccggtcgc ggcggcgctc ctcgacggca gagttggtgc caggttggcg    300
gatgattgat gccgaatatt acgcgaccaa ttctcgaggc aaatgaactg tgagctactg    360
agttgcaggc attgacagcc atcccatttc tatcatacag ttacggacgc atcacgagta    420
ggtgataagc ctagcagatt gcggcagttg gcaaaatcag ctattactaa taattaaaaa    480
ctttcggagc acatcac                                                    497
```

<210> SEQ ID NO 104
<211> LENGTH: 1509
<212> TYPE: DNA
<213> ORGANISM: Artificial Sequence
<220> FEATURE:
<223> OTHER INFORMATION: codon optimized GlpK

<400> SEQUENCE: 104

```
atgaccgaaa aaaatatat cgtcgcgttg gatcaaggca ccaccagcag ccgcgcggtc       60
```

-continued

```
gtcatggatc acgatgcgaa catcatcagc gtcagccaac gcgaattcga acaaatctat    120
ccgaaaccgg gctgggtcga acacgatccg atggaaatct gggcgaccca aagcagcacc    180
ttggtcgaag tcttggcgaa agcggatatc agcagcgatc aaatcgcggc gatcggcatc    240
accaaccaac gcgaaaccac catcgtctgg aaaaagaaa ccggcaaacc gatctataac     300
gcgatcgtct ggcaatgccg ccgcaccgcg gaaatctgcg aacacttgaa acgcgatggc    360
ttggaagatt atatccgcag caacaccggc ttggtcatcg atccgtattt cagcggcacc    420
aaagtcaaat ggatcttgga tcacgtcgaa ggcagccgcg aacgcgcgcg ccgcggcgaa    480
ttgttgttcg gcaccgtcga tacctggttg atctggaaaa tgacccaagg ccgcgtccac    540
gtcaccgatt ataccaacgc gagccgcacc atgttgttca acatccacac cttggattgg    600
gatgataaaa tgttggaagt cttggatatc ccgcgcgaaa tgttgccgga agtccgccgc    660
agcagcgaag tctatggcca aaccaacatc ggcggcaaag gcggcacccg catcccgatc    720
agcggcatcg cggcgatca acaagcggcg ttgttcggcc aattgtgcgt caaagaaggc     780
atggcgaaaa acacctatgg caccggctgc ttcatgttga tgaacaccgg cgaaaaagcg    840
gtcaaaagcg aaaacggctt gttgaccacc atcgcgtgcg gcccgaccgg cgaagtcaac    900
tatgcgttgg aaggcgcggt cttcatggcg ggcgcgagca tccaatggtt gcgcgatgaa    960
atgaaattga tcaacgatgc gtatgatagc gaatatttcg cgaccaaagt ccaaaacacc   1020
aacggcgtct atgtcgtccc ggcgttcacc ggcttgggcg cgccgtattg ggatccgtat   1080
gcgcgcggcg cgatcttcgg cttgaccccg ggcgtcaacg cgaaccacat catccgcgcg   1140
accttggaaa gcatcgcgta tcaaacccgc gatgtcttgg aagcgatgca agcggatagc   1200
ggcatccgct tgcacgcgtt gcgcgtcgat ggcggcgcgg tcgcgaacaa cttcttgatg   1260
caattccaaa gcgatatctt gggcacccgc gtcgaacgcc cggaagtccg cgaagtcacc   1320
gcgttgggcg cggcgtattt ggcgggcttg gcggtcggct tctggcaaaa cttggatgaa   1380
ttgcaagaaa aagcggtcat cgaacgcgaa ttccgcccgg gcatcgaaac caccgaacgc   1440
aactatcgct atgcgggctg gaaaaaagcg gtcaaacgcg cgatggcgtg gaagaacac    1500 gatgaataa                                                           1509
```

<210> SEQ ID NO 105
<211> LENGTH: 30
<212> TYPE: DNA
<213> ORGANISM: Artificial Sequence
<220> FEATURE:
<223> OTHER INFORMATION: Intergenic region

<400> SEQUENCE: 105

```
taataattaa aaactttcgg agcacatcac                                       30
```

<210> SEQ ID NO 106
<211> LENGTH: 1506
<212> TYPE: DNA
<213> ORGANISM: Artificial Sequence
<220> FEATURE:
<223> OTHER INFORMATION: codon optimized GlpD

<400> SEQUENCE: 106

```
atggaaacca aagatttgat cgtcatcggc ggcggcatca cggcgcgggg catcgcggcg     60
gatgcggcgg gccgcggctt gagcgtcttg atgttggaag cgcaagattt ggcgtgcgcg    120
accagcagcg cgagcagcaa attgatccac ggcggcttgc gctatttgga acactatgaa    180
```

| ttccgcttgg tcagcgaagc gttggcggaa cgcgaagtct tgttgaaaat ggcgccgcac | 240 |
| atcgcgttcc cgatgcgctt ccgcttgccg caccgcccgc acttgcgccc ggcgtggatg | 300 |
| atccgcatcg gcttgttcat gtatgatcac ttgggcaaac gcaccagctt gccgggcagc | 360 |
| accggcttgc gcttcggcgc gaacagcgtc ttgaaaccgg aaatcaaacg cggcttcgaa | 420 |
| tatagcgatt gctgggtcga tgatgcgcgc ttggtcttgg cgaacgcgca aatggtcgtc | 480 |
| cgcaaaggcg gcgaagtctt gacccgcacc cgcgcgacca gcgcgcgccg cgaaaacggc | 540 |
| ttgtggatcg tcgaagcgga agatatcgat accggcaaaa aatatagctg gcaagcgcgc | 600 |
| ggcttggtca cgcgaccgg cccgtgggtc aaacaattct cgatgatgg catgcacttg | 660 |
| ccgagcccgt atggcatccg cttgatcaaa ggcagccaca tcgtcgtccc gcgcgtccac | 720 |
| acccaaaaac aagcgtatat cttgcaaaac gaagataaac gcatcgtctt cgtcatcccg | 780 |
| tggatggatg aattcagcat catcggcacc accgatgtcg aatataaagg cgatccgaaa | 840 |
| gcggtcaaaa tcgaagaaag cgaaatcaac tatttgttga acgtctataa cacccacttc | 900 |
| aaaaaacaat tgagccgcga tgatatcgtc tggacctata cgcgcgtccg cccgttgtgc | 960 |
| gatgatgaaa gcgatagccc gcaagcgatc acccgcgatt ataccttgga tatccacgat | 1020 |
| gaaaacggca aagcgccgtt gttgagcgtc ttcggcggca aattgaccac ctatcgcaaa | 1080 |
| ttggcggaac acgcgttgga aaaattgacc ccgtattatc aaggcatcgg cccggcgtgg | 1140 |
| accaaagaaa gcgtcttgcc gggcggcgcg atcgaaggcg atcgcgatga ttatgcggcg | 1200 |
| cgcttgcgcc gccgctatcc gttcttgacc gaaagcttgg cgcgccacta tgcgcgcacc | 1260 |
| tatggcagca cagcgaatt gttgttgggc aacgcgggca ccgtcagcga tttgggcgaa | 1320 |
| gatttcggcc acgaattcta tgaagcggaa ttgaaatatt tggtcgatca cgaatgggtc | 1380 |
| cgccgcgcgg atgatgcgtt gtggcgccgc accaaacaag gcatgtggtt gaacgcggat | 1440 |
| caacaaagcc gcgtcagcca atggttggtc gaatataccc aacaacgctt gagcttggcg | 1500 |
| agctaa | 1506 |

<210> SEQ ID NO 107
<211> LENGTH: 30
<212> TYPE: DNA
<213> ORGANISM: Artificial Sequence
<220> FEATURE:
<223> OTHER INFORMATION: Intergenic region

<400> SEQUENCE: 107

| taataattaa aaactttcgg agcacatcac | 30 |

<210> SEQ ID NO 108
<211> LENGTH: 846
<212> TYPE: DNA
<213> ORGANISM: Artificial Sequence
<220> FEATURE:
<223> OTHER INFORMATION: codon optimized GlpF

<400> SEQUENCE: 108

| atgagccaaa ccagcacctt gaaaggccaa tgcatcgcgg aattcttggg caccggcttg | 60 |
| ttgatcttct cggcgtcgg ctgcgtcgcg gcgttgaaag tcgcgggcgc gagcttcggc | 120 |
| caatgggaaa tcagcgtcat ctggggcttg ggcgtcgcga tggcgatcta tttgaccgcg | 180 |
| ggcgtcagcg gcgcgcactt gaacccggcg gtcaccatcg cgttgtggtt gttcgcgtgc | 240 |
| ttcgataaac gcaaagtcat cccgttcatc gtcagccaag tcgcgggcgc gttctgcgcg | 300 |
| gcggcgttgg tctatggctt gtattataac ttgttcttcg atttcgaaca aacccaccac | 360 |

```
atcgtccgcg gcagcgtcga aagcgtcgat ttggcgggca ccttcagcac ctatccgaac    420
ccgcacatca acttcgtcca agcgttcgcg gtcgaaatgg tcatcaccgc gatcttgatg    480
ggcttgatct tggcgttgac cgatgatggc aacggcgtcc cgcgcggccc gttggcgccg    540
ttgttgatcg gcttgttgat cgcggtcatc ggcgcgagca tgggcccgtt gaccggcttc    600
gcgatgaacc cggcgcgcga tttcggcccg aaagtcttcg cgtggttggc gggctggggc    660
aacgtcgcgt tcaccggcgg ccgcgatatc ccgtatttct tggtcccgtt gttcggcccg    720
atcgtcggcg cgatcgtcgg cgcgttcgcg tatcgcaaat tgatcggccg ccacttgccg    780
tgcgatatct gcgtcgtcga agaaaaagaa accaccaccc cgagcgaaca aaaagcgagc    840
ttgtaa                                                              846

<210> SEQ ID NO 109
<211> LENGTH: 4418
<212> TYPE: DNA
<213> ORGANISM: Artificial Sequence
<220> FEATURE:
<223> OTHER INFORMATION: Glycerol Utilization Pathway Operon

<400> SEQUENCE: 109
ttcggaatcc ctgacgggaa ttggcccgaa gaaggcagat gccatcgttc agtatcgaaa     60
ggaacatggg gattttcagt cattgaagga tctggagaat gtcagcggca ttggcgagaa    120
aacccttcag gccaatgaaa aagacattcg cttcacggat gatttgagcg ataagtcatc    180
cgcggaaaaa ggtgcggtag ctgtggataa aaaaggcgcc agatagtaag cgctaaggat    240
tggggtgcgt cgccggtcgc ggcggcgctc ctcgacggca gagttggtgc caggttggcg    300
gatgattgat gccgaatatt acgcgaccaa ttctcgaggc aaatgaactg tgagctactg    360
agttgcaggc attgacagcc atcccatttc tatcatacag ttacggacgc atcacgagta    420
ggtgataagc ctagcagatt gcggcagttg caaaatcag ctattactaa taattaaaaa    480
ctttcggagc acatcacatg accgaaaaaa aatatatcgt cgcgttggat caaggcacca    540
ccagcagccg cgcggtcgtc atggatcacg atgcgaacat catcagcgtc agccaacgcg    600
aattcgaaca aatctatccg aaaccgggct gggtcgaaca cgatccgatg gaaatctggg    660
cgacccaaag cagcaccttg gtcgaagtct tggcgaaagc ggatatcagc agcgatcaaa    720
tcgcggcgat cggcatcacc aaccaacgcg aaaccaccat cgtctgggaa aaagaaaccg    780
gcaaaccgat ctataacgcg atcgtctggc aatgccgccg caccgcggaa atctgcgaac    840
acttgaaacg cgatggcttg aagattata tccgcagcaa caccggcttg gtcatcgatc    900
cgtatttcag cggcaccaaa gtcaaatgga tcttggatca cgtcgaaggc agccgcgaac    960
gcgcgcgccc cggcgaattg ttgttcggca ccgtcgacac ctggttgatc tggaaaatga   1020
cccaaggccg cgtccacgtc accgattata ccaacgcgag ccgcaccatg ttgttcaaca   1080
tccacacctt ggattgggat gataaaatgt tggaagtctt ggatatcccg cgcgaaatgt   1140
tgccggaagt ccgccgcagc agcgaagtct atggccaaac caacatcggc ggcaaaggcg   1200
gcacccgcat cccgatcagc ggcatcgcgg gcgatcaaca agcggcgttg ttcggccaat   1260
tgtgcgtcaa agaaggcatg gcgaaaaaca cctatgcac cggctgcttc atgttgatga   1320
acaccggcga aaagcggtc aaaagcgaaa acggcttgtt gaccaccatc gcgtgcggcc   1380
cgaccggcga agtcaactat gcgttggaag gcgcggtctt catggcgggc gcgagcatcc   1440
aatggttgcg cgatgaaatg aaattgatca acgatgcgta tgatagcgaa tatttcgcga   1500
```

```
ccaaagtcca aaacaccaac ggcgtctatg tcgtcccggc gttcaccggc ttgggcgcgc    1560
cgtattggga tccgtatgcg cgcggcgcga tcttcggctt gacccgcggc gtcaacgcga    1620
accacatcat ccgcgcgacc ttggaaagca tcgcgtatca aacccgcgat gtcttggaag    1680
cgatgcaagc ggatagcggc atccgcttgc acgcgttgcg cgtcgatggc ggcgcggtcg    1740
cgaacaactt cttgatgcaa ttccaaagcg atatcttggg cacccgcgtc gaacgcccgg    1800
aagtccgcga agtcaccgcg ttgggcgcgg cgtatttggc gggcttggcg gtcggcttct    1860
ggcaaaactt ggatgaattg caagaaaaag cggtcatcga acgcgaattc cgcccgggca    1920
tcgaaaccac cgaacgcaac tatcgctatg cgggctggaa aaaagcggtc aaacgcgcga    1980
tggcgtggga agaacacgat gaataataat aattaaaaac tttcggagca catcacatgg    2040
aaaccaaaga tttgatcgtc atcggcggcg gcatcaacgg cgcgggcatc gcggcggatg    2100
cggcgggccg cggcttgagc gtcttgatgt tggaagcgca agatttggcg tgcgcgacca    2160
gcagcgcgag cagcaaattg atccacggcg gcttgcgcta tttggaacac tatgaattcc    2220
gcttggtcag cgaagcgttg gcggaacgcg aagtcttgtt gaaaatggcg ccgcacatcg    2280
cgttcccgat gcgcttccgc ttgccgcacc gcccgcactt gcgcccggcg tggatgatcc    2340
gcatcggctt gttcatgtat gatcacttgg caaacgcac cagcttgccg gcagcaccg    2400 gcttgcgctt cggcgcgaac agcgtcttga accggaaat caaacgcggc ttcgaatata    2460
gcgattgctg ggtcgatgat gcgcgcttgg tcttggcgaa cgcgcaaatg gtcgtccgca    2520
aaggcggcga agtcttgacc cgcacccgcg cgaccagcgc gcgccgcgaa acggcttgt    2580 ggatcgtcga agcggaagat atcgataccg gcaaaaaata tagctggcaa gcgcgcggct    2640
tggtcaacgc gaccggcccg tgggtcaaac aattcttcga tgatggcatg cacttgccga    2700
gcccgtatgg catccgcttg atcaaaggca gccacatcgt cgtcccgcgc gtccacaccc    2760
aaaaacaagc gtatatcttg caaaacgaag ataaacgcat cgtcttcgtc atcccgtgga    2820
tggatgaatt cagcatcatc ggcaccaccg atgtcgaata taaaggcgat ccgaaagcgg    2880
tcaaaatcga agaaagcgaa atcaactatt tgttgaacgt ctataacacc cacttcaaaa    2940
aacaattgag ccgcgatgat atcgtctgga cctatagcgg cgtccgcccg ttgtgcgatg    3000
atgaaagcga tagcccgcaa gcgatcaccc gcgattatac cttggatatc cacgatgaaa    3060
acggcaaagc gccgttgttg agcgtcttcg gcggcaaatt gaccacctat cgcaaattgg    3120
cggaacacgc gttggaaaaa ttgacccgt attatcaagg catcggcccg gcgtggacca    3180
aagaaagcgt cttgccgggc ggcgcgatcg aaggcgatcg cgatgattat gcggcgcgct    3240
tgcgccgccg ctatccgttc ttgaccgaaa gcttggcgcg ccactatgcg cgcacctatg    3300
gcagcaacag cgaattgttg ttgggcaacg cgggcaccgt cagcgatttg ggcgaagatt    3360
tcggccacga attctatgaa gcggaattga atatttggt cgatcacgaa tgggtccgcc    3420
gcgcggatga tgcgttgtgg cgccgcacca acaaggcat gtggttgaac gcggatcaac    3480
aaagccgcgt cagccaatgg ttggtcgaat atacccaaca acgcttgagc ttggcgagct    3540
aataataatt aaaaactttc ggagcacatc acatgagcca aaccagcacc ttgaaaggcc    3600
aatgcatcgc ggaattcttg gcaccggct tgttgatctt cttcggcgtc ggctgcgtcg    3660
cggcgttgaa agtcgcgggc gcgagcttcg gccaatggga aatcagcgtc atctgggct    3720 tgggcgtcgc gatggcgatc tatttgaccg cgggcgtcag cggcgcgcac ttgaacccgg    3780
cggtcaccat cgcgttgtgg ttgttcgcgt gcttcgataa acgcaaagtc atcccgttca    3840
tcgtcagcca agtcgcgggc gcgttctgcg cggcggcgtt ggtctatggc ttgtattata    3900
```

```
acttgttctt cgatttcgaa caaacccacc acatcgtccg cggcagcgtc gaaagcgtcg    3960
atttggcggg caccttcagc acctatccga acccgcacat caacttcgtc caagcgttcg    4020
cggtcgaaat ggtcatcacc gcgatcttga tgggcttgat cttggcgttg accgatgatg    4080
gcaacggcgt cccgcgcggc ccgttggcgc cgttgttgat cggcttgttg atcgcggtca    4140
tcggcgcgag catgggcccg ttgaccggct tcgcgatgaa cccggcgcgc gatttcggcc    4200
cgaaagtctt cgcgtggttg gcgggctggg caacgtcgc gttcaccggc ggccgcgata    4260
tcccgtattt cttggtcccg ttgttcggcc cgatcgtcgg cgcgatcgtc ggcgcgttcg    4320
cgtatcgcaa attgatcggc cgccacttgc cgtgcgatat ctgcgtcgtc gaagaaaaag    4380
aaaccaccac cccgagcgaa caaaaagcga gcttgtaa                           4418

<210> SEQ ID NO 110
<211> LENGTH: 229
<212> TYPE: DNA
<213> ORGANISM: Artificial Sequence
<220> FEATURE:
<223> OTHER INFORMATION: MDH promoter

<400> SEQUENCE: 110
tttgcctcga tcggcggtcc ttgtgacagg gagatattcc cgacggatcc ggggcattcg      60
agcggaaccg cccgccgtgg gagttttttcc agcgagcatt cgagagtttt tcaaggcggc     120
ttcgaggggt tattccgtaa cgccgccgac atgatctgtc ccagaatctc cgccgctgtt     180
cgtagagcgc cgatgcaggg tcggcatcaa tcattcttgg aggagacac                 229

<210> SEQ ID NO 111
<211> LENGTH: 1959
<212> TYPE: DNA
<213> ORGANISM: Artificial Sequence
<220> FEATURE:
<223> OTHER INFORMATION: codon optimized AcsA

<400> SEQUENCE: 111
atgtcgcaga tccataagca taccatcccg gcgaacatcg cggaccgctg cctgatcaac      60
ccgcagcagt atgaggcgat gtatcagcag tcgatcaacg tcccggacac cttctggggc     120
gagcagggca agatcctgga ctggatcaag ccgtatcaga aggtcaagaa cacctcgttc     180
gcgccgggca acgtctcgat caagtggtat gaggacggca ccctgaacct ggcggcgaac     240
tgcctggacc gccatctgca ggagaacggc gaccgcaccg cgatcatctg ggagggcgac     300
gacgcgtcgc agtcgaagca tatctcgtat aaggagctgc atcgcgacgt ctgccgcttc     360
gcgaacaccc tgctggagct gggcatcaag aagggcgacg tcgtcgcgat ctatatgccg     420
atggtcccgg aggcggcgt cgcgatgctg cgtgcgcgc catcggcgc ggtccattcg     480 gtcatcttcg cggcttctc gccggaggcg gtcgcgggcc gcatcatcga ctcgaactcg     540
cgcctggtca tcacctcgga cgagggcgtc cgcgcgggcc gtcgatccc gctgaagaag     600 aacgtcgacg acgcgctgaa gaacccgaac gtcacctcgg tcgagcatgt cgtcgtcctg     660
aagcgcaccg gcggcaagat cgactggcag gagggccgcg acctgtggtg gcatgacctg     720
gtcgagcagg cgtcggacca gcatcaggcg gaggagatga acgcggagga cccgctgttc     780
atcctgtata cctcgggctc gaccggcaag ccgaagggcg tcctgcatac caccggcggc     840
tatctggtct atgcggcgct gaccttcaag tatgtcttcg actatcatcc gggcgacatc     900
tattggtgca ccgcggacgt cggctggtc accggccatt cgtatctgct gtatggcccg     960
```

```
ctggcgtgcg gcgcgaccac cctgatgttc gagggcgtcc cgaactggcc gaccccggcg    1020
cgcatggcgc aggtcgtcga caagcatcag gtcaacatcc tgtataccgc gccgaccgcg    1080
atccgcgcgc tgatggcgga gggcgacaag gcgatcgagg gcaccgaccg ctcgtcgctg    1140
cgcatcctgg gctcggtcgg cgagccgatc aacccggagg cgtgggagtg gtattggaag    1200
aagatcggca acgagaagtg cccggtcgtc gacacctggt ggcagaccga gaccggcggc    1260
ttcatgatca ccccgctgcc gggcgcgacc gagctgaagg cgggctcggc gacccgcccg    1320
ttcttcggcg tccagccggc gctggtcgac aacgagggca cccgctggag gggcgcgacc    1380
gagggctcgc tggtcatcac cgactcgtgg ccggggccagg cgcgcaccct gttcggcgac    1440
catgagcgct tcgagcagac ctatttctcg accttcaaga acatgtattt ctcgggcgac    1500
ggcgcgcgcc gcgacgagga cggctattat tggatcaccg gccgcgtcga cgacgtcctg    1560
aacgtctcgg gccatcgcct gggcaccgcg gagatcgagt cggcgctggt cgcgcatccg    1620
aagatcgcgg aggcggcggt cgtcggcatc ccgcataaca tcaagggcca ggcgatctat    1680
gcgtatgtca ccctgaacca tggcgaggag ccgtcgccgg agctgtatgc ggaggtccgc    1740
aactgggtcc gcaaggagat cggcccgctg gcgaccccgg acgtcctgca ttggaccgac    1800
tcgctgccga gacccgctc gggcaagatc atgcgccgca tcctgcgcaa gatcgcggcg    1860
ggcgacacct cgaacctggg cgacacctcg accctggcgg acccgggcgt cgtcgagaag    1920
ctgctggagg agaagcaggc gatcgcgatg ccgtcgtga                           1959
```

<210> SEQ ID NO 112
<211> LENGTH: 19
<212> TYPE: DNA
<213> ORGANISM: Artificial Sequence
<220> FEATURE:
<223> OTHER INFORMATION: Intergenic Region

<400> SEQUENCE: 112

```
tcattcttgg aggagacac                                                   19
```

<210> SEQ ID NO 113
<211> LENGTH: 1650
<212> TYPE: DNA
<213> ORGANISM: Artificial Sequence
<220> FEATURE:
<223> OTHER INFORMATION: codon opitmized ActP

<400> SEQUENCE: 113

```
atgaagcgcg tcctgaccgc gctggcggcg accctgccgt cgcggcgaa cgcggcggac     60 gcgatctcgg gcgcggtcga gcgccagccg accaactggc aggcgatcat catgttcctg    120
atcttcgtcg tcttcacccct gggcatcacc tattgggcgt cgaagcgcgt ccgctcgcgc    180
tcggactatt ataccgcggg cggcaacatc accggcttcc agaacggcct ggcgatcgcg    240
ggcgactata tgtcggcggc gtcgttcctg ggcatctcgg cgctggtctt cacctcgggc    300
tatgacggcc tgatctattc gctgggcttc ctggtcggct ggcgatcat cctgttcctg    360 atcgcggagc gcctgcgcaa cctgggccgc tataccttcg cggacgtcgc gtcgtatcgc    420
ctgaagcagg gcccgatccg catcctgtcg cgtgcggct cgctggtcgt cgtcgcgctg    480
tatctgatcg cgcagatggt cggcgcgggc aagctgatcg agctgctgtt cggcctgaac    540
tatcatatcg cggtcgtcct ggtcggcgtc ctgatgatga tgtatgtcct gttcggcggc    600
atgctggcga ccacctgggt ccagatcatc aaggcggtcc tgctgctgtt cggcgcgtcg    660
ttcatggcgt tcatggtcat gaagcatgtc ggcttctcgt tcaacaacct gttctcggag    720
```

```
gcgatggcgg tccatccgaa gggcgtcgac atcatgaagc cgggcggcct ggtcaaggac      780
ccgatctcgg cgctgtcgct gggcctgggc ctgatgttcg gcaccgcggg cctgccgcat      840
atcctgatgc gcttcttcac cgtctcggac gcgcgcgagg cgcgcaagtc ggtcttctat      900
gcgaccggct tcatgggcta tttctatatc ctgaccttca tcatcggctt cggcgcgatc      960
atgctggtcg gcgcgaaccc ggagtataag gacgcggcgg ccatctgat cggcggcaac     1020 aacatggcgc cggtccatct ggcgaacgcg gtcggcggca acctgttcct gggcttcatc     1080
tcggcggtcg cgttcgcgac catcctggcg gtcgtcgcgg gcctgaccct ggcgggcgcg     1140
tcggcggtct cgcatgacct gtatgcgaac gtcttcaaga agggcgcgac cgagcgcgag     1200
gagctgcgcg tctcgaagat caccgtcctg atcctgggcg tcatcgcgat catcctgggc     1260
gtcctgttcg agaaccagaa catcgcgttc atggtcggcc tggcgttcgc gatcgcggcg     1320
tcgtgcaact ccccgatcat cctgctgtcg atgtattggt cgaagctgac cacccgcggc     1380
gcgatgatgg gcggctggct gggcctgatc accgcggtcg tcctgatgat cctgggcccg     1440
accatctggg tccagatcct gggccatgag aaggcgatct ccccgtatga gtatccggcg     1500
ctgttctcga tcaccgtcgc gttcctgggc atctggttct tctcggcgac cgacaactcg     1560
gcggagggcg cgcgcgagcg cgagctgttc cgcgcgcagt tcatccgctc gcagaccggc     1620
ttcggcgtcg agcagggccg cgcgcattga                                      1650

<210> SEQ ID NO 114
<211> LENGTH: 3857
<212> TYPE: DNA
<213> ORGANISM: Artificial Sequence
<220> FEATURE:
<223> OTHER INFORMATION: Acetate Utilization Pathway Operon

<400> SEQUENCE: 114
tttgcctcga tcggcggtcc ttgtgacagg gagatattcc cgacggatcc ggggcattcg       60
agcggaaccg cccgccgtgg gagttttttcc agcgagcatt cgagagtttt tcaaggcggc      120
ttcgaggggt tattccgtaa cgccgccgac atgatctgtc ccagaatctc cgccgctgtt      180
cgtagagcgc cgatgcaggg tcggcatcaa tcattcttgg aggagacaca tgtcgcagat      240
ccataagcat accatcccgg cgaacatcgc ggaccgctgc ctgatcaacc cgcagcagta      300
tgaggcgatg tatcagcagt cgatcaacgt cccggacacc ttctggggcg agcagggcaa      360
gatcctggac tggatcaagc cgtatcagaa ggtcaagaac acctcgttcg cgccgggcaa      420
cgtctcgatc aagtggtatg aggacggcac cctgaacctg gcggcgaact gcctggaccg      480
ccatctgcag gagaacggcg accgcaccgc gatcatctgg gagggcgacg acgcgtcgca      540
gtcgaagcat atctcgtata aggagctgca tcgcgacgtc tgccgcttcg cgaacaccct      600
gctggagctg ggcatcaaga agggcgacgt cgtcgcgatc tatatgccga tggtcccgga      660
ggcggcggtc gcgatgctgg cgtgcgcgcg catcggcgcg gtccattcgg tcatcttcgg      720
cggcttctcg ccggaggcgg tcgcgggccg catcatcgac tcgaactcgc gcctggtcat      780
cacctcggac gagggcgtcc gcgcgggccg ctcgatcccg ctgaagaaga acgtcgacga      840
cgcgctgaag aacccgaacg tcacctcggt cgagcatgtc gtcgtcctga gcgcaccgg     900 cggcaagatc gactggcagg agggccgcga cctgtggtgg catgacctgg tcgagcaggc      960 gtcgaccag catcaggcgg aggagatgaa cgcggaggac ccgctgttca tcctgtatac     1020
ctcgggctcg accggcaagc cgaagggcgt cctgcatacc accggcggct atctggtcta     1080
```

```
tgcggcgctg accttcaagt atgtcttcga ctatcatccg ggcgacatct attggtgcac    1140
cgcggacgtc ggctgggtca ccggccattc gtatctgctg tatggcccgc tggcgtgcgg    1200
cgcgaccacc ctgatgttcg agggcgtccc gaactggccg accccggcgc gcatggcgca    1260
ggtcgtcgac aagcatcagg tcaacatcct gtataccgcg ccgaccgcga tccgcgcgct    1320
gatggcggag ggcgacaagg cgatcgaggg caccgaccgc tcgtcgctgc gcatcctggg    1380
ctcggtcggc gagccgatca cccggaggc gtgggagtgg tattggaaga agatcggcaa    1440
cgagaagtgc ccggtcgtcg cacctggtg gcagaccgag accggcggct tcatgatcac    1500
cccgctgccg ggcgcgaccg agctgaaggc gggctcggcg acccgcccgt tcttcggcgt    1560
ccagccggcg ctggtcgaca acgagggcaa cccgctggag ggcgcgaccg agggctcgct    1620
ggtcatcacc gactcgtggc cgggccaggc gcgcaccctg ttcggcgacc atgagcgctt    1680
cgagcagacc tatttctcga ccttcaagaa catgtatttc tcgggcgacg gcgcgcgccg    1740
cgacgaggac ggctattatt ggatcaccgg ccgcgtcgac gacgtcctga acgtctcggg    1800
ccatcgcctg ggcaccgcgg agatcgagtc ggcgctggtc gcgcatccga agatcgcgga    1860
ggcggcggtc gtcggcatcc cgcataacat caagggccag gcgatctatg cgtatgtcac    1920
cctgaaccat ggcgaggagc cgtcgccgga gctgtatgcg gaggtccgca actgggtccg    1980
caaggagatc ggcccgctgg cgaccccgga cgtcctgcat tggaccgact cgctgccgaa    2040
gacccgctcg ggcaagatca tgcgccgcat cctgcgcaag atcgcggcgg gcgacacctc    2100
gaacctgggc gacacctcga ccctggcgga cccgggcgtc gtcgagaagc tgctggagga    2160
gaagcaggcg atcgcgatgc cgtcgtgatc attcttggag gagacacatg aagcgcgtcc    2220
tgaccgcgct ggcggcgacc ctgccgttcg cggcgaacgc ggcggacgcg atctcgggcg    2280
cggtcgagcg ccagccgacc aactggcagg cgatcatcat gttcctgatc ttcgtcgtct    2340
tcaccctggg catcacctat gggcgtcga agcgcgtccg ctcgcgctcg gactattata    2400 ccgcgggcg caacatcacc ggcttccaga acggcctggc gatcgcgggc gactatatgt    2460
cggcggcgtc gttcctgggc atctcggcgc tggtcttcac ctcgggctat gacggcctga    2520
tctattcgct gggcttcctg gtcggctggc cgatcatcct gttcctgatc gcggagcgcc    2580
tgcgcaacct gggccgctat accttcgcgg acgtcgcgtc gtatcgcctg aagcagggcc    2640
cgatccgcat cctgtcggcg tgcggctcgc tggtcgtcgt cgcgctgtat ctgatcgcgc    2700
agatggtcgg cgcgggcaag ctgatcgagc tgctgttcgg cctgaactat catatcgcgg    2760
tcgtcctggt cggcgtcctg atgatgatgt atgtcctgtt cggcggcatg ctggcgacca    2820
cctgggtcca gatcatcaag gcggtcctgc tgctgttcgg cgcgtcgttc atggcgttca    2880
tggtcatgaa gcatgtcggc ttctcgttca caacctgtt ctcggaggcg atggcggtcc    2940
atccgaaggg cgtcgacatc atgaagccgg cggcctggt caaggacccg atctcggcgc    3000
tgtcgctggg cctgggcctg atgttcggca ccgcgggcct gccgcatatc ctgatgcgct    3060
tcttcaccgt ctcggacgcg cgcgaggcgc gcaagtcggt cttctatgcg accggcttca    3120
tgggctattt ctatatcctg accttcatca tcggcttcgg cgcgatcatg ctggtcggcg    3180
cgaacccgga gtataaggac gcggcgggcc atctgatcgg cggcaacaac atggcggcgg    3240
tccatctggc gaacgcggtc ggcggcaacc tgttcctggg cttcatctcg gcggtcgcgt    3300
tcgcgaccat cctggcggtc gtcggggcc tgacccggc gggcgcgtcg cggtctcgc    3360 atgacctgta tgcgaacgtc ttcaagaagg gcgcgaccga gcgcgaggag ctgcgcgtct    3420
cgaagatcac cgtcctgatc ctgggcgtca tcgcgatcat cctgggcgtc ctgttcgaga    3480
```

```
accagaacat cgcgttcatg gtcggcctgg cgttcgcgat cgcggcgtcg tgcaacttcc    3540
cgatcatcct gctgtcgatg tattggtcga agctgaccac ccgcggcgcg atgatgggcg    3600
gctggctggg cctgatcacc gcggtcgtcc tgatgatcct gggcccgacc atctgggtcc    3660
agatcctggg ccatgagaag gcgatcttcc cgtatgagta tccggcgctg ttctcgatca    3720
ccgtcgcgtt cctgggcatc tggttcttct cggcgaccga caactcggcg agggcgcgc    3780 gcgagcgcga gctgttccgc gcgcagttca tccgctcgca gaccggcttc ggcgtcgagc    3840
agggccgcgc gcattga                                                  3857
```

<210> SEQ ID NO 115
<211> LENGTH: 229
<212> TYPE: DNA
<213> ORGANISM: Artificial Sequence
<220> FEATURE:
<223> OTHER INFORMATION: MDH promoter

<400> SEQUENCE: 115

```
tttgcctcga tcggcggtcc ttgtgacagg gagatattcc cgacggatcc ggggcattcg     60
agcggaaccg cccgccgtgg gagttttttcc agcgagcatt cgagagttttt tcaaggcggc    120 ttcgaggggt tattccgtaa cgccgccgac atgatctgtc ccagaatctc cgccgctgtt    180
cgtagagcgc cgatgcaggg tcggcatcaa tcattcttgg aggagacac                229
```

<210> SEQ ID NO 116
<211> LENGTH: 1959
<212> TYPE: DNA
<213> ORGANISM: Artificial Sequence
<220> FEATURE:
<223> OTHER INFORMATION: codon optimized AcsA

<400> SEQUENCE: 116

```
atgagccaga tccacaagca caccatcccg gccaacatcg ccgaccgctg cctgatcaac     60
ccgcagcagt acgaggccat gtaccagcag agcatcaacg tcccggacac cttctggggc    120
gagcagggca agatcctgga ctggatcaag ccgtaccaga aggtcaagaa caccagcttc    180
gccccgggca acgtcagcat caagtggtac gaggacggca ccctgaacct ggccgccaac    240
tgcctggacc gccacctgca ggagaacggc gaccgcaccg ccatcatctg ggagggcgac    300
gacgccagcc agagcaagca catcagctac aaggagctgc accgcgacgt ctgccgcttc    360
gccaacaccc tgctggagct gggcatcaag aagggcgacg tcgtcgccat ctacatgccg    420
atggtcccgg aggccgccgt cgccatgctg gcctgcgccc gcatcggcgc cgtccacagc    480
gtcatcttcg gcggcttcag cccggaggcc gtcgccggcc gcatcatcga cagcaacagc    540
cgcctggtca tcaccagcga cgagggcgtc cgcgccggcc gcagcatccc gctgaagaag    600
aacgtcgacg acgccctgaa gaacccgaac gtcaccagcg tcgagcacgt cgtcgtcctg    660
aagcgcaccg cggcaagat cgactggcag gagggccgcg acctgtggtg cacgacctg    720 gtcgagcagg ccagcgacca gcaccaggcc gaggagatga cgccgagga cccgctgttc    780 atcctgtaca ccagcggcag caccggcaag ccgaagggcg tcctgcacac caccggcggc    840
tacctggtct acgccgccct gaccttcaag tacgtcttcg actaccaccc gggcgacatc    900
tactggtgca ccgccgacgt cggctgggtc accggccaca gctacctgct gtacggcccg    960
ctggcctgcg gcgccaccac cctgatgttc gagggcgtcc cgaactggcc gaccccggcc   1020
cgcatggccc aggtcgtcga caagcaccag gtcaacatcc tgtacaccgc cccgaccgcc   1080
```

```
atccgcgccc tgatggccga gggcgacaag gccatcgagg gcaccgaccg cagcagcctg      1140
cgcatcctgg gcagcgtcgg cgagccgatc aacccggagg cctggagtg gtactggaag      1200 aagatcggca acgagaagtg cccggtcgtc gacacctggt ggcagaccga gaccggcggc      1260
ttcatgatca ccccgctgcc gggcgccacc gagctgaagg ccggcagcgc cacccgcccg      1320
ttcttcggcg tccagccggc cctggtcgac aacgagggca acccgctgga gggcgccacc      1380
gagggcagcc tggtcatcac cgacagctgg ccgggccagg cccgcaccct gttcggcgac      1440
cacgagcgct tcgagcagac ctacttcagc accttcaaga acatgtactt cagcggcgac      1500 ggcgccgcc gcgacgagga cggctactac tggatcaccg ccgcgtcga cgacgtcctg      1560 aacgtcagcg ccaccgcct gggcaccgcc gagatcgaga gcgccctggt cgcccacccg      1620
aagatcgccg aggccgccgt cgtcggcatc ccgcacaaca tcaagggcca ggccatctac      1680
gcctacgtca ccctgaacca cggcgaggag ccgagcccgg agctgtacgc cgaggtccgc      1740
aactgggtcc gcaaggagat cggcccgctg gccaccccgg acgtcctgca ctggaccgac      1800
agcctgccga agaccccgcag cggcaagatc atgcccgcga tcctgcgcaa gatcgccgcc      1860
ggcgacacca gcaacctggg cgacaccagc accctggccg acccgggcgt cgtcgagaag      1920
ctgctggagg agaagcaggc catcgccatg ccgagctga                            1959
```

<210> SEQ ID NO 117
<211> LENGTH: 19
<212> TYPE: DNA
<213> ORGANISM: Artificial Sequence
<220> FEATURE:
<223> OTHER INFORMATION: Intergenic Region

<400> SEQUENCE: 117

```
tcattcttgg aggagacac                                                    19
```

<210> SEQ ID NO 118
<211> LENGTH: 1650
<212> TYPE: DNA
<213> ORGANISM: Artificial Sequence
<220> FEATURE:
<223> OTHER INFORMATION: Codon optimized ActP

<400> SEQUENCE: 118

```
atgaagcgcg tcctgaccgc cctggccgcc ccctgccgt cgccgccaa cgccgccgac       60 gccatcagcg gcgccgtcga gcgccagccg accaactggc aggccatcat catgttcctg     120
atcttcgtcg tcttcaccct gggcatcacc tactgggcca gcaagcgcgt ccgcagccgc     180
agcgactact acaccgccgg cggcaacatc accggcttcc agaacggcct ggccatcgcc     240
ggcgactaca tgagcgccgc cagcttcctg ggcatcagcg ccctggtctt caccagcggc     300
tacgacggcc tgatctacag cctgggcttc ctggtcggct ggccgatcat cctgttcctg     360
atcgccgagc gcctgcgcaa cctgggccgc tacaccttcg ccgacgtcgc cagctaccgc     420
ctgaagcagg gcccgatccg catcctgagc gcctgcggca gcctggtcgt cgtcgccctg     480
tacctgatcg cccagatggt cggcgccggc aagctgatcg agctgctgtt cggcctgaac     540
taccacatcg ccgtcgtcct ggtcggcgtc ctgatgatga tgtacgtcct gttcggcggc     600
atgctggcca ccacctgggt ccagatcatc aaggccgtcc tgctgctgtt cggcgccagc     660
ttcatggcct tcatggtcat gaagcacgtc ggcttcagct tcaacaacct gttcagcgag     720
gccatggccg tccacccgaa gggcgtcgac atcatgaagc gggcggcct ggtcaaggac     780 ccgatcagcg ccctgagcct gggcctgggc ctgatgttcg gcaccgccgg cctgccgcac     840
```

```
atcctgatgc gcttcttcac cgtcagcgac gcccgcgagg cccgcaagag cgtcttctac    900
gccaccggct tcatgggcta cttctacatc ctgaccttca tcatcggctt cggcgccatc    960
atgctggtcg cgccaacccc ggagtacaag gacgccgccg ccacctgatc ggcggcaac    1020
aacatggccc ccgtccacct ggccaacgcc gtcggcggca acctgttcct gggcttcatc   1080
agcgccgtcg ccttcgccac catcctggcc gtcgtcgccg gcctgaccct ggccggcgcc   1140
agcgccgtca gccacgacct gtacgccaac gtcttcaaga agggcgccac cgagcgcgag   1200
gagctgcgcg tcagcaagat caccgtcctg atcctgggcg tcatcgccat catcctgggc   1260
gtcctgttcg agaaccagaa catcgccttc atggtcggcc tggccttcgc catcgccgcc   1320
agctgcaact ccccgatcat cctgctgagc atgtactgga gcaagctgac cacccgcggc   1380
gccatgatgg gcggctggct gggcctgatc accgccgtcg tcctgatgat cctgggcccg   1440
accatctggg tccagatcct gggccacgag aaggccatct ccccgtacga gtacccggcc   1500
ctgttcagca tcaccgtcgc cttcctgggc atctggttct tcagcgccac cgacaacagc   1560
gccgagggcg cccgcgagcg cgagctgttc cgcgcccagt tcatccgcag ccagaccggc   1620
ttcggcgtcg agcagggccg cgcccactga                                    1650

<210> SEQ ID NO 119
<211> LENGTH: 3857
<212> TYPE: DNA
<213> ORGANISM: Artificial Sequence
<220> FEATURE:
<223> OTHER INFORMATION: Acetate Utilization Pathway Operon

<400> SEQUENCE: 119
tttgcctcga tcggcggtcc ttgtgacagg gagatattcc cgacggatcc ggggcattcg     60
agcggaaccg cccgccgtgg gagttttttcc agcgagcatt cgagagtttt tcaaggcggc    120
ttcgagggggt tattccgtaa cgccgccgac atgatctgtc ccagaatctc cgccgctgtt    180
cgtagagcgc cgatgcaggg tcggcatcaa tcattcttgg aggagacaca tgagccagat    240
ccacaagcac accatcccgg ccaacatcgc cgaccgctgc ctgatcaacc cgcagcagta    300
cgaggccatg taccagcaga gcatcaacgt cccggacacc ttctggggcg agcagggcaa    360
gatcctggac tggatcaagc cgtaccagaa ggtcaagaac accagcttcg ccccgggcaa    420
cgtcagcatc aagtggtacg aggacggcac cctgaacctg gccgccaact gcctggaccg    480
ccacctgcag gagaacggcg accgcaccgc catcatctgg gagggcgacg acgccagcca    540
gagcaagcac atcagctaca aggagctgca ccgcgacgtc tgccgcttcg ccaacaccct    600
gctggagctg ggcatcaaga agggcgacgt cgtcgccatc tacatgccga tggtcccgga    660
ggccgccgtc gccatgctgg cctgcgcccc catcggcgcc gtccacagcg tcatcttcgg    720
cggcttcagc ccggaggccg tcgccggccg catcatcgac agcaacagcc gcctggtcat    780
caccagcgac gagggcgtcc gcgccggccg cagcatcccg ctgaagaaga acgtcgacga    840
cgccctgaag aacccgaacg tcaccagcgt cgagcacgtc gtcgtcctga gcgcaccgg     900
cggcaagatc gactggcagg agggccgcga cctgtggtgg cacgacctgg tcgagcaggc    960
cagcgaccag caccaggccg aggagatgaa cgccgaggac ccgctgttca tcctgtacac   1020
cagcggcagc accggcaagc cgaagggcgt cctgcacacc accggcggct acctggtcta   1080
cgccgccctg accttcaagt acgtcttcga ctaccacccg ggcgacatct actggtgcac   1140
cgccgacgtc ggctgggtca ccggccacag ctacctgctg tacggcccgc tggcctgcgg   1200
```

| | |
|---|---|
| cgccaccacc ctgatgttcg agggcgtccc gaactggccg accccggccc gcatggccca | 1260 |
| ggtcgtcgac aagcaccagg tcaacatcct gtacaccgcc ccgaccgcca tccgcgccct | 1320 |
| gatggccgag ggcgacaagg ccatcgaggg caccgaccgc agcagcctgc gcatcctggg | 1380 |
| cagcgtcggc gagccgatca acccggaggc ctgggagtgg tactggaaga agatcggcaa | 1440 |
| cgagaagtgc ccggtcgtcg acacctggtg gcagaccgag accggcggct tcatgatcac | 1500 |
| cccgctgccg ggcgccaccg agctgaaggc cggcagcgcc acccgcccgt tcttcggcgt | 1560 |
| ccagccggcc ctggtcgaca acgagggcaa cccgctggag ggcgccaccg agggcagcct | 1620 |
| ggtcatcacc gacagctggc cgggccaggc ccgcaccctg ttcggcgacc acgagcgctt | 1680 |
| cgagcagacc tacttcagca ccttcaagaa catgtacttc agcggcgacg gcgcccgccg | 1740 |
| cgacgaggac ggctactact ggatcaccgg ccgcgtcgac gacgtcctga acgtcagcgg | 1800 |
| ccaccgcctg ggcaccgccg agatcgagag cgccctggtc gcccacccga gatcgccga | 1860 |
| ggccgccgtc gtcggcatcc cgcacaacat caagggccag gccatctacg cctacgtcac | 1920 |
| cctgaaccac ggcgaggagc cgagcccgga gctgtacgcc gaggtccgca actgggtccg | 1980 |
| caaggagatc ggcccgctgg ccaccccgga cgtcctgcac tggaccgaca gcctgccgaa | 2040 |
| gacccgcagc ggcaagatca tgcgccgcat cctgcgcaag atcgccgccg cgacaccag | 2100 |
| caacctgggc gacaccagca ccctggccga cccgggcgtc gtcgagaagc tgctggagga | 2160 |
| gaagcaggcc atcgccatgc cgagctgatc attcttggag gagacacatg aagcgcgtcc | 2220 |
| tgaccgccct ggccgccacc ctgccgttcg ccgccaacgc cgccgacgcc atcagcggcg | 2280 |
| ccgtcgagcg ccagccgacc aactggcagg ccatcatcat gttcctgatc ttcgtcgtct | 2340 |
| tcaccctggg catcacctac tgggccagca agcgcgtccg cagccgcagc gactactaca | 2400 |
| ccgccggcg caacatcacc ggcttccaga acggcctggc catcgccggc gactacatga | 2460 |
| gcgccgccag cttcctgggc atcagcgccc tggtcttcac cagcggctac gacggcctga | 2520 |
| tctacagcct gggcttcctg gtcggctggc cgatcatcct gttcctgatc gccgagcgcc | 2580 |
| tgcgcaacct gggccgctac accttcgccg acgtcgccag ctaccgcctg aagcagggcc | 2640 |
| cgatccgcat cctgagcgcc tgcggcagcc tggtcgtcgt cgccctgtac ctgatcgccc | 2700 |
| agatggtcgg cgccggcaag ctgatcgagc tgctgttcgg cctgaactac cacatcgccg | 2760 |
| tcgtcctggt cggcgtcctg atgatgatgt acgtcctgtt cggcggcatg ctggccacca | 2820 |
| cctgggtcca gatcatcaag gccgtcctgc tgctgttcgg cgccagcttc atggccttca | 2880 |
| tggtcatgaa gcacgtcggc ttcagcttca acaacctgtt cagcgaggcc atggccgtcc | 2940 |
| acccgaaggg cgtcgacatc atgaagccgg gcggcctggt caaggacccg atcagcgccc | 3000 |
| tgagcctggg cctgggcctg atgttcggca ccgccggcct gccgcacatc ctgatgcgct | 3060 |
| tcttcaccgt cagcgacgcc cgcgaggccc gcaagagcgt cttctacgcc accggcttca | 3120 |
| tgggctactt ctacatcctg accttcatca tcggcttcgg cgccatcatg ctggtcggcg | 3180 |
| ccaacccgga gtacaaggac gccgccggcc acctgatcgg cggcaacaac atggccgccg | 3240 |
| tccacctggc caacgccgtc ggcggcaacc tgttcctggg cttcatcagc gccgtcgcct | 3300 |
| tcgccaccat cctggccgtc gtccgccgcc tgacccggc cggcgccagc gccgtcagcc | 3360 |
| acgacctgta cgccaacgtc ttcaagaagg cgccaccga gcgcgaggag ctgcgcgtca | 3420 |
| gcaagatcac cgtcctgatc ctgggcgtca tcgccatcat cctgggcgtc ctgttcgaga | 3480 |
| accagaacat cgccttcatg gtcggcctgg ccttcgccat cgccgccagc tgcaacttcc | 3540 |
| cgatcatcct gctgagcatg tactggagca agctgaccac ccgcggcgcc atgatgggcg | 3600 |

```
gctggctggg cctgatcacc gccgtcgtcc tgatgatcct gggcccgacc atctgggtcc    3660
agatcctggg ccacgagaag gccatcttcc cgtacgagta cccggccctg ttcagcatca    3720
ccgtcgcctt cctgggcatc tggttcttca gcgccaccga caacagcgcc gagggcgccc    3780
gcgagcgcga gctgttccgc gcccagttca tccgcagcca gaccggcttc ggcgtcgagc    3840
agggccgcgc ccactga                                                    3857
```

<210> SEQ ID NO 120
<211> LENGTH: 497
<212> TYPE: DNA
<213> ORGANISM: Artificial Sequence
<220> FEATURE:
<223> OTHER INFORMATION: HPS promoter

<400> SEQUENCE: 120

```
ttcggaatcc ctgacgggaa ttggcccgaa gaaggcagat gccatcgttc agtatcgaaa     60
ggaacatggg gattttcagt cattgaagga tctggagaat gtcagcggca ttggcgagaa    120
aacccttcag gccaatgaaa aagacattcg cttcacggat gatttgagcg ataagtcatc    180
cgcggaaaaa ggtgcggtag ctgtggataa aaaaggcgcc agatagtaag cgctaaggat    240
tggggtgcgt cgccggtcgc ggcggcgctc ctcgacggca gagttggtgc caggttggcg    300
gatgattgat gccgaatatt acgcgaccaa ttctcgaggc aaatgaactg tgagctactg    360
agttgcaggc attgacagcc atcccatttc tatcatacag ttacggacgc atcacgagta    420
ggtgataagc ctagcagatt gcggcagttg gcaaaatcag ctattactaa taattaaaaa    480
ctttcggagc acatcac                                                   497
```

<210> SEQ ID NO 121
<211> LENGTH: 1959
<212> TYPE: DNA
<213> ORGANISM: Artificial Sequence
<220> FEATURE:
<223> OTHER INFORMATION: codon optimized AcsA

<400> SEQUENCE: 121

```
atgagccaaa tccacaaaca ccatcccg gcgaacatcg cggatcgctg cttgatcaac     60
ccgcaacaat atgaagcgat gtatcaacaa agcatcaacg tcccggatac cttctggggc    120
gaacaaggca aatcttgga ttggatcaaa ccgtatcaaa aagtcaaaaa caccagcttc    180
gcgccgggca acgtcagcat caaatggtat gaagatggca ccttgaactt ggcggcgaac    240
tgcttggatc gccacttgca agaaaacggc gatcgcaccg cgatcatctg gaaggcgat    300 gatgcgagcc aaagcaaaca catcagctat aaagaattgc accgcgatgt ctgccgcttc    360 gcgaacaccct tgttggaatt gggcatcaaa aaggcgatg tcgtcgcgat ctatatgccg    420
atggtcccgg aagcggcggt cgcgatgttg gcgtgcgcgc catcggcgc ggtccacagc    480 gtcatcttcg gcggcttcag cccggaagcg gtcgcgggcc gcatcatcga tagcaacagc    540
cgcttggtca tcaccagcga tgaaggcgtc gcgcgggcc gcagcatccc gttgaaaaaa    600
aacgtcgatg atgcgttgaa aaacccgaac gtcaccagcg tcgaacacgt cgtcgtcttg    660
aaacgcaccg cggcaaaat cgattggcaa gaaggccgcg atttgtggtg cacgatttg    720 gtcgaacaag cgagcgatca cacccaagcg gaagaaatga cgcggaaga tccgttgttc    780 atcttgtata ccagcggcag caccggcaaa ccgaaaggcg tcttgcacac caccggcggc    840
tatttggtct atgcggcgtt gaccttcaaa tatgtcttcg attatcaccc gggcgatatc    900
```

```
tattggtgca ccgcggatgt cggctgggtc accggccaca gctatttgtt gtatggcccg    960
ttggcgtgcg gcgcgaccac cttgatgttc gaaggcgtcc cgaactggcc gaccccggcg   1020
cgcatggcgc aagtcgtcga taaacaccaa gtcaacatct tgtataccgc gccgaccgcg   1080
atccgcgcgt tgatggcgga aggcgataaa gcgatcgaag caccgatcg cagcagcttg    1140
cgcatcttgg gcagcgtcgg cgaaccgatc aacccggaag cgtgggaatg gtattggaaa   1200
aaaatcggca acgaaaaatg cccggtcgtc gatacctggt ggcaaaccga accggcggc    1260
ttcatgatca ccccgttgcc gggcgcgacc gaattgaaag cgggcagcgc gacccgcccg   1320
ttcttcggcg tccaaccggc gttggtcgat aacgaaggca accgttggaa aggcgcgacc   1380
gaaggcagct tggtcatcac cgatagctgg ccgggccaag cgcgcacctt gttcggcgat   1440
cacgaacgct tcaacaaac ctatttcagc accttcaaaa acatgtattt cagcggcgat    1500
ggcgcgcgcc gcgatgaaga tggctattat tggatcaccg gccgcgtcga tgatgtcttg   1560
aacgtcagcg gccaccgctt gggcaccgcg gaaatcgaaa gcgcgttggt cgcgcacccg   1620
aaaatcgcgg aagcggcggt cgtcggcatc ccgcacaaca tcaaaggcca agcgatctat   1680
gcgtatgtca ccttgaacca cggcgaagaa ccgagcccgg aattgtatgc ggaagtccgc   1740
aactgggtcc gcaaagaaat cggcccgttg gcgaccccgg atgtcttgca ctggaccgat   1800
agcttgccga aacccgcag cggcaaaatc atgcgccgca tcttgcgcaa aatcgcggcg    1860
ggcgatacca gcaacttggg cgataccagc accttggcgg atccgggcgt cgtcgaaaaa   1920
ttgttggaag aaaaacaagc gatcgcgatg ccgagctaa                          1959

<210> SEQ ID NO 122
<211> LENGTH: 30
<212> TYPE: DNA
<213> ORGANISM: Artificial Sequence
<220> FEATURE:
<223> OTHER INFORMATION: Intergenic Region

<400> SEQUENCE: 122
taataattaa aaactttcgg agcacatcac                                      30

<210> SEQ ID NO 123
<211> LENGTH: 1650
<212> TYPE: DNA
<213> ORGANISM: Artificial Sequence
<220> FEATURE:
<223> OTHER INFORMATION: codon optimized ActP

<400> SEQUENCE: 123
atgaaacgcg tcttgaccgc gttggcggcg accttgccgt tcgcggcgaa cgcggcggat     60
gcgatcagcg cgcggtcga acgccaaccg accaactggc aagcgatcat catgttcttg    120
atcttcgtcg tcttcaccct gggcatcacc tattgggcga gcaaacgcgt ccgcagccgc    180
agcgattatt ataccgcggg cggcaacatc accggcttcc aaaacggctt ggcgatcgcg    240
ggcgattata tgagcgcggc gagcttcttg ggcatcagcg cgttggtctt caccagcggc    300
tatgatggct tgatctatag cttgggcttc ttggtcggct ggccgatcat cttgttcttg    360
atcgcggaac gcttgcgcaa cttggccgc ataccttcg cggatgtcgc gagctatcgc     420
ttgaaacaag gcccgatccg catcttgagc gcgtgcggca gcttggtcgt cgtcgcgttg    480
tatttgatcg cgcaaatggt cggcgcgggc aaattgatcg aattgttgtt cggcttgaac    540
tatcacatcg cggtcgtctt ggtcggcgtc ttgatgatga tgtatgtctt gttcggcggc    600
atgttggcga ccacctgggt ccaaatcatc aaagcggtct tgttgttgtt cggcgcgagc    660
```

```
ttcatggcgt tcatggtcat gaaacacgtc ggcttcagct tcaacaactt gttcagcgaa      720
gcgatggcgg tccacccgaa aggcgtcgat atcatgaaac cgggcggctt ggtcaaagat      780
ccgatcagcg cgttgagctt gggcttgggc ttgatgttcg gcaccgcggg cttgccgcac      840
atcttgatgc gcttcttcac cgtcagcgat gcgcgcgaag cgcgcaaaag cgtcttctat      900
gcgaccggct tcatgggcta tttctatatc ttgaccttca tcatcggctt cggcgcgatc      960
atgttggtcg gcgcgaaccc ggaatataaa gatgcggcgg gccacttgat cggcggcaac     1020
aacatggcgg cggtccactt ggcgaacgcg gtcggcggca acttgttctt gggcttcatc     1080
agcgcggtcg cgttcgcgac catcttggcg gtcgtcgcgg gcttgacctt ggcgggcgcg     1140
agcgcggtca gccacgattt gtatgcgaac gtcttcaaaa aaggcgcgac cgaacgcgaa     1200
gaattgcgcg tcagcaaaat caccgtcttg atcttgggcg tcatcgcgat catcttgggc     1260
gtcttgttcg aaaaccaaaa catcgcgttc atggtcggct ggcgttcgc gatcgcggcg     1320 agctgcaact tcccgatcat cttgttgagc atgtattgga gcaaattgac cacccgcggc     1380
gcgatgatgg gcggctggtt gggcttgatc accgcggtcg tcttgatgat cttgggcccg     1440
accatctggg tccaaatctt gggccacgaa aaagcgatct tcccgtatga atatccggcg     1500
ttgttcagca tcaccgtcgc gttcttgggc atctggttct tcagcgcgac cgataacagc     1560
gcggaaggcg cgcgcgaacg cgaattgttc cgcgcgcaat tcatccgcag ccaaaccggc     1620
ttcggcgtcg aacaaggccg cgcgcactaa                                      1650
```

<210> SEQ ID NO 124
<211> LENGTH: 4136
<212> TYPE: DNA
<213> ORGANISM: Artificial Sequence
<220> FEATURE:
<223> OTHER INFORMATION: Acetate Utilization Pathway Operon
<400> SEQUENCE: 124

```
ttcggaatcc ctgacgggaa ttggcccgaa gaaggcagat gccatcgttc agtatcgaaa       60
ggaacatggg gattttcagt cattgaagga tctggagaat gtcagcggca ttggcgagaa      120
aacccttcag gccaatgaaa aagacattcg cttcacggat gatttgagcg ataagtcatc      180
cgcggaaaaa ggtgcggtag ctgtggataa aaaaggcgcc agatagtaag cgctaaggat      240
tggggtgcgt cgccggtcgc ggcggcgctc ctcgacggca gagttggtgc caggttggcg      300
gatgattgat gccgaatatt acgcgaccaa ttctcgaggc aaatgaactg tgagctactg      360
agttgcaggc attgacagcc atcccatttc tatcatacag ttacggacgc atcacgagta      420
ggtgataagc ctagcagatt gcggcagttg gcaaaatcag ctattactaa taattaaaaa      480
ctttcggagc acatcacatg agccaaatcc acaaacacac catcccggcg aacatcgcgg      540
atcgctgctt gatcaacccg caacaatatg aagcgatgta tcaacaaagc atcaacgtcc      600
cggatacctt ctgggcgaa caaggcaaaa tcttggattg gatcaaaccg tatcaaaaag      660
tcaaaaacac cagcttcgcg ccgggcaacg tcagcatcaa atggtatgaa gatggcacct      720
tgaacttggc ggcgaactgc ttggatcgcc acttgcaaga aaacggcgat cgcaccgcga      780
tcatctggga aggcgatgat gcgagccaaa gcaaacacat cagctataaa gaattgcacc      840
gcgatgtctg ccgcttcgcg aacaccttgt tggaattggg catcaaaaaa ggcgatgtcg      900
tcgcgatcta tatgccgatg gtcccggaag cggcggtcgc gatgttggcg tgcgcgcgca      960
tcggcgcggt ccacagcgtc atcttcggcg gcttcagccc ggaagcggtc gcgggccgca     1020
```

```
tcatcgatag caacagccgc ttggtcatca ccagcgatga aggcgtccgc gcgggccgca   1080
gcatcccgtt gaaaaaaaac gtcgatgatg cgttgaaaaa cccgaacgtc accagcgtcg   1140
aacacgtcgt cgtcttgaaa cgcaccggcg gcaaaatcga ttggcaagaa ggccgcgatt   1200
tgtggtggca cgatttggtc gaacaagcga gcgatcaaca ccaagcggaa gaaatgaacg   1260
cggaagatcc gttgttcatc ttgtatacca gcggcagcac cggcaaaccg aaaggcgtct   1320
tgcacaccac cggcggctat ttggtctatg cggcgttgac cttcaaatat gtcttcgatt   1380
atcacccggg cgatatctat tggtgcaccg cggatgtcgg ctgggtcacc ggccacagct   1440
atttgttgta tggcccgttg gcgtgcgcg cgaccaccett gatgttcgaa ggcgtcccga   1500
actggccgac cccggcgcgc atggcgcaag tcgtcgataa acaccaagtc aacatcttgt   1560
ataccgcgcc gaccgcgatc cgcgcgttga tggcggaagg cgataaagcg atcgaaggca   1620
ccgatcgcag cagcttgcgc atcttgggca gcgtcggcga accgatcaac ccggaagcgt   1680
gggaatggta ttggaaaaaa atcggcaacg aaaaatgccc ggtcgtcgat acctggtggc   1740
aaaccgaaac cggcggcttc atgatcaccc cgttgccggg cgcgaccgaa ttgaaagcgg   1800
gcagcgcgac ccgcccgttc ttcggcgtcc aaccggcgtt ggtcgataac gaaggcaacc   1860
cgttggaagg cgcgaccgaa ggcagcttgg tcatcaccga tagctggccg ggccaagcgc   1920
gcaccttgtt cggcgatcac gaacgcttcg aacaaaccta tttcagcacc ttcaaaaaca   1980
tgtatttcag cggcgatggc gcgcgccgcg atgaagatgg ctattattgg atcaccggcc   2040
gcgtcgatga tgtcttgaac gtcagcggcc accgcttggg caccgcggaa atcgaaagcg   2100
cgttggtcgc gcaccgaaa atcgcggaag cggcggtcgt cggcatcccg cacaacatca   2160
aaggccaagc gatctatgcg tatgtcacct tgaaccacgg cgaagaaccg agcccggaat   2220
tgtatgcgga agtccgcaac tgggtccgca agaaatcgg cccgttggcg accccggatg   2280
tcttgcactg gaccgatagc ttgccgaaaa cccgcagcgg caaaatcatg cgccgcatct   2340
tgcgcaaaat cgcggcgggc gataccagca acttgggcga taccagcacc ttggcggatc   2400
cgggcgtcgt cgaaaaattg ttggaagaaa acaagcgat cgcgatgccg agctaataat   2460
aattaaaaac tttcggagca catcacgta aacgcgtctt gaccgcgttg gcggcgacct   2520
tgccgttcgc ggcgaacgcg gcggatgcga tcagcggcgc ggtcgaacgc caaccgacca   2580
actggcaagc gatcatcatg ttcttgatct tcgtcgtctt caccttgggc atcacctatt   2640
gggcgagcaa acgcgtccgc agccgcagcg attattatac cgcgggcggc aacatcaccg   2700
gcttccaaaa cggcttggcg atcgcggcg attatatgag cgcggcgagc ttcttgggca   2760
tcagcgcgtt ggtcttcacc agcggctatg atggcttgat ctatagcttg gcttcttgg   2820 tcggctggcc gatcatcttg ttcttgatcg cggaacgctt gcgcaacttg gccgctata   2880 ccttcgcgga tgtcgcgagc tatcgcttga acaaggccc gatccgcatc ttgagcgcgt   2940
gcggcagctt ggtcgtcgtc gcgttgtatt tgatcgcgca aatggtcggc gcgggcaaat   3000
tgatcgaatt gttgttcggc ttgaactatc acatcgcggt cgtcttggtc ggcgtcttga   3060
tgatgatgta tgtcttgttc ggcggcatgt tggcgaccac ctgggtccaa atcatcaaag   3120
cggtcttgtt gttgttcggc gcgagcttca tggcgttcat ggtcatgaaa cacgtcggct   3180
tcagcttcaa caacttgttc agcgaagcga tggcggtcca cccgaaaggc gtcgatatca   3240
tgaaaccggg cggcttggtc aaagatccga tcagcgcgtt gagcttgggc ttgggcttga   3300
tgttcggcac cgcgggcttg ccgcacatct tgatgcgctt cttcaccgtc agcgatgcgc   3360
gcgaagcgcg caaaagcgtc ttctatgcga ccggcttcat gggctatttc tatatcttga   3420
```

```
ccttcatcat cggcttcggc gcgatcatgt tggtcggcgc gaacccggaa tataaagatg    3480
cggcgggcca cttgatcggc ggcaacaaca tggcggcggt ccacttggcg aacgcggtcg    3540
gcggcaactt gttcttgggc ttcatcagcg cggtcgcgtt cgcgaccatc ttggcggtcg    3600
tcgcgggctt gaccttggcg ggcgcgagcg cggtcagcca cgatttgtat gcgaacgtct    3660
tcaaaaaagg cgcgaccgaa cgcgaagaat tgcgcgtcag caaaatcacc gtcttgatct    3720
tgggcgtcat cgcgatcatc ttgggcgtct tgttcgaaaa ccaaaacatc gcgttcatgg    3780
tcggcttggc gttcgcgatc gcggcgagct gcaacttccc gatcatcttg ttgagcatgt    3840
attggagcaa attgaccacc cgcggcgcga tgatgggcgg ctggttgggc ttgatcaccg    3900
cggtcgtctt gatgatcttg ggcccgacca tctgggtcca aatcttgggc cacgaaaaag    3960
cgatcttccc gtatgaatat ccggcgttgt tcagcatcac cgtcgcgttc ttgggcatct    4020
ggttcttcag cgcgaccgat aacagcgcgg aaggcgcgcg cgaacgcgaa ttgttccgcg    4080
cgcaattcat ccgcagccaa accggcttcg gcgtcgaaca aggccgcgcg cactaa      4136

<210> SEQ ID NO 125
<211> LENGTH: 229
<212> TYPE: DNA
<213> ORGANISM: Artificial Sequence
<220> FEATURE:
<223> OTHER INFORMATION: MDH promoter

<400> SEQUENCE: 125
tttgcctcga tcggcggtcc ttgtgacagg gagatattcc cgacggatcc ggggcattcg      60
agcggaaccg cccgccgtgg gagttttccc agcgagcatt cgagagtttt tcaaggcggc     120
ttcgaggggt tattccgtaa cgccgccgac atgatctgtc ccagaatctc cgccgctgtt     180
cgtagagcgc cgatgcaggg tcggcatcaa tcattcttgg aggagacac               229

<210> SEQ ID NO 126
<211> LENGTH: 990
<212> TYPE: DNA
<213> ORGANISM: Artificial Sequence
<220> FEATURE:
<223> OTHER INFORMATION: codon optimized LdhD

<400> SEQUENCE: 126
atgaagctgg cggtctattc gaccaagcag tatgacaaga agtatctgca gcaggtcaac     60
gagtcgttcg gcttcgagct ggagttcttc gacttcctgc tgaccgagaa gaccgcgaag    120
accgcgaacg gctgcgaggc ggtctgcatc ttcgtcaacg acgacggctc cgcgcccggtc   180 ctggaggagc tgaagaagca tggcgtcaag tatatcgcgc tgcgctgcgc gggcttcaac    240
aacgtcgacc tggacgcggc gaaggagctg ggcctgaagg tcgtccgcgt cccggcgtat    300
gacccggagg cggtcgcgga gcatgcgatc ggcatgatga tgaccctgaa ccgccgcatc    360
catcgcgcgt atcagcgcac ccgcgacgcg aacttctcgc tggagggcct gaccggcttc    420
accatgtatg gcaagaccgc gggcgtcatc ggcaccggca agatcggcgt cgcgatgctg    480
cgcatcctga gggcttcgg catgcgcctg ctggcgttcg acccgtatcc gtcggcggcg    540
gcgctggagc tgggcgtcga gtatgtcgac ctgccgaccc tgttctcgga gtcggacgtc    600
atctcgctgc attgcccgct gaccccggag aactatcatc tgctgaacga ggcggcgttc    660
gagcagatga gaaacggcgt catgatcgtc aacacctcgc gcggcgcgct gatcgactcg    720
caggcggcga tcgaggcgct gaagaaccag aagatcggct cgctgggcat ggacgtctat    780
```

| gagaacgagc gcgacctgtt cttcgaggac aagtcgaacg acgtcatcca ggacgacgtc | 840 |
| ttccgccgcc tgtcggcgtg ccataacgtc ctgttcaccg gccatcaggc gttcctgacc | 900 |
| gcggaggcgc tgacctcgat ctcgcagacc accctgcaga acctgtcgaa cctggagaag | 960 |
| ggcgagacct gcccgaacga gctggtctga | 990 |

<210> SEQ ID NO 127
<211> LENGTH: 19
<212> TYPE: DNA
<213> ORGANISM: Artificial Sequence
<220> FEATURE:
<223> OTHER INFORMATION: Intergenic Region

<400> SEQUENCE: 127

| tcattcttgg aggagacac | 19 |

<210> SEQ ID NO 128
<211> LENGTH: 1656
<212> TYPE: DNA
<213> ORGANISM: Artificial Sequence
<220> FEATURE:
<223> OTHER INFORMATION: codon optimized LctP

<400> SEQUENCE: 128

| atgaacctgt ggcagcagaa ctatgacccg gcgggcaaca tctggctgtc gtcgctgatc | 60 |
| gcgtcgctgc cgatcctgtt cttcttcttc gcgctgatca agctgaagct gaagggctat | 120 |
| gtcgcggcgt cgtggaccgt cgcgatcgcg ctggcggtcg cgctgctgtt ctataagatg | 180 |
| ccggtcgcga acgcgctggc gtcggtcgtc tatggcttct tctatggcct gtggccgatc | 240 |
| gcgtggatca tcatcgcggc ggtcttcgtc tataagatct cggtcaagac cggccagttc | 300 |
| gacatcatcc gctcgtcgat cctgtcgatc accccggacc agcgcctgca gatgctgatc | 360 |
| gtcggcttct gcttcggcgc gttcctggag ggcgcggcgg gcttcggcgc gccggtcgcg | 420 |
| atcaccgcgg cgctgctggt cggcctgggc ttcaagccgc tgtatgcggc gggcctgtgc | 480 |
| ctgatcgtca acaccgcgcc ggtcgcgttc ggcgcgatgg gcatcccgat cctggtcgcg | 540 |
| ggccaggtca ccggcatcga ctcgttcgag atcggccaga tggtcggccg ccagctgccg | 600 |
| ttcatgacca tcatcgtcct gttctggatc atggcgatca tggacggctg gcgcggcatc | 660 |
| aaggagacct ggccggcggt cgtcgtcgcg ggcggctcgt tcgcgatcgc gcagtatctg | 720 |
| tcgtcgaact tcatcggccc ggagctgccg gacatcatct cgtcgctggt ctcgctgctg | 780 |
| tgcctgaccc tgttcctgaa cgcgctggcag ccggtccgcg tcttccgctt cggcgacctg | 840 |
| ggcgcgtcgc aggtcgacat gaccctggcg cataccggct ataccgcggg ccaggtcctg | 900 |
| cgcgcgtgga ccccgttcct gttcctgacc gcgaccgtca cctgtggtc gatcccgccg | 960 |
| ttcaaggcgc tgttcgcgtc gggcggcgcg ctgtatgagt gggtcatcaa catcccggtc | 1020 |
| ccgtatctgg acaagctggt cgcgcgcatg ccgccggtcg tctcggaggc gaccgcgtat | 1080 |
| gcggcggtct tcaagttcga ctggttctcg gcgaccggca ccgcgatcct gttcgcggcg | 1140 |
| ctgctgtcga tcgtctggct gaagatgaag ccgtcggacg cgatctcgac cttcggctcg | 1200 |
| accctgaagg agctggcgct gccgatctat tcgatcggca tggtcctggc gttcgcgttc | 1260 |
| atctcgaact attcgggcct gtcgtcgacc ctggcgctgg cgctggcgca taccggccat | 1320 |
| gcgttcacct tcttctcgcc gttcctgggc tggctgggcg tcttcctgac cggctcggac | 1380 |
| acctcgtcga acgcgctgtt cgcggcgctg caggcgaccg cggcgcagca gatcggcgtc | 1440 |
| tcggacctgc tgctggtcgc ggcgaacacc accggcggcg tcaccggcaa gatgatctcg | 1500 |

```
ccgcagtcga tcgcgatcgc gtgcgcggcg gtcggcctgg tcggcaagga gtcggacctg    1560
ttccgcttca ccgtcaagca ttcgctgatc ttcacctgca tcgtcggcgt catcaccacc    1620
ctgcaggcgt atgtcctgac ctggatgatc ccgtga                              1656
```

<210> SEQ ID NO 129
<211> LENGTH: 2894
<212> TYPE: DNA
<213> ORGANISM: Artificial Sequence
<220> FEATURE:
<223> OTHER INFORMATION: Lactate Utilization Pathway Operon

<400> SEQUENCE: 129

```
tttgcctcga tcggcggtcc ttgtgacagg gagatattcc cgacggatcc ggggcattcg      60
agcggaaccg cccgccgtgg gagttttttcc agcgagcatt cgagagtttt tcaaggcggc    120
ttcgaggggt tattccgtaa cgccgccgac atgatctgtc ccagaatctc cgccgctgtt    180
cgtagagcgc cgatgcaggg tcggcatcaa tcattcttgg aggagacaca tgaagctggc    240
ggtctattcg accaagcagt atgacaagaa gtatctgcag caggtcaacg agtcgttcgg    300
cttcgagctg gagttcttcg acttcctgct gaccgagaag accgcgaaga ccgcgaacgg    360
ctgcgaggcg gtctgcatct tcgtcaacga cgacggctcg cgcccggtcc tggaggagct    420
gaagaagcat ggcgtcaagt atatcgcgct gcgctgcgcg gcttcaacaa cgtcgacct    480 ggacgcggcg aaggagctgg gcctgaaggt cgtccgcgtc ccggcgtatg acccggaggc    540
ggtcgcggag catgcgatcg gcatgatgat gaccctgaac cgccgcatcc atcgcgcgta    600
tcagcgcacc cgcgacgcga acttctcgct ggagggcctg accggcttca ccatgtatgg    660
caagaccgcg ggcgtcatcg gcaccggcaa gatcggcgtc gcgatgctgc gcatcctgaa    720
gggcttcggc atgcgcctgc tggcgttcga cccgtatccg tcggcggcgg cgctggagct    780
gggcgtcgag tatgtcgacc tgccgaccct gttctcggag tcggacgtca tctcgctgca    840
ttgcccgctg accccggaga actatcatct gctgaacgag gcggcgttcg agcagatgaa    900
gaacggcgtc atgatcgtca acacctcgcg cggcgcgctg atcgactcgc aggcggcgat    960
cgaggcgctg aagaaccaga agatcggctc gctgggcatg gacgtctatg agaacgagcg   1020
cgacctgttc ttcgaggaca gtcgaacga cgtcatccag gacgacgtct tccgccgcct   1080
gtcggcgtgc cataacgtcc tgttcaccgg ccatcaggcg ttcctgaccg cggaggcgct   1140
gacctcgatc tcgcagacca ccctgcagaa cctgtcgaac ctggagaagg gcgagacctg   1200
cccgaacgag ctggtctgat cattcttgga ggagacacat gaacctgtgg cagcagaact   1260
atgacccggc gggcaacatc tggctgtcgt cgctgatcgc gtcgctgccg atcctgttct   1320
tcttcttcgc gctgatcaag ctgaagctga agggctatgt cgcggcgtcg tggaccgtcg   1380
cgatcgcgct ggcggtcgcg ctgctgttct ataagatgcc ggtcgcgaac gcgctggcgt   1440
cggtcgtcta tggcttcttc tatggcctgt ggccgatcgc gtggatcatc atcgcggcgg   1500
tcttcgtcta taagatctcg gtcaagaccg gccagttcga catcatccgc tcgtcgatcc   1560
tgtcgatcac cccggaccag cgcctgcaga tgctgatcgt cggcttctgc ttcggcgcgt   1620
tcctggaggg cgcggcgggc ttcggcgcgc ggtcgcgat caccgcggcg ctgctggtcg   1680
gcctgggctt caagccgctg tatgcggcgg gcctgtgcct gatcgtcaac accgcgccgg   1740
tcgcgttcgg cgcgatgggc atcccgatcc tggtcgcggg ccaggtcacc ggcatcgact   1800
cgttcgagat cggccagatg gtcggccgcc agctgccgtt catgaccatc atcgtcctgt   1860
```

-continued

```
tctggatcat ggcgatcatg gacggctggc gcggcatcaa ggagacctgg ccggcggtcg    1920
tcgtcgcggg cggctcgttc gcgatcgcgc agtatctgtc gtcgaacttc atcggcccgg    1980
agctgccgga catcatctcg tcgctggtct cgctgctgtg cctgaccctg ttcctgaagc    2040
gctggcagcc ggtccgcgtc ttccgcttcg gcgacctggg cgcgtcgcag gtcgacatga    2100
ccctggcgca taccggctat accgcgggcc aggtcctgcg cgcgtggacc ccgttcctgt    2160
tcctgaccgc gaccgtcacc ctgtggtcga tcccgccgtt caaggcgctg ttcgcgtcgg    2220
gcggcgcgct gtatgagtgg gtcatcaaca tcccggtccc gtatctggac aagctggtcg    2280
cgcgcatgcc gccggtcgtc tcggaggcga ccgcgtatgc ggcggtcttc aagttcgact    2340
ggttctcggc gaccggcacc gcgatcctgt tcgcggcgct gctgtcgatc gtctggctga    2400
agatgaagcc gtcggacgcg atctcgacct tcggctcgac cctgaaggag ctggcgctgc    2460
cgatctattc gatcggcatg gtcctggcgt tcgcgttcat ctcgaactat tcgggcctgt    2520
cgtcgaccct ggcgctggcg ctggcgcata ccgccatgc gttcaccttc ttctcgccgt    2580
tcctgggctg gctgggcgtc ttcctgaccg gctcggacac ctcgtcgaac gcgctgttcg    2640
cggcgctgca ggcgaccgcg gcgcagcaga tcggcgtctc ggacctgctg ctggtcgcgg    2700
cgaacaccac cggcggcgtc accggcaaga tgatctcgcc gcagtcgatc gcgatcgcgt    2760
gcgcggcggt cggcctggtc ggcaaggagt cggacctgtt ccgcttcacc gtcaagcatt    2820
cgctgatctt cacctgcatc gtcggcgtca tcaccaccct gcaggcgtat gtcctgacct    2880
ggatgatccc gtga                                                     2894
```

<210> SEQ ID NO 130
<211> LENGTH: 229
<212> TYPE: DNA
<213> ORGANISM: Artificial Sequence
<220> FEATURE:
<223> OTHER INFORMATION: MDH promoter

<400> SEQUENCE: 130

```
tttgcctcga tcggcggtcc ttgtgacagg gagatattcc cgacggatcc ggggcattcg     60
agcggaaccg cccgccgtgg gagttttttcc agcgagcatt cgagagttttt tcaaggcggc    120 ttcgagggggt tattccgtaa cgccgccgac atgatctgtc ccagaatctc cgccgctgtt   180
cgtagagcgc cgatgcaggg tcggcatcaa tcattcttgg aggagacac                229
```

<210> SEQ ID NO 131
<211> LENGTH: 990
<212> TYPE: DNA
<213> ORGANISM: Artificial Sequence
<220> FEATURE:
<223> OTHER INFORMATION: codon optimized LdhD

<400> SEQUENCE: 131

```
atgaagctgg ccgtctacag caccaagcag tacgacaaga agtacctgca gcaggtcaac     60
gagagcttcg gcttcgagct ggagttcttc gacttcctgc tgaccgagaa gaccgccaag    120
accgccaacg gctgcgaggc cgtctgcatc ttcgtcaacg acgacggcag ccgcccggtc    180
ctggaggagc tgaagaagca cggcgtcaag tacatcgccc tgcgctgcgc cggcttcaac    240
aacgtcgacc tggacgccgc caaggagctg ggcctgaagg tcgtccgcgt cccggcctac    300
gacccggagg ccgtcgccga gcacgccatc ggcatgatga tgaccctgaa ccgccgcatc    360
caccgcgcct accagcgcac ccgcgacgcc aacttcagcc tggagggcct gaccggcttc    420
accatgtacg gcaagaccgc cggcgtcatc ggcaccggca agatcggcgt cgccatgctg    480
```

```
cgcatcctga agggcttcgg catgcgcctg ctggccttcg acccgtaccc gagcgccgcc     540
gccctggagc tgggcgtcga gtacgtcgac ctgccgaccc tgttcagcga gagcgacgtc     600
atcagcctgc actgcccgct gaccccggag aactaccacc tgctgaacga ggccgccttc     660
gagcagatga agaacggcgt catgatcgtc aacaccagcc gcggcgccct gatcgacagc     720
caggccgcca tcgaggccct gaagaaccag aagatcggca gcctgggcat ggacgtctac     780
gagaacgagc gcgacctgtt cttcgaggac aagagcaacg acgtcatcca ggacgacgtc     840
ttccgccgcc tgagcgcctg ccacaacgtc ctgttcaccg gccaccaggc cttcctgacc     900
gccgaggccc tgaccagcat cagccagacc accctgcaga acctgagcaa cctggagaag     960
ggcgagacct gcccgaacga gctggtctga                                       990

<210> SEQ ID NO 132
<211> LENGTH: 19
<212> TYPE: DNA
<213> ORGANISM: Artificial Sequence
<220> FEATURE:
<223> OTHER INFORMATION: Intergenic Region

<400> SEQUENCE: 132
tcattcttgg aggagacac                                                    19

<210> SEQ ID NO 133
<211> LENGTH: 1656
<212> TYPE: DNA
<213> ORGANISM: Artificial Sequence
<220> FEATURE:
<223> OTHER INFORMATION: codon optimized LctP

<400> SEQUENCE: 133
atgaacctgt ggcagcagaa ctacgacccg gccggcaaca tctggctgag cagcctgatc      60
gccagcctgc cgatcctgtt cttcttcttc gccctgatca agctgaagct gaagggctac     120
gtcgccgcca gctggaccgt cgccatcgcc ctggccgtcg ccctgctgtt ctacaagatg     180
ccggtcgcca acgccctggc cagcgtcgtc tacggcttct tctacggcct gtggccgatc     240
gcctggatca tcatcgccgc cgtcttcgtc tacaagatca gcgtcaagac cggccagttc     300
gacatcatcc gcagcagcat cctgagcatc accccggacc agcgcctgca gatgctgatc     360
gtcggcttct gcttcggcgc cttcctggag ggcgccgccg gcttcggcgc ccgggtcgcc     420
atcaccgccg ccctgctggt cggcctgggc ttcaagccgc tgtacgccgc cggcctgtgc     480
ctgatcgtca acaccgcccc ggtcgccttc ggcgccatgg gcatcccgat cctggtcgcc     540
ggccaggtca ccggcatcga cagcttcgag atcggccaga tggtcggccg ccagctgccg     600
ttcatgacca tcatcgtcct gttctggatc atggccatca tggacggctg gcgcggcatc     660
aaggagacct ggccggccgt cgtcgtcgcc ggcggcagct tcgccatcgc ccagtacctg     720
agcagcaact tcatcggccc ggagctgccg acatcatca gcagcctggt cagcctgctg     780
tgcctgaccc tgttcctgaa cgctggcag ccggtccgcg tcttccgctt cggcgacctg     840
ggcgccagcc aggtcgacat gaccctggcc cacaccggct acaccgcggg ccaggtcctg     900
cgcgcctgga cccgttcct gttcctgacc gccaccgtca ccctgtggag catcccgccg     960
ttcaaggccc tgttcgccag cggcggcgcc ctgtacgagt gggtcatcaa catcccggtc    1020
ccgtacctgg acaagctggt cgcccgcatg ccgccggtcg tcagcgaggc caccgcctac    1080
gccgccgtct tcaagttcga ctggttcagc gccaccggca ccgccatcct gttcgccgcc    1140
```

```
ctgctgagca tcgtctggct gaagatgaag ccgagcgacg ccatcagcac cttcggcagc    1200
accctgaagg agctggccct gccgatctac agcatcggca tggtcctggc cttcgccttc    1260
atcagcaact acagcggcct gagcagcacc ctggccctgg ccctggccca caccggccac    1320
gccttcacct tcttcagccc gttcctgggc tggctgggcg tcttcctgac cggcagcgac    1380
accagcagca acgccctgtt cgccgccctg caggccaccg ccgcccagca gatcggcgtc    1440
agcgacctgc tgctggtcgc cgccaacacc accggcggcg tcaccggcaa gatgatcagc    1500
ccgcagagca tcgccatcgc ctgcgccgcc gtcggcctgg tcggcaagga gagcgacctg    1560
ttccgcttca ccgtcaagca cagcctgatc ttcacctgca tcgtcggcgt catcaccacc    1620
ctgcaggcct acgtcctgac ctggatgatc ccgtga                              1656
```

<210> SEQ ID NO 134
<211> LENGTH: 2894
<212> TYPE: DNA
<213> ORGANISM: Artificial Sequence
<220> FEATURE:
<223> OTHER INFORMATION: Lactate Utilization Pathway Operon

<400> SEQUENCE: 134

```
tttgcctcga tcggcggtcc ttgtgacagg gagatattcc cgacggatcc ggggcattcg      60
agcggaaccg cccgccgtgg gagttttttcc agcgagcatt cgagagtttt tcaaggcggc    120
ttcgaggggt tattccgtaa cgccgccgac atgatctgtc ccagaatctc cgccgctgtt    180
cgtagagcgc cgatgcaggg tcggcatcaa tcattcttgg aggagacaca tgaagctggc    240
cgtctacagc accaagcagt acgacaagaa gtacctgcag caggtcaacg agagcttcgg    300
cttcgagctg gagttcttcg acttcctgct gaccgagaag accgccaaga ccgccaacgg    360
ctgcgaggcc gtctgcatct tcgtcaacga cgacggcagc cgcccggtcc tggaggagct    420
gaagaagcac ggcgtcaagt acatcgccct gcgctgcgcc ggcttcaaca cgtcgacct    480 ggacgccgcc aaggagctgg gcctgaaggt cgtccgcgtc ccggcctacg acccggaggc    540
cgtcgccgag cacgccatcg gcatgatgat gaccctgaac cgccgcatcc accgcgccta    600
ccagcgcacc cgcgacgcca acttcagcct ggagggcctg accggcttca ccatgtacgg    660
caagaccgcc ggcgtcatcg gcaccggcaa gatcggcgtc gccatgctgc gcatcctgaa    720
gggcttcggc atgcgcctgc tggccttcga cccgtacccg agcgccgccg ccctggagct    780
gggcgtcgag tacgtcgacc tgccgaccct gttcagcgag agcgacgtca tcagcctgca    840
ctgcccgctg accccggaga actaccacct gctgaacgag gccgccttcg agcagatgaa    900
gaacggcgtc atgatcgtca acaccagccg cggcgccctg atcgacagcc aggccgccat    960
cgaggccctg aagaaccaga gatcggcag cctgggcatg gacgtctacg agaacgagcg    1020
cgacctgttc ttcgaggaca gagcaacga cgtcatccag gacgacgtct ccgccgcct    1080 gagcgccctgc cacaacgtcc tgttcaccgg ccaccaggcc ttcctgaccg ccgaggccct    1140
gaccagcatc agccagacca ccctgcagaa cctgagcaac ctggagaagg gcgagacctg    1200
cccgaacgag ctggtctgat cattcttgga ggagacacat gaacctgtgg cagcagaact    1260 acgaccggc cggcaacatc tggctgagca gcctgatcgc cagcctgccg atcctgttct    1320
tcttcttcgc cctgatcaag ctgaagctga agggctacgt cgccgccagc tggaccgtcg    1380
ccatcgccct ggccgtcgcc ctgctgttct acacaagatgcc ggtcgccaac gccctggcca    1440
gcgtcgtcta cggcttcttc tacgccctgt ggccgatcgc ctggatcatc atcgccgccg    1500
tcttcgtcta caagatcagc gtcaagaccg gccagttcga catcatccgc agcagcatcc    1560
```

```
tgagcatcac cccggaccag cgcctgcaga tgctgatcgt cggcttctgc ttcggcgcct    1620
tcctggaggg cgccgccggc ttcggcgccc cggtcgccat caccgccgcc ctgctggtcg    1680
gcctgggctt caagccgctg tacgccgccg gcctgtgcct gatcgtcaac accgccccgg    1740
tcgccttcgg cgccatgggc atcccgatcc tggtcgccgg ccaggtcacc ggcatcgaca    1800
gcttcgagat cggccagatg gtcggccgcc agctgccgtt catgaccatc atcgtcctgt    1860
tctggatcat ggccatcatg gacggctggc gcggcatcaa ggagacctgg ccggccgtcg    1920
tcgtcgccgg cggcagcttc gccatcgccc agtacctgag cagcaacttc atcggcccgg    1980
agctgccgga catcatcagc agcctggtca gcctgctgtg cctgaccctg ttcctgaagc    2040
gctggcagcc ggtccgcgtc ttccgcttcg gcgacctggg cgccagccag gtcgacatga    2100
ccctggccca caccggctac accgccggcc aggtcctgcg cgcctggacc ccgttcctgt    2160
tcctgaccgc caccgtcacc ctgtggagca tcccgccgtt caaggccctg ttcgccagcg    2220
gcggcgccct gtacgagtgg gtcatcaaca tcccggtccc gtacctggac aagctggtcg    2280
cccgcatgcc gccggtcgtc agcgaggcca ccgcctacgc cgccgtcttc aagttcgact    2340
ggttcagcgc caccggcacc gccatcctgt tcgccgccct gctgagcatc gtctggctga    2400
agatgaagcc gagcgacgcc atcagcacct tcggcagcac cctgaaggag ctggccctgc    2460
cgatctacag catcggcatg gtcctggcct tcgccttcat cagcaactac agcggcctga    2520
gcagcaccct ggccctggcc ctggcccaca ccggccacgc cttcaccttc ttcagcccgt    2580
tcctgggctg gctgggcgtc ttcctgaccg gcagcgacac cagcagcaac gccctgttcg    2640
ccgccctgca ggccaccgcc gcccagcaga tcggcgtcag cgacctgctg ctggtcgccg    2700
ccaacaccac cggcggcgtc accggcaaga tgatcagccc gcagagcatc gccatcgcct    2760
gcgccgccgt cggcctggtc ggcaaggaga gcgacctgtt ccgcttcacc gtcaagcaca    2820
gcctgatctt cacctgcatc gtcggcgtca tcaccaccct gcaggcctac gtcctgacct    2880
ggatgatccc gtga                                                     2894

<210> SEQ ID NO 135
<211> LENGTH: 497
<212> TYPE: DNA
<213> ORGANISM: Artificial Sequence
<220> FEATURE:
<223> OTHER INFORMATION: HPS promoter

<400> SEQUENCE: 135
ttcggaatcc ctgacgggaa ttggcccgaa gaaggcagat gccatcgttc agtatcgaaa     60
ggaacatggg gattttcagt cattgaagga tctggagaat gtcagcggca ttggcgagaa    120 aaccccttcag gccaatgaaa aagacattcg cttcacggat gatttgagcg ataagtcatc    180
cgcggaaaaa ggtgcggtag ctgtggataa aaaaggcgcc agatagtaag cgctaaggat    240
tggggtgcgt cgccggtcgc ggcggcgctc ctcgacggca gagttggtgc caggttggcg    300
gatgattgat gccgaatatt acgcgaccaa ttctcgaggc aaatgaactg tgagctactg    360
agttgcaggc attgacagcc atcccatttc tatcatacag ttacggacgc atcacgagta    420
ggtgataagc ctagcagatt gcggcagttg caaaatcag ctattactaa taattaaaaa    480
ctttcggagc acatcac                                                  497

<210> SEQ ID NO 136
<211> LENGTH: 990
<212> TYPE: DNA
```

<213> ORGANISM: Artificial Sequence
<220> FEATURE:
<223> OTHER INFORMATION: codon optimized LdhD

<400> SEQUENCE: 136

| | | |
|---|---|---|
| atgaaattgg cggtctatag caccaaacaa tatgataaaa aatatttgca acaagtcaac | 60 |
| gaaagcttcg gcttcgaatt ggaattcttc gatttcttgt tgaccgaaaa aaccgcgaaa | 120 |
| accgcgaacg gctgcgaagc ggtctgcatc ttcgtcaacg atgatggcag ccgcccggtc | 180 |
| ttggaagaat tgaaaaaaca cggcgtcaaa tatatcgcgt tgcgctgcgc gggcttcaac | 240 |
| aacgtcgatt tggatgcggc gaaagaattg ggcttgaaag tcgtccgcgt cccggcgtat | 300 |
| gatccggaag cggtcgcgga cacgcgatc ggcatgatga tgaccttgaa ccgccgcatc | 360 |
| caccgcgcgt atcaacgcac ccgcgatgcg aacttcagct tggaaggctt gaccggcttc | 420 |
| accatgtatg gcaaaaccgc gggcgtcatc ggcaccggca aaatcggcgt cgcgatgttg | 480 |
| cgcatcttga aaggcttcgg catgcgcttg ttggcgttcg atccgtatcc gagcgcggcg | 540 |
| gcgttggaat gggcgtcga atatgtcgat ttgccgacct tgttcagcga aagcgatgtc | 600 |
| atcagcttgc actgcccgtt gaccccggaa actatcact tgttgaacga agcggcgttc | 660 |
| gaacaaatga aaaacggcgt catgatcgtc aacaccagcc gcggcgcgtt gatcgatagc | 720 |
| caagcggcga tcgaagcgtt gaaaaaccaa aaaatcggca gcttgggcat ggatgtctat | 780 |
| gaaaacgaac gcgatttgtt cttcgaagat aaaagcaacg atgtcatcca agatgatgtc | 840 |
| ttccgccgct tgagcgcgtg ccacaacgtc ttgttcaccg gccaccaagc gttcttgacc | 900 |
| gcggaagcgt tgaccagcat cagccaaacc accttgcaaa acttgagcaa cttggaaaaa | 960 |
| ggcgaaaccct gcccgaacga attggtctaa | 990 |

<210> SEQ ID NO 137
<211> LENGTH: 30
<212> TYPE: DNA
<213> ORGANISM: Artificial Sequence
<220> FEATURE:
<223> OTHER INFORMATION: Intergenic Region

<400> SEQUENCE: 137

| | | |
|---|---|---|
| taataattaa aaactttcgg agcacatcac | 30 |

<210> SEQ ID NO 138
<211> LENGTH: 1656
<212> TYPE: DNA
<213> ORGANISM: Artificial Sequence
<220> FEATURE:
<223> OTHER INFORMATION: codon optimized LctP

<400> SEQUENCE: 138

| | | |
|---|---|---|
| atgaacttgt ggcaacaaaa ctatgatccg gcgggcaaca tctggttgag cagcttgatc | 60 |
| gcgagcttgc cgatcttgtt cttcttcttc gcgttgatca aattgaaatt gaaaggctat | 120 |
| gtcgcggcga gctggaccgt cgcgatcgcg ttggcggtcg cgttgttgtt ctataaaatg | 180 |
| ccggtcgcga acgcgttggc gagcgtcgtc tatggcttct tctatggctt gtggccgatc | 240 |
| gcgtggatca tcatcgcggc ggtcttcgtc tataaaatca gcgtcaaaac cggccaattc | 300 |
| gatatcatcc gcagcagcat cttgagcatc accccggatc aacgcttgca aatgttgatc | 360 |
| gtcggcttct gcttcggcgc gttcttggaa ggcgcggcgg gcttcggcgc gccggtcgcg | 420 |
| atcaccgcgg cgttgttggt cggcttgggc ttcaaaccgt tgtatgcggc gggcttgtgc | 480 |
| ttgatcgtca acaccgcgcc ggtcgcgttc ggcgcgatgg gcatcccgat cttggtcgcg | 540 |

```
ggccaagtca ccggcatcga tagcttcgaa atcggccaaa tggtcggccg ccaattgccg        600
ttcatgacca tcatcgtctt gttctggatc atggcgatca tggatggctg gcgcggcatc        660
aaagaaacct ggccggcggt cgtcgtcgcg ggcggcagct cgcgatcgc gcaatatttg         720 agcagcaact tcatcggccc ggaattgccg gatatcatca gcagcttggt cagcttgttg        780
tgcttgacct tgttcttgaa acgctggcaa ccggtccgcg tcttccgctt cggcgatttg        840
ggcgcgagcc aagtcgatat gaccttggcg cacaccggct ataccgcggg ccaagtcttg        900
cgcgcgtgga ccccgttctt gttcttgacc gcgaccgtca ccttgtggag catcccgccg        960
ttcaaagcgt tgttcgcgag cggcggcgcg ttgtatgaat gggtcatcaa catcccggtc       1020
ccgtatttgg ataaattggt cgcgcgcatg ccgccggtcg tcagcgaagc gaccgcgtat       1080
gcggcggtct tcaaattcga ttggttcagc gcgaccggca ccgcgatctt gttcgcggcg       1140
ttgttgagca tcgtctggtt gaaaatgaaa ccgagcgatg cgatcagcac cttcggcagc       1200
accttgaaag aattggcgtt gccgatctat agcatcggca tggtcttggc gttcgcgttc       1260
atcagcaact atagcggctt gagcagcacc ttggcgttgg cgttggcgca caccggccac       1320
gcgttcacct tcttcagccc gttcttgggc tggttgggcg tcttcttgac cggcagcgat       1380
accagcagca acgcgttgtt cgcggcgttg caagcgaccg cggcgcaaca aatcggcgtc       1440
agcgatttgt tgttggtcgc ggcgaacacc accggcggcg tcaccggcaa aatgatcagc       1500
ccgcaaagca tcgcgatcgc gtgcgcggcg gtcggcttgg tcggcaaaga aagcgatttg       1560
ttccgcttca ccgtcaaaca cagcttgatc ttcacctgca tcgtcggcgt catcaccacc       1620
ttgcaagcgt atgtcttgac ctggatgatc ccgtaa                                  1656

<210> SEQ ID NO 139
<211> LENGTH: 3173
<212> TYPE: DNA
<213> ORGANISM: Artificial Sequence
<220> FEATURE:
<223> OTHER INFORMATION: Lactate Utilization Pathway Operon

<400> SEQUENCE: 139
ttcggaatcc ctgacgggaa ttggcccgaa gaaggcagat gccatcgttc agtatcgaaa         60
ggaacatggg gattttcagt cattgaagga tctggagaat gtcagcggca ttggcgagaa        120
aacccttcag gccaatgaaa aagacattcg cttcacggat gatttgagcg ataagtcatc        180
cgcggaaaaa ggtgcggtag ctgtggataa aaaaggcgcc agatagtaag cgctaaggat        240
tggggtgcgt cgccggtcgc ggcggcgctc ctcgacggca gagttggtgc caggttggcg        300
gatgattgat gccgaatatt acgcgaccaa ttctcgaggc aaatgaactg tgagctactg        360
agttgcaggc attgacagcc atcccatttc tatcatacag ttacggacgc atcacgagta        420
ggtgataagc ctagcagatt gcggcagttg gcaaaatcag ctattactaa taattaaaaa        480
ctttcggagc acatcacatg aaattggcgg tctatagcac caaacaatat gataaaaaat        540
atttgcaaca agtcaacgaa agcttcggct tcgaattgga attcttcgat tcttgttga         600 ccgaaaaaac cgcgaaaacc gcgaacggct gcgaagcggt ctgcatcttc gtcaacgatg        660
atggcagccg cccggtcttg gaagaattga aaaaacacgg cgtcaaatat atcgcgttgc        720
gctgcgcggg cttcaacaac gtcgatttgg atgcggcgaa agaattgggc ttgaaagtcg        780
tccgcgtccc ggcgtatgat ccggaagcgg tcgcggaaca cgcgatcggc atgatgatga        840
ccttgaaccg ccgcatccac cgcgcgtatc aacgcacccg cgatgcgaac ttcagcttgg        900
```

-continued

```
aaggcttgac cggcttcacc atgtatggca aaaccgcggg cgtcatcggc accggcaaaa   960
tcggcgtcgc gatgttgcgc atcttgaaag gcttcggcat gcgcttgttg gcgttcgatc  1020
cgtatccgag cgcggcggcg ttggaattgg gcgtcgaata tgtcgatttg ccgaccttgt  1080
tcagcgaaag cgatgtcatc agcttgcact gcccgttgac cccggaaaac tatcacttgt  1140
tgaacgaagc ggcgttcgaa caaatgaaaa acggcgtcat gatcgtcaac accagccgcg  1200
gcgcgttgat cgatagccaa gcggcgatcg aagcgttgaa aaaccaaaaa atcggcagct  1260
tgggcatgga tgtctatgaa acgaacgcg atttgttctt cgaagataaa agcaacgatg  1320
tcatccaaga tgatgtcttc cgccgcttga gcgcgtgcca acgtcttg ttcaccggcc   1380
accaagcgtt cttgaccgcg gaagcgttga ccagcatcag ccaaaccacc ttgcaaaact  1440
tgagcaactt ggaaaaaggc gaaacctgcc cgaacgaatt ggtctaataa taattaaaaa  1500
ctttcggagc acatcacatg aacttgtggc aacaaaacta tgatccggcg ggcaacatct  1560
ggttgagcag cttgatcgcg agcttgccga tcttgttctt cttcttcgcg ttgatcaaat  1620
tgaaattgaa aggctatgtc gcggcgagct ggaccgtcgc gatcgcgttg gcggtcgcgt  1680
tgttgttcta taaaatgccg gtcgcgaacg cgttggcgag cgtcgtctat ggcttcttct  1740
atggcttgtg gccgatcgcg tggatcatca tcgcggcggt cttcgtctat aaaatcagcg  1800
tcaaaaccgg ccaattcgat atcatccgca gcagcatctt gagcatcacc ccggatcaac  1860
gcttgcaaat gttgatcgtc ggcttctgct tcggcgcgtt cttggaaggc gcggcgggct  1920
tcggcgcgcc ggtcgcgatc accgcggcgt tgttggtcgg cttgggcttc aaaccgttgt  1980
atgcggcggg cttgtgcttg atcgtcaaca ccgcgccggt cgcgttcggc gcgatgggca  2040
tcccgatctt ggtcgcgggc caagtcaccg gcatcgatag cttcgaaatc ggccaaatgg  2100
tcggccgcca attgccgttc atgaccatca tcgtcttgtt ctggatcatg gcgatcatgg  2160
atggctggcg cggcatcaaa gaaacctggc cggcggtcgt cgtcgcgggc ggcagcttcg  2220
cgatcgcgca atatttgagc agcaacttca tcggcccgga attgccggat atcatcagca  2280
gcttggtcag cttgttgtgc ttgaccttgt tcttgaaacg ctggcaaccg gtccgcgtct  2340
tccgcttcgg cgatttgggc gcgagccaag tcgatatgac cttggcgcac accggctata  2400
ccgcgggcca agtcttgcgc gcgtggaccc cgttcttgtt cttgaccgcg accgtcacct  2460
tgtggagcat cccgccgttc aaagcgttgt tcgcgagcgg cggcgcgttg tatgaatggg  2520
tcatcaacat cccggtcccg tatttggata aattggtcgc gcgcatgccg ccggtcgtca  2580
gcgaagcgac cgcgtatgcg gcggtcttca aattcgattg gttcagcgcg accggcaccg  2640
cgatcttgtt cgcggcgttg ttgagcatcg tctggttgaa aatgaaaccg agcgatgcga  2700
tcagcacctt cggcagcacc ttgaaagaat tggcgttgcc gatctatagc atcggcatgg  2760
tcttggcgtt cgcgttcatc agcaactata gcggcttgag cagcaccttg gcgttggcgt  2820
tggcgcacac cggccacgcg ttcaccttct tcagcccgtt cttgggctgg ttgggcgtct  2880
tcttgaccgg cagcgatacc agcagcaacg cgttgttcgc ggcgttgcaa gcgaccgcgg  2940
cgcaacaaat cggcgtcagc gatttgttgt tggtcgcggc gaacaccacc ggcggcgtca  3000
ccggcaaaat gatcagcccg caaagcatcg cgatcgcgtg cgcggcggtc ggcttggtcg  3060
gcaaagaaag cgatttgttc cgcttcaccg tcaaacacag cttgatcttc acctgcatcg  3120
tcggcgtcat caccaccttg caagcgtatg tcttgacctg gatgatcccg taa          3173
```